US012545656B2

(12) United States Patent
Park et al.

(10) Patent No.: US 12,545,656 B2
(45) Date of Patent: Feb. 10, 2026

(54) ORGANIC LIGHT-EMITTING COMPOUND AND ORGANIC ELECTROLUMINESCENT DEVICE USING THE SAME

(71) Applicant: SOLUS ADVANCED MATERIALS CO., LTD., Iksan-si (KR)

(72) Inventors: Woo Jae Park, Yongin-si (KR); Min Sik Eum, Yongin-si (KR); Jae Yi Sim, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 951 days.

(21) Appl. No.: 16/632,009

(22) PCT Filed: Jul. 2, 2018

(86) PCT No.: PCT/KR2018/007482

§ 371 (c)(1),
(2) Date: Jan. 17, 2020

(87) PCT Pub. No.: WO2019/017616

PCT Pub. Date: Jan. 24, 2019

(65) Prior Publication Data

US 2020/0168805 A1 May 28, 2020

(30) Foreign Application Priority Data

Jul. 20, 2017 (KR) ........................ 10-2017-0092063

(51) Int. Cl.

| | |
|---|---|
| ***C07D 401/04*** | (2006.01) |
| ***C07D 401/10*** | (2006.01) |
| ***C07D 403/10*** | (2006.01) |
| ***H10K 50/16*** | (2023.01) |
| ***H10K 50/17*** | (2023.01) |
| ***H10K 85/60*** | (2023.01) |
| *H10K 50/15* | (2023.01) |

(52) U.S. Cl.

CPC ......... *C07D 401/04* (2013.01); *C07D 401/10* (2013.01); *H10K 85/654* (2023.02); *H10K 50/15* (2023.02); *H10K 50/166* (2023.02); *H10K 50/17* (2023.02); *H10K 50/171* (2023.02)

(58) Field of Classification Search

CPC ............................ C07D 401/10; C07D 403/10

See application file for complete search history.

(56) References Cited

U.S. PATENT DOCUMENTS

| | | | | |
|---|---|---|---|---|
| 10,276,800 | B2 * | 4/2019 | Hayashi | C09K 11/06 |
| 2007/0051944 | A1 † | 3/2007 | Vestweber | |
| 2017/0186967 | A1 * | 6/2017 | Hayashi | H01L 51/0056 |
| 2017/0213982 | A1 * | 7/2017 | Hayama | H10K 85/623 |
| 2017/0346009 | A1 * | 11/2017 | Yokoyama | C09B 1/00 |
| 2017/0346015 | A1 * | 11/2017 | Hayashi | C09B 57/008 |
| 2018/0006235 | A1 * | 1/2018 | Yokoyama | H01L 51/006 |
| 2019/0106391 | A1 * | 4/2019 | Wucherer-Plietker | C07D 213/16 |

FOREIGN PATENT DOCUMENTS

| | | | | |
|---|---|---|---|---|
| CN | 106573911 | A | 4/2017 | |
| CN | 107759608 | A | 3/2018 | |
| CN | 110494426 | A | 11/2019 | |
| CN | 110622332 | A | 12/2019 | |
| JP | 2018-531883 | A | 11/2018 | |
| KR | 10-2012-0038032 | A | 4/2012 | |
| KR | 10-2013-0060157 | A | 6/2013 | |
| KR | 10-2016-0010730 | A | 1/2016 | |
| KR | 10-2016-0027985 | A | 3/2016 | |
| KR | 10-2017-0016936 | A | 2/2017 | |
| KR | 10-2017-0065711 | A | 6/2017 | |
| KR | 10-2017-0086211 | A | 7/2017 | |
| KR | 10-1755986 | B1 | 7/2017 | |
| KR | 10-2017-0111802 | A | 10/2017 | |
| KR | 10-2018-0127639 | A | 11/2018 | |
| KR | 10-2018-0130329 | A | 12/2018 | |
| WO | 2015/190400 | A1 | 12/2015 | |
| WO | 2016/076384 | A1 | 5/2016 | |
| WO | 2016/105141 | A2 | 6/2016 | |
| WO | WO 2016/175292 | * | 11/2016 | |
| WO | WO-2017016630 | A1 * | 2/2017 | C07D 251/24 |
| WO | 2017/157983 | A1 | 9/2017 | |
| WO | 2018/221930 | A1 | 12/2018 | |

OTHER PUBLICATIONS

International Search Report for PCT/KR2018/007482, dated Oct. 15, 2018.

Communication dated Oct. 9, 2023, issued in Chinese Application No. 202211257812.5.

* cited by examiner
† cited by third party

*Primary Examiner* — Bruck Kifle
*Assistant Examiner* — Kevin S Martin
(74) *Attorney, Agent, or Firm* — Sughrue Mion, PLLC

(57) ABSTRACT

The present disclosure relates to a novel organic compound and an organic EL device including the organic compound. The compound according to the present disclosure may be used in an organic layer of an organic EL device, more specifically, in a light emitting layer, a light emitting auxiliary layer, an electron transport auxiliary layer, or an electron transporting layer and may improve driving voltage, luminous efficiency, and lifespan characteristics of the organic EL device.

14 Claims, No Drawings

ORGANIC LIGHT-EMITTING COMPOUND AND ORGANIC ELECTROLUMINESCENT DEVICE USING THE SAME

CROSS REFERENCE TO RELATED APPLICATIONS

This application is a National Stage of International Application No. PCT/KR2018/007482 filed Jul. 2, 2018, claiming priority based on Korean Patent Application No. 10-2017-0092063 filed Jul. 20, 2017.

TECHNICAL FIELD

The present disclosure relates to a novel light-emitting organic compound and an organic electroluminescent device using the same, and more particularly, to a compound having excellent electron transporting ability and light emitting performance and an organic electroluminescence device improved in terms of luminous efficiency, driving voltage, lifespan and the like by including the compound in one or more organic layers.

DISCUSSION OF RELATED ART

Starting from Bernanose's observation of light emission from organic thin films in the 1950s, the study on organic electroluminescent devices (hereinafter, "EL devices") led to blue electroluminescence using anthracene monocrystals in 1965, and Tang suggested in 1987 an organic EL device in a stack structure which may be divided into functional layers of hole layers and light emitting layers. Then, in order to develop highly efficient, long lifespan organic EL devices, organic layers each having distinctive characteristics have been introduced in the EL devices, which led to the development of specialized materials used therein.

In organic EL devices, upon application of voltage between two electrodes, holes are injected from an anode into an organic layer and electrons are injected from a cathode into the organic layer. Injected holes and electrons meet each other to form excitons, and light emission occurs when the excitons fall to a ground state. In this case, materials used for the organic layer may be classified into, for example, light emitting materials, hole injection materials, hole transporting materials, electron transporting materials and electron injection materials depending on their function.

Materials forming a light emitting layer of an organic EL device may be classified into blue, green and red light emitting materials depending on their emission colors. Besides, yellow and orange light emitting materials may be used as such a light emitting material to realize better natural colors. In addition, a host/dopant system may be employed in the light emitting material to increase color purity and luminous efficiency through energy transfer. Dopant materials may be classified into fluorescent dopants using organic materials and phosphorescent dopants using metal complex compounds which include heavy atoms such as Ir and Pt. The developed phosphorescent materials may improve the luminous efficiency theoretically up to four times as compared to fluorescent materials, so attention is given to phosphorescent dopants as well as phosphorescent host materials.

To date, NPB, BCP and $Alq_3$, for example, are widely known as hole injection materials, hole transporting materials, electron transporting materials, and electron injection materials, and anthracene derivatives have been reported as light emitting materials. Particularly, metal complex compounds including Ir, such as FIrpic, Ir $(ppy)_3$, and (acac)Ir $(btp)_2$, are used as phosphorescent dopant materials of blue, green, and red colors, and 4,4-dicarbazolybiphenyl, (CBP) is used as phosphorescent host materials:

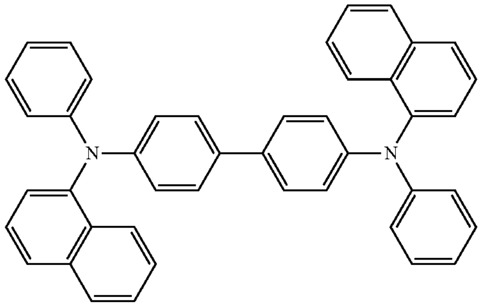

NP6

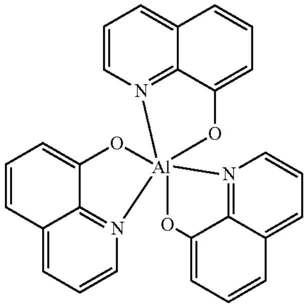

Alq3

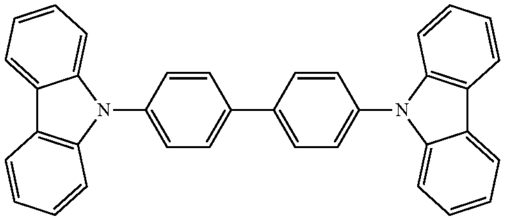

CBP

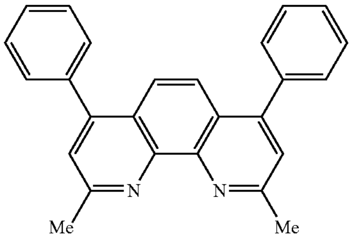

BCP

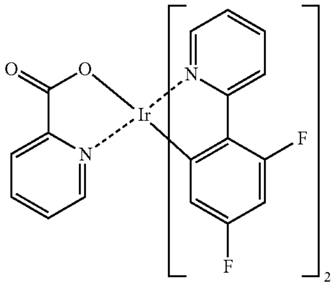

FIrpic

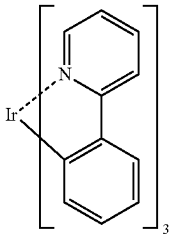

Ir(ppy)3

-continued

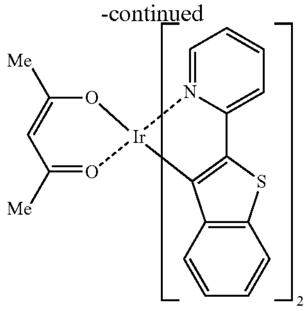

(acac)Ir(btp)$_2$

However, since conventional materials for organic layers have low glass transition temperatures, thus having poor thermal stability, and have low triplet energy, organic EL devices in which such conventional materials are used in the organic layers do not exhibit satisfactory current efficiency and lifespan characteristics. Accordingly, there is a demand for materials of organic layers that are excellent in performance.

PRIOR ART DOCUMENT

Patent Literature

Korean Laid-Open Patent Publication No. 2016-0078237

DETAILED DESCRIPTION OF THE INVENTION

Technical Objectives

The present disclosure is directed to providing a novel compound that has excellent heat resistance characteristics, carrier transporting ability and light emitting performance and thus may be used as a material for an organic layer of an organic electroluminescent device, specifically a material for a light emitting layer, a material for an electron transport auxiliary layer, a material for a light emitting auxiliary layer, or a material for an electron transporting layer.

The present disclosure is also directed to providing an organic electroluminescent device that has a low driving voltage, high luminous efficiency, and improved lifespan characteristics by including the novel compound.

Technical Solution to the Problem

In order to achieve the above object, the present disclosure provides a compound represented by the following Chemical Formula 1:

[Chemical Formula 1]

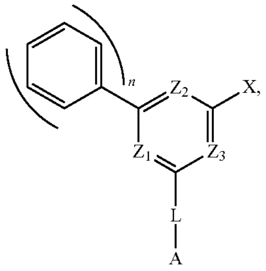

where in Chemical Formula 1, $Z_1$ to $Z_3$ are each independently nitrogen or carbon, and include at least two nitrogens, and X is represented by the following Chemical Formula 2 or Chemical Formula 3,

[Chemical Formula 2]

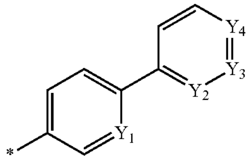

[Chemical Formula 3]

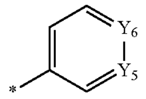

in Chemical Formula 2 and Chemical Formula 3, one of $Y_1$ to $Y_4$ is nitrogen and the others are carbons, and one of $Y_5$ and $Y_6$ is nitrogen and the other is carbon,

* means a site where a bond with Chemical Formula 1 is made, n is an integer ranging from 1 to 3, L is a single bond, or selected from the group consisting of a $C_6$ to $C_{18}$ arylene group and a heteroarylene group having 5 to 18 nuclear atoms, and A is represented by the following Chemical Formula 4, and

[Chemical Formula 4]

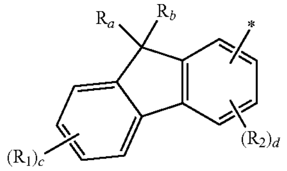

in Chemical Formula 4, $R_a$ and $R_b$ are the same as or different from each other, each independently a $C_1$ to $C_{40}$ alkyl group or a $C_6$ to $C_{60}$ aryl group, or bound with each other to form a fused ring, $R_1$ and $R_2$ are the same as or different from each other, each independently selected from the group consisting of: hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ phosphine group, a $C_1$ to $C_{40}$ phosphine oxide group, and a $C_6$ to $C_{60}$ arylamine group, or bound with an adjacent group to form a fused ring, c is an integer ranging from 0 to 4, d is an integer ranging from 0 to 3,

* means a site where a bond with Chemical Formula 1 is made, the alkyl group and the aryl group of $R_a$ and $R_b$, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the phosphine group, the phosphine oxide group, and the arylamine group of $R_1$ and $R_2$, and the arylene group and the heteroarylene group of L are each independently substituted or unsubstituted with one or more kinds of substituents selected from the group consisting of: deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ phosphine group, a $C_1$ to $C_{40}$ phosphine oxide group, and a $C_6$ to $C_{60}$ arylamine group, and when the substituents are plural in number, the plurality of substituents are the same as or different from each other.

The present disclosure also provides an organic electroluminescent device that includes an anode, a cathode and one or more organic layers disposed between the anode and the cathode. At least one of the one or more organic layers includes the compound represented by Chemical Formula 1. The organic layer including the compound represented by Chemical Formula 1 may be selected from the group consisting of: a hole injection layer, a hole transporting layer, a light emitting auxiliary layer, a light emitting layer, an electron transporting layer, and an electron injection layer. In such a case, the compound represented by Chemical Formula 1 may be used as a material of an electron transporting layer and an electron transport auxiliary layer.

Effects of the Invention

A compound represented by Chemical Formula 1 may be used as a material for an organic layer of an organic electroluminescent device by virtue of its excellent heat resistance characteristics, carrier transporting ability and light emitting performance.

In addition, an organic electroluminescent device including the compound according to an embodiment of the present disclosure may be greatly improved in terms of light emitting performance, driving voltage, lifespan, efficiency, etc., and such an organic electroluminescent device may be effectively applied to a full color display panel and the like.

MODES FOR CARRYING OUT THE INVENTION

Hereinafter, embodiments of the present disclosure will be described in detail.

<Organic Compound>

A novel organic compound according to the present disclosure is a compound, represented by the above Chemical Formula 1, that has a structure, as a basic skeleton, in which a fluorene moiety is bound to an electron withdrawing group (EWG) where a pyridine moiety is bound to triazine or pyrimidine.

The compound represented by Chemical Formula 1 not only is electrochemically stable and excellent in electron transporting properties but also has high triplet energy, excellent glass transition temperature and improved thermal stability, because pyrimidine (or triazine) that has excellent electron withdrawing characteristics is bound to pyridine moiety therein. In addition, since the compound represented by Chemical Formula 1 has a higher molecular weight than that of materials of conventional organic EL devices, it has a high glass transition temperature and excellent thermal stability.

Accordingly, since the compound represented by Chemical Formula 1 has excellent electron transporting ability and luminescence properties, it may be used as a material of one of a hole injection layer, a hole transporting layer, a light emitting layer, an electron transporting layer, and an electron injection layer, which are organic layers of organic EL devices. Preferably, it may be used as a material of one of a light emitting layer of green phosphorescence, an electron transporting layer, and an electron transport auxiliary layer further laminated on the electron transporting layer.

Specifically, since the compound represented by Chemical Formula 1 has a high triplet energy, due to triplet-triplet fusion (TTF) effects, it may be used as a material for the electron transport auxiliary layer, thus exhibiting greatly increased efficiency. In addition, excitons generated in the light emitting layer may be substantially prevented from being diffused into the electron transporting layer or the hole transporting layer which are adjacent to the light emitting layer. The number of excitons contributing to light emission in the light emitting layer may increase, and thus luminous efficiency of the device may be improved. Further, durability and stability of the device may be improved, and thus the lifespan of the device may be efficiently increased. The organic EL device to which such a compound represented by the above Chemical Formula 1 is applied exhibits physical characteristics that the lifespan of the organic EL device is improved because such an organic EL device is generally capable of operating at a low voltage.

Accordingly, when the compound represented by Chemical Formula 1 is used in an organic EL device, not only excellent thermal stability and carrier transporting ability (particularly, electron transporting ability and light emitting performance) may be expected, but also the driving voltage, efficiency, lifespan and the like of the device may be improved.

In addition, the compound represented by Chemical Formula 1 is considerably advantageous for electron transporting and shows long lifespan characteristics. The excellent electron transporting ability of such a compound may provide high efficiency and fast mobility in organic EL devices, and it is easy to adjust a HOMO and LUMO energy level depending on the direction or position of substituents. Accordingly, high electron transporting ability may be provided in the organic EL device using such a compound.

Specifically, the compound represented by Chemical Formula 1 according to the present disclosure may be represented by any one of the following Chemical Formula 5 to Chemical Formula 10.

[Chemical Formula 5]

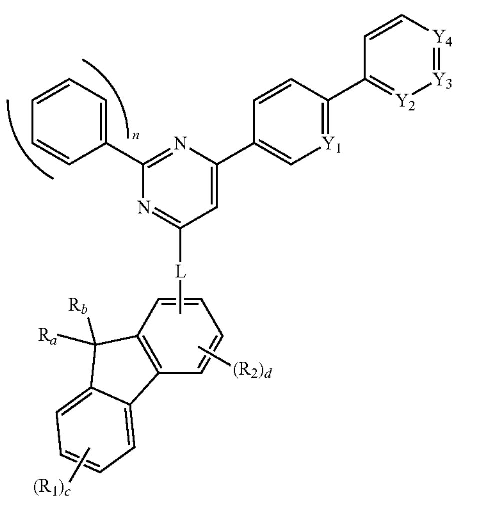

[Chemical Formula 6]

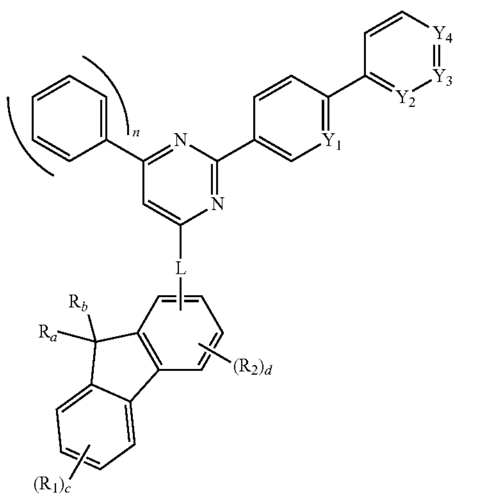

[Chemical Formula 7]

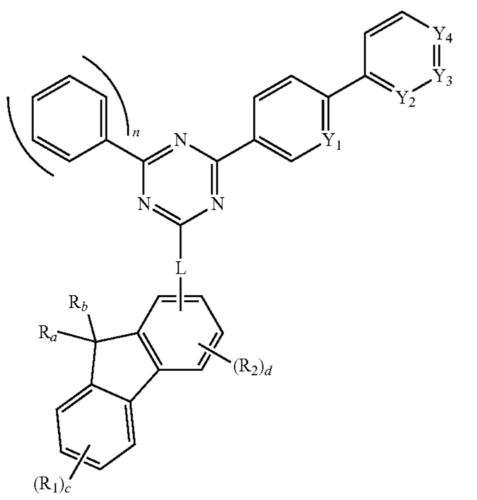

-continued

[Chemical Formula 8]

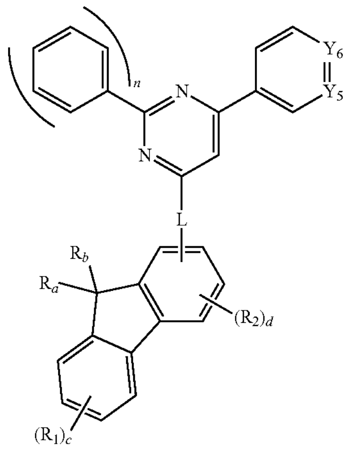

[Chemical Formula 9]

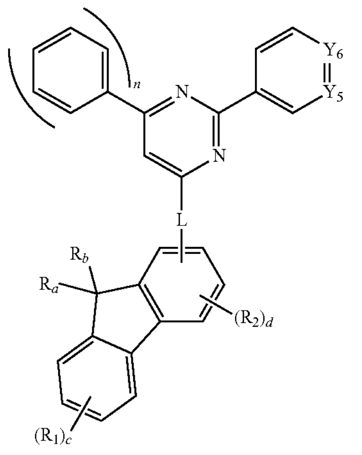

[Chemical Formula 10]

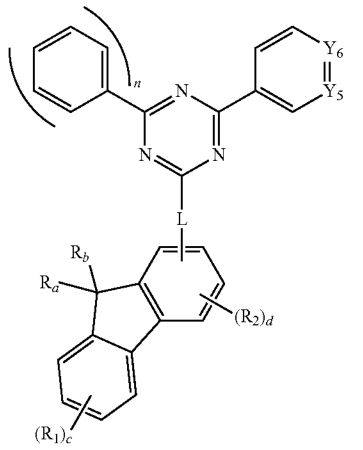

In Chemical Formula 5 to Chemical Formula 10, $R_a$, $R_b$, $R_1$, $R_2$, $Y_1$ to $Y_6$, L, c, d and n are the same as those defined in Chemical Formula 1, respectively.

Preferably, in Chemical Formula 1, X may be selected from the group consisting of the following structures represented by X-1 to X-6.

X-1

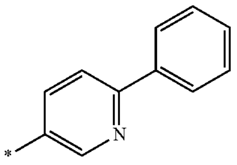

X-2

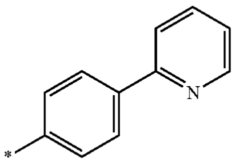

X-3

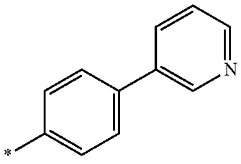

X-4

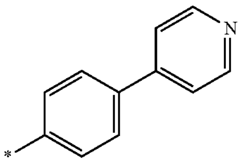

X-5

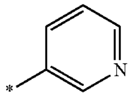

X-6

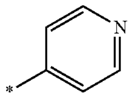

Preferably, in Chemical Formula 1, a structure represented by

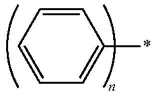

(* is a site where a bond is made) may be selected from the group consisting of the following structures represented by Ar-1 to Ar-5.

Ar-1

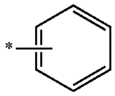

Ar-2

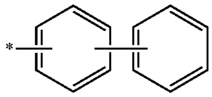

-continued

Ar-3

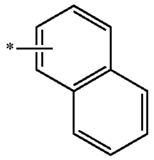

Ar-4

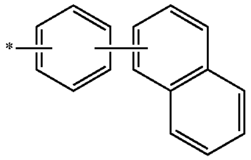

Ar-5

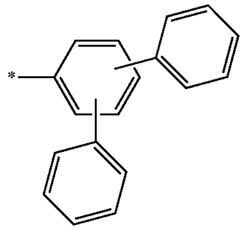

Preferably, $R_a$ and $R_b$ may each independently be a methyl group or a phenyl group or may be combined with each other to form a fused ring represented by

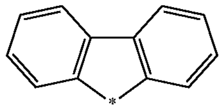 [SMILES: *1c2ccccc2c2ccccc12]

(* is a site where a bond is made).

Preferably, in Chemical Formula 1, A may be selected from the group consisting of the following structures represented by A-1 to A-6.

A-1

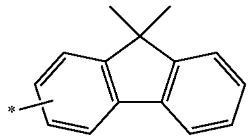

A-2

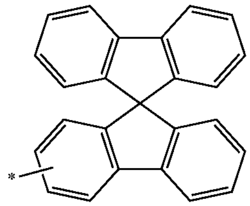

A-3

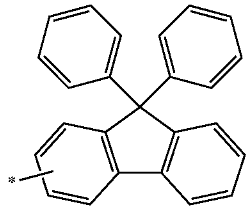

-continued

A-4

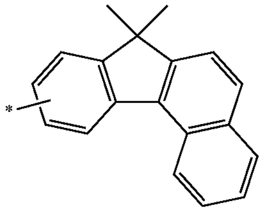

A-5

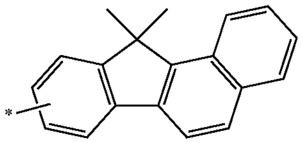

A-6

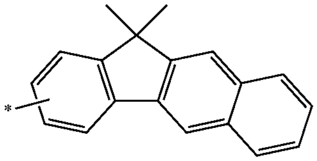

Preferably, in Chemical Formula 1, L may be a single bond or a linking group selected from the following structures represented by L-1 to L-7.

L-1

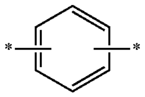

L-2

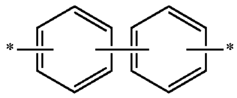

L-3

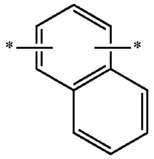

L-4

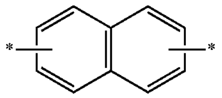

L-5

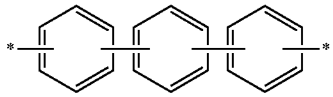

L-6

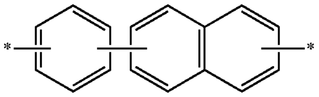

L-7

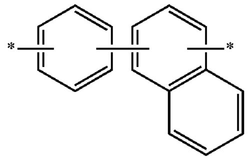

The compound, described above, represented by the above Chemical Formula 1 according to the present disclosure may be more specifically embodied as a compound represented by any one of Compounds 1 to 750 exemplified below. However, the compound represented by Chemical Formula 1 of the present disclosure is not limited by those illustrated below.

1

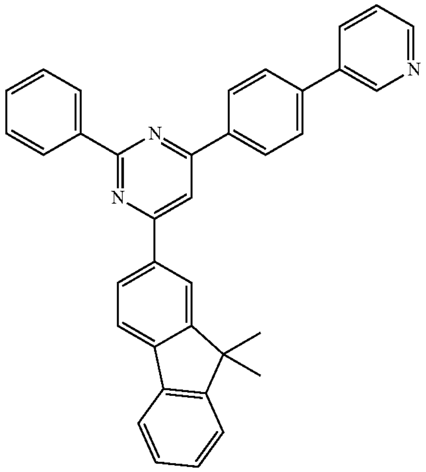

2

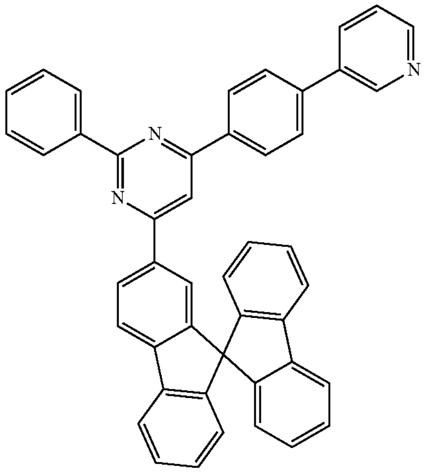

3

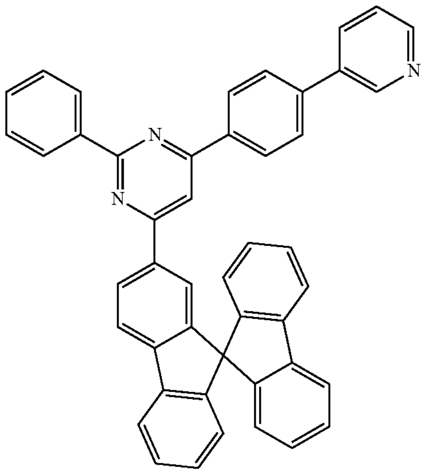

-continued
4
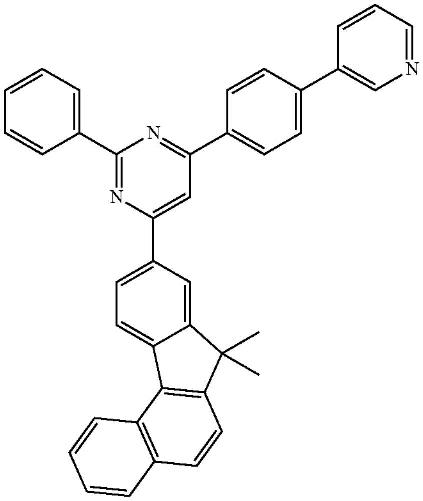
5
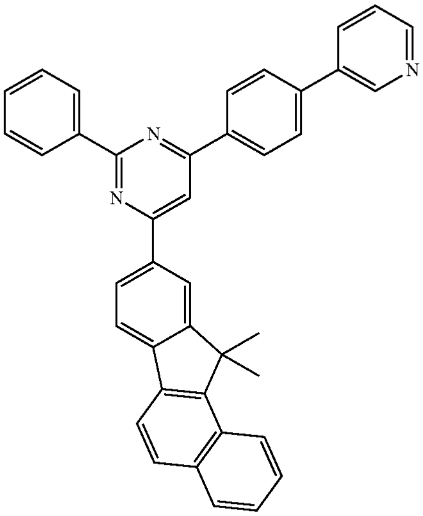
6
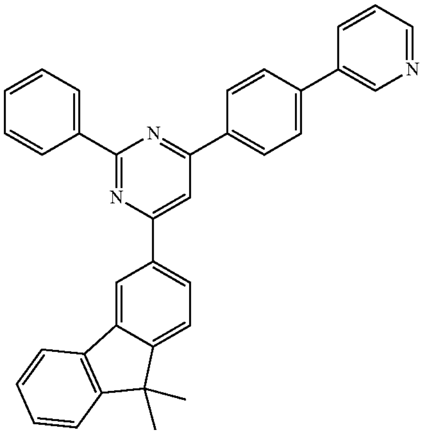
-continued
7
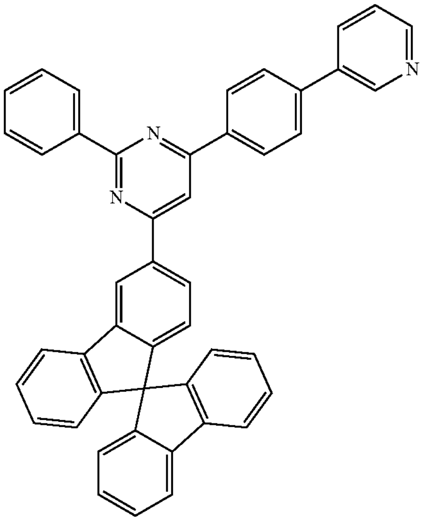
8
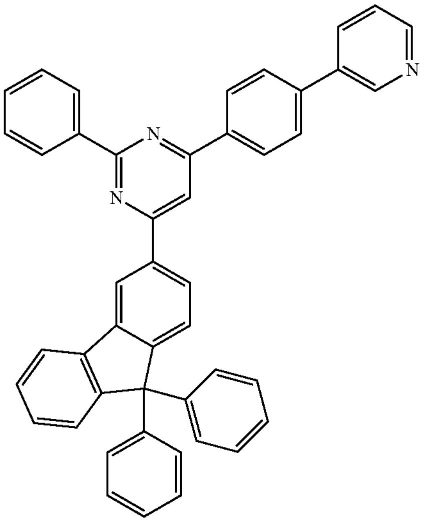
9
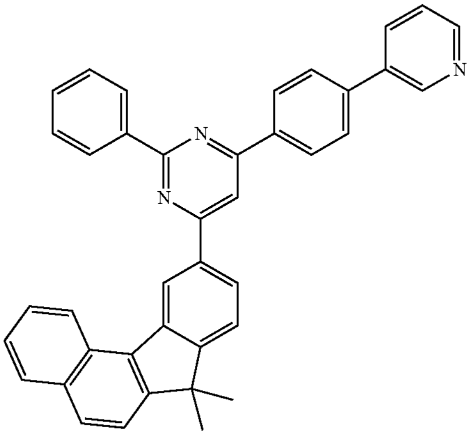

-continued
10
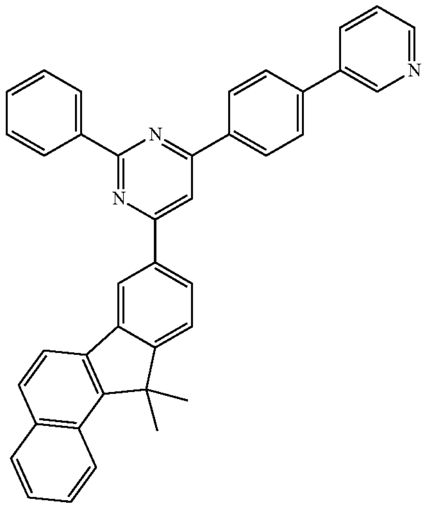
11
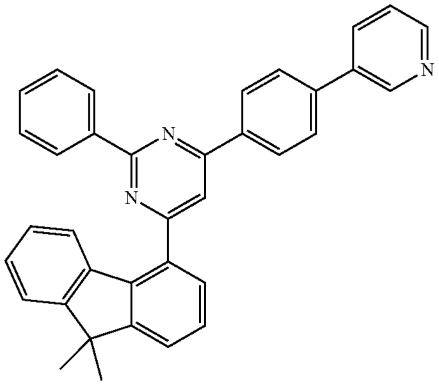
12
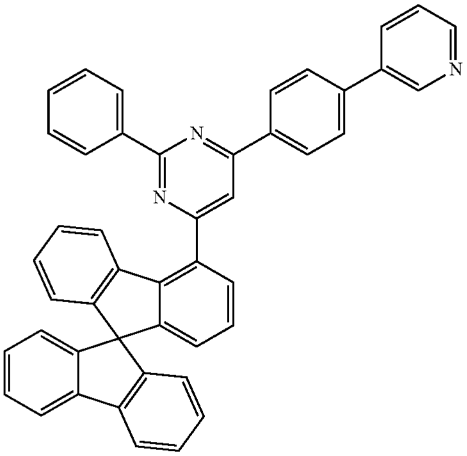
-continued
13
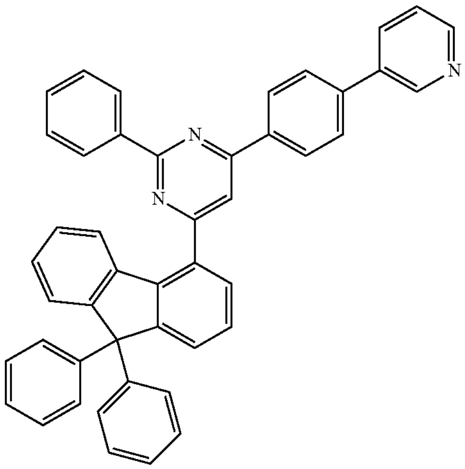
14
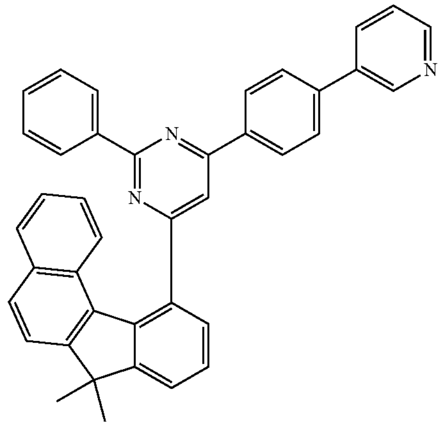
15
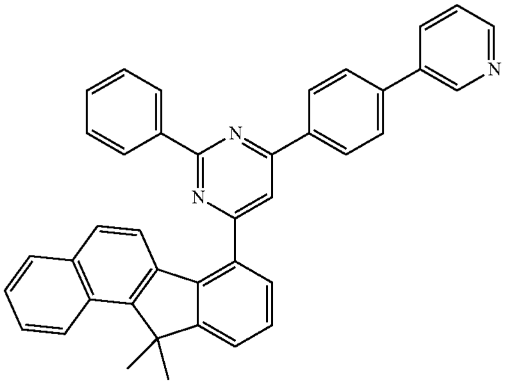

-continued
16
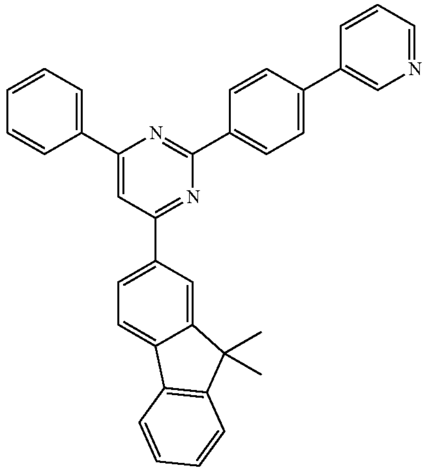
17
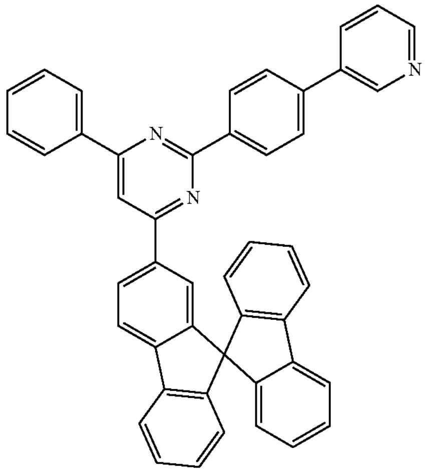
18
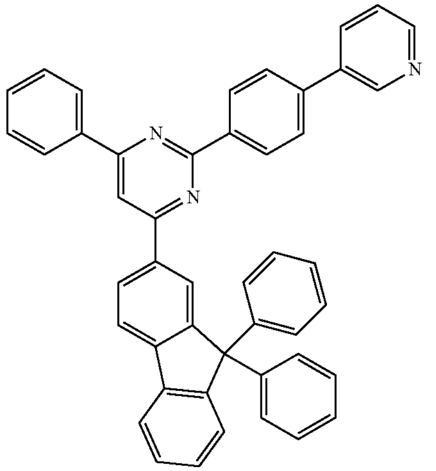
-continued
19
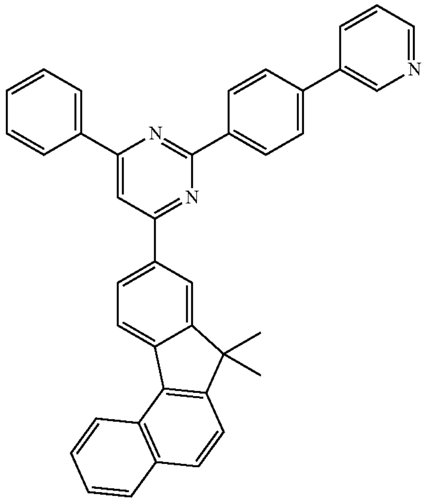
20
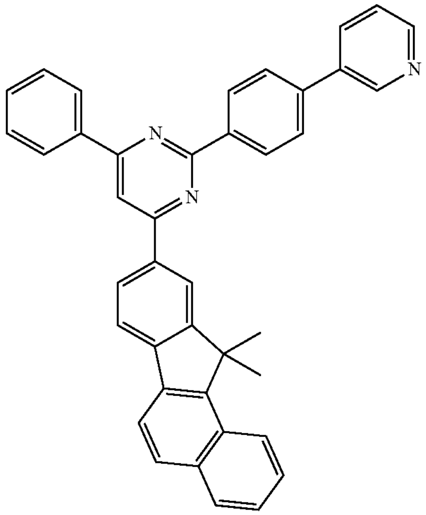
21
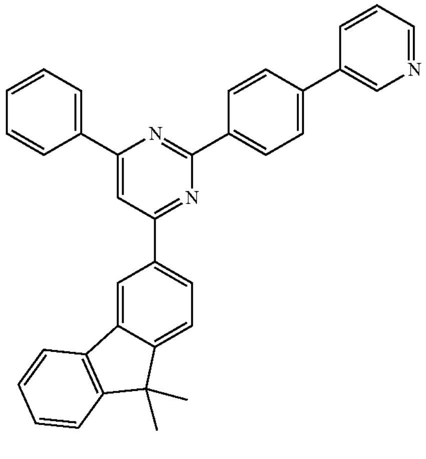

-continued
22
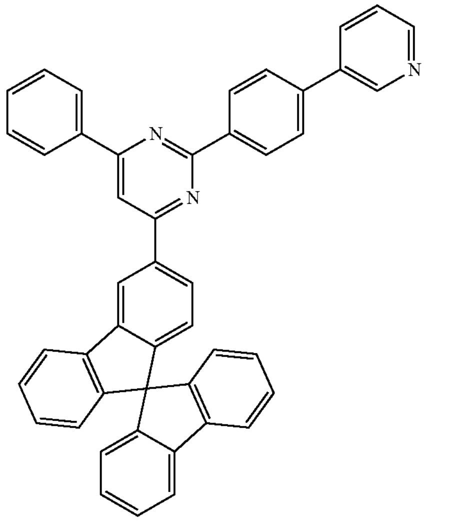
23
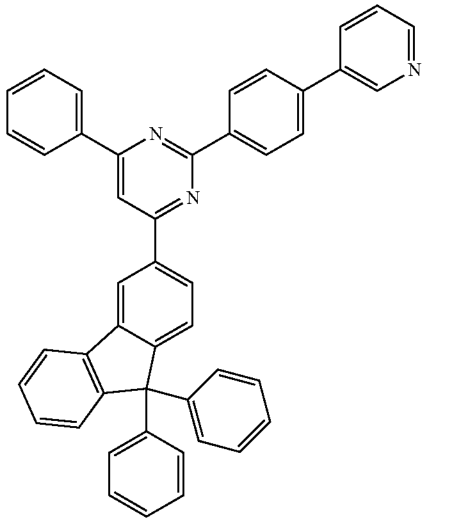
24
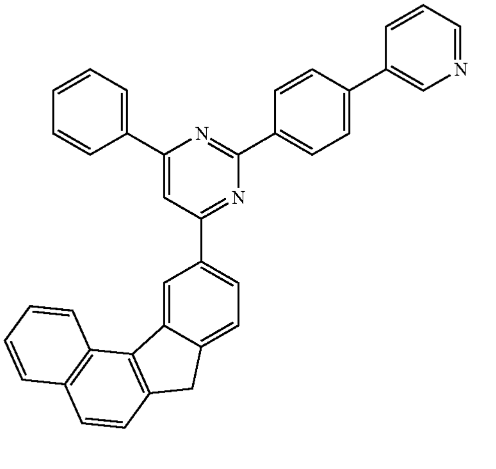
-continued
25
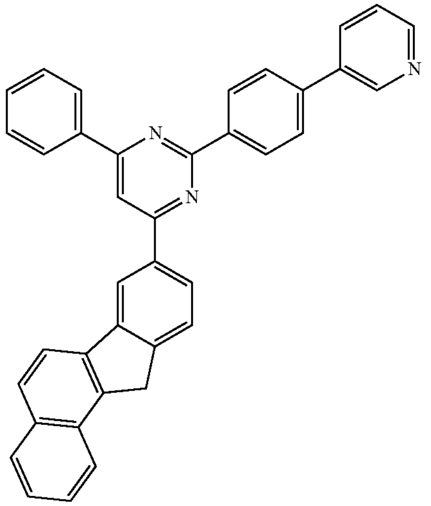
26
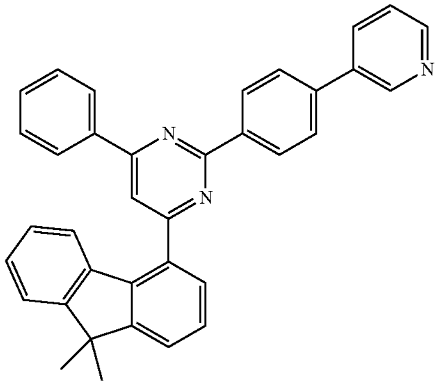
27
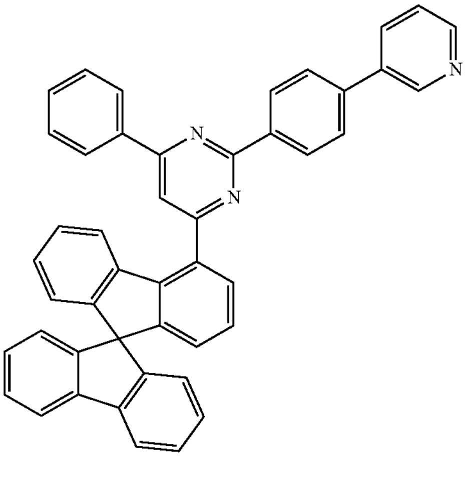

-continued
28
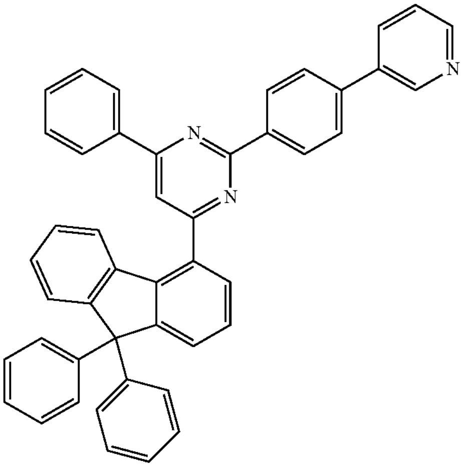
29
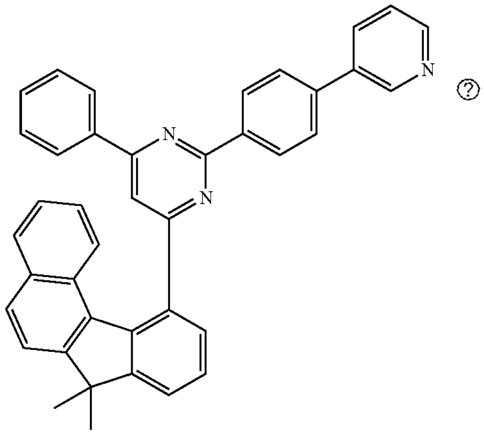
30
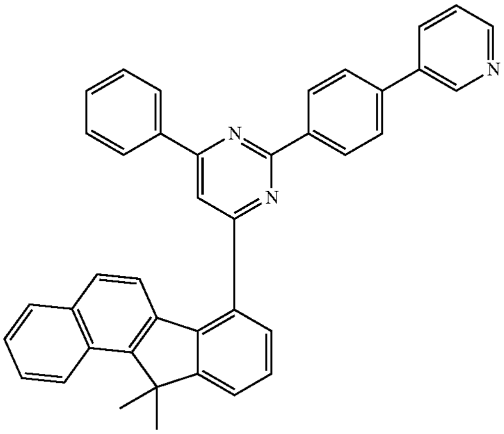
-continued
31
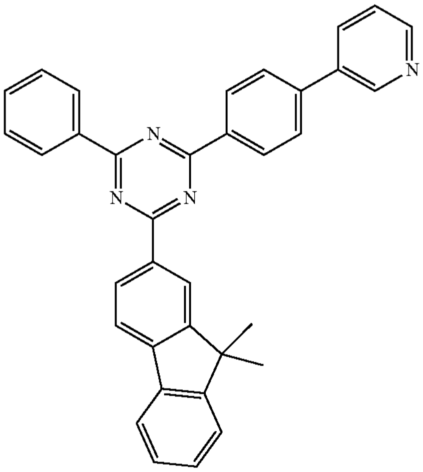
32
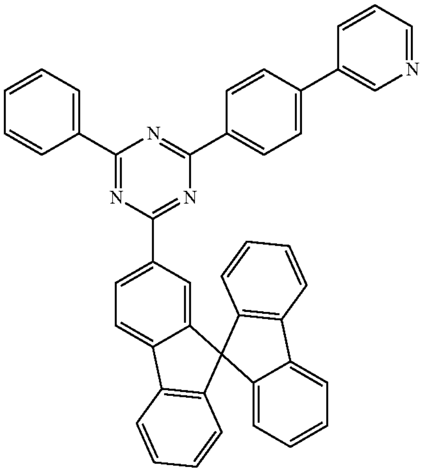
33
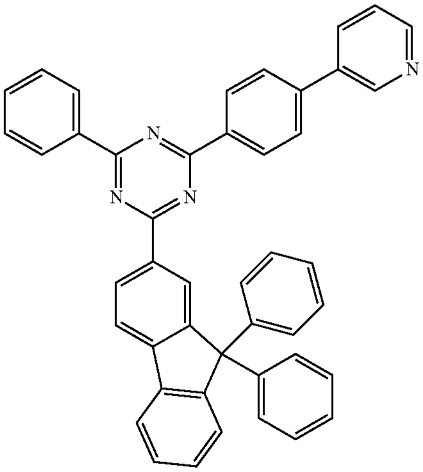

-continued
34
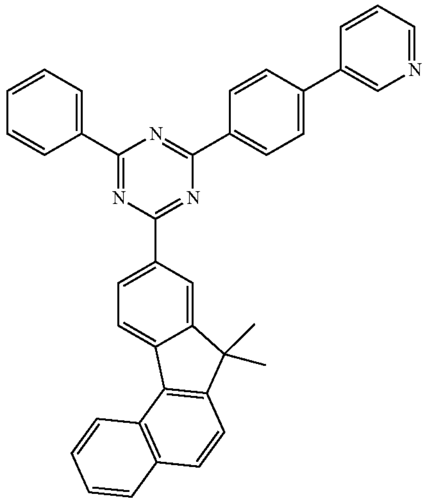
35
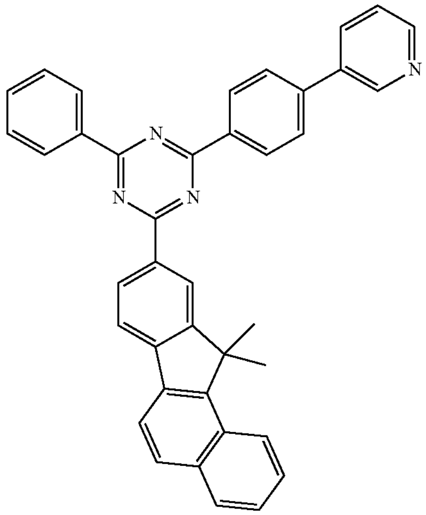
36
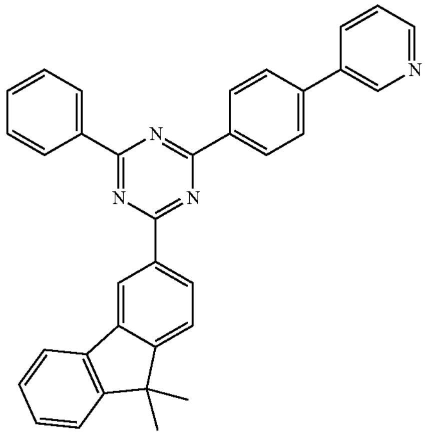
-continued
37
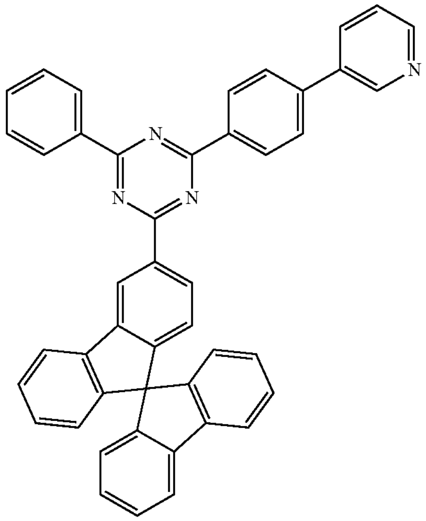
38
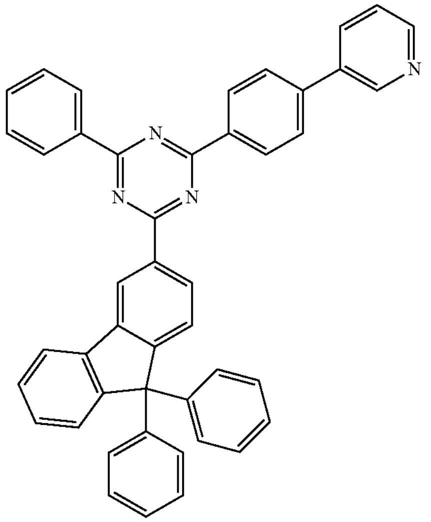
39
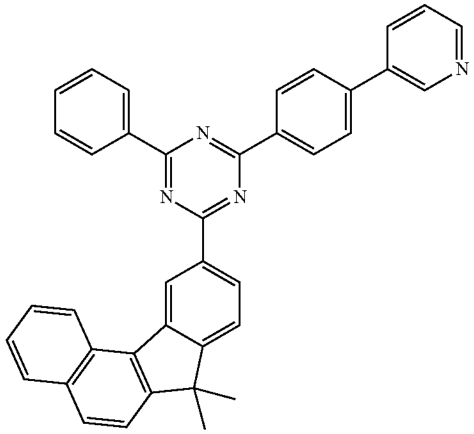

-continued
40
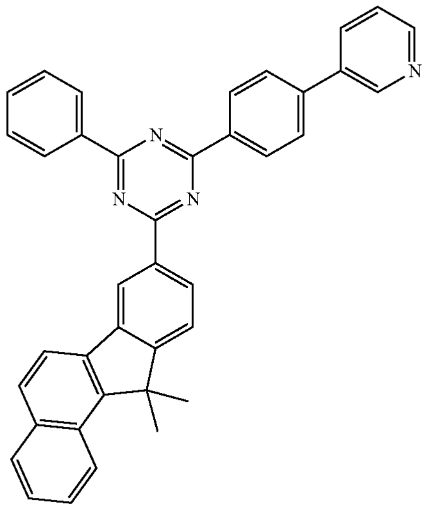
41
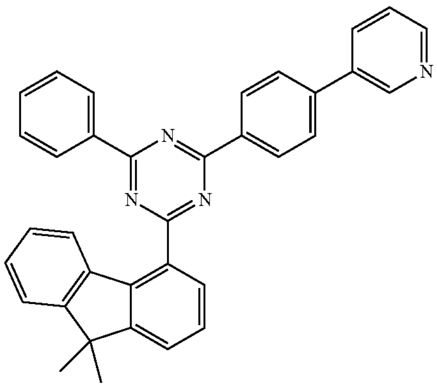
42
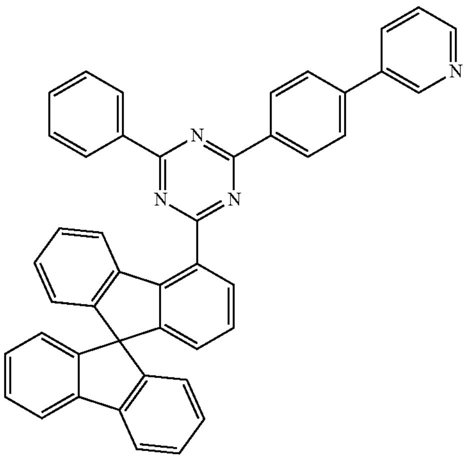
-continued
43
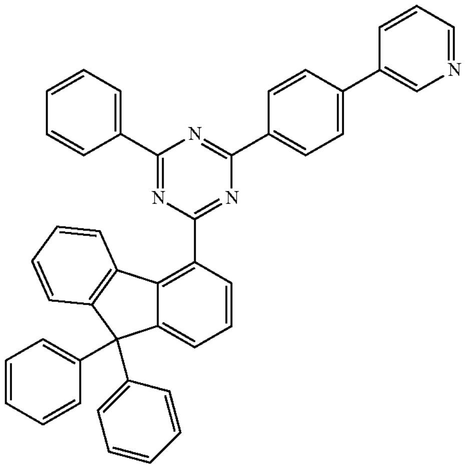
44
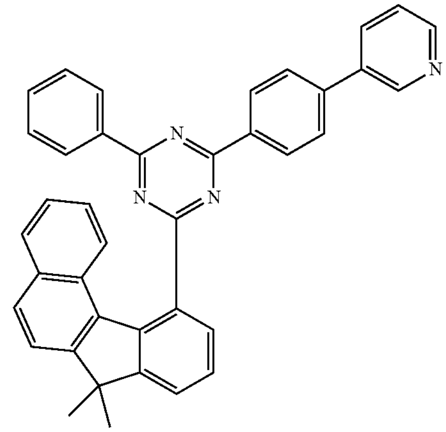
45
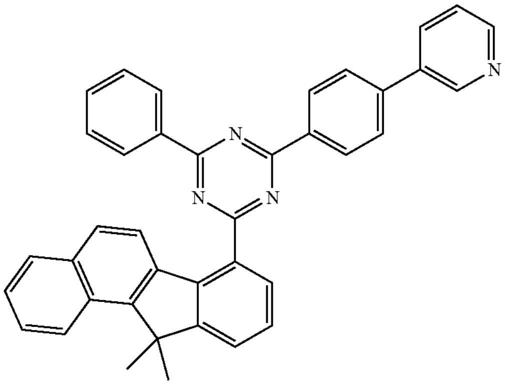

-continued
46
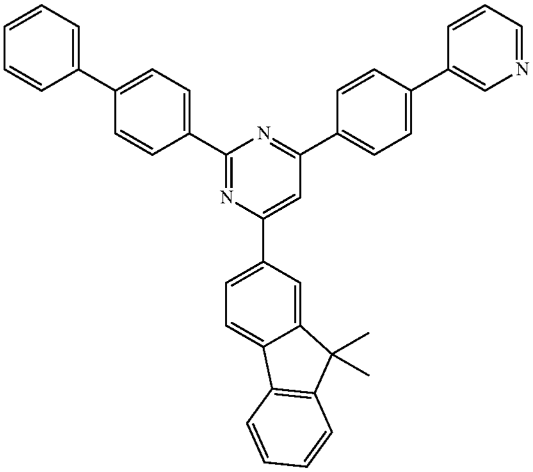
47
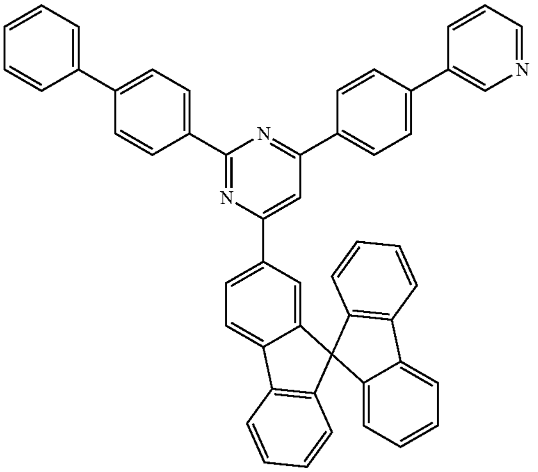
48
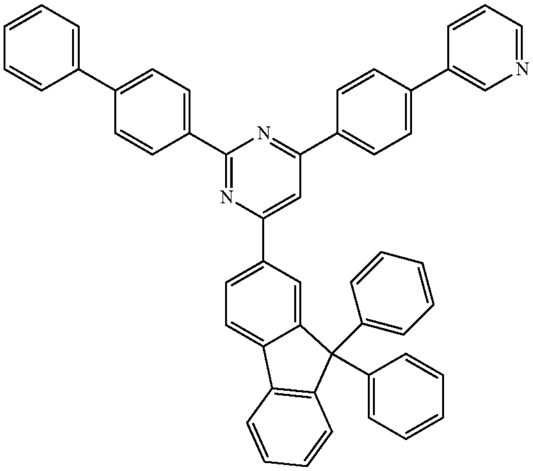
-continued
49
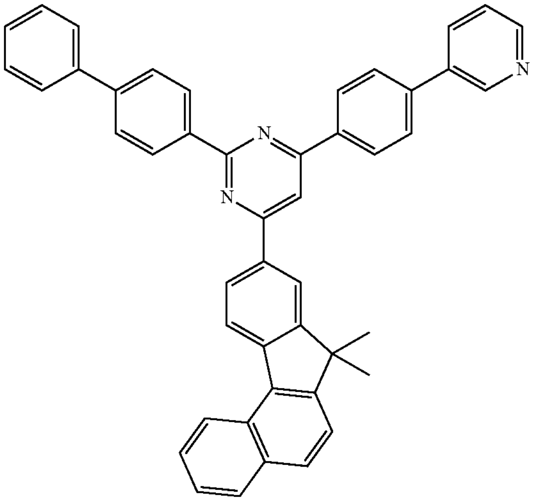
50
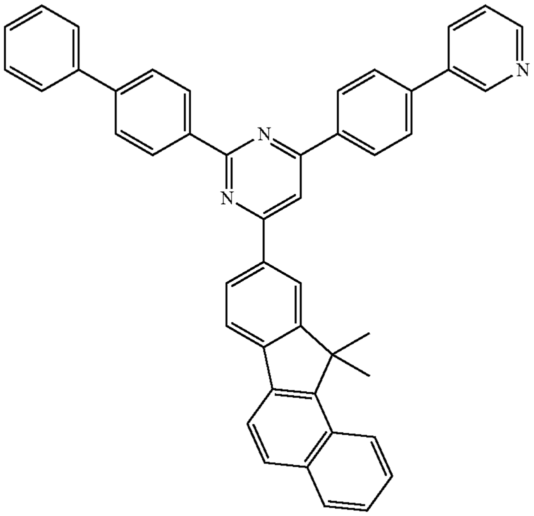
51
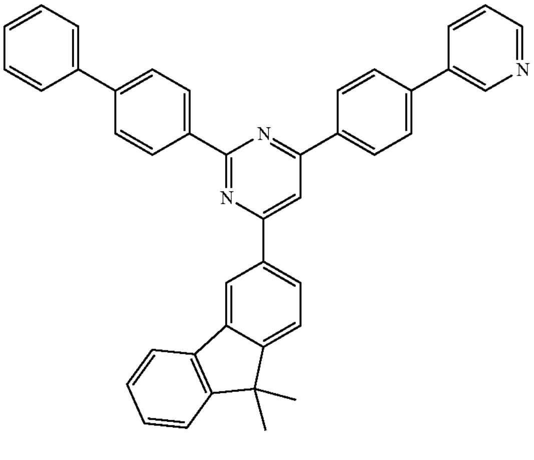

-continued
52
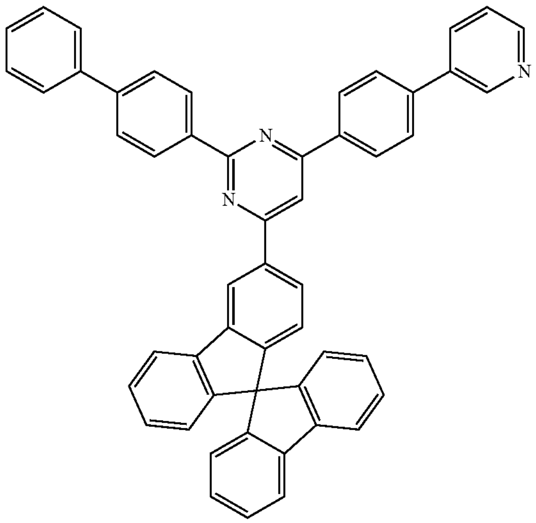
53
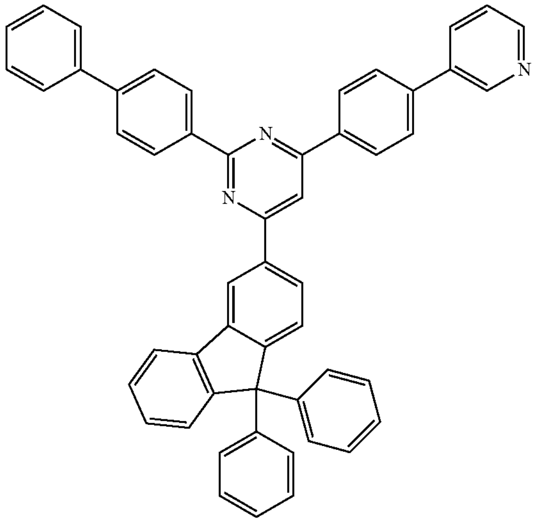
54
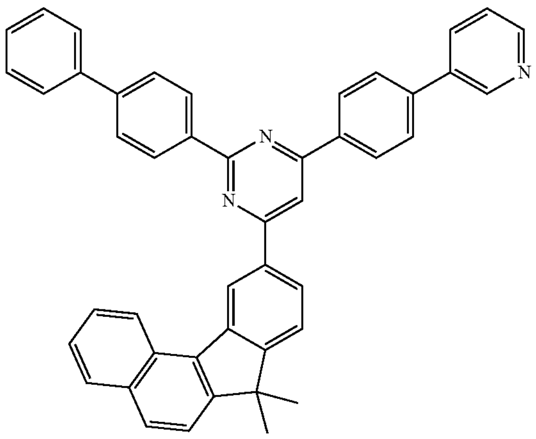
-continued
55
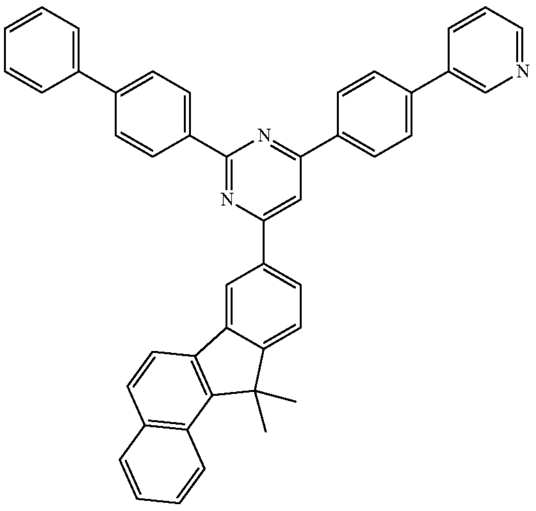
56
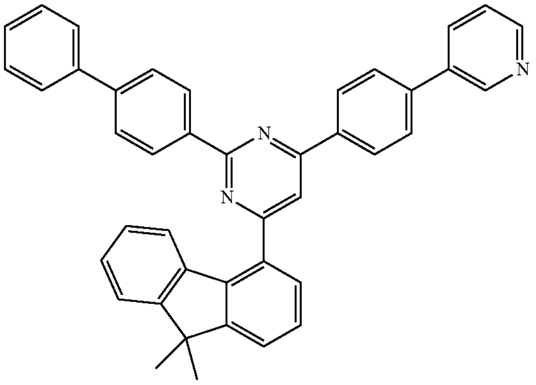
57
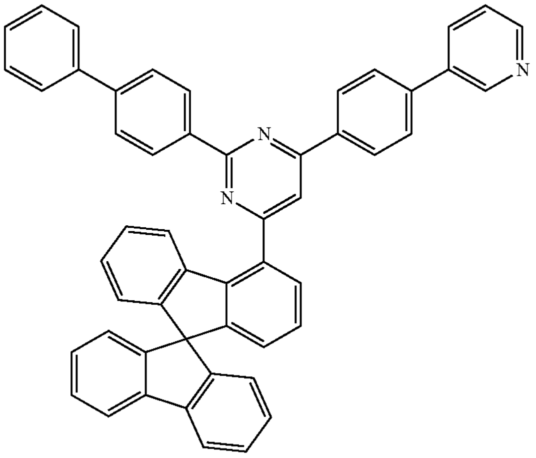

-continued
58
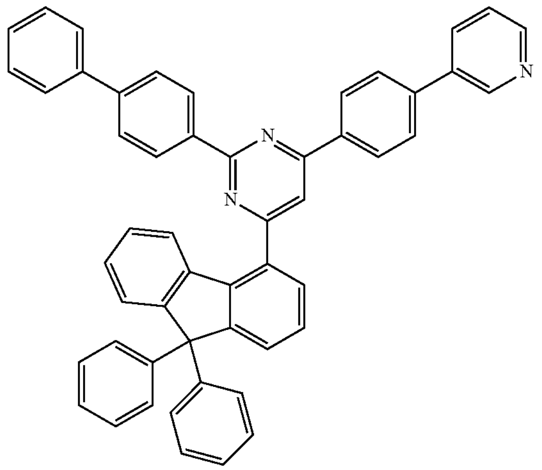
59
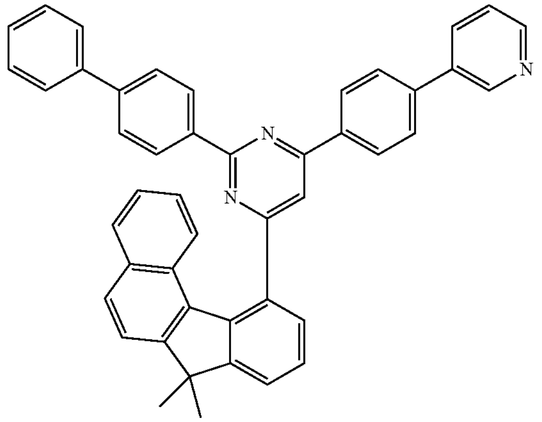
60
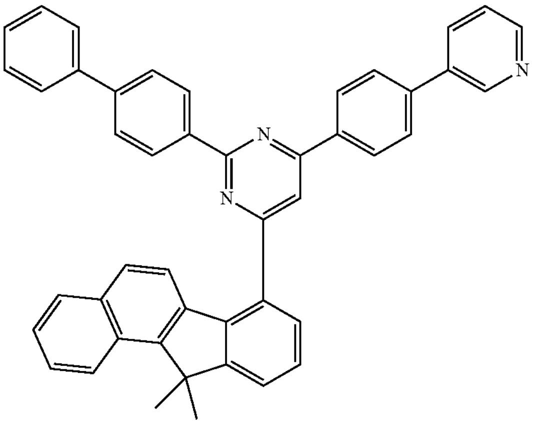
-continued
61
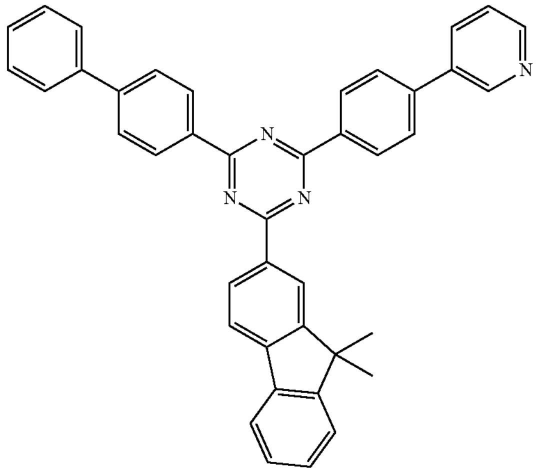
62
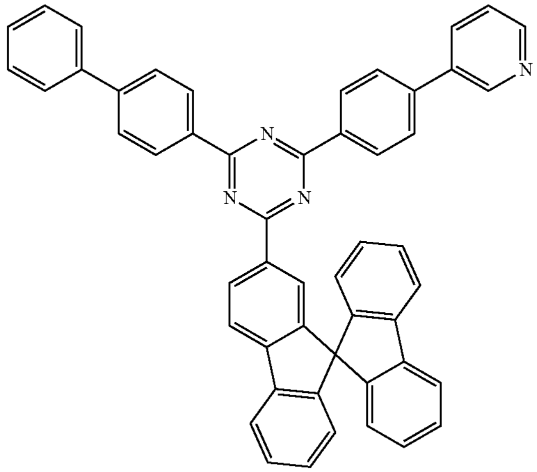
63
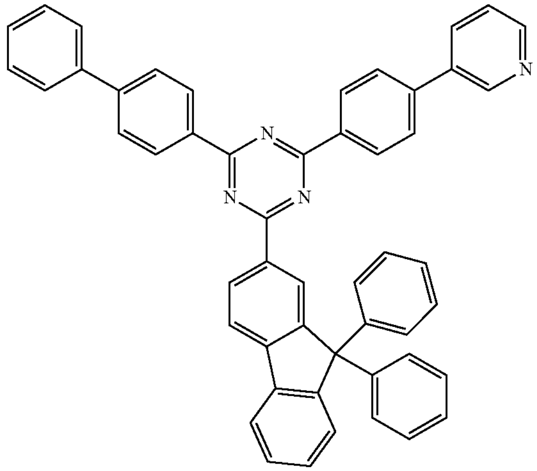

-continued
64
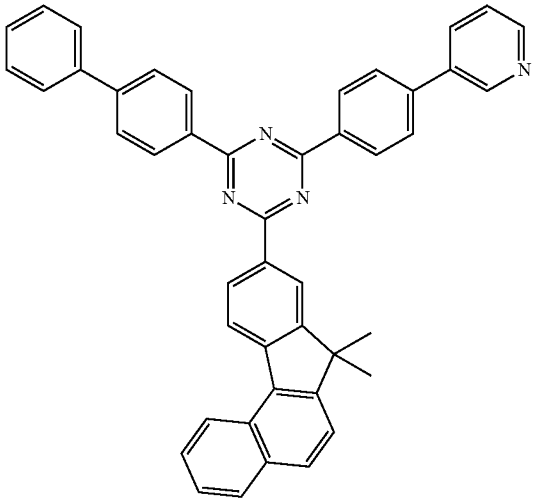
65
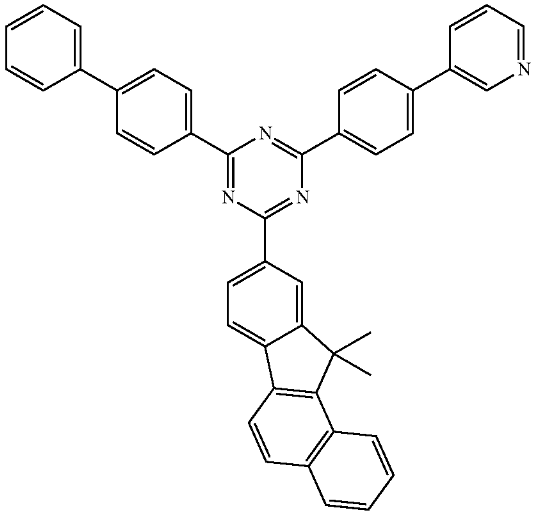
66
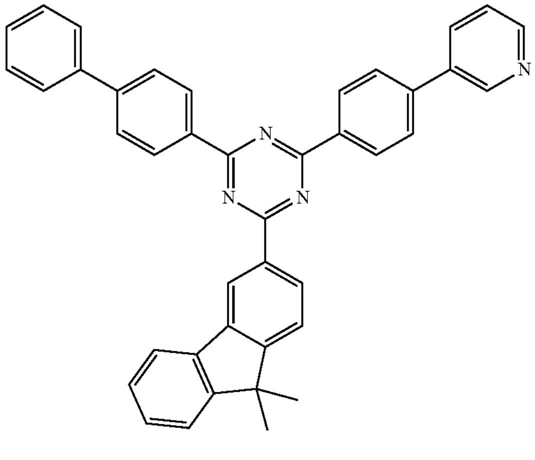
-continued
67
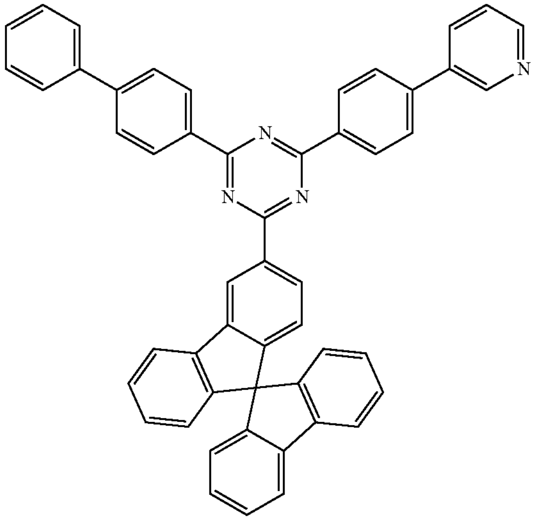
68
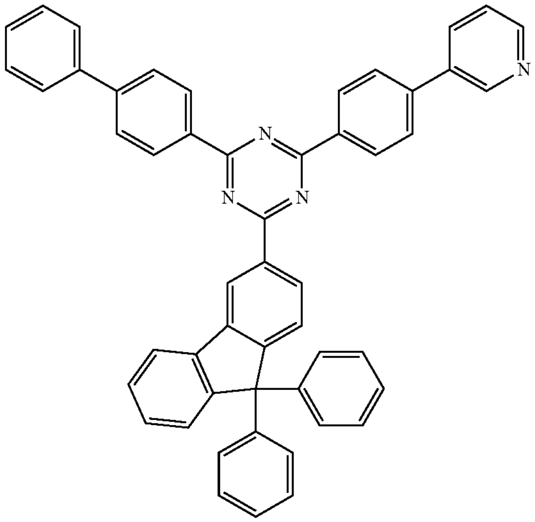
69
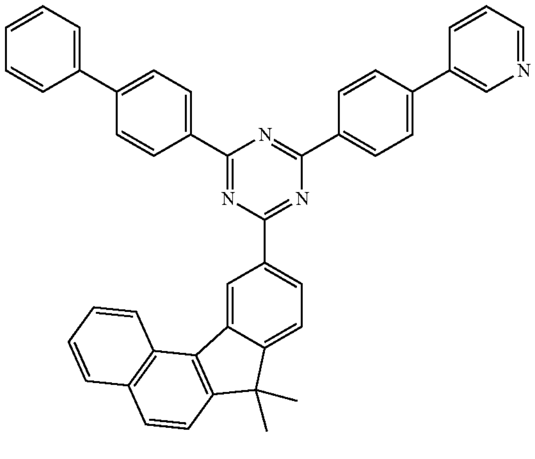

-continued
70
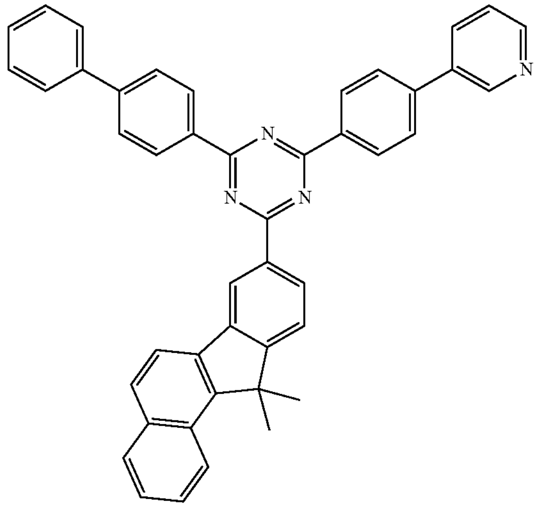
71
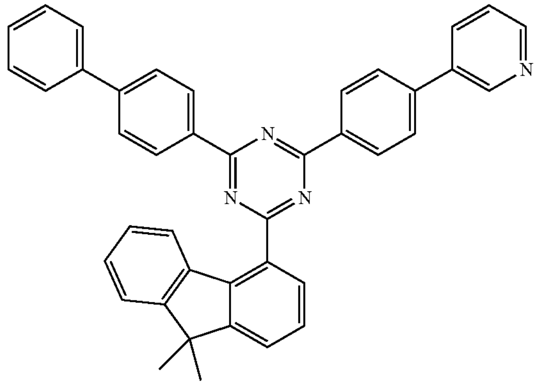
72
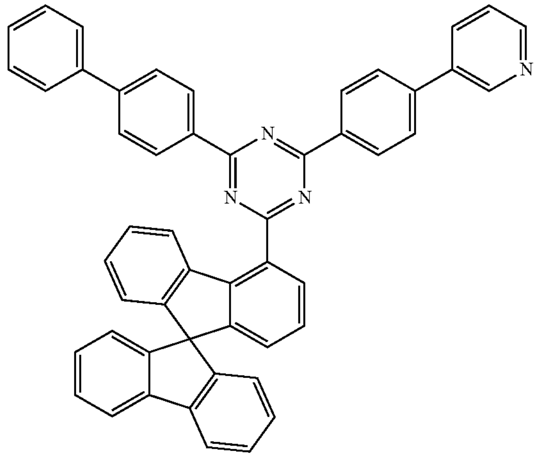
-continued
73
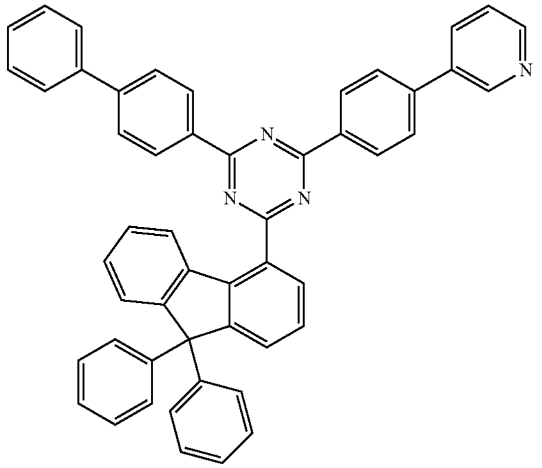
74
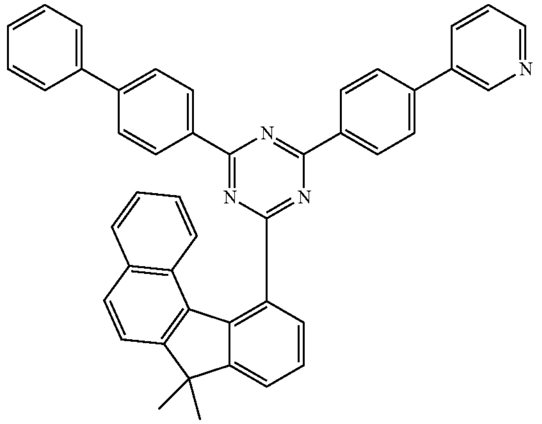
75
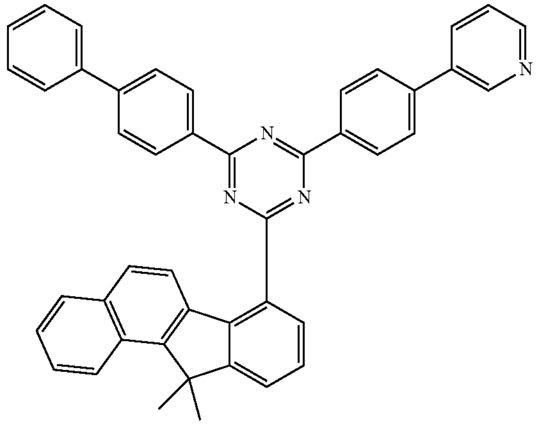

-continued
76
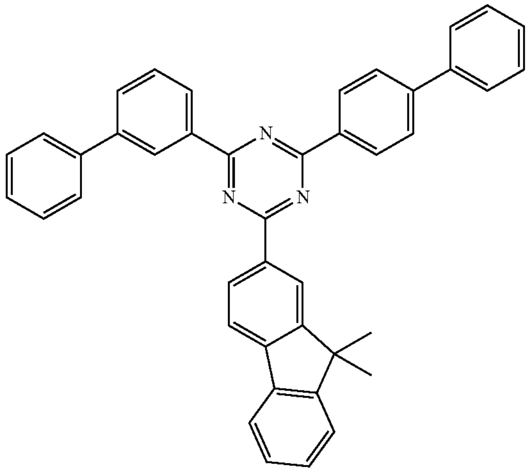
77
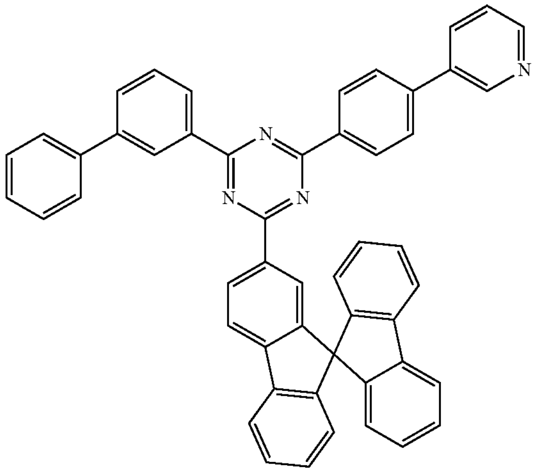
78
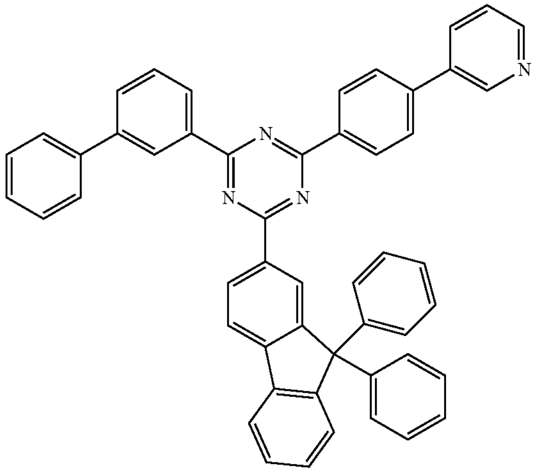
-continued
79
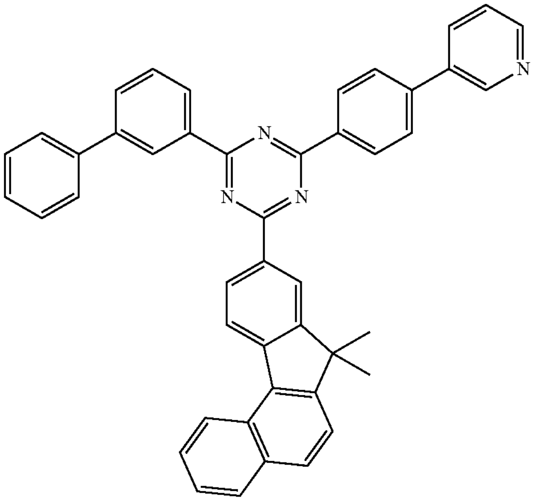
80
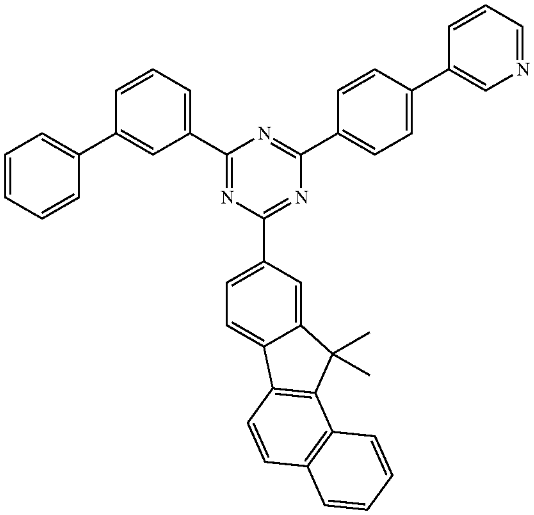
81
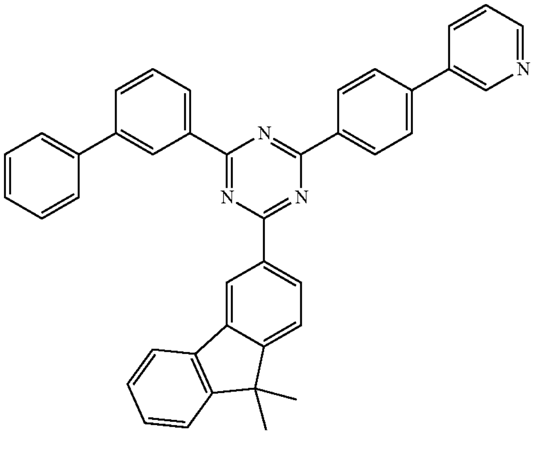

82
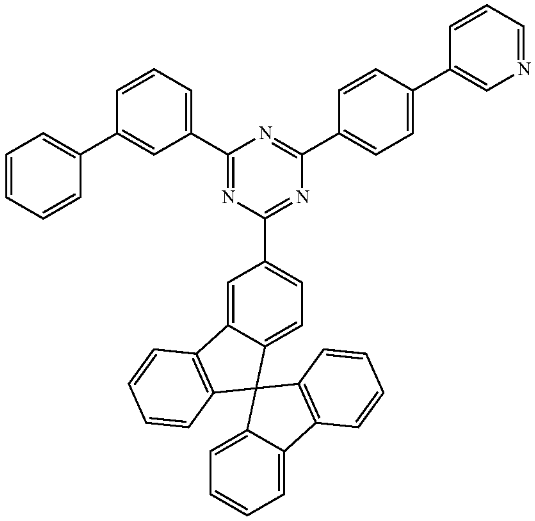
83
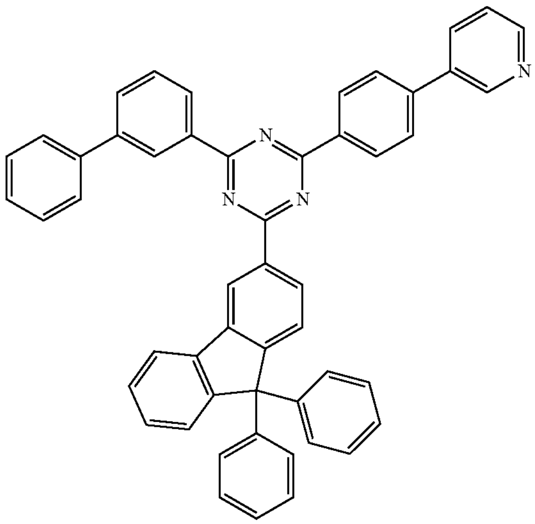
84
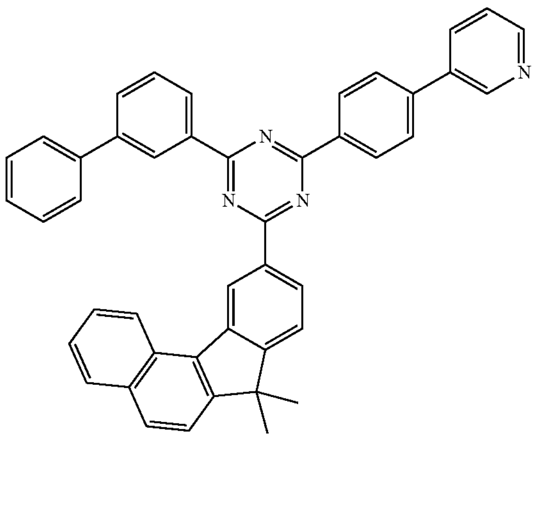
85
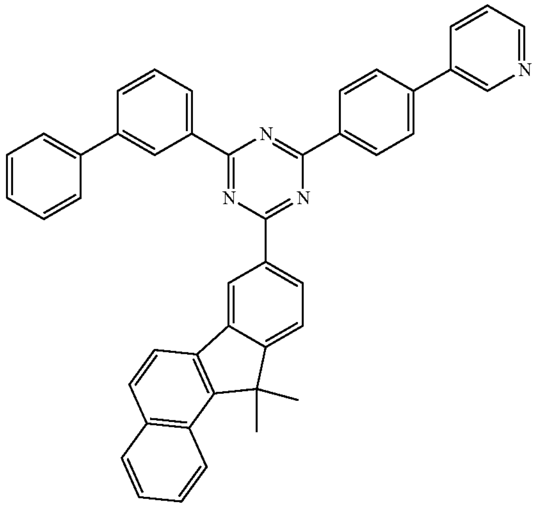
86
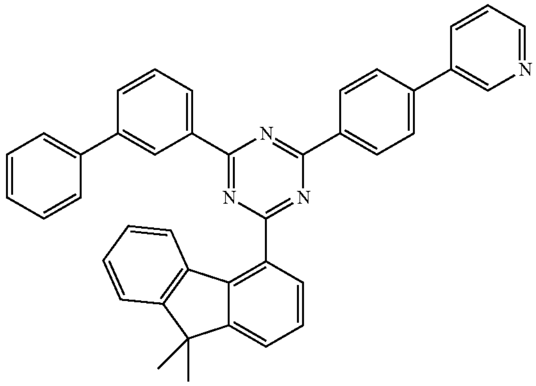
87
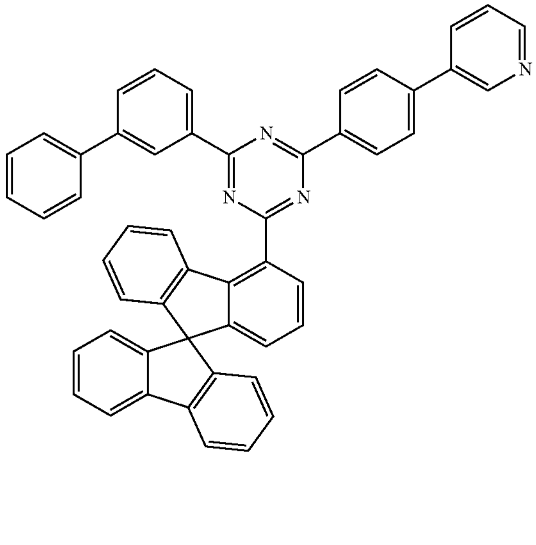

-continued
88
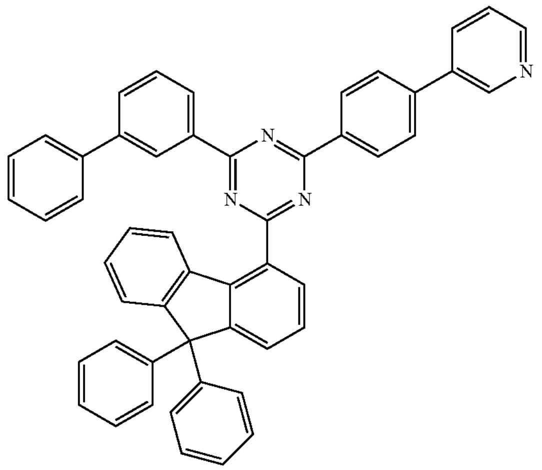
89
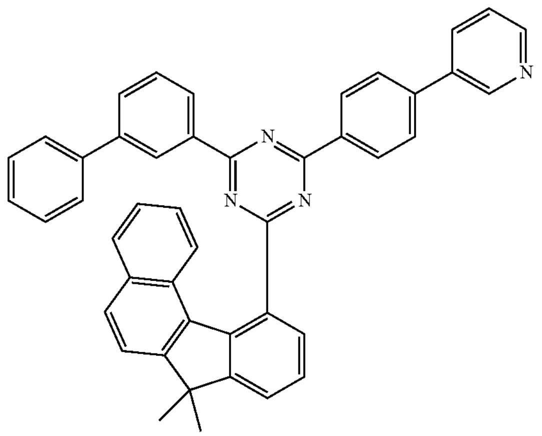
90
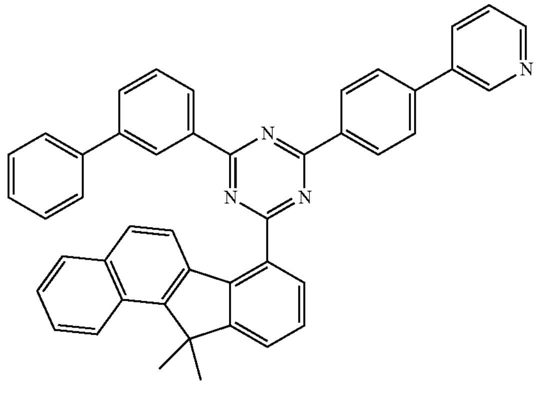
-continued
91
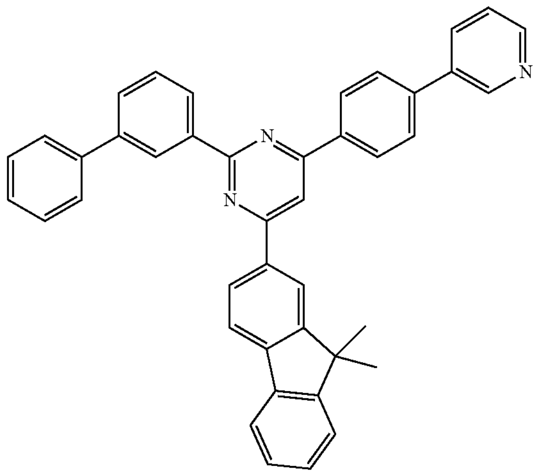
92
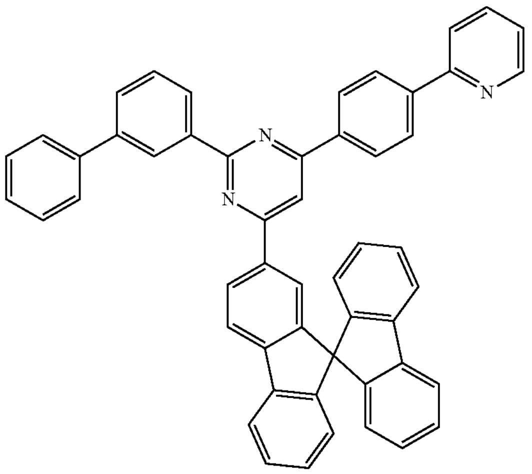
93
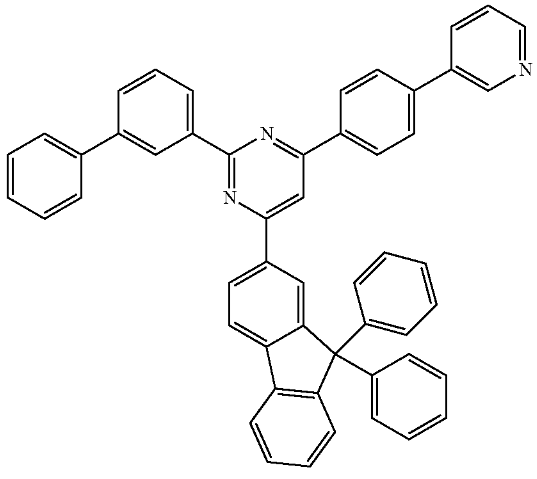

-continued
94
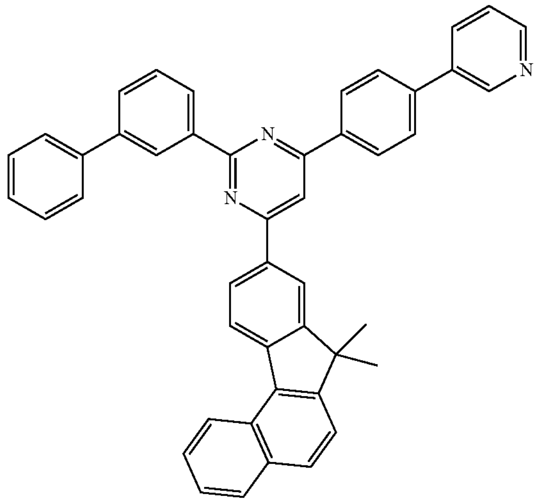
95
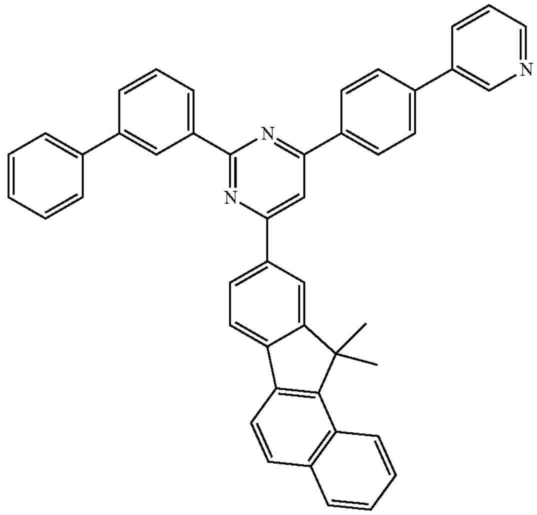
96
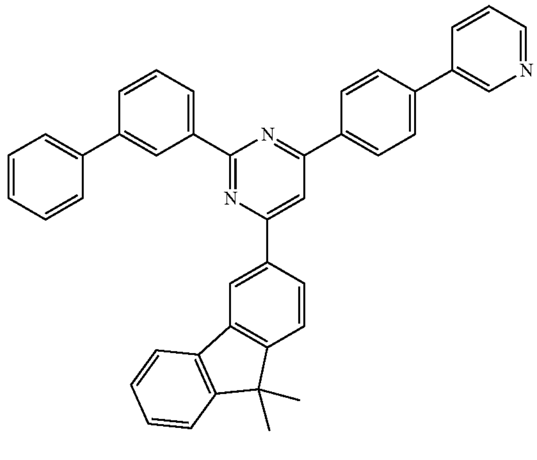
-continued
97
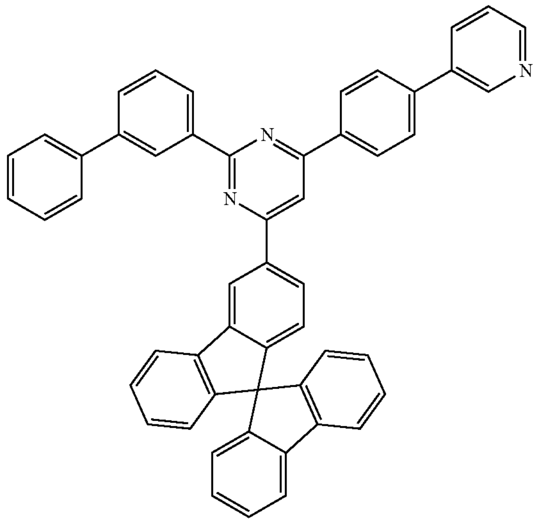
98
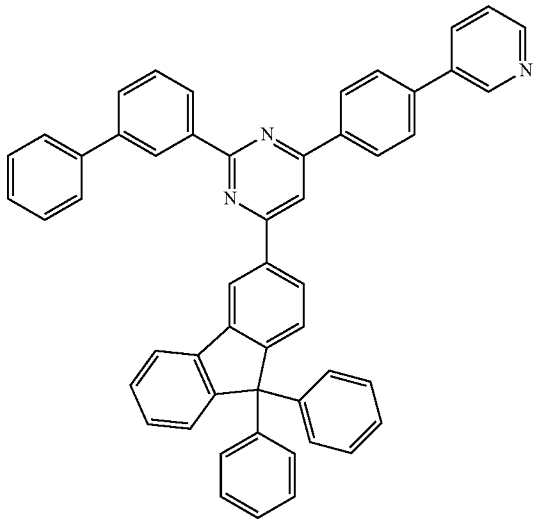
99
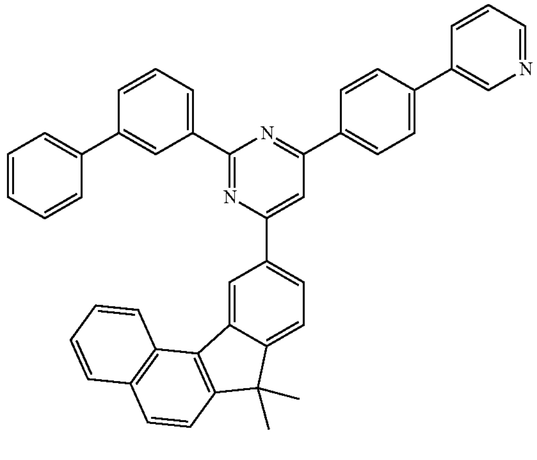

-continued
100
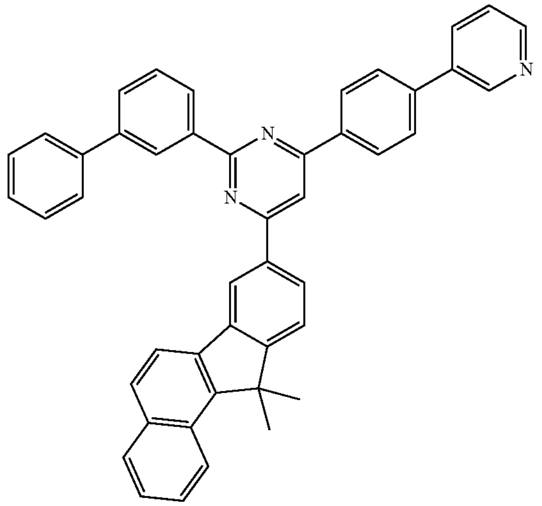
101
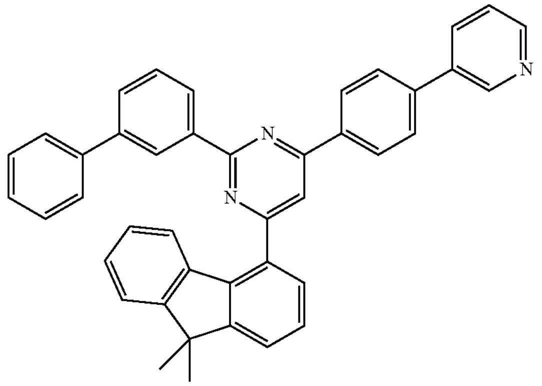
102
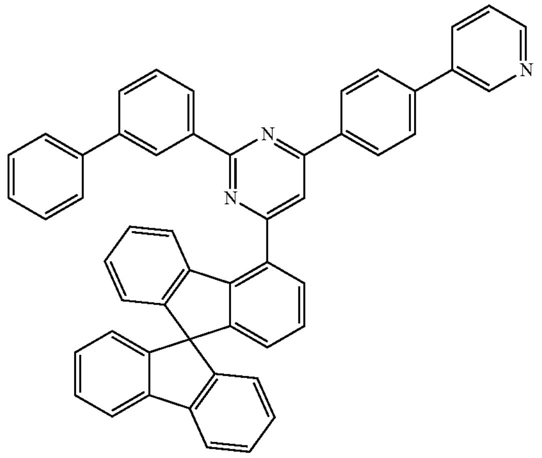
-continued
103
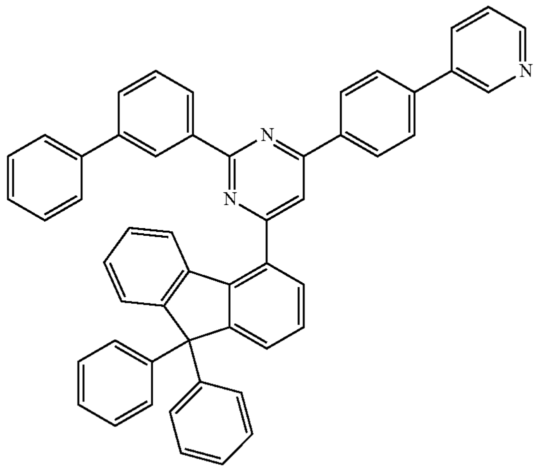
104
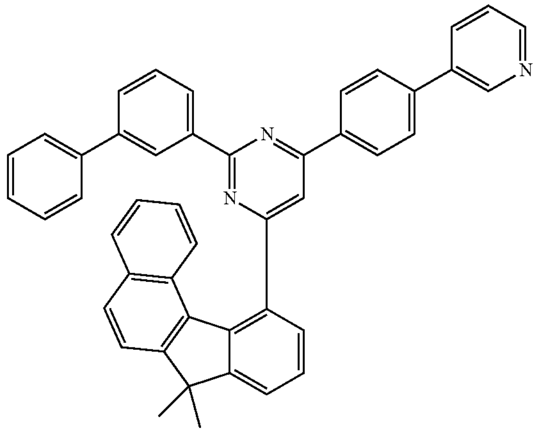
105
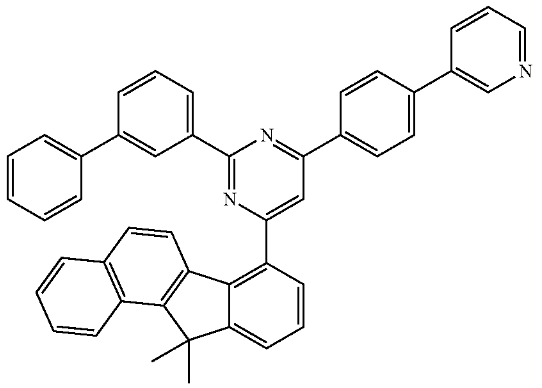

-continued
106
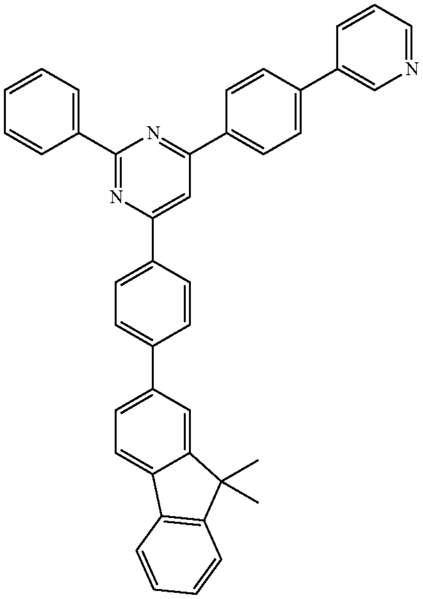
107
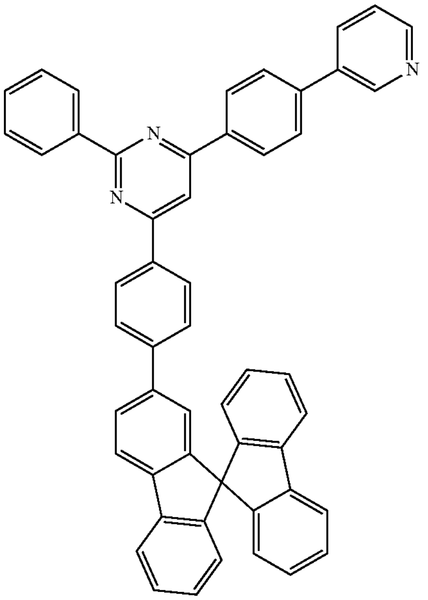
-continued
108
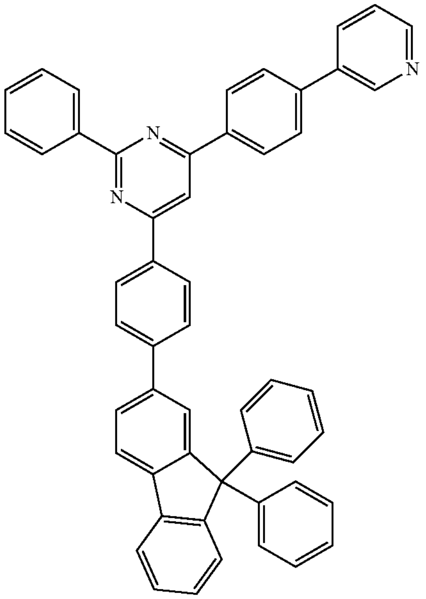
109
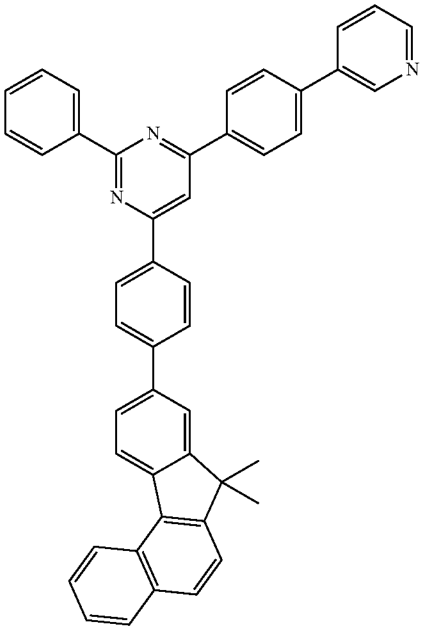

-continued
110
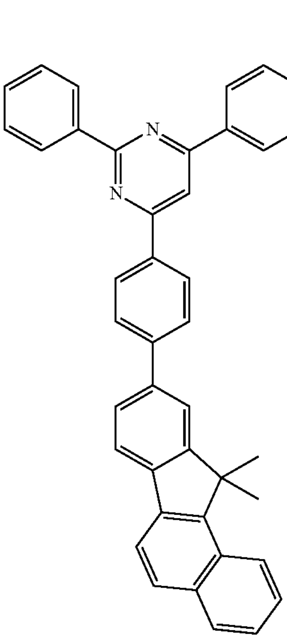
111
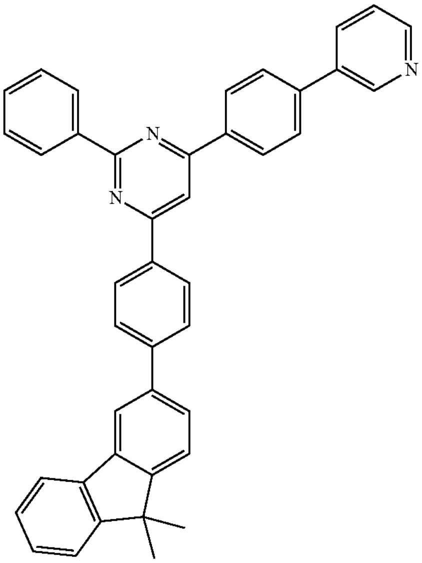
-continued
112
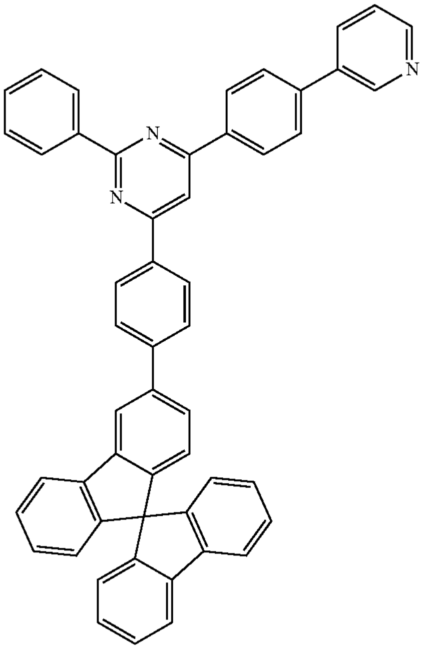
113
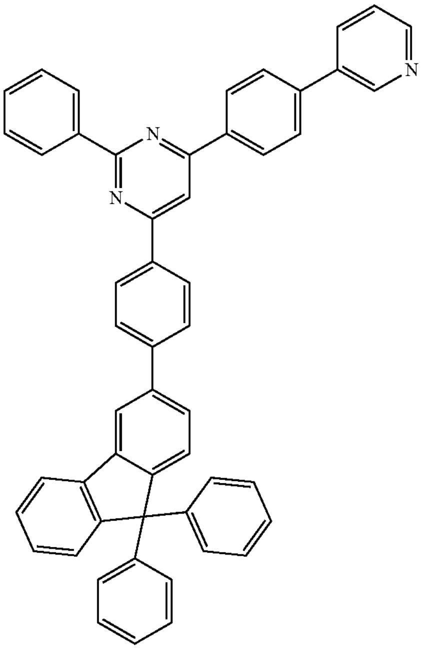

-continued
114
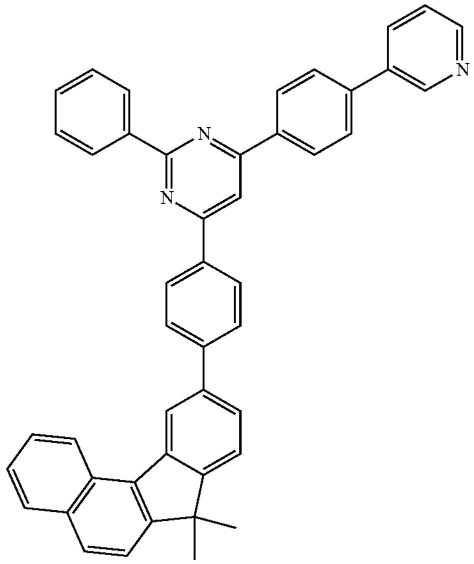
116
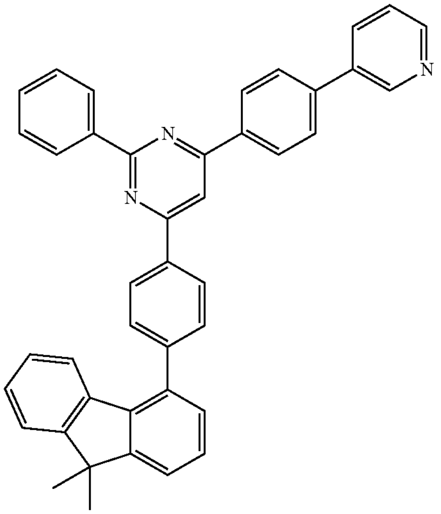
115
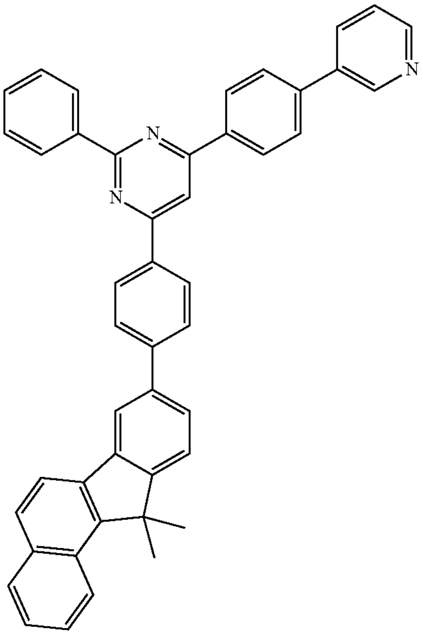
117
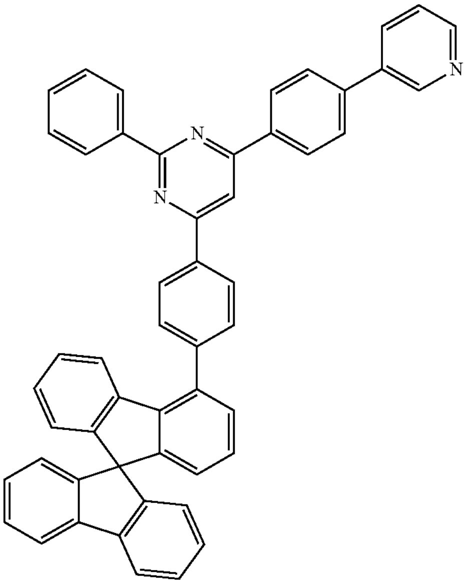
-continued -continued
118
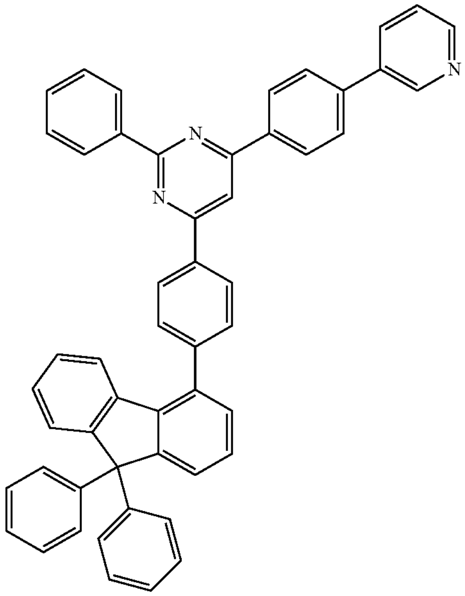
119
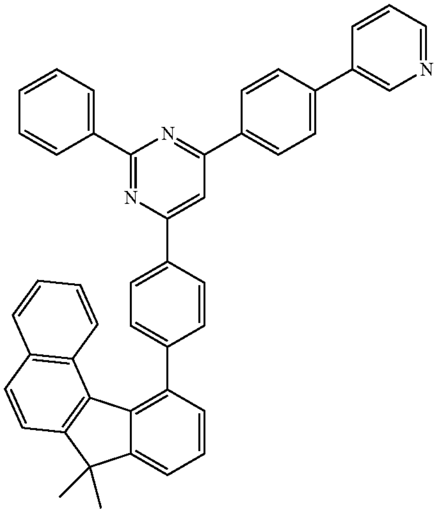
120
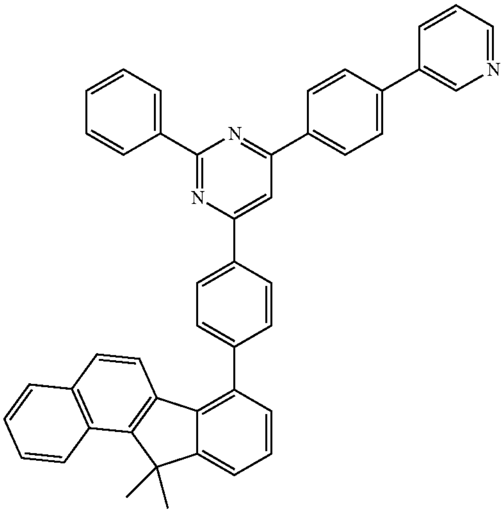
-continued
121
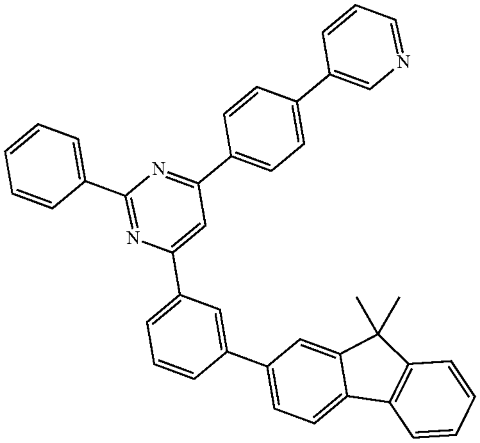
122
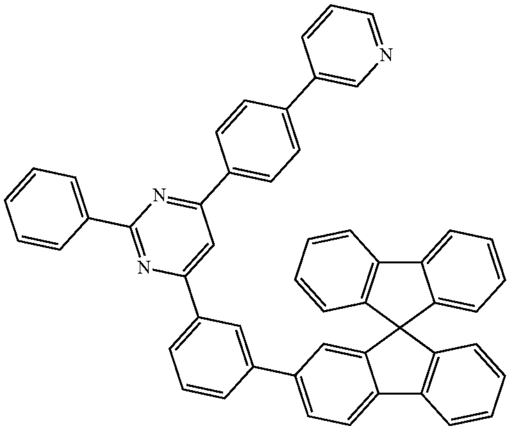
123
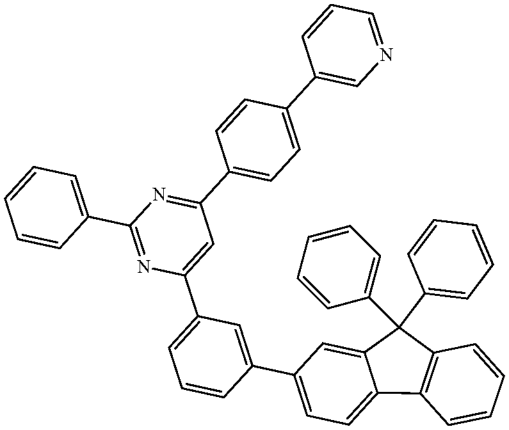

-continued
124
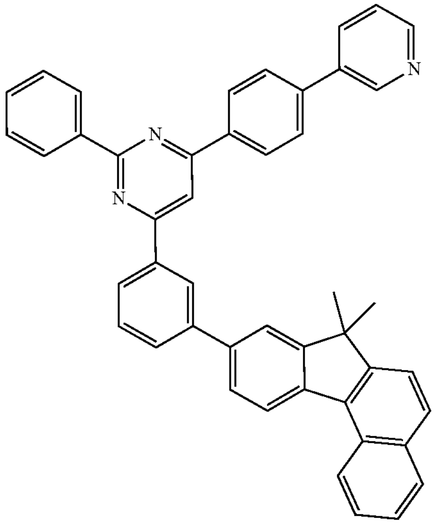
125
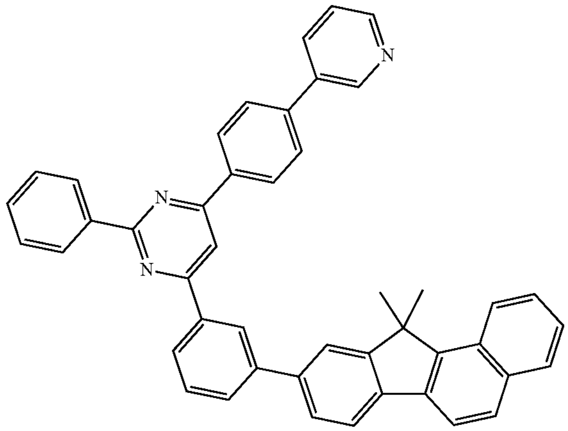
126
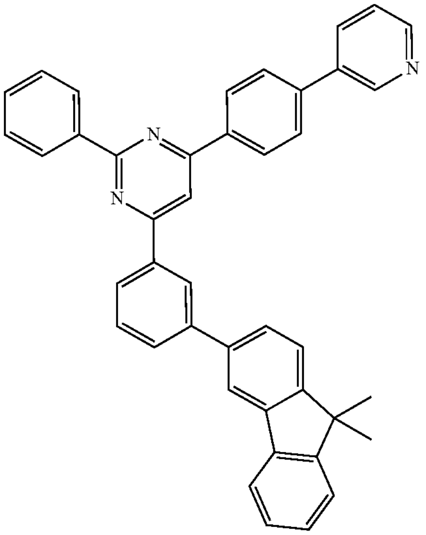
-continued
127
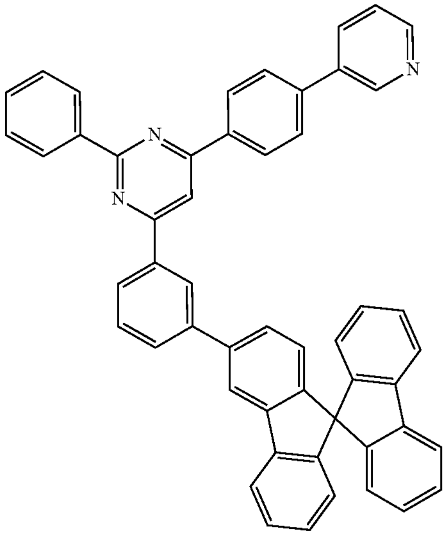
128
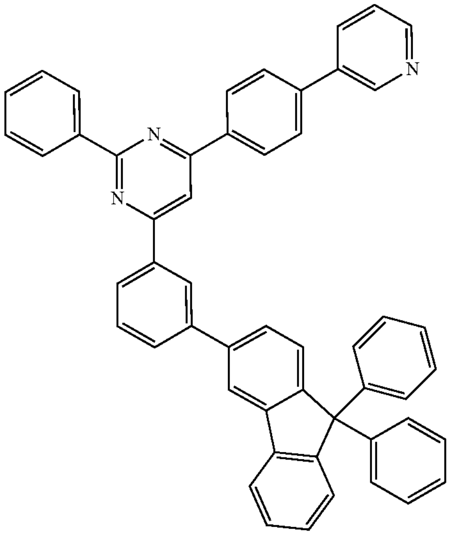
129
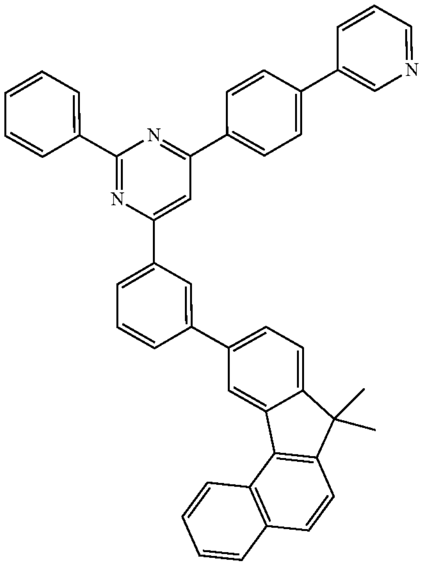

-continued
130
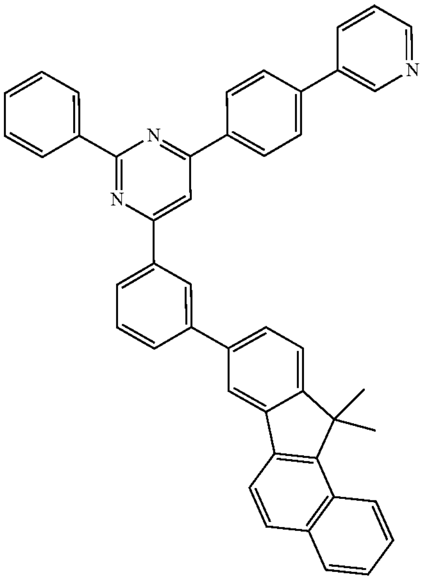
131
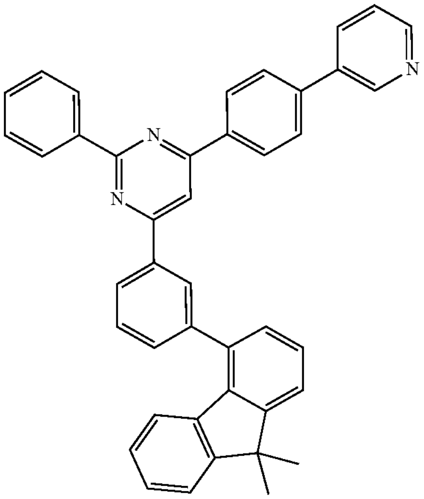
132
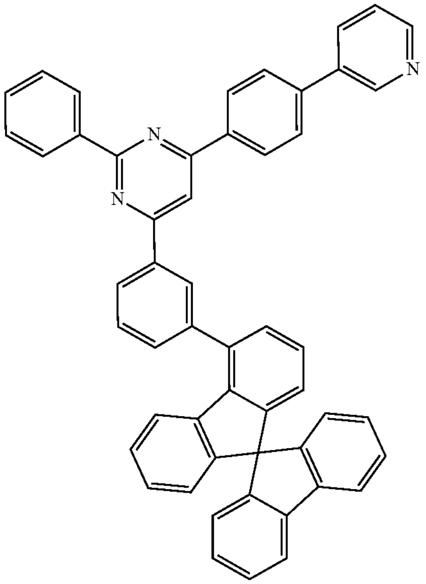
-continued
133
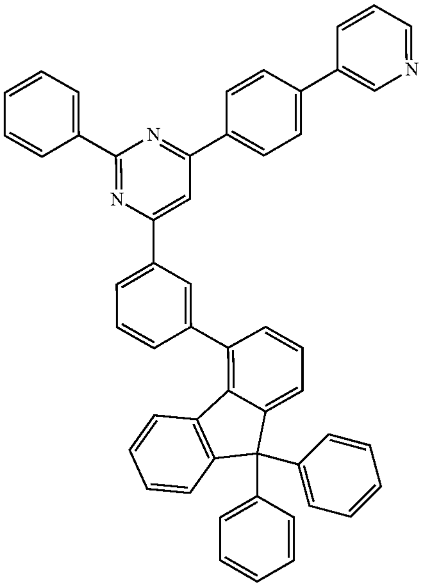
134
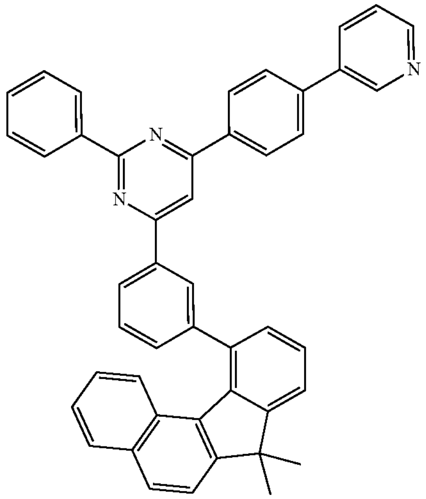
135
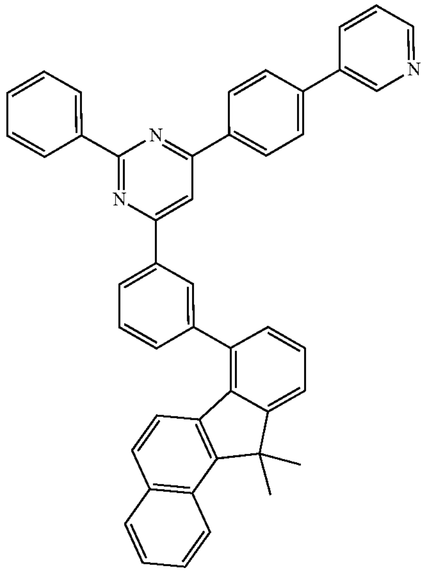

-continued
136
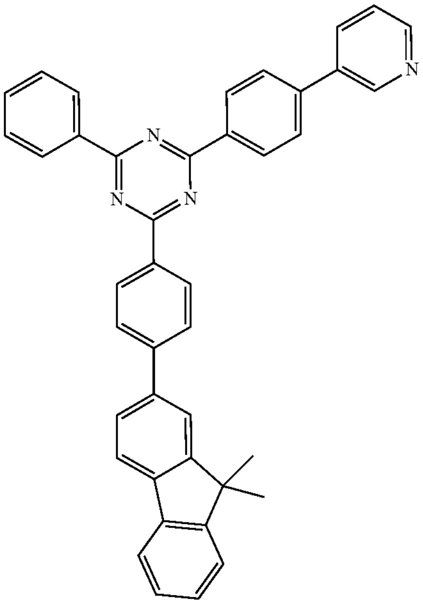
137
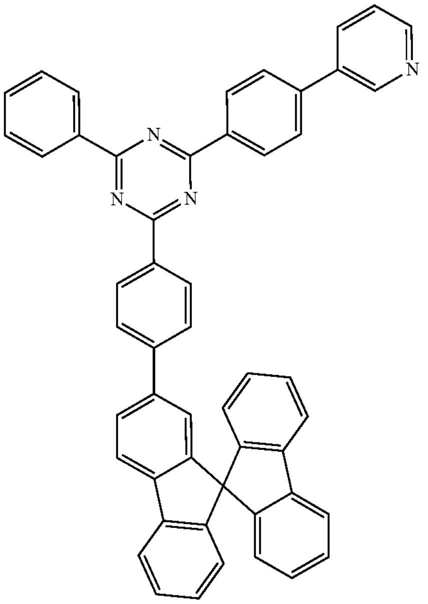
-continued
138
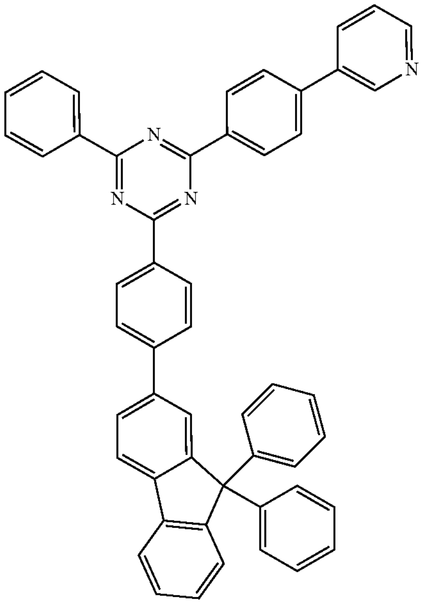
139
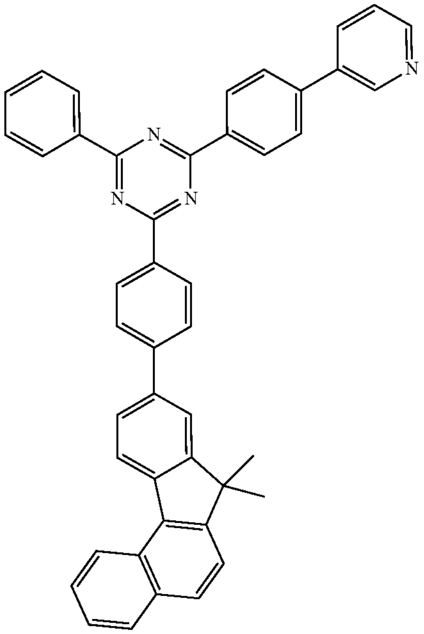

-continued
140
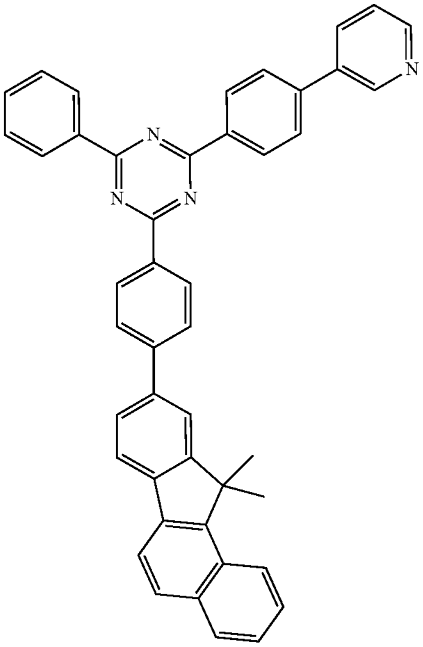
141
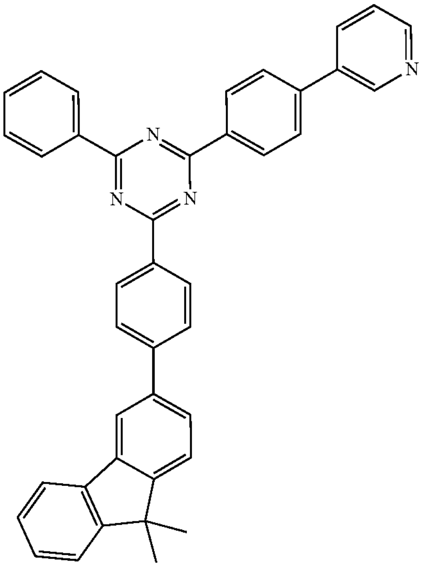
-continued
142
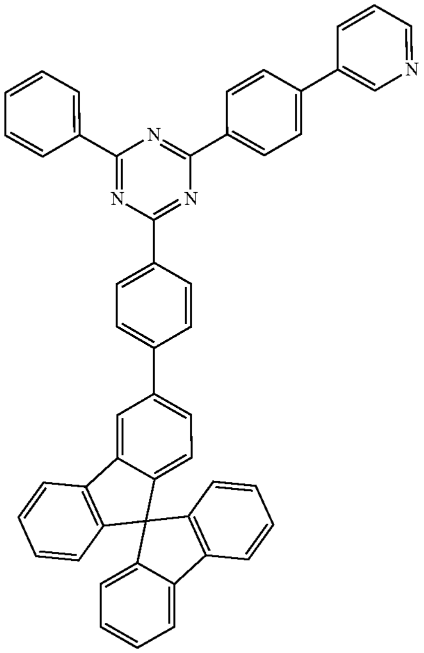
143
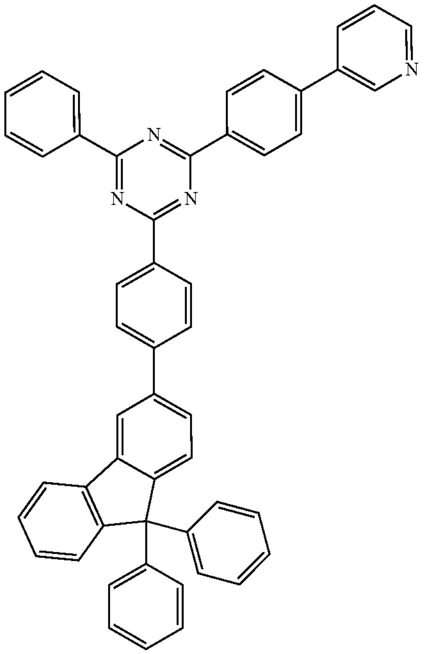

-continued
144
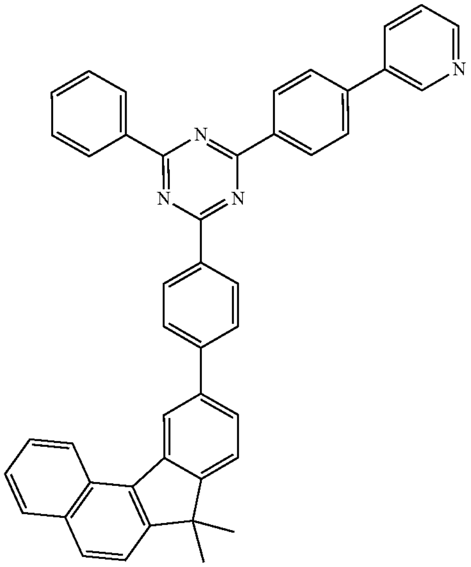
145
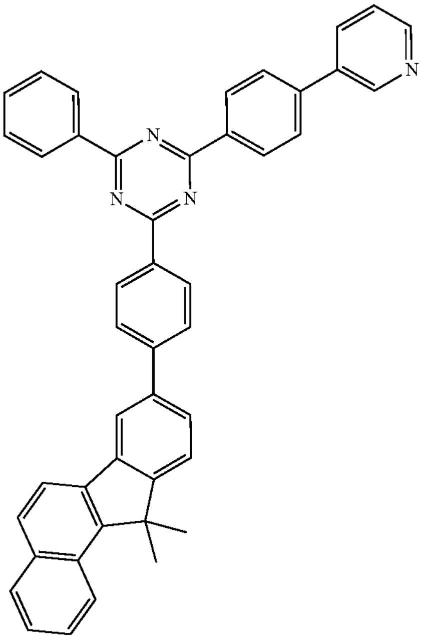
-continued
146
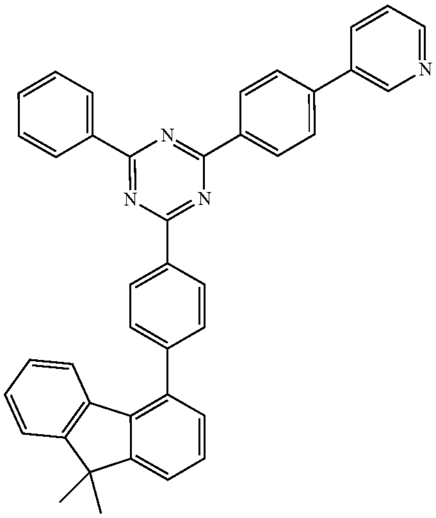
147
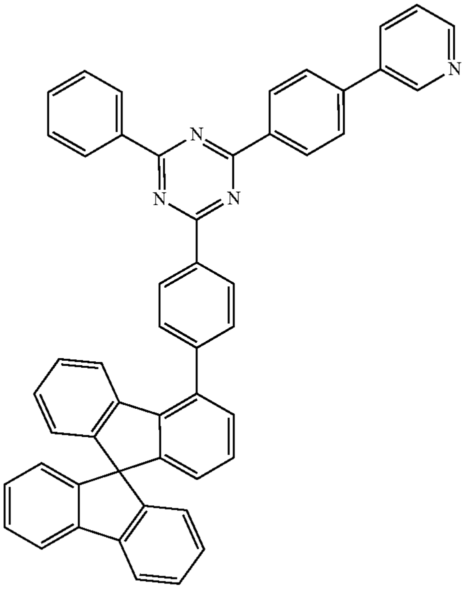

-continued
148
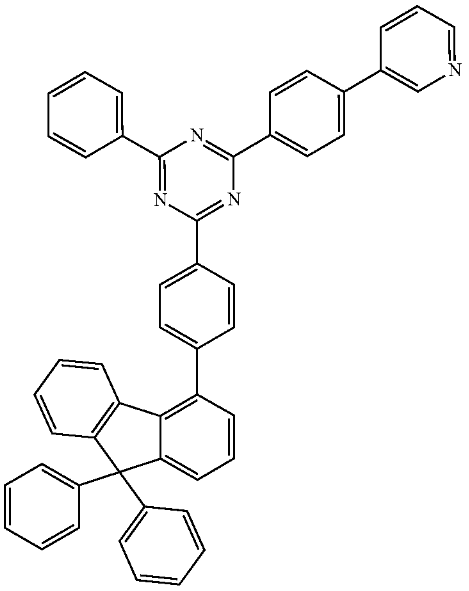
149
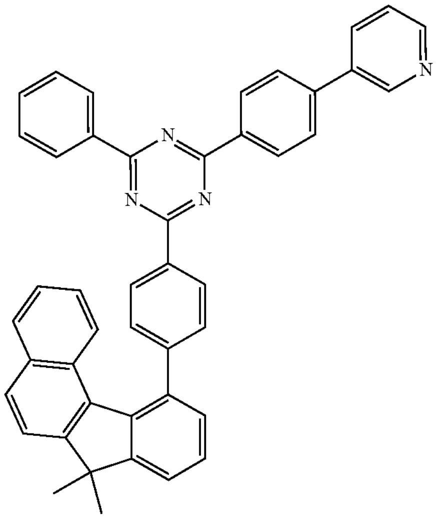
150
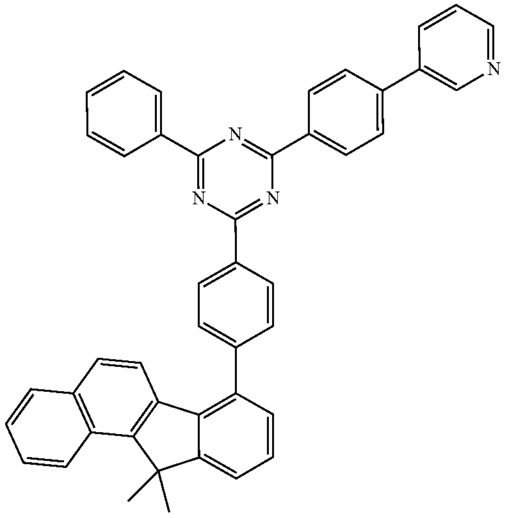
-continued
151
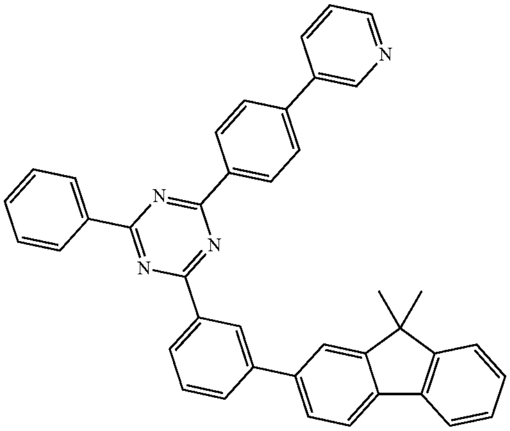
152
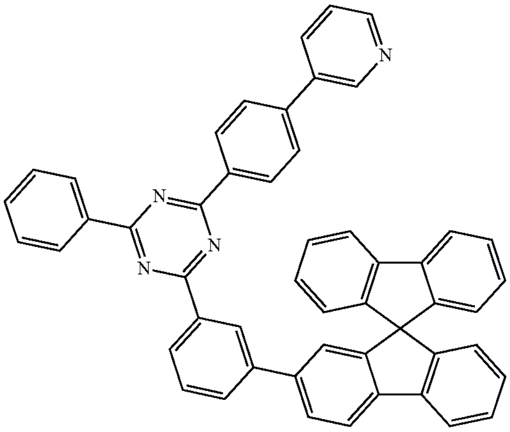
153
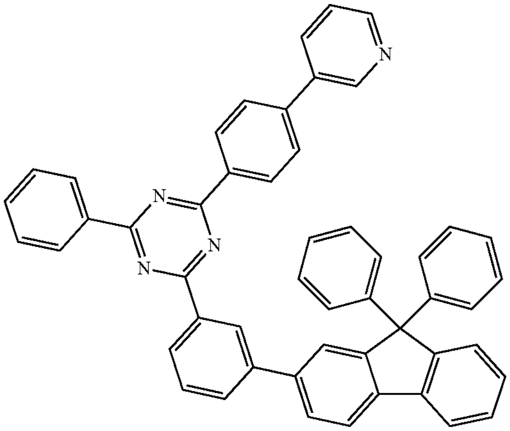

-continued
154
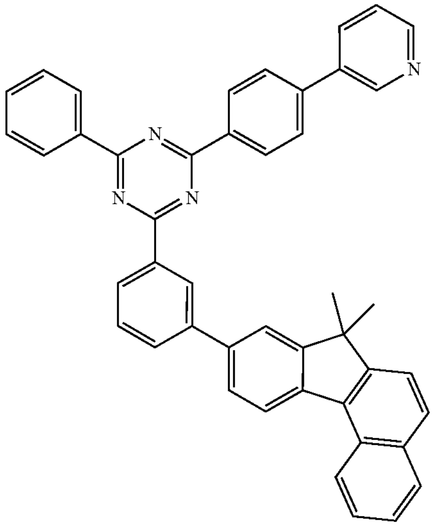
155
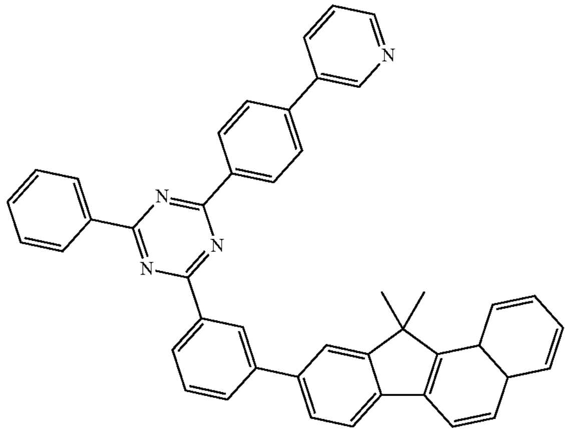
156
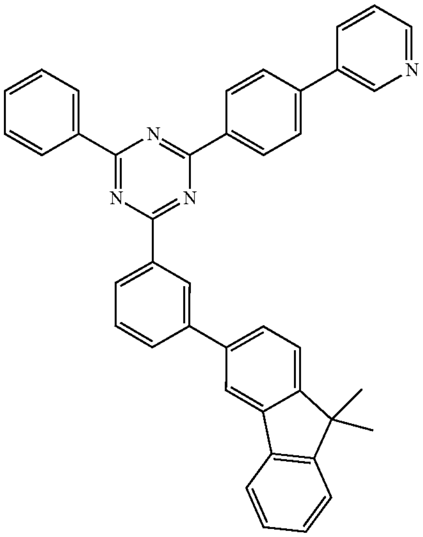
-continued
157
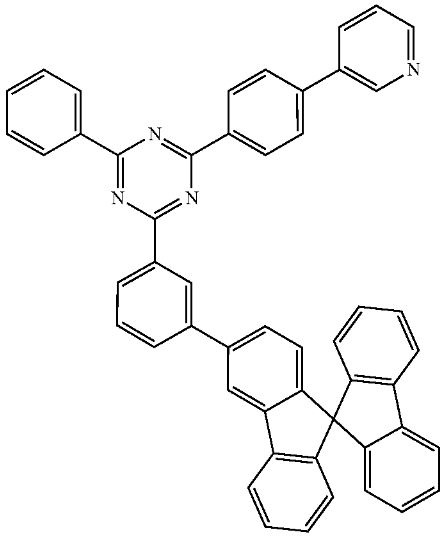
158
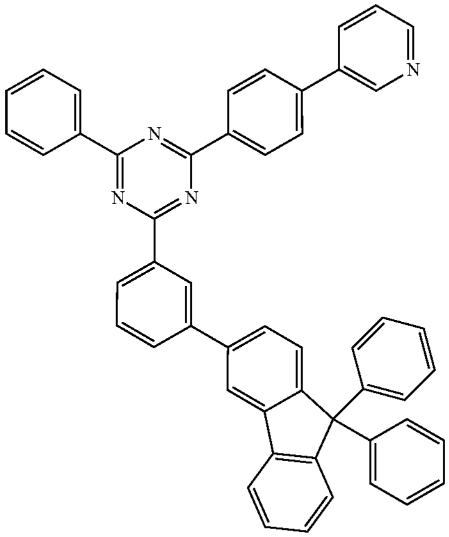
159
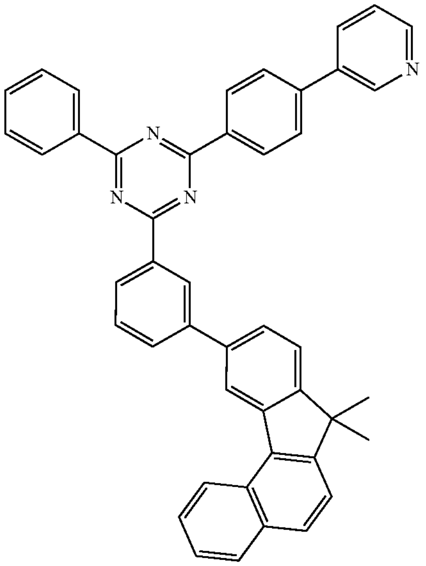

-continued
160
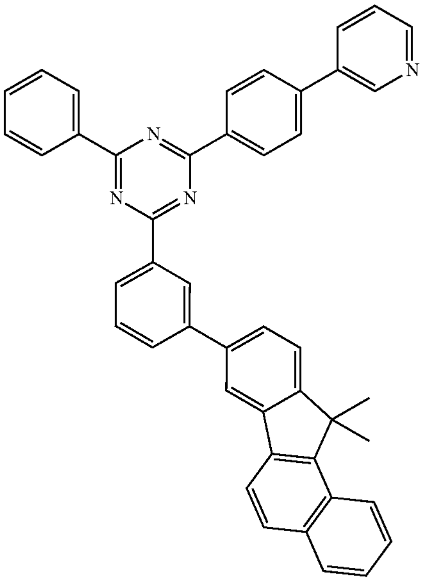
161
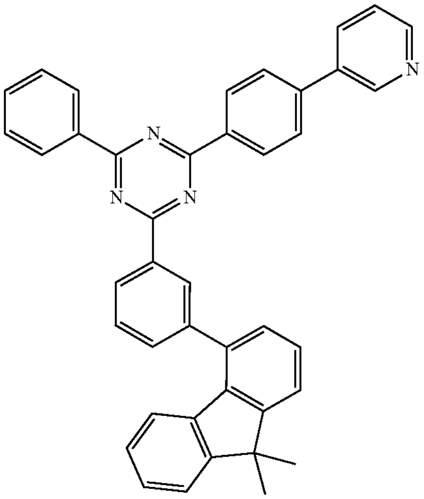
162
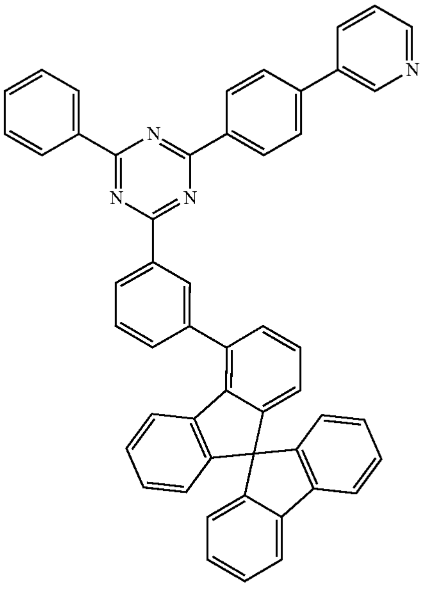
-continued
163
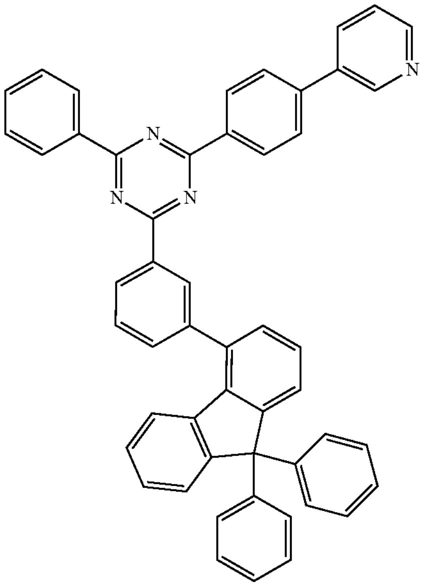
164
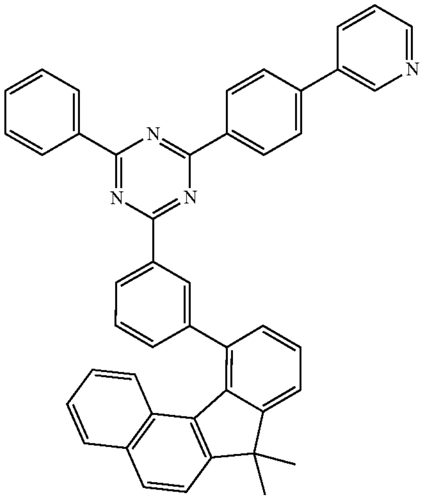
165
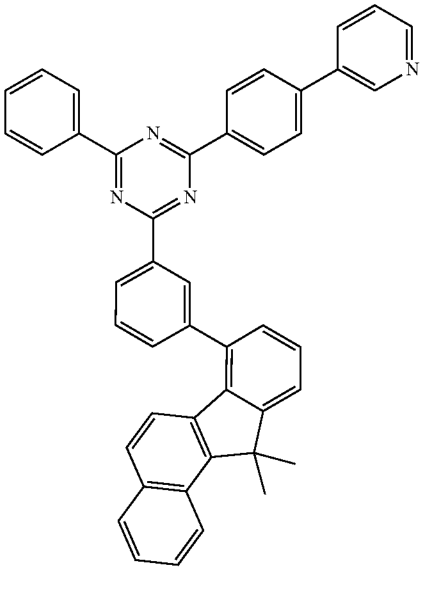

-continued
166
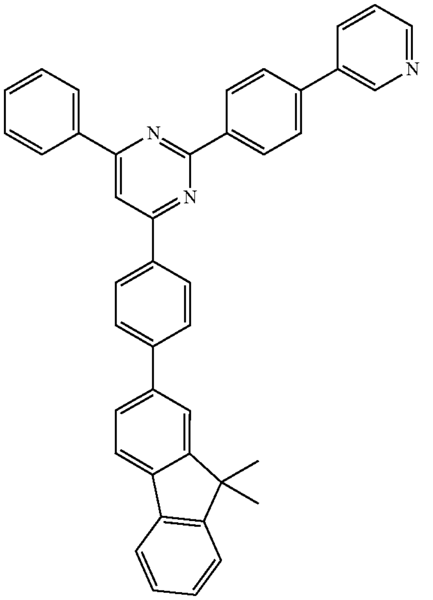
167
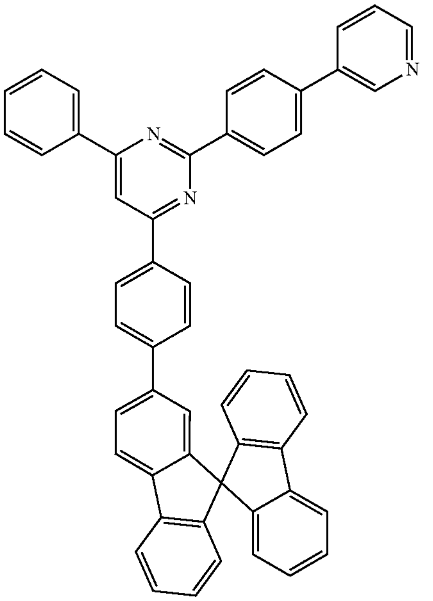
-continued
168
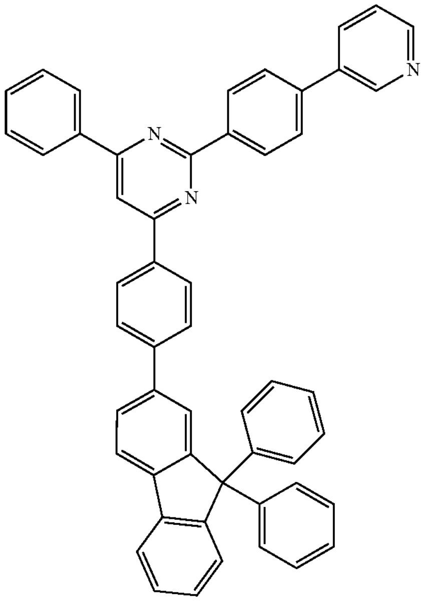
169
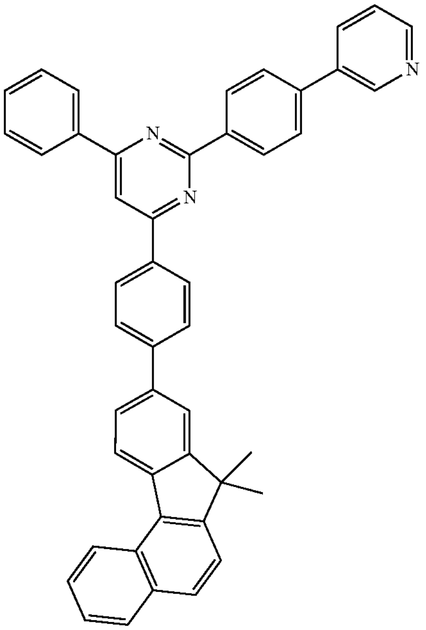

-continued
170
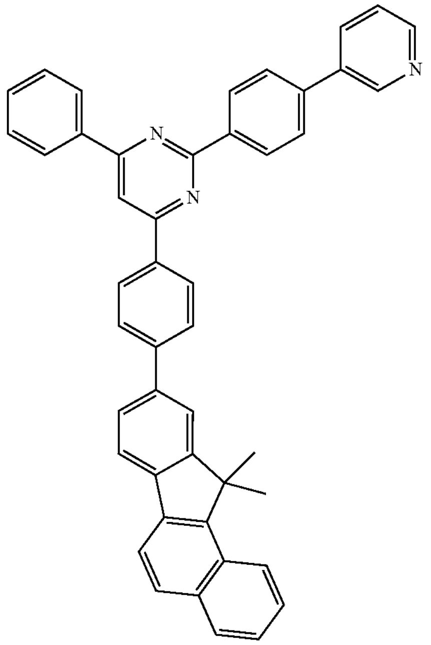
171
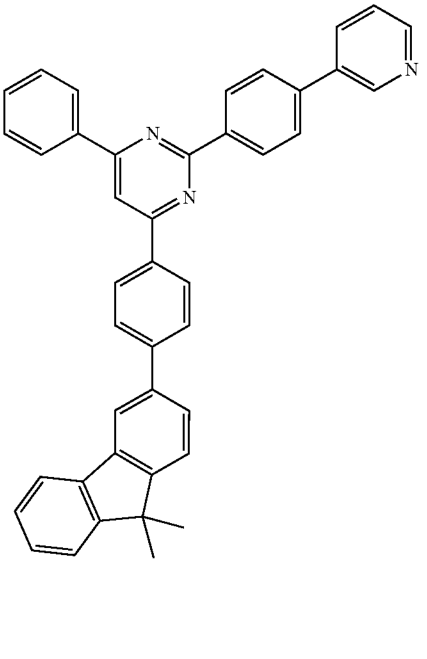
-continued
172
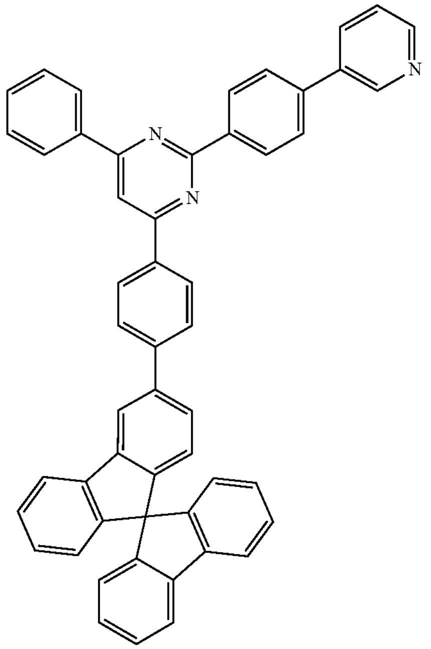
173
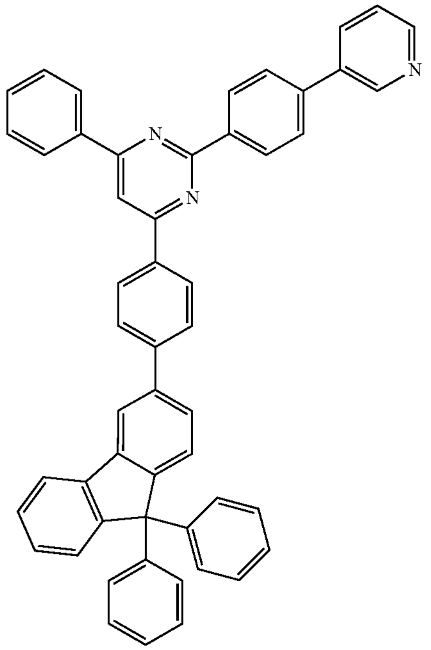

-continued
174
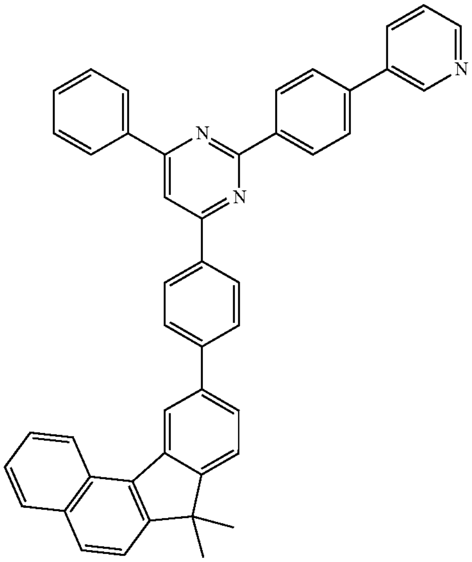
175
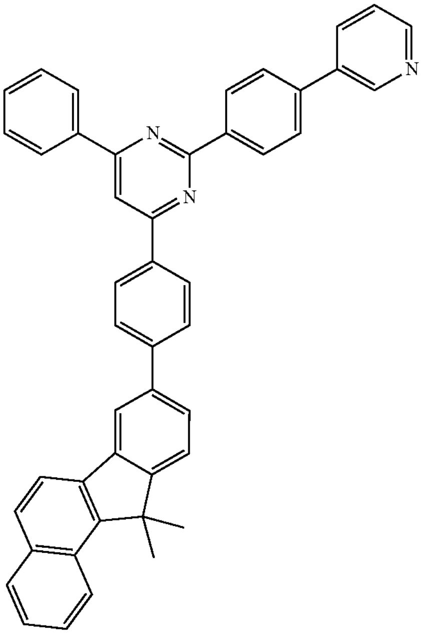
-continued
176
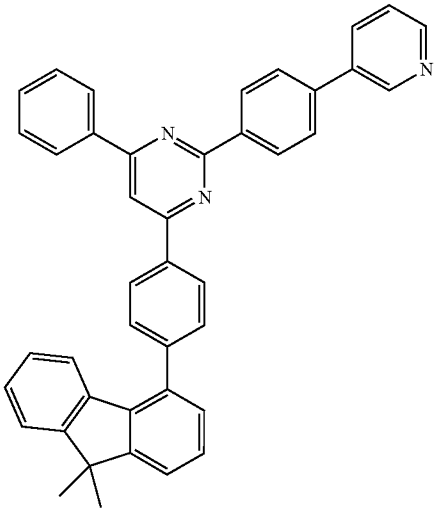
177
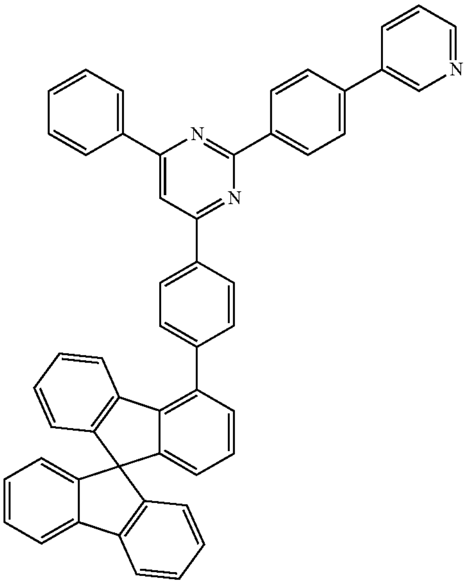

-continued
178
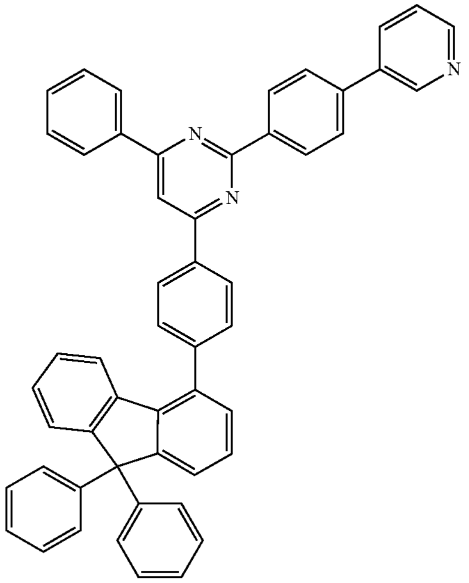
179
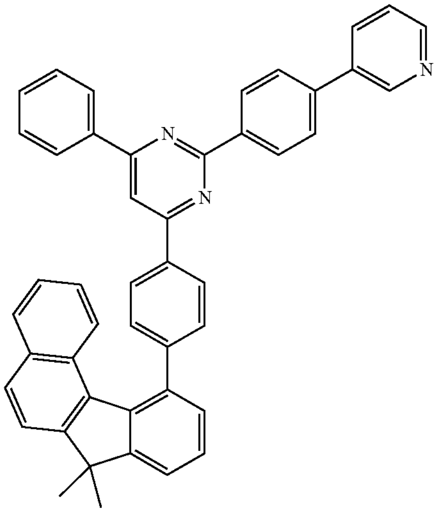
180
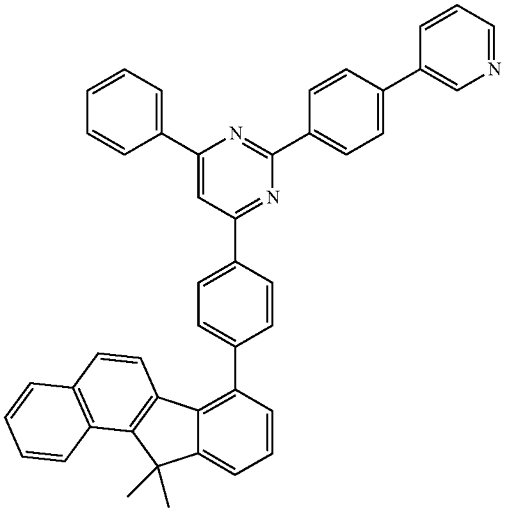
-continued
181
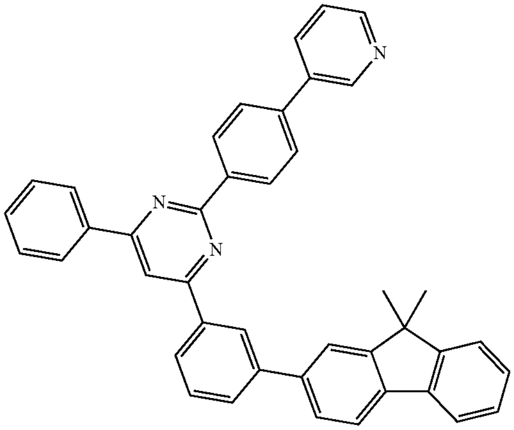
182
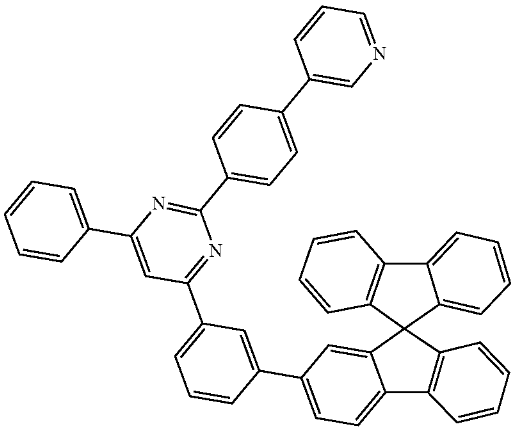
183
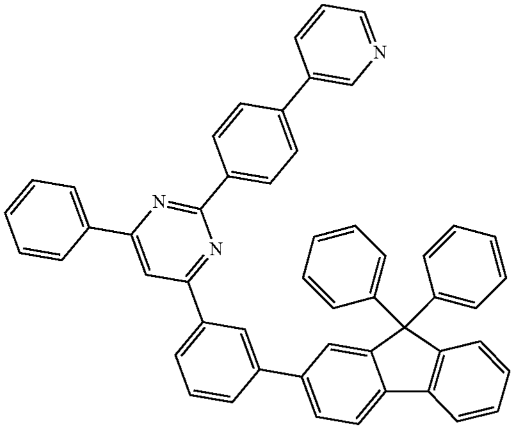

-continued
184
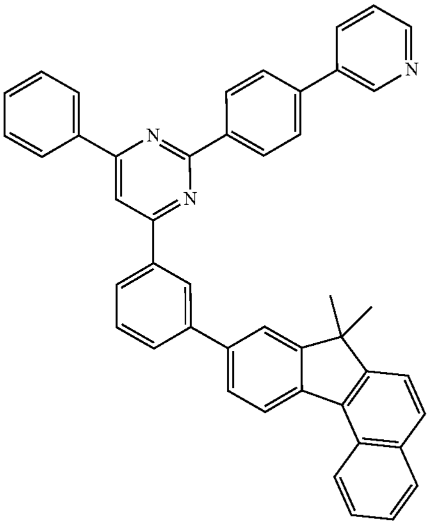
185
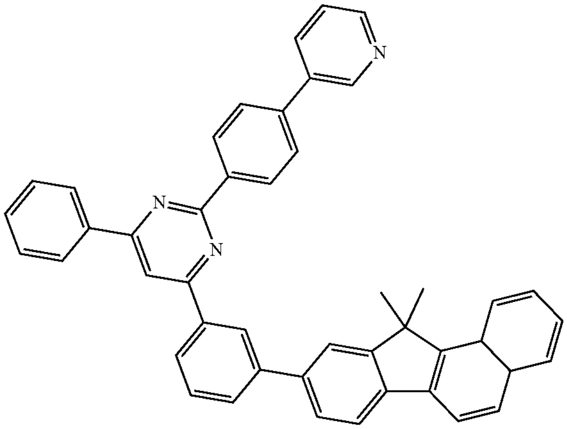
186
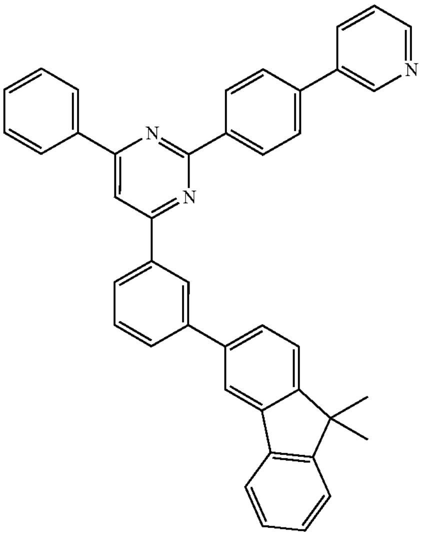
-continued
187
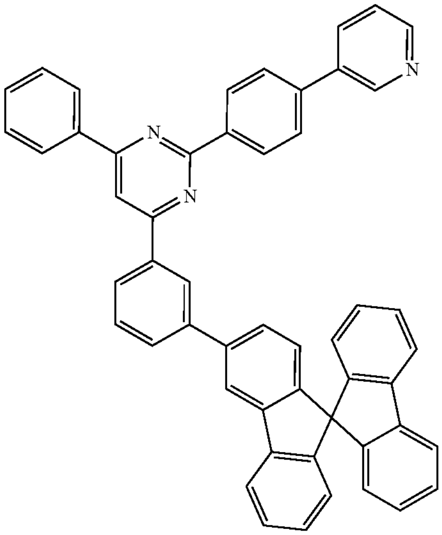
188
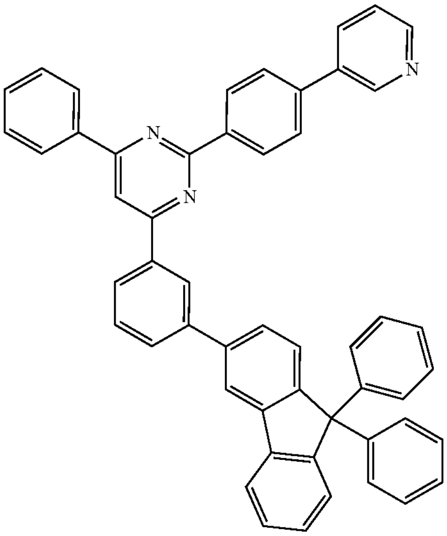
189
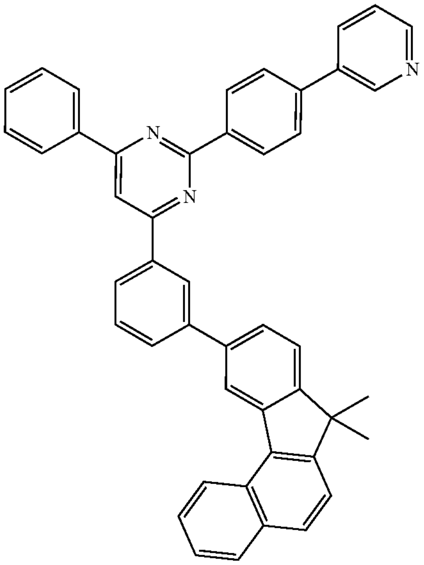

-continued
190
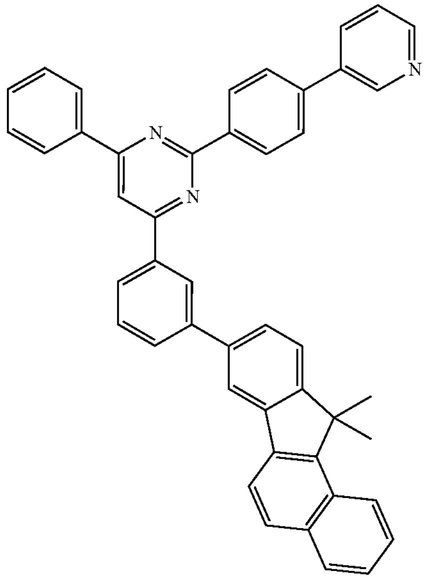
191
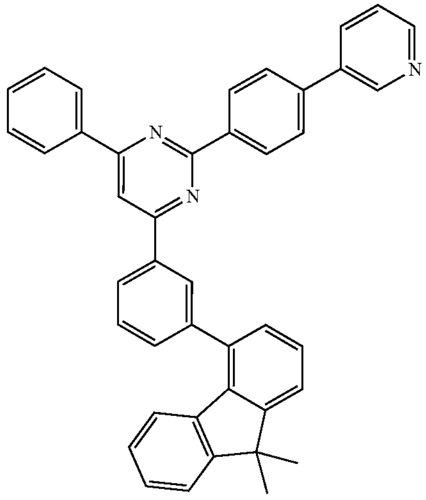
192
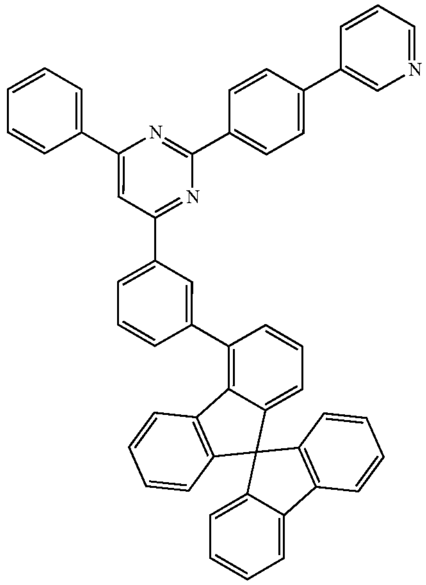
-continued
193
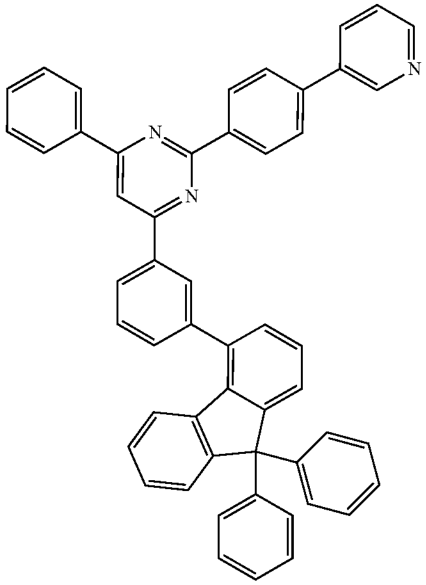
194
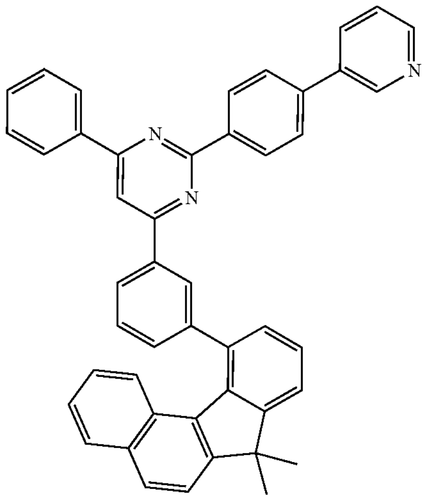
195
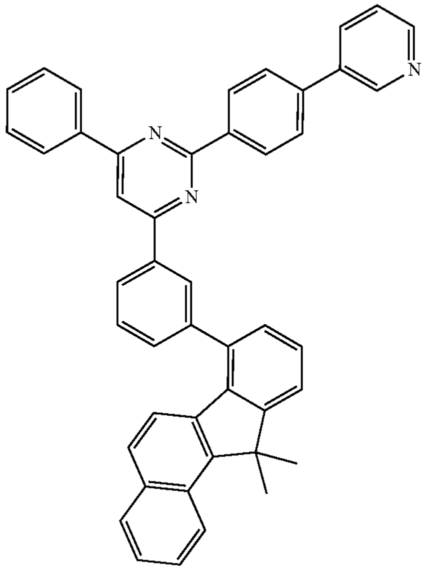

-continued
196
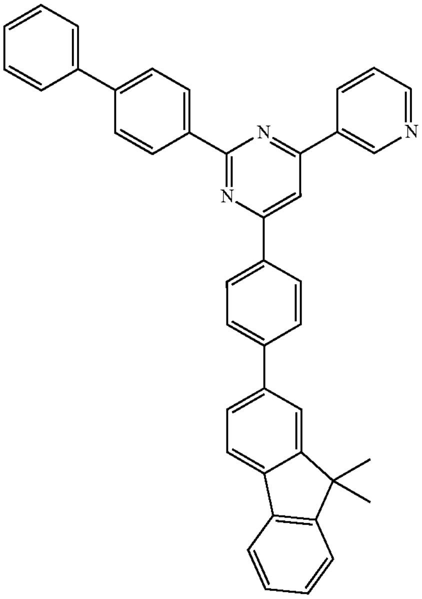
197
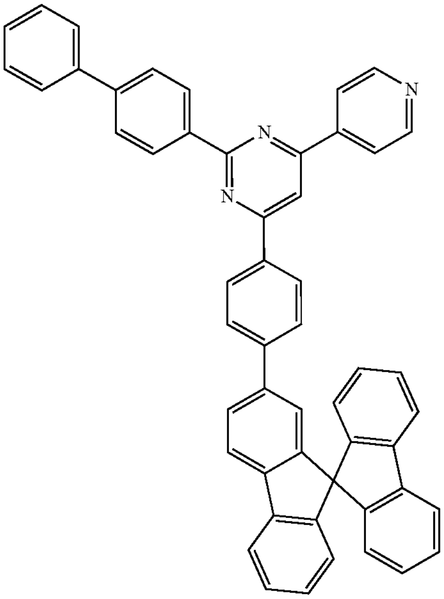
-continued
198
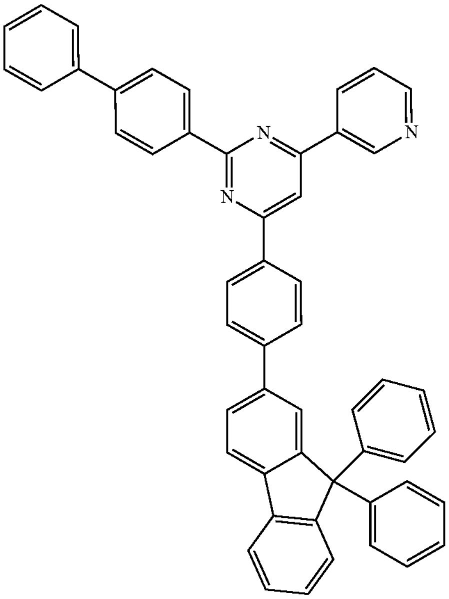
199
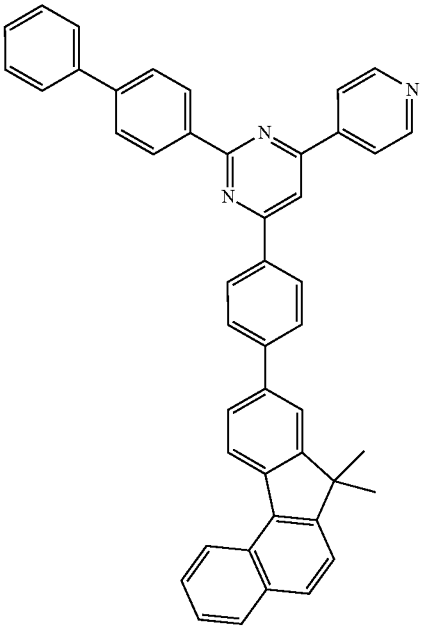

-continued
200
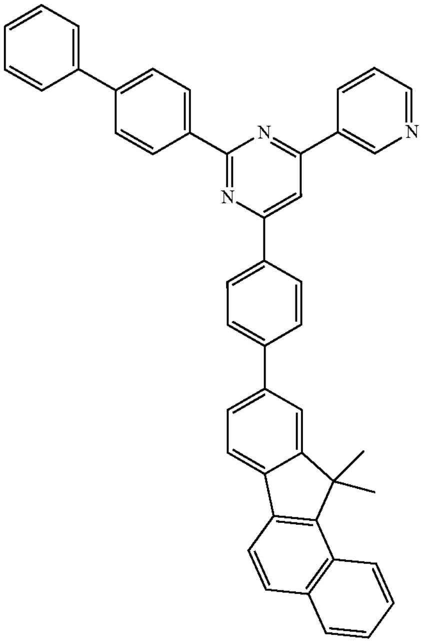
201
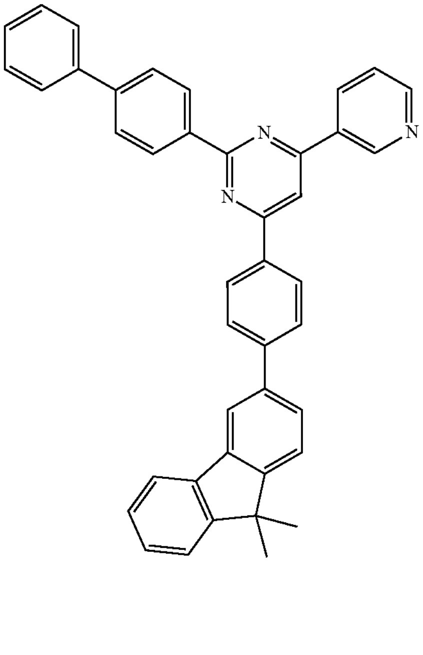
-continued
202
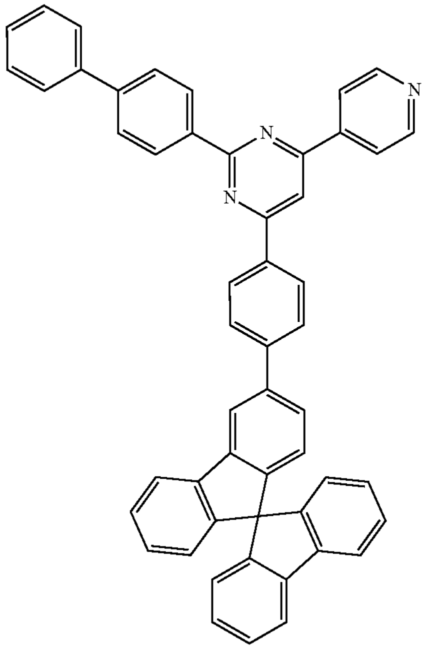
203
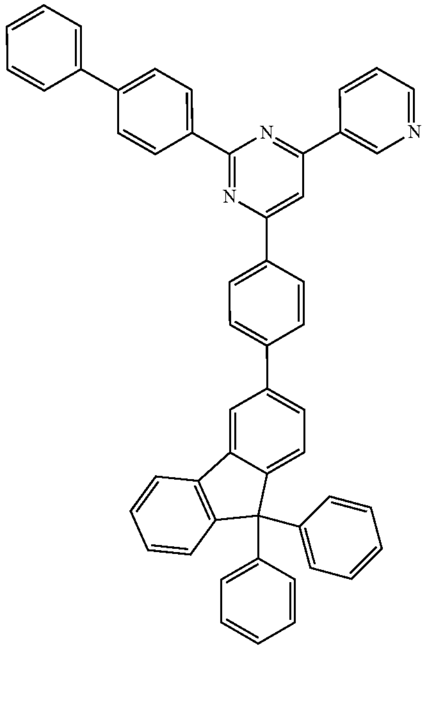

-continued
204
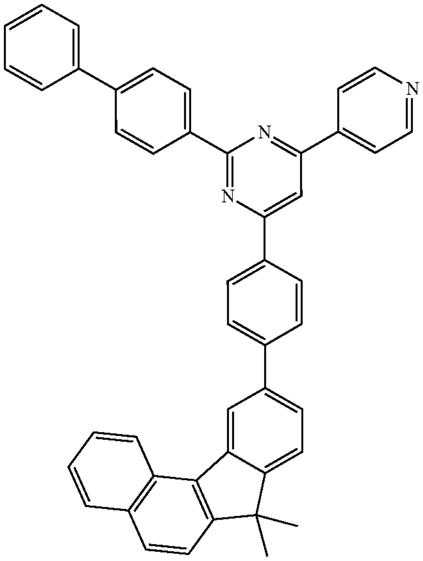
205
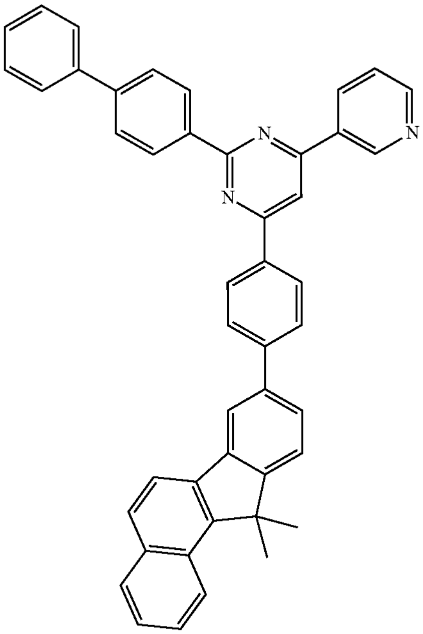
-continued
206
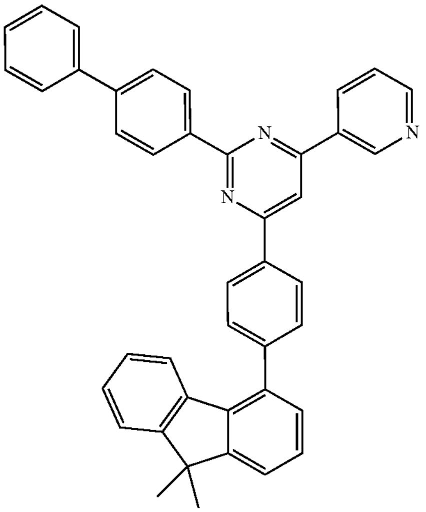
207
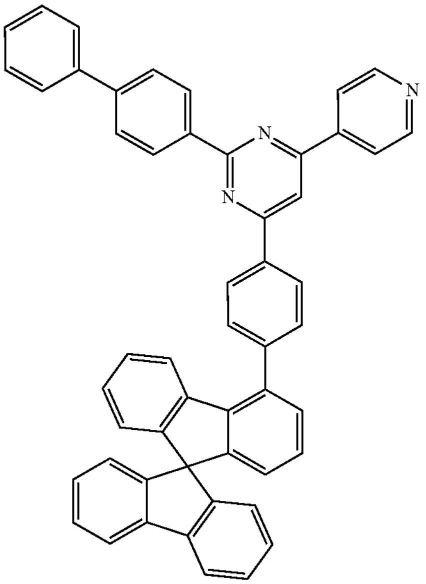

-continued
208
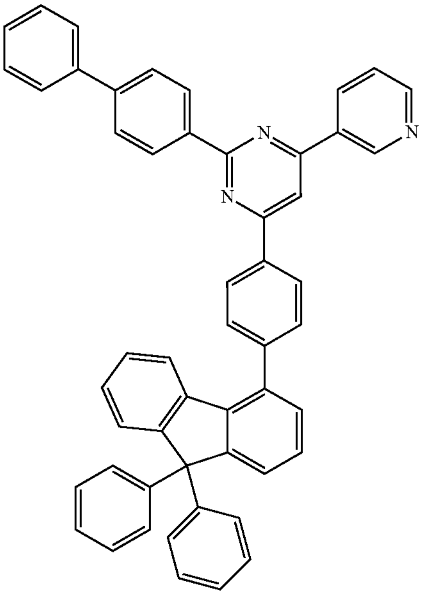
209
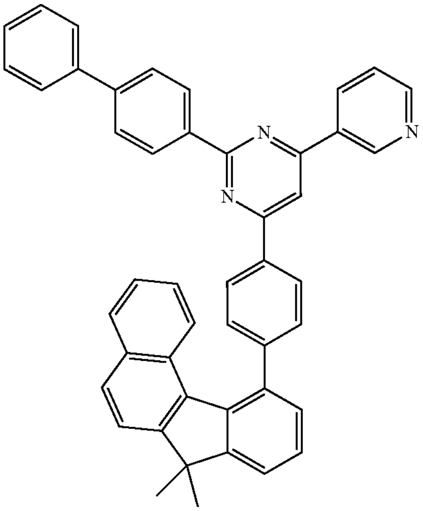
210
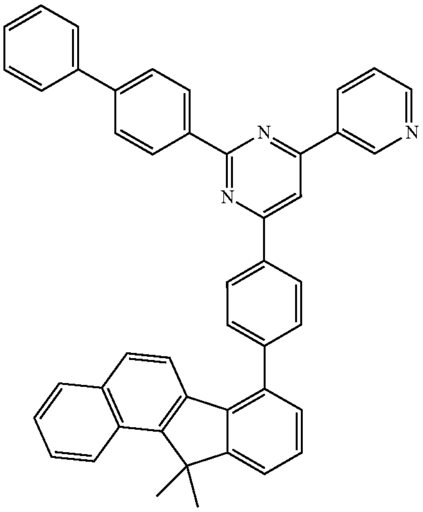
-continued
211
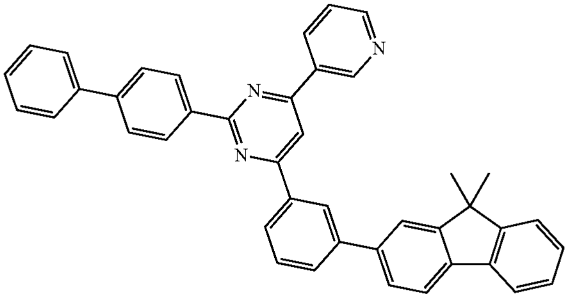
212
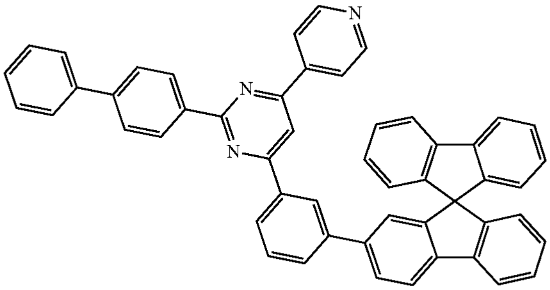
213
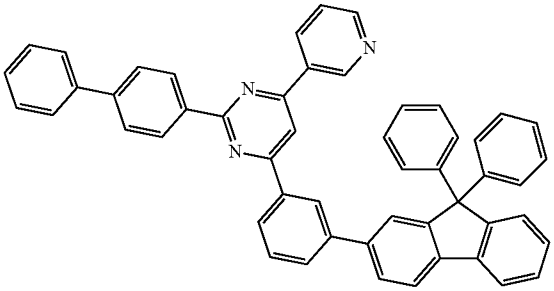
214
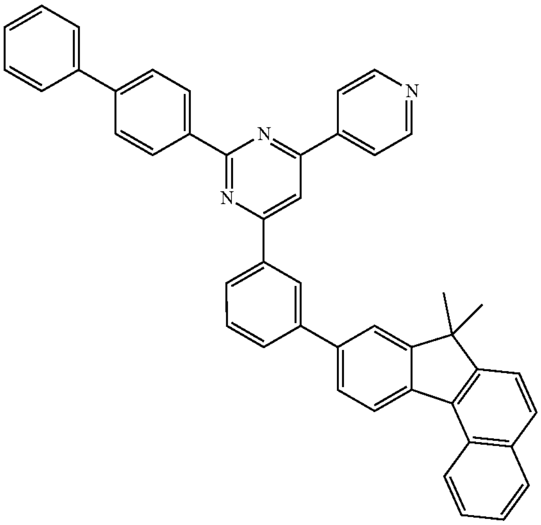

-continued
215
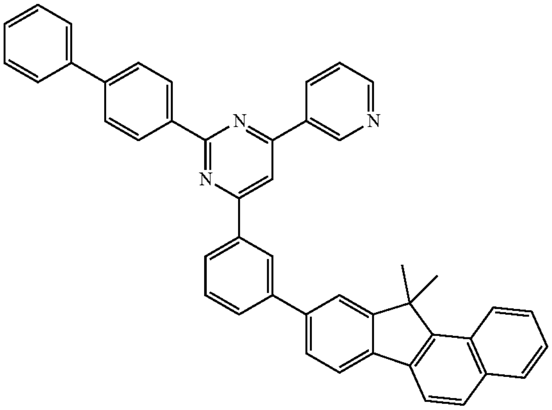
216
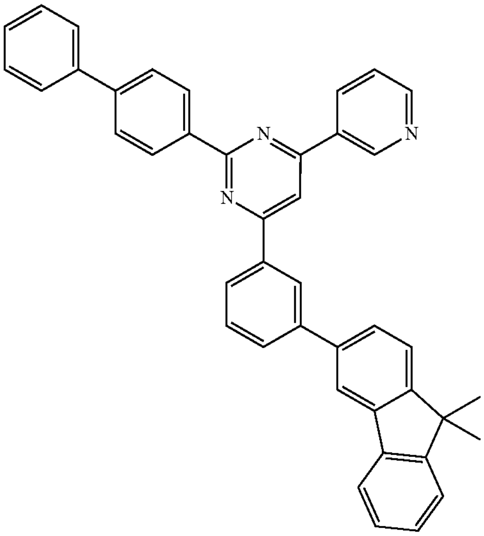
217
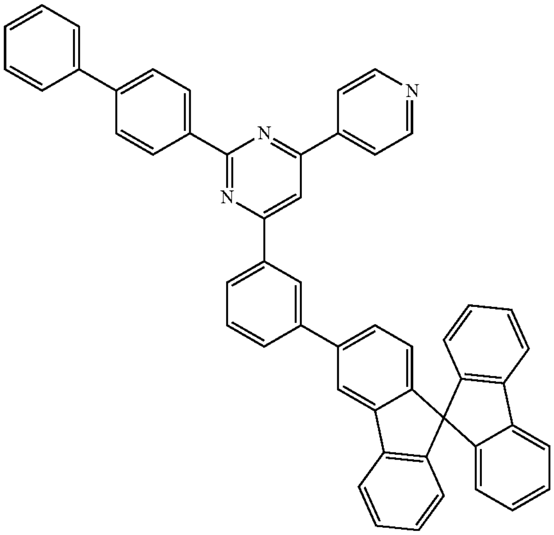
-continued
218
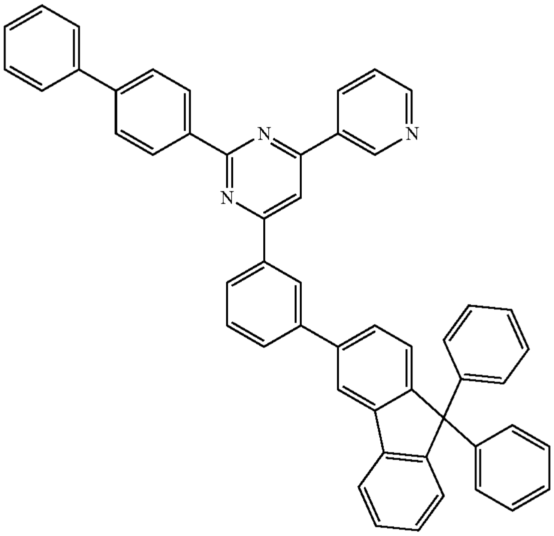
219
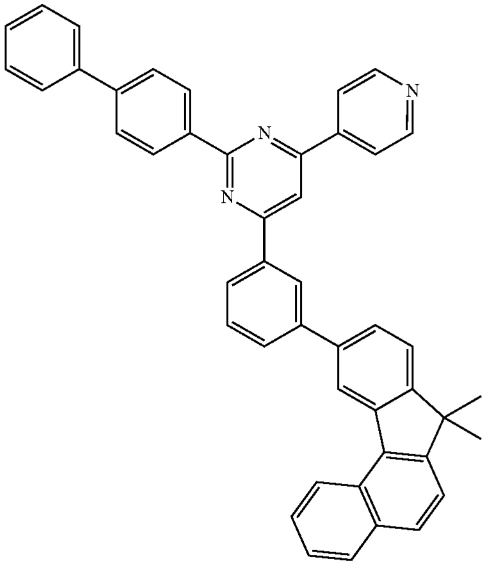

-continued
220
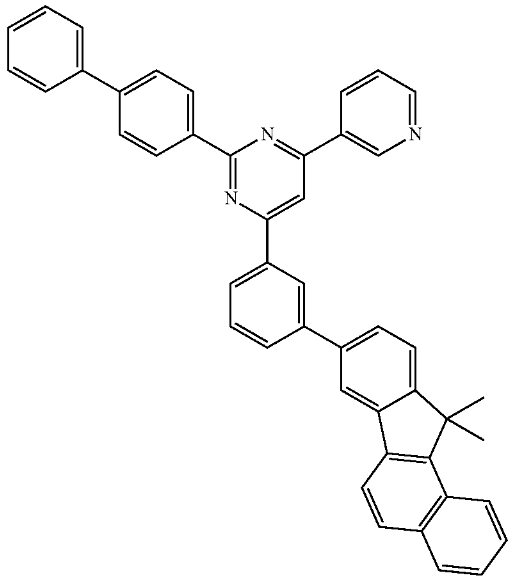
221
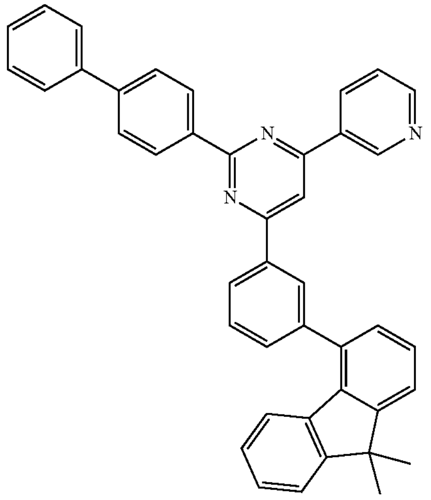
-continued
222
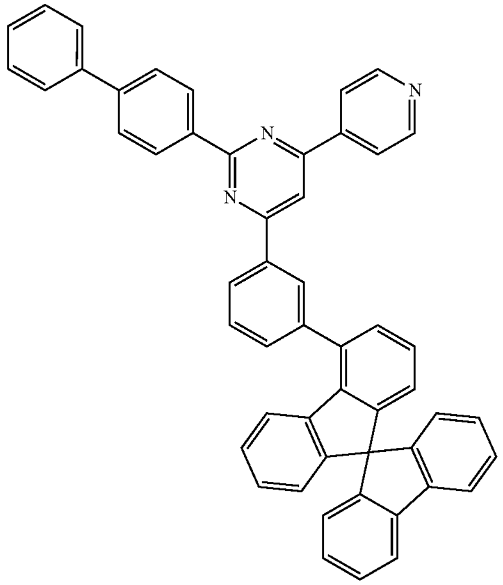
223
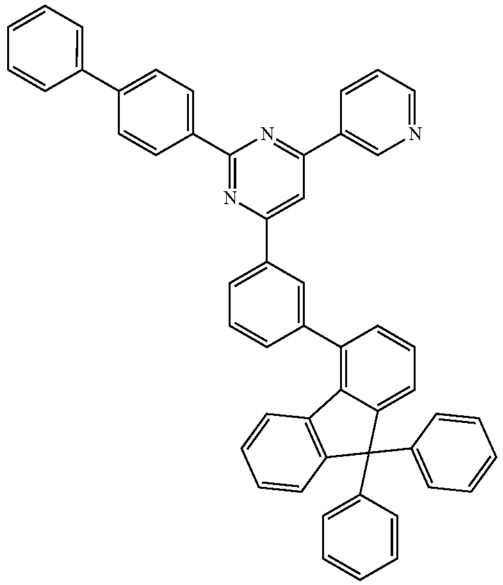
224
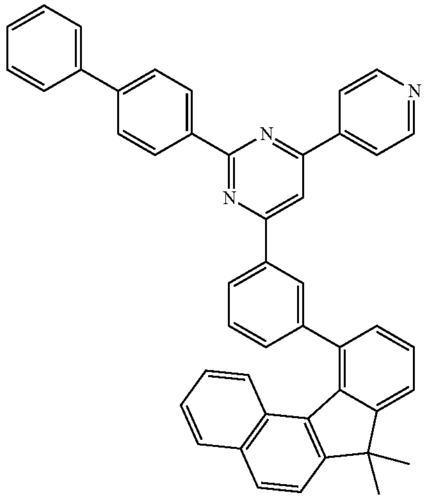

-continued
225
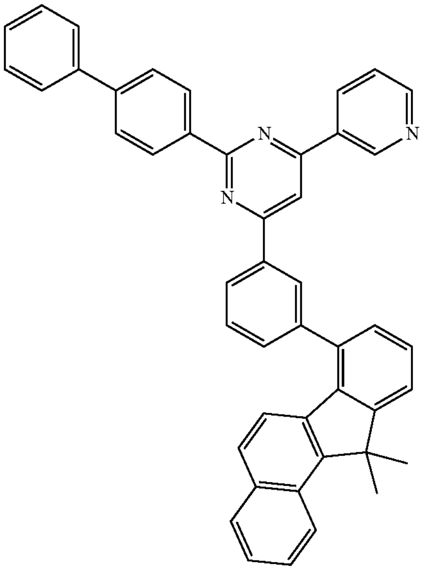
226
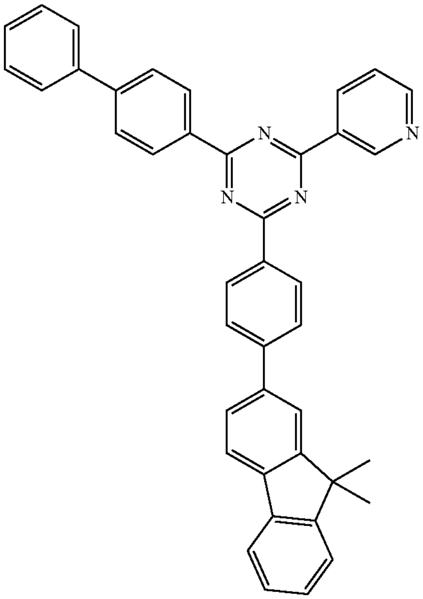
-continued
227
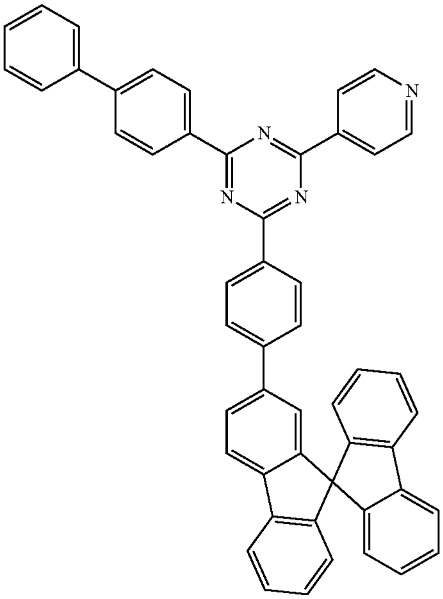
228
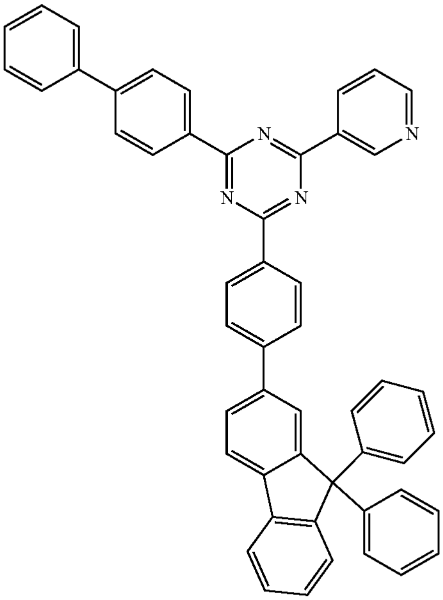

-continued
229
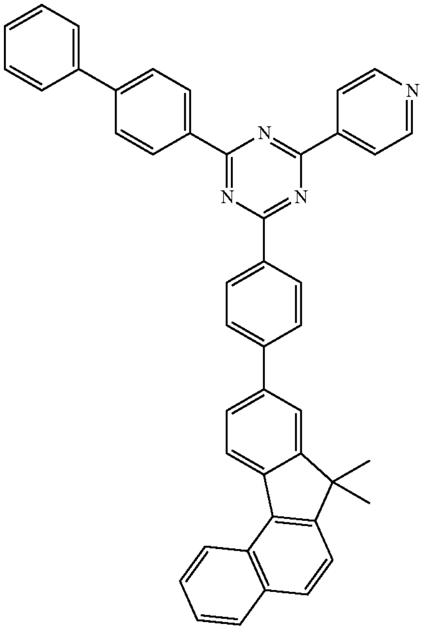
-continued
231
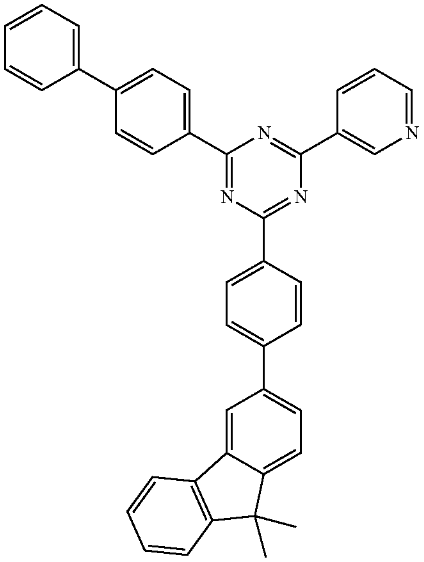
230
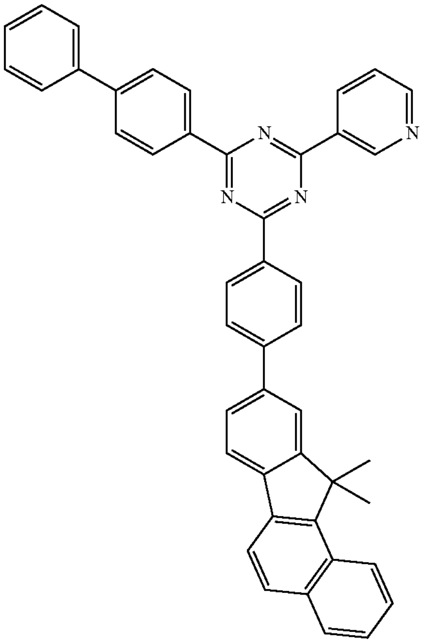
232
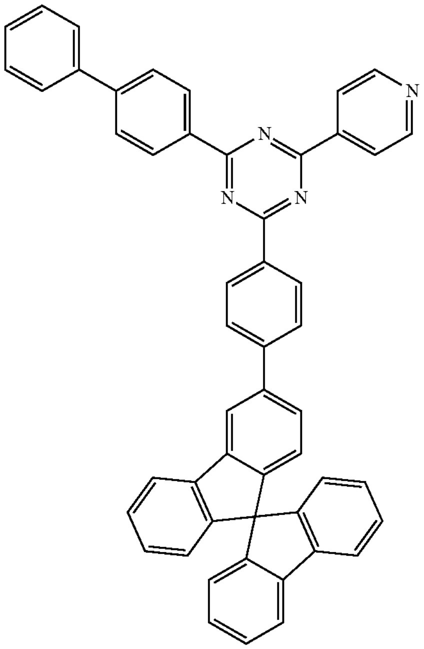

233
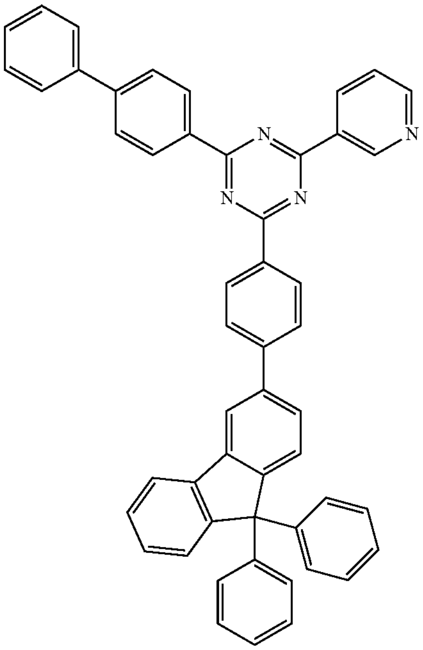
234
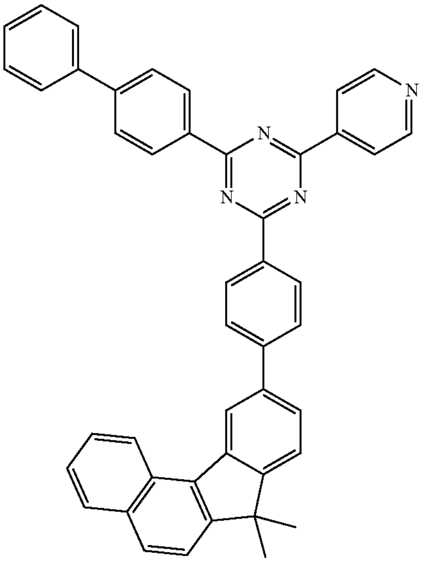
235
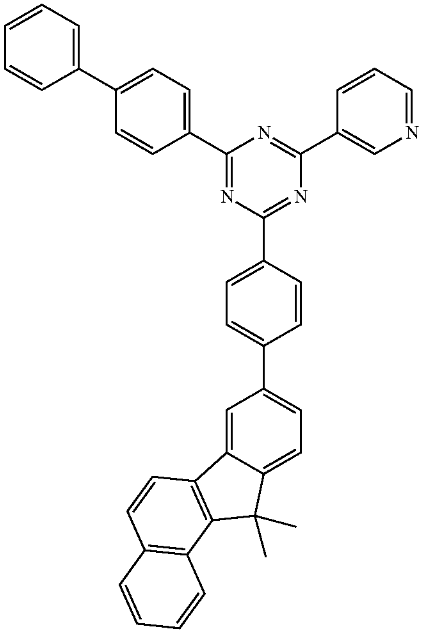
236
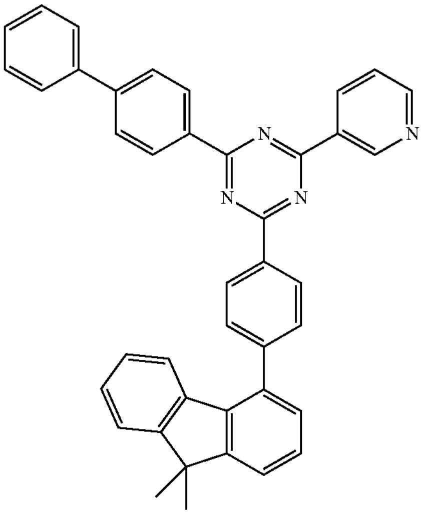

-continued
237
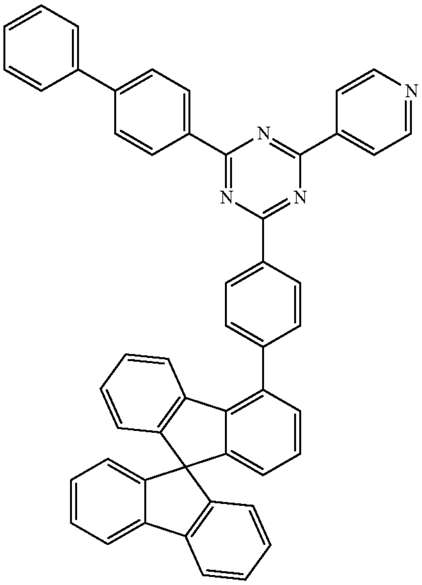
238
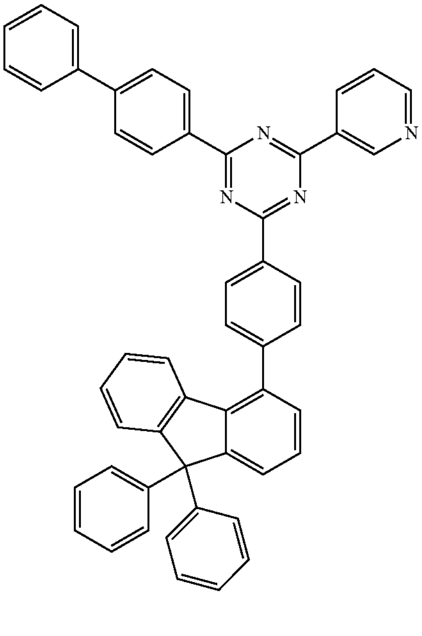
-continued
239
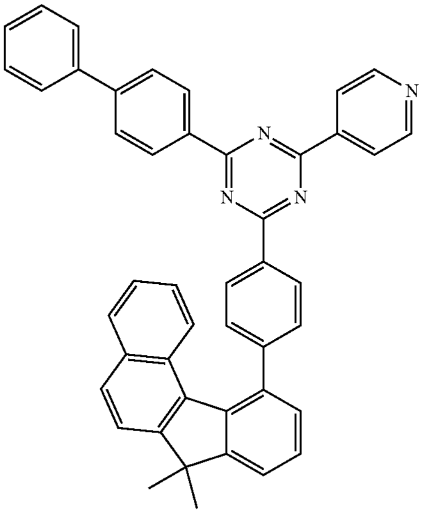
240
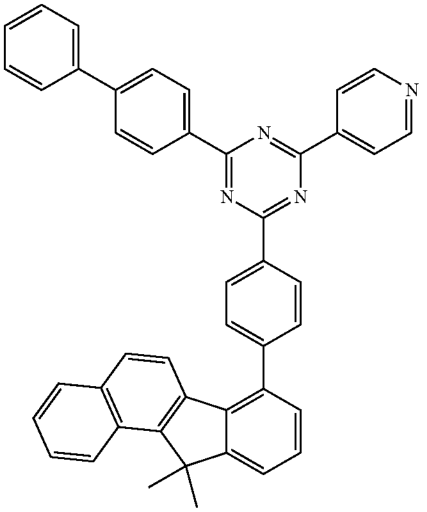
241
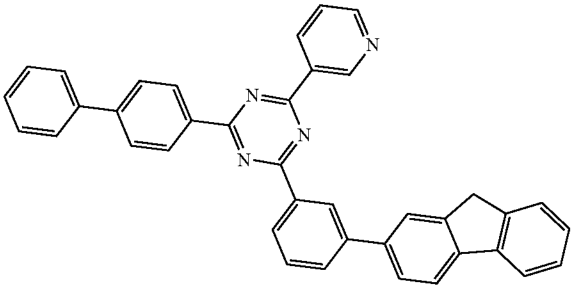
242
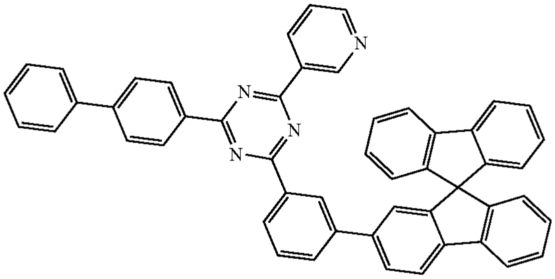

-continued
243
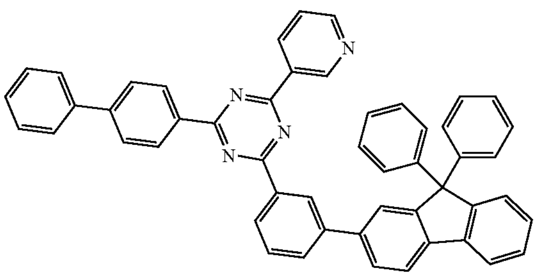
244
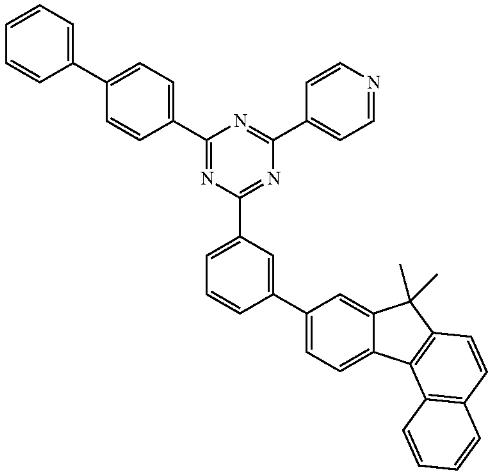
245
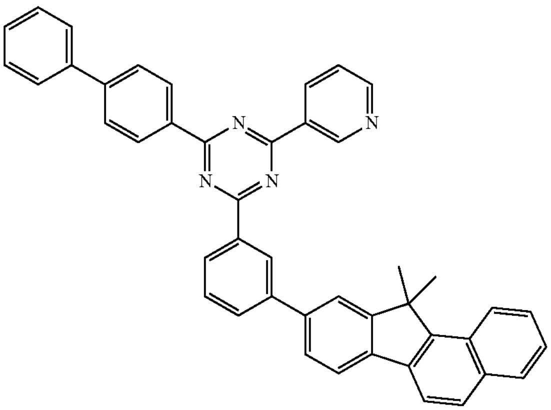
-continued
246
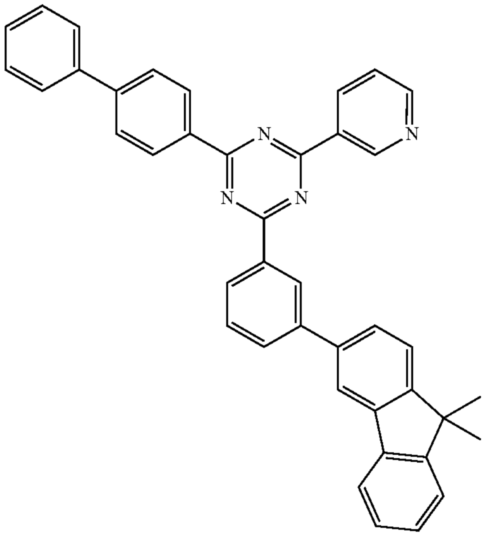
247
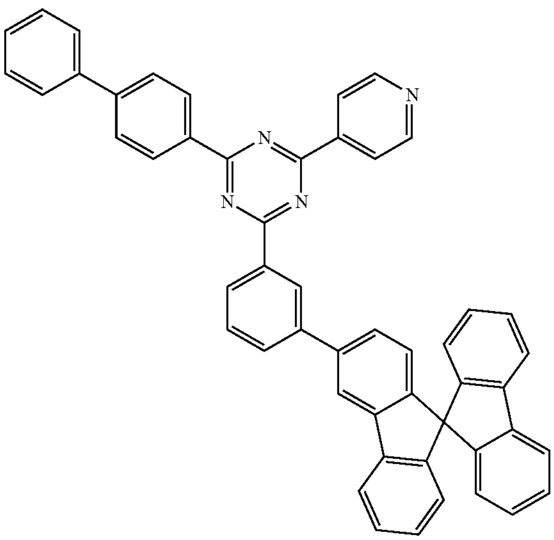
248
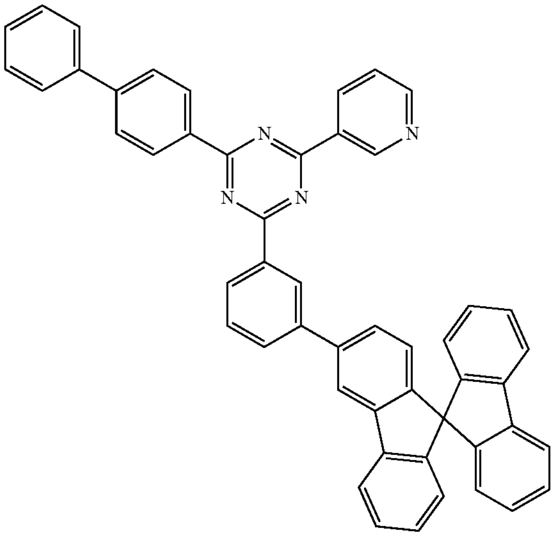

-continued
249
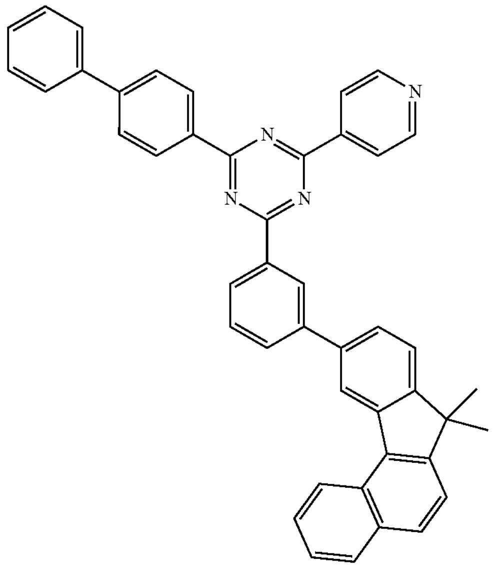
250
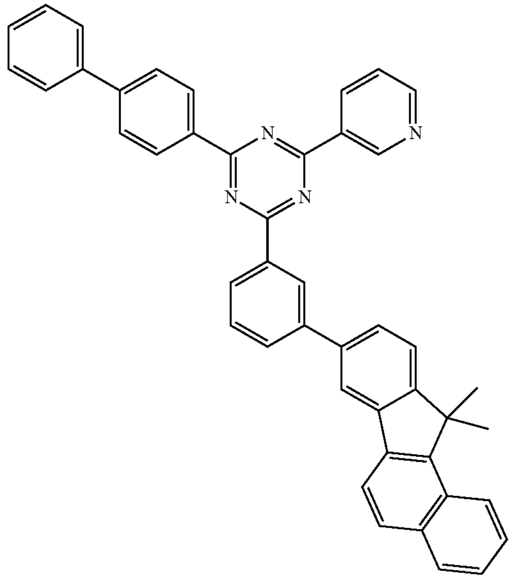
251
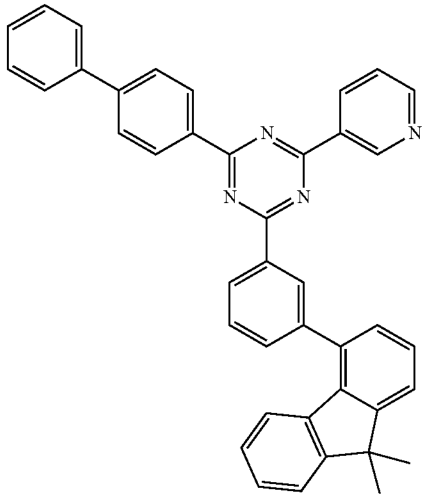
-continued
252
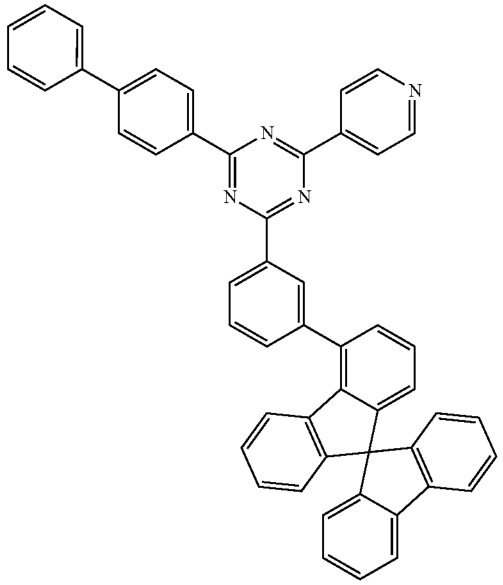
253
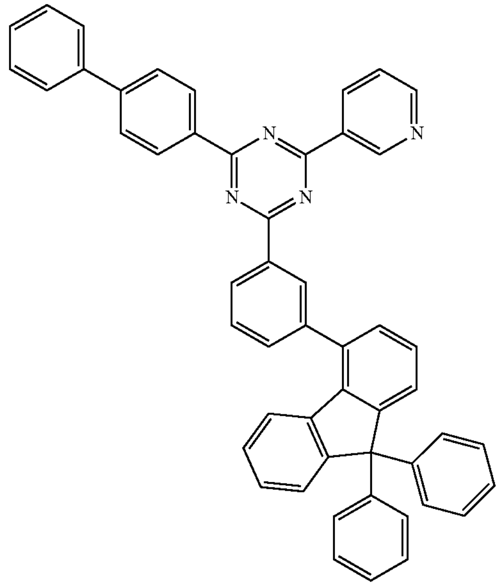

-continued
254
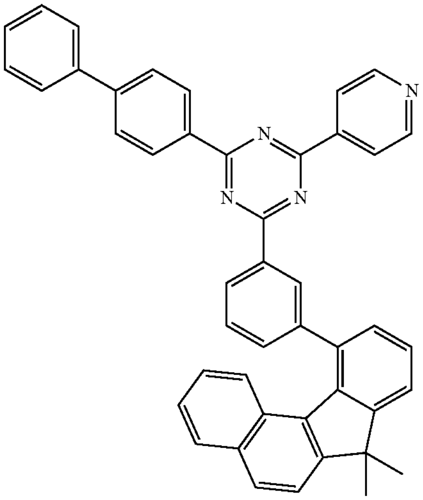
255
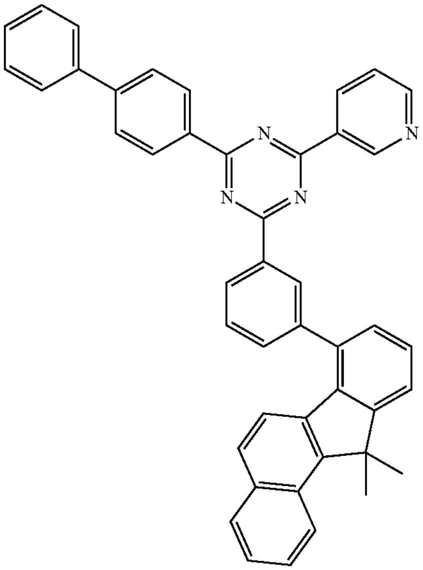
256
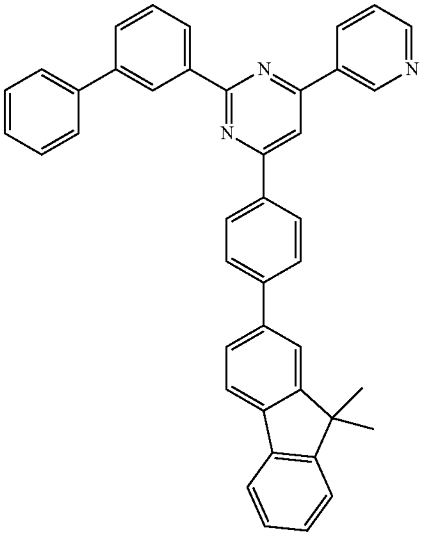
-continued
257
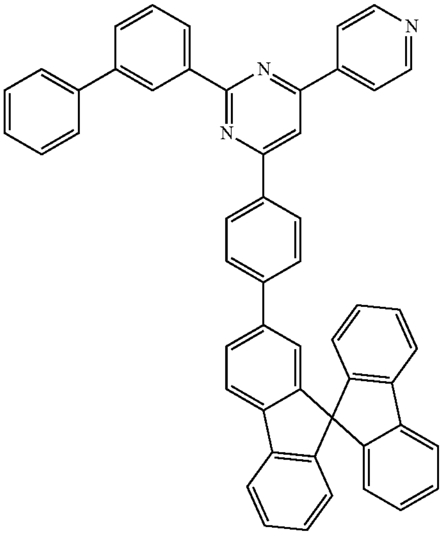
258
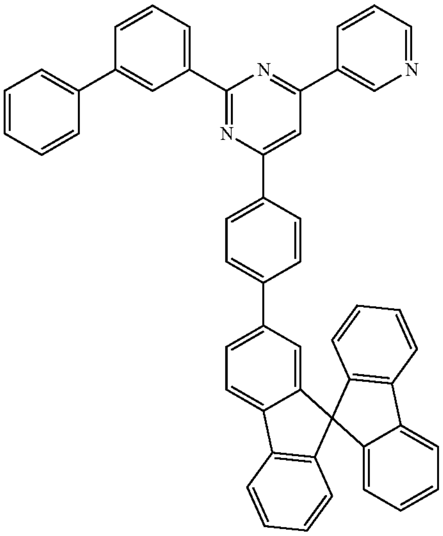
259
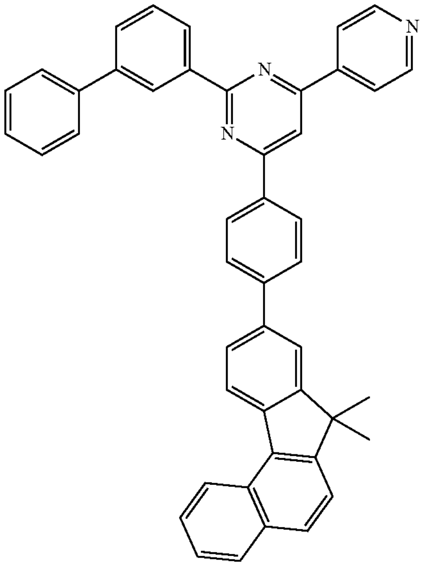

-continued
260
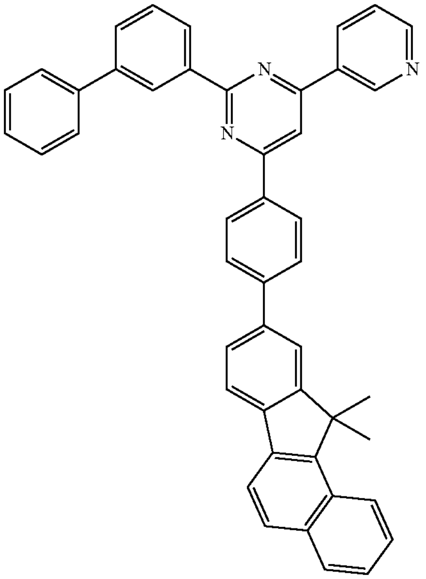
261
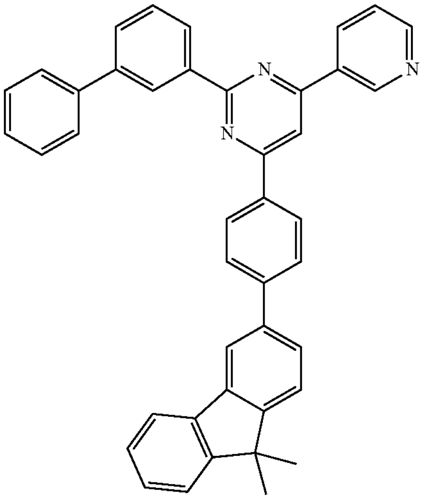
262
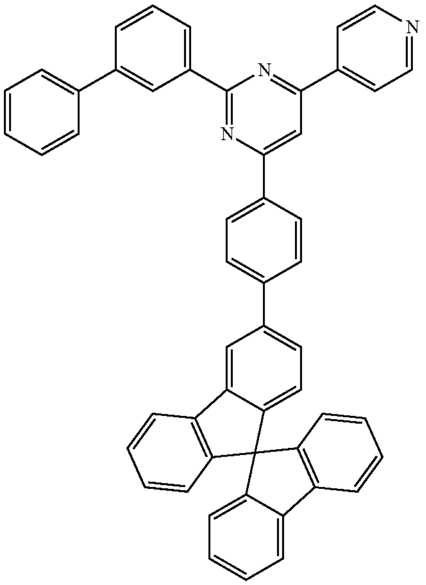
-continued
263
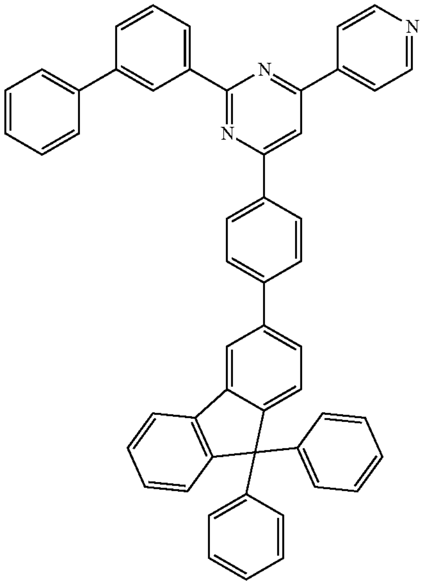
264
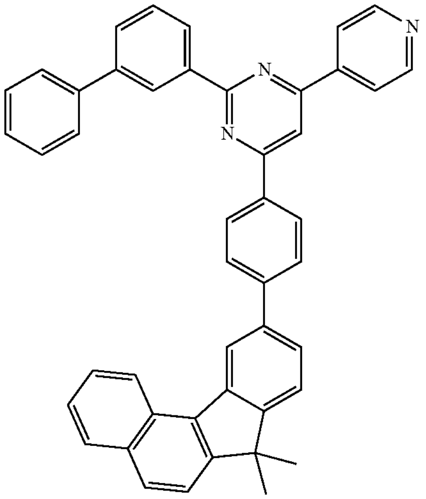
265
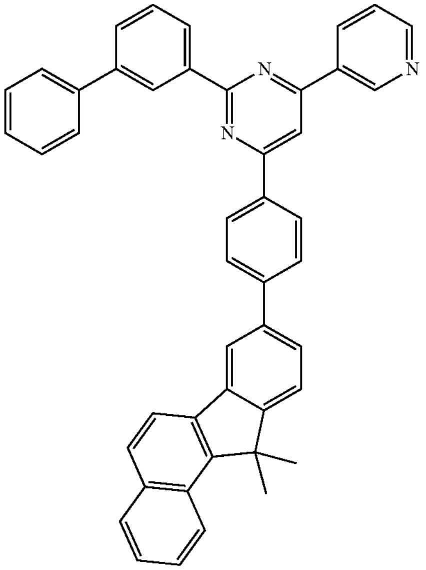

-continued
266
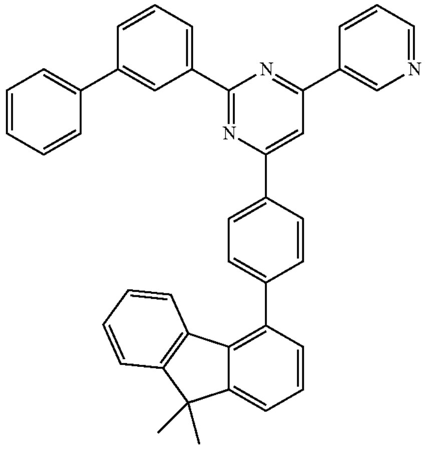
267
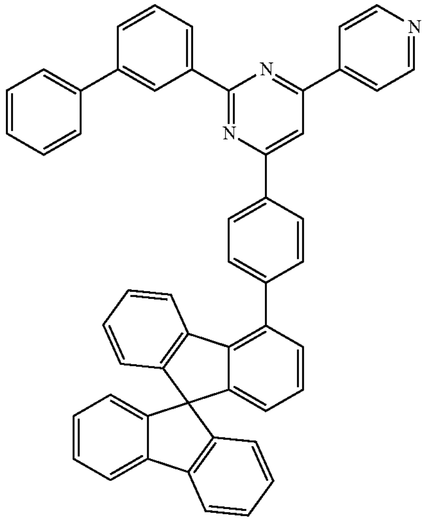
268
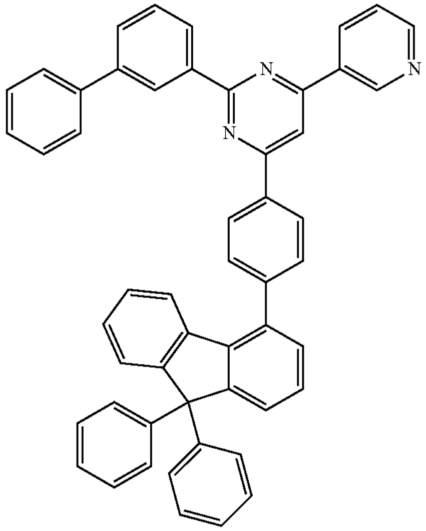
-continued
269
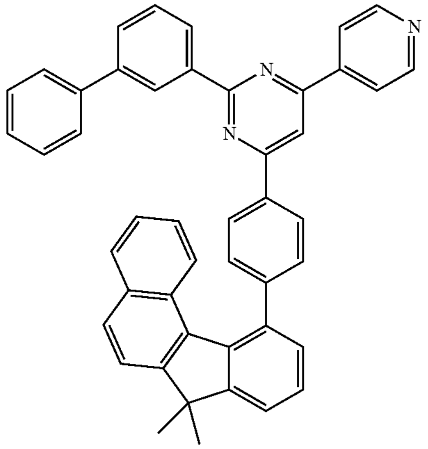
270
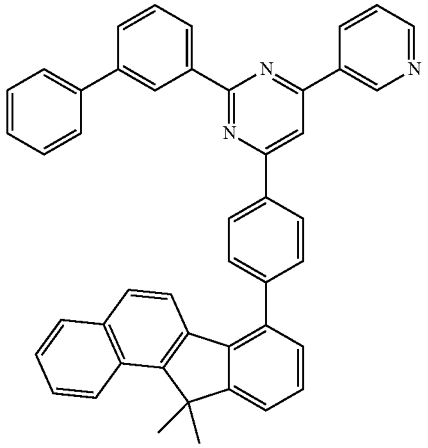
271
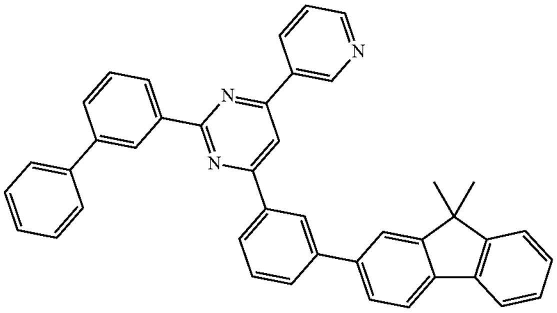
272
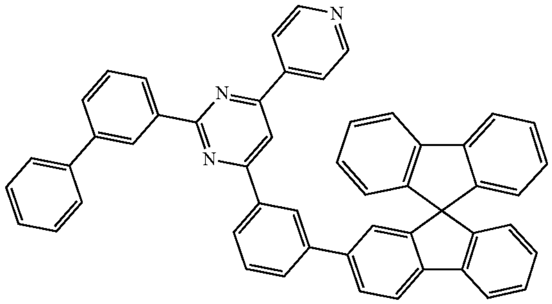

-continued
273
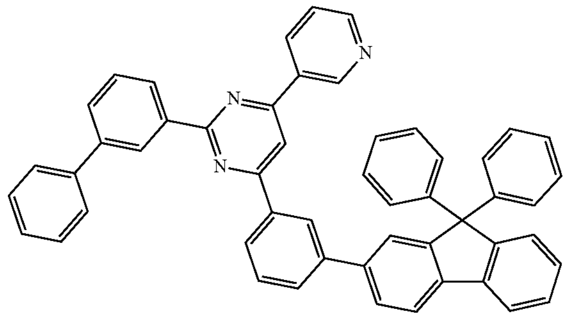
274
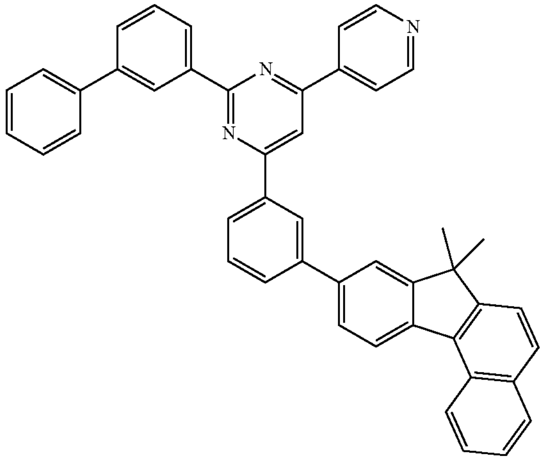
275
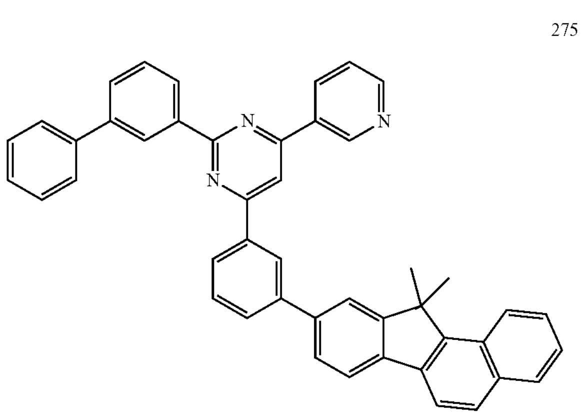
-continued
276
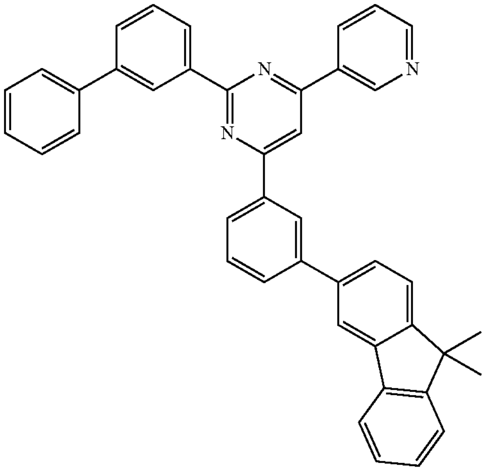
277
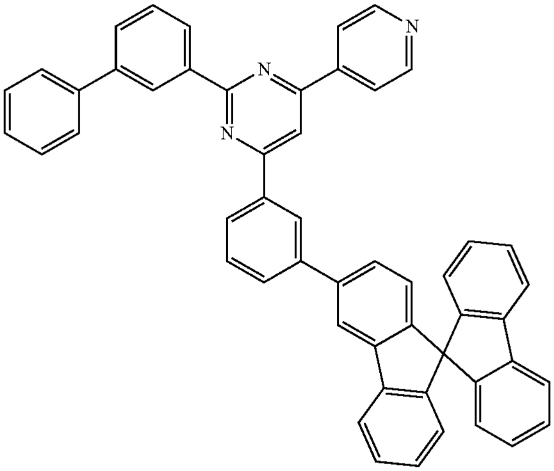
278
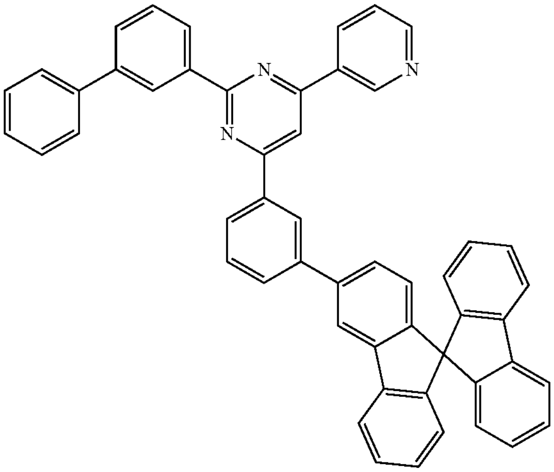

-continued
279
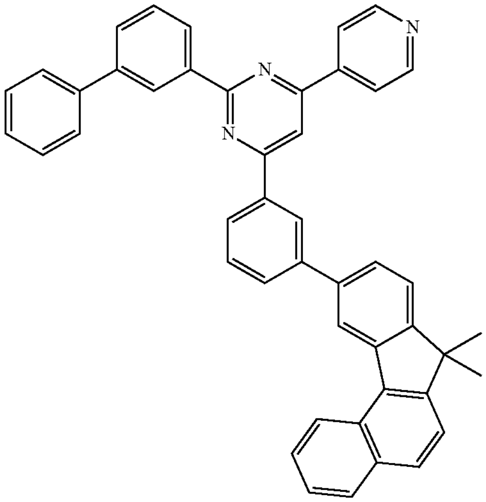
280
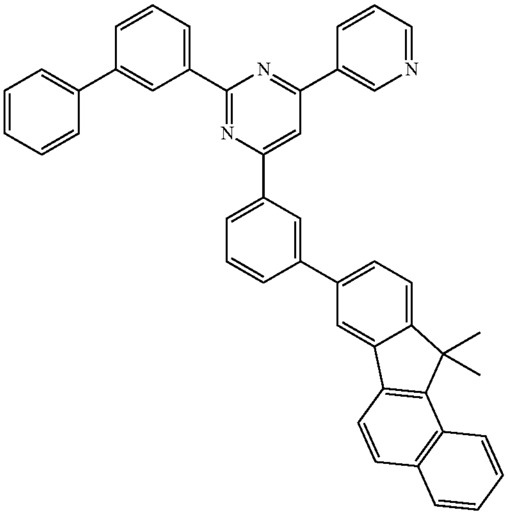
281
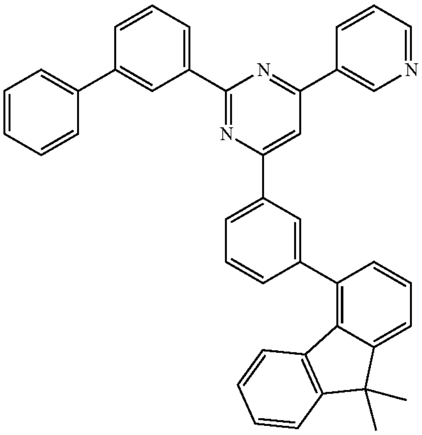
-continued
282
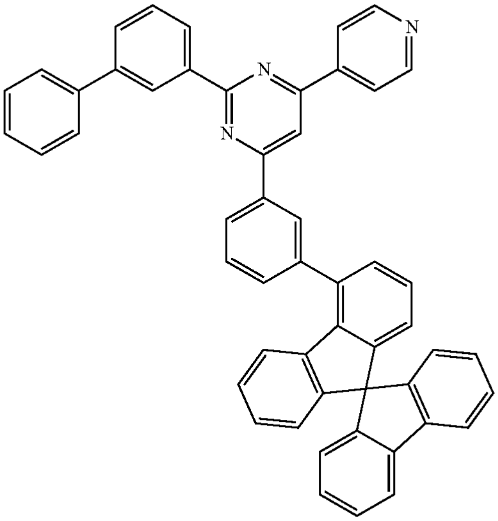
283
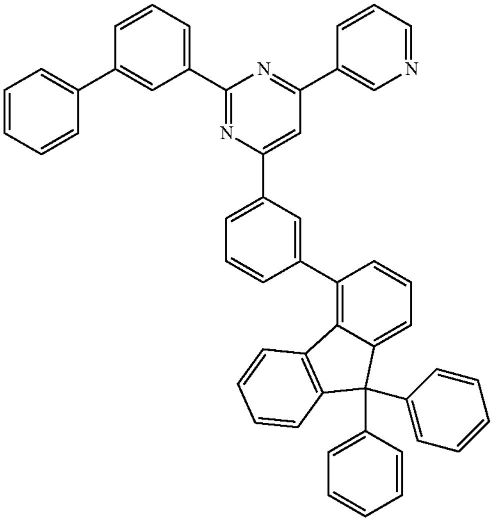
284
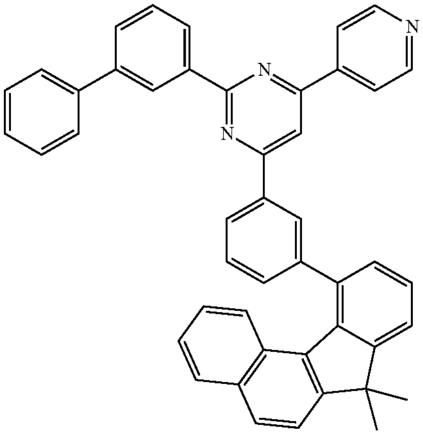

-continued
285
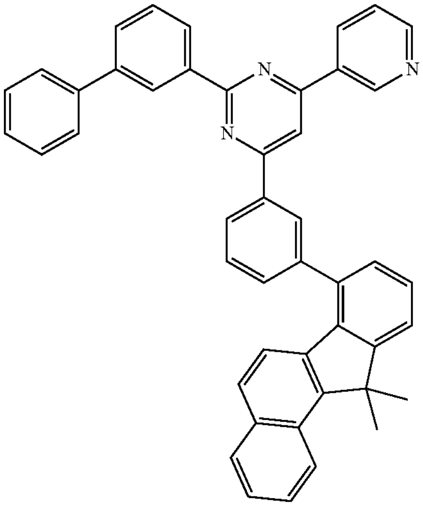
286
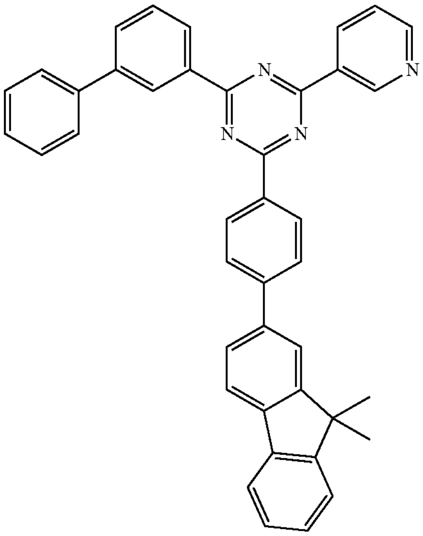
287
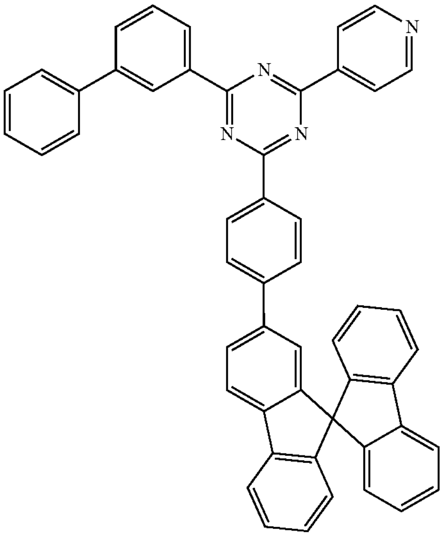
-continued
288
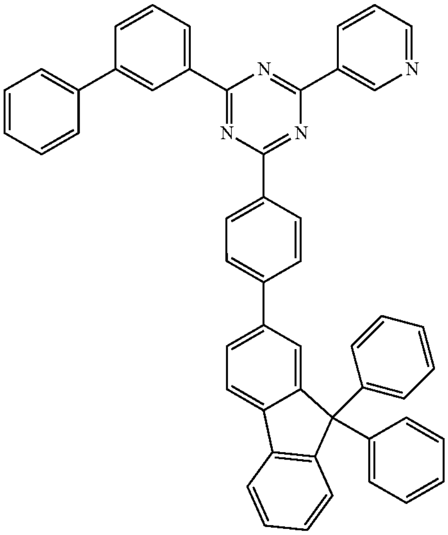
289
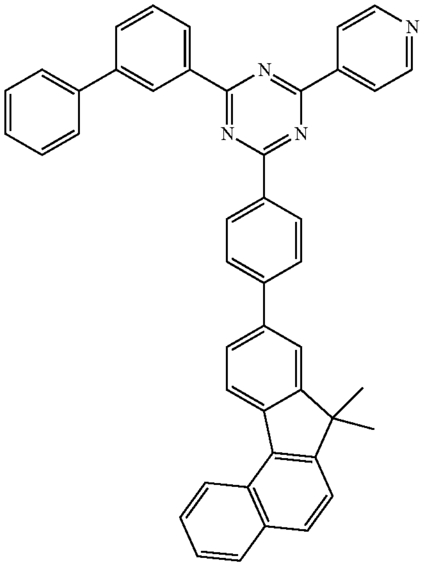

290
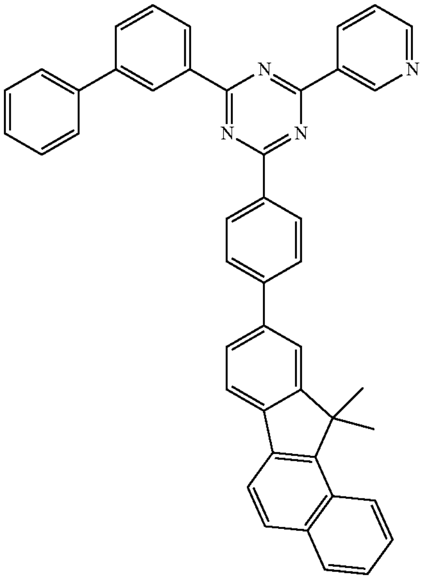
291
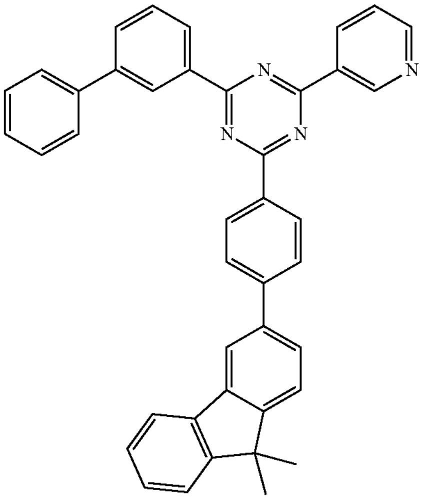
292
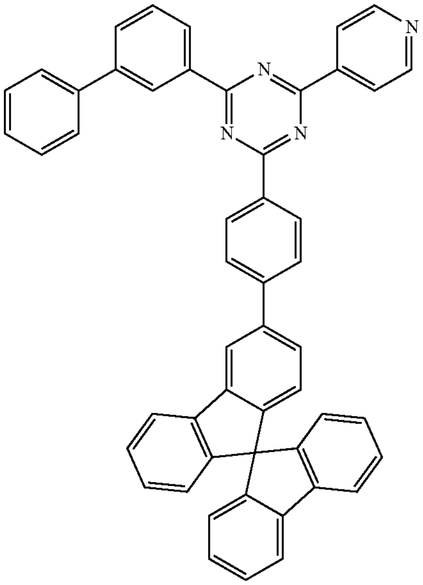
293
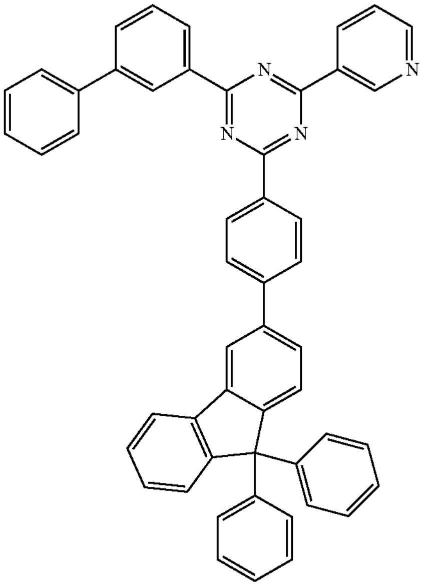
294
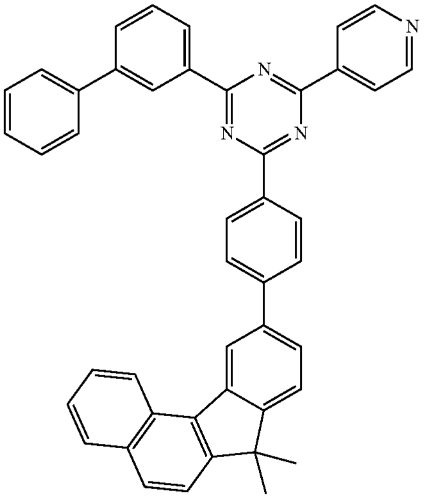

-continued
295
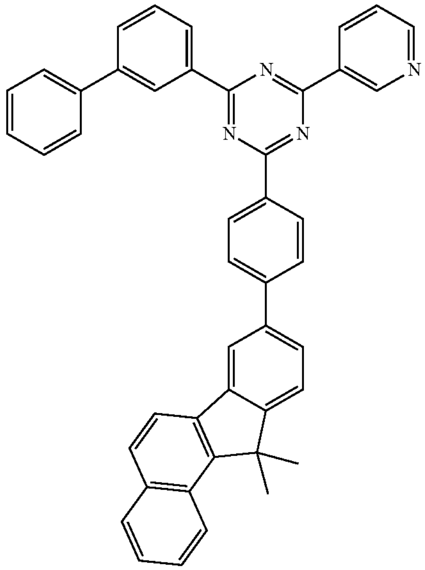
296
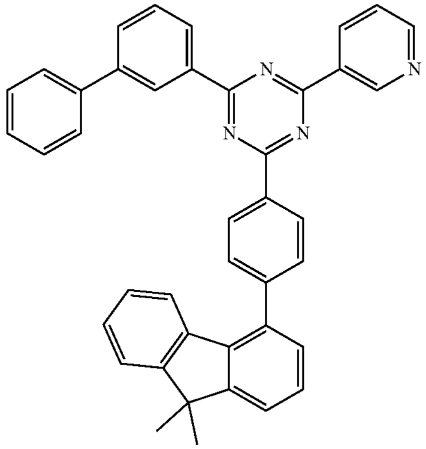
297
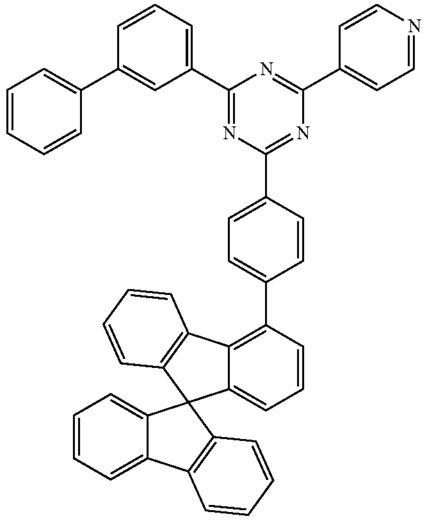
298
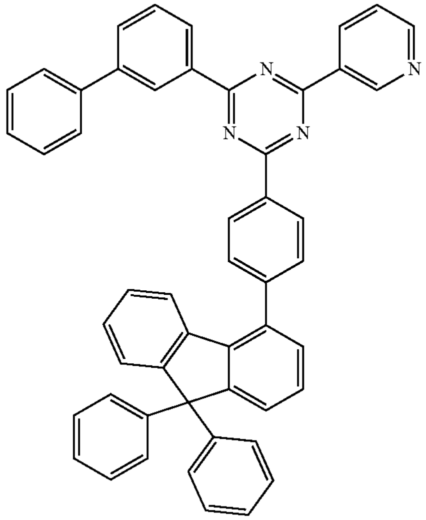
⑦

-continued
299
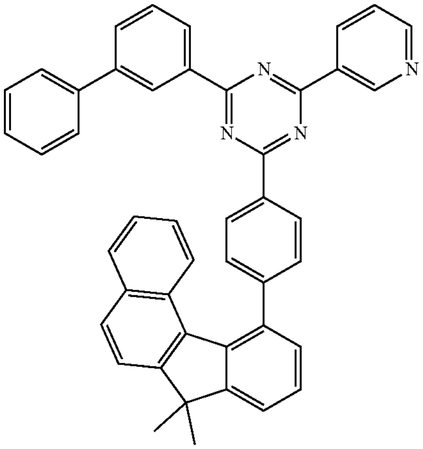
300
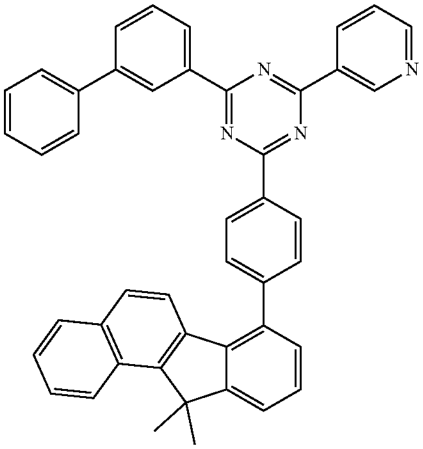
301
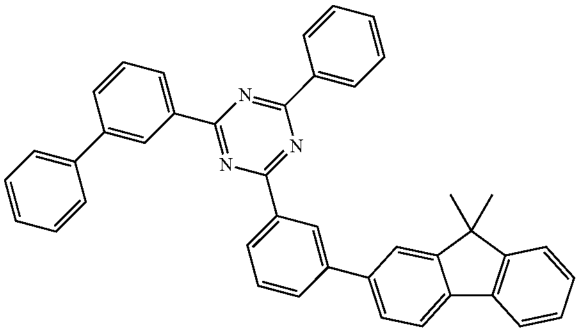
302
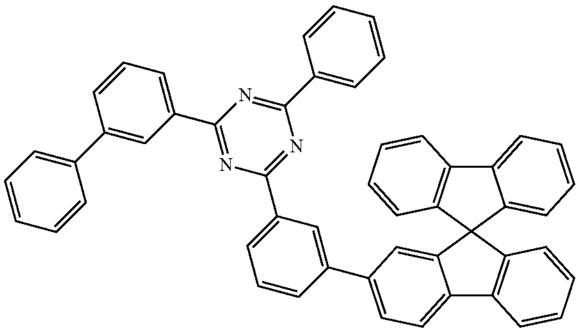
-continued
303
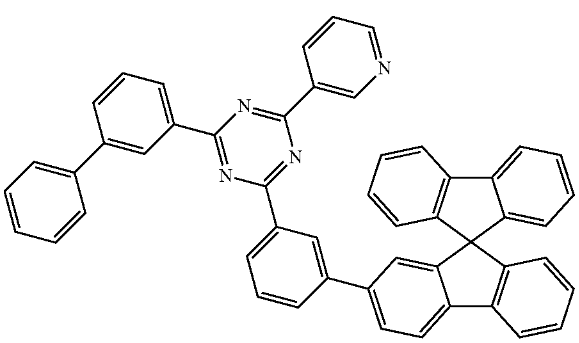
304
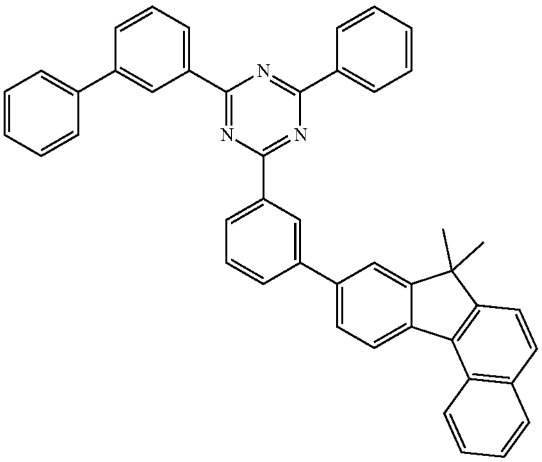
305
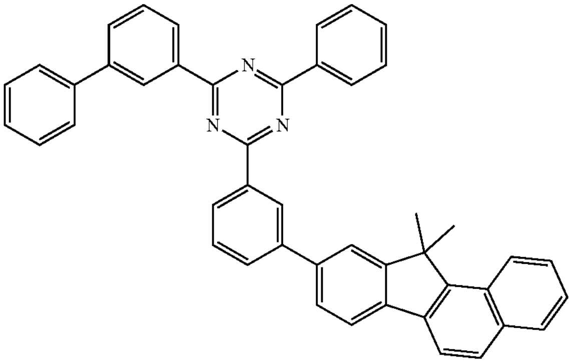

-continued
306
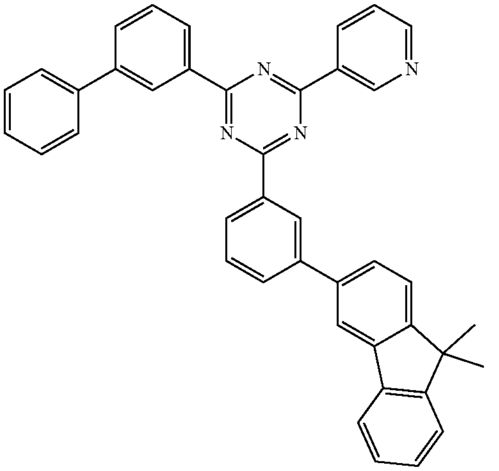
307
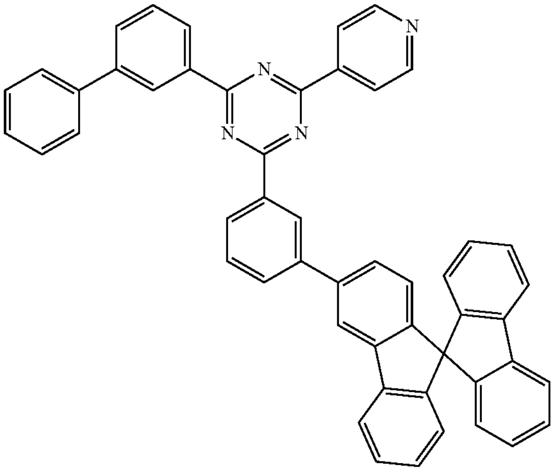
308
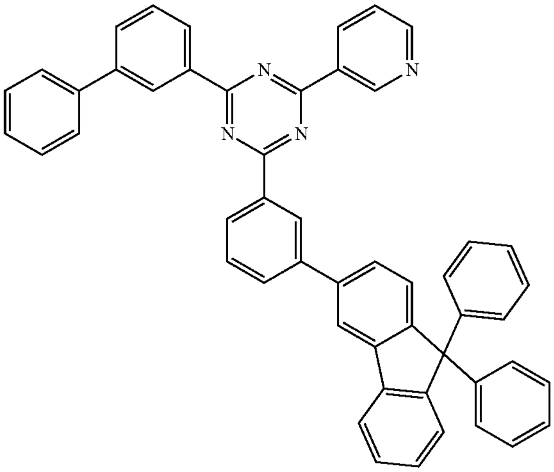
-continued
309
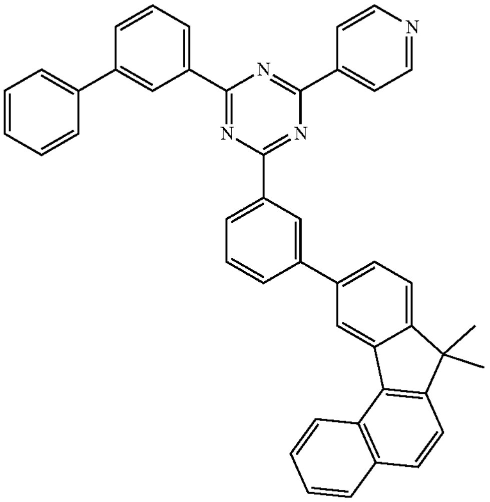
310
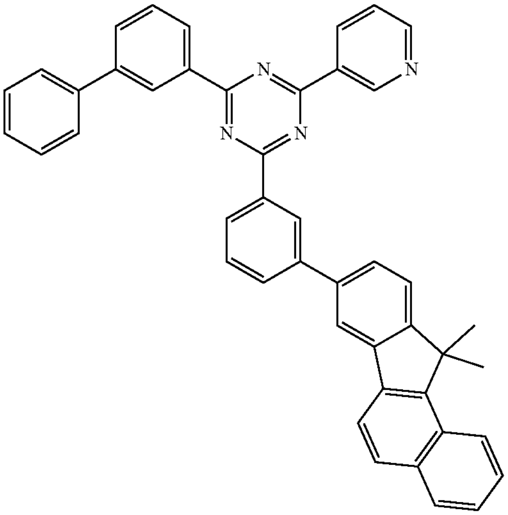
311
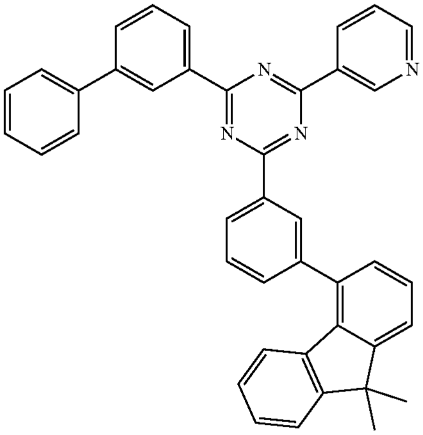

312
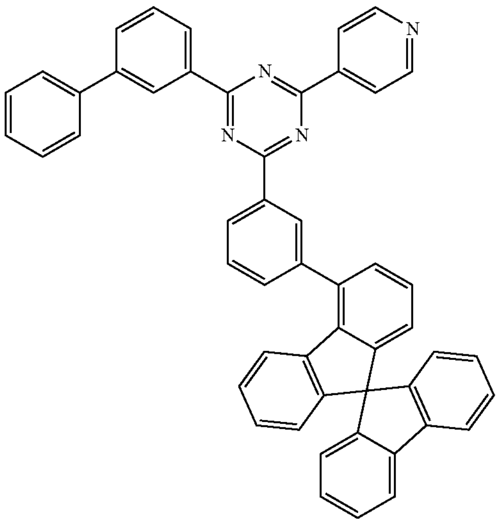
313
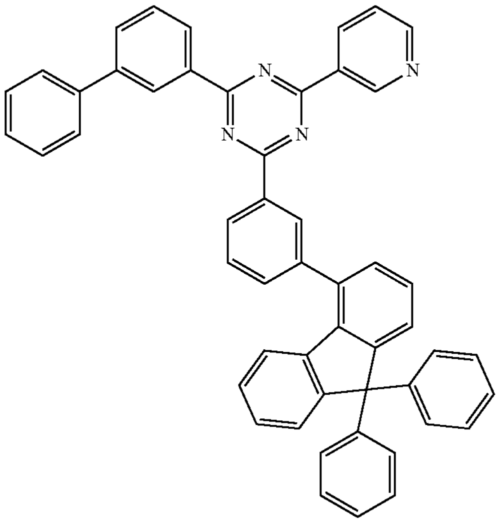
314
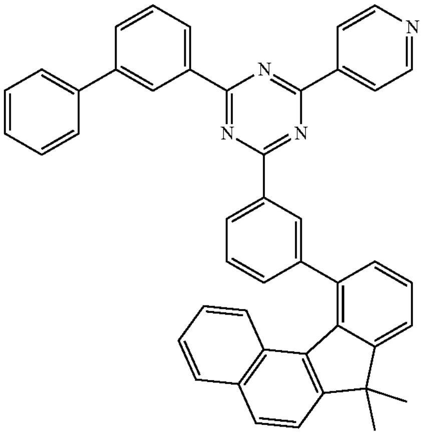
315
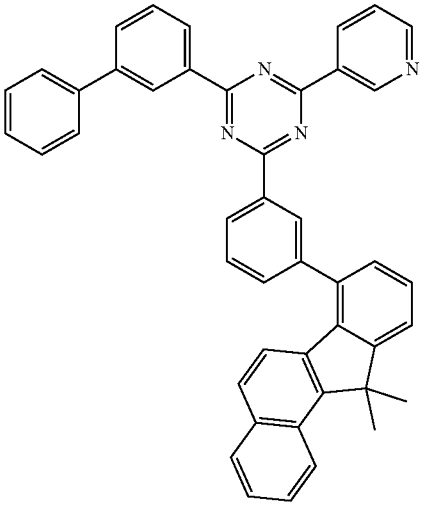
316
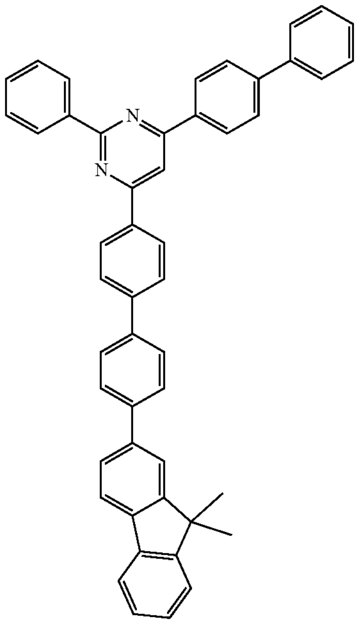

-continued
317
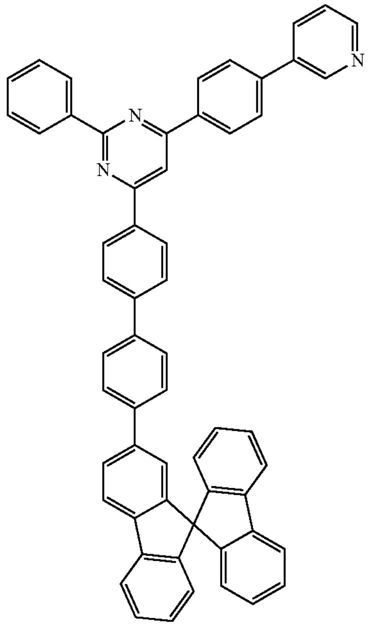
318
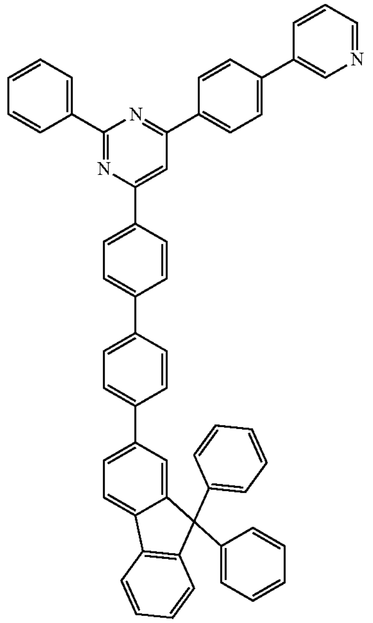
-continued
319
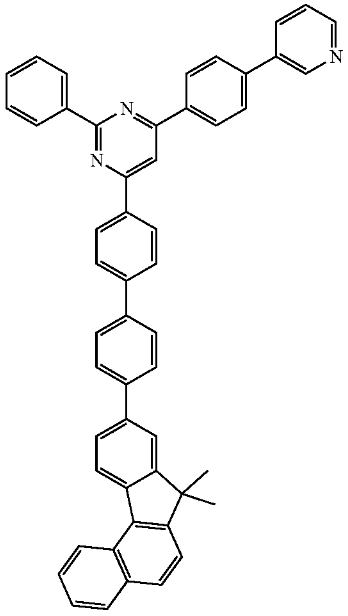
320
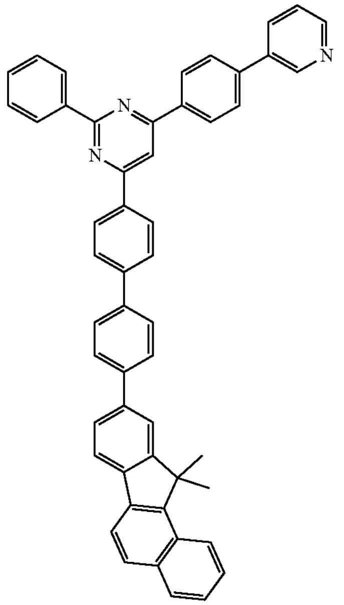

-continued
321
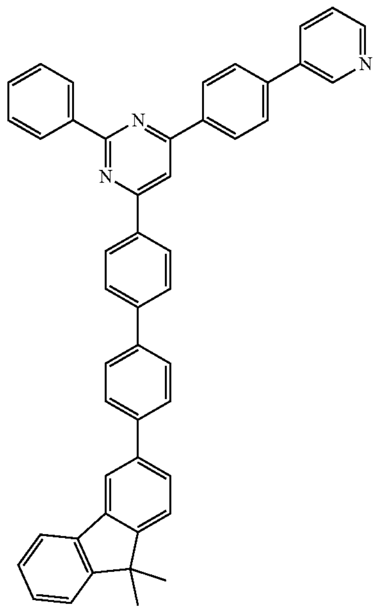
323
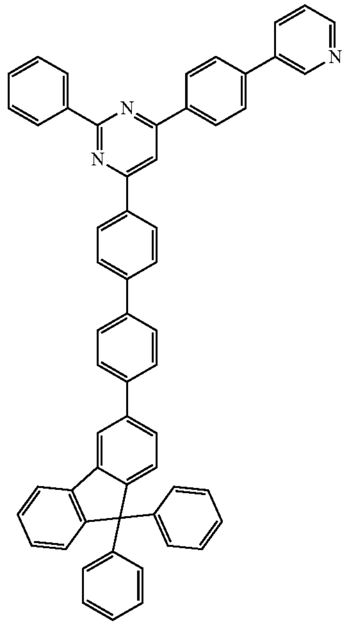
322
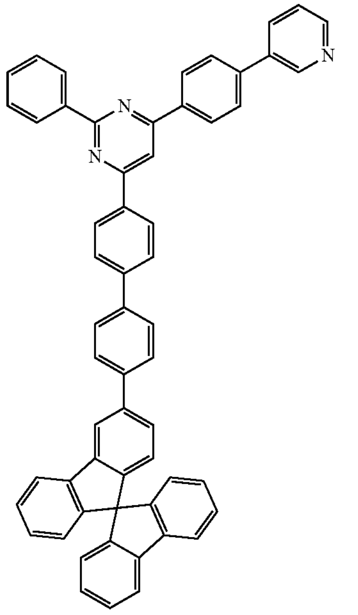
324
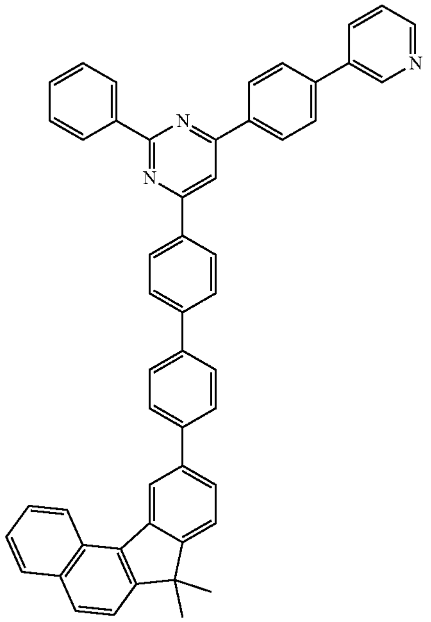

-continued
325
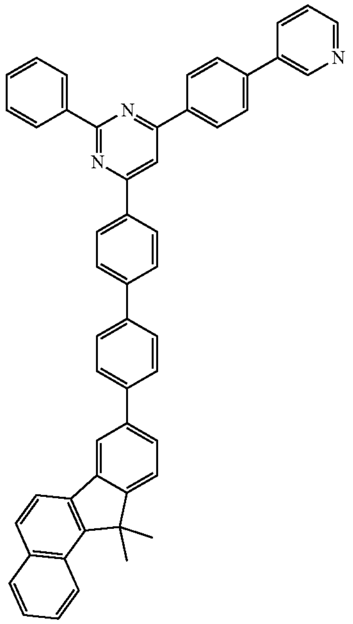
326
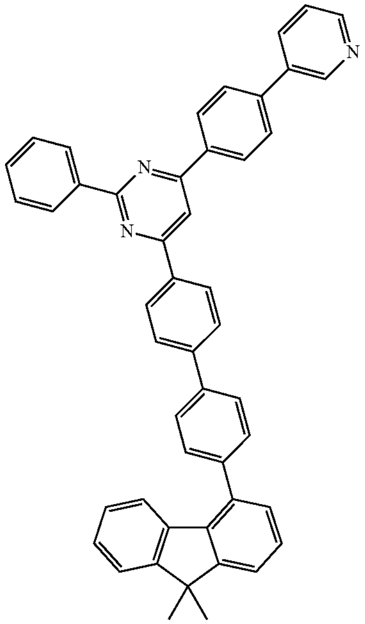
-continued
327
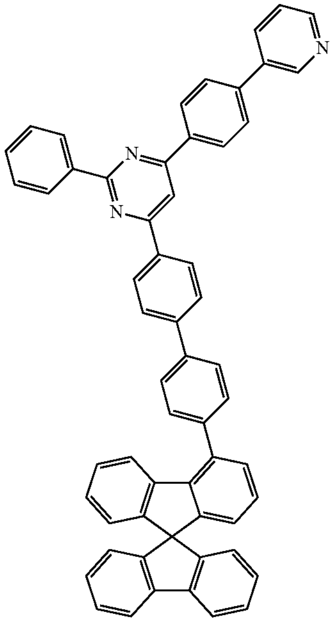
328
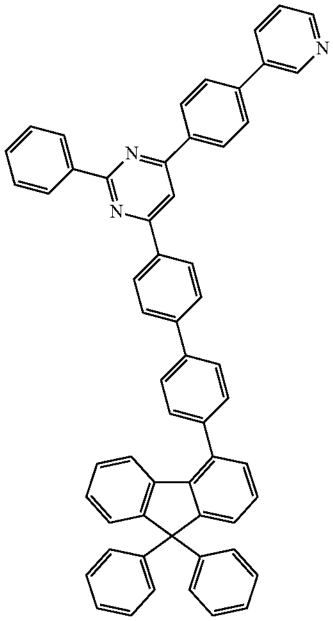

-continued
329
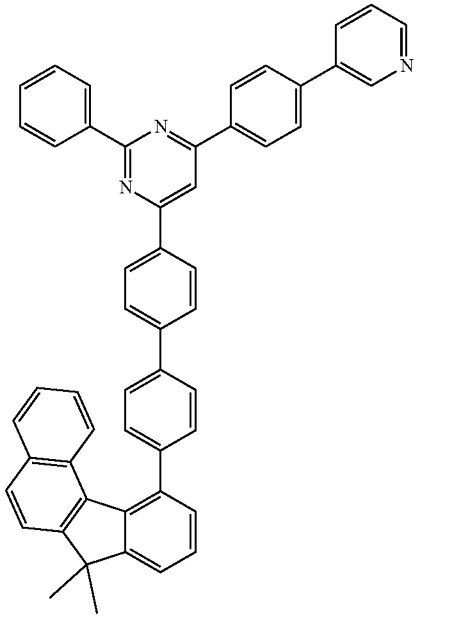
330
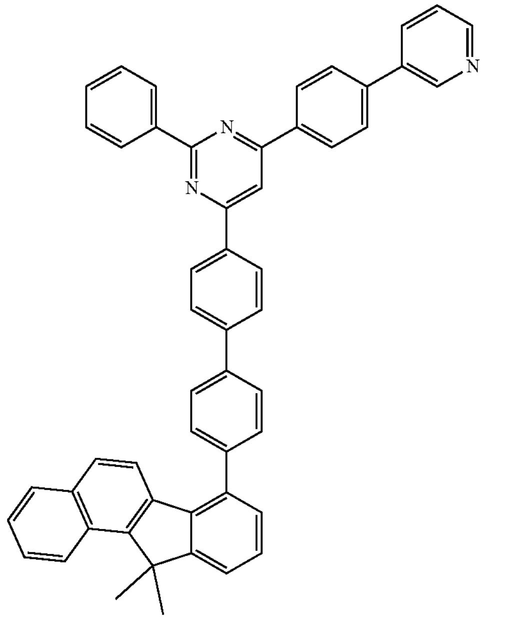
-continued
331
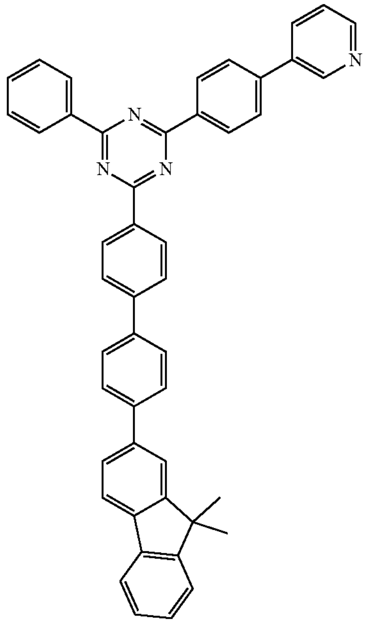
332
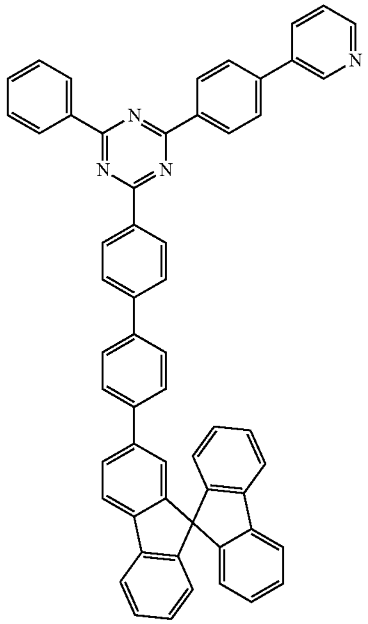

-continued
333
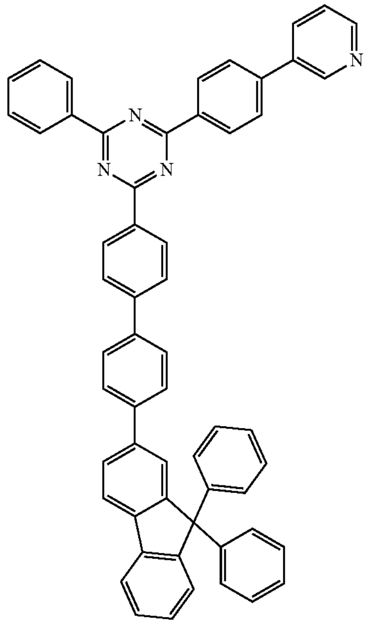
334
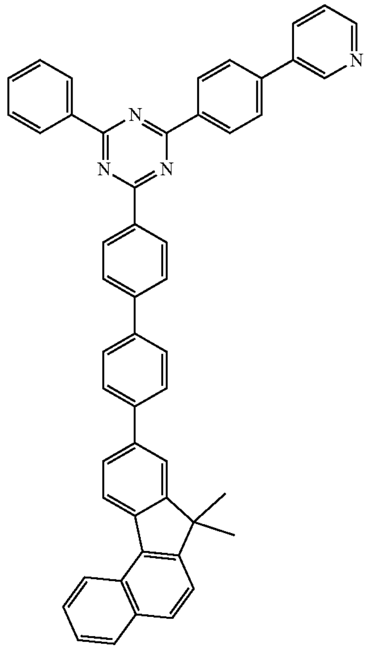
-continued
335
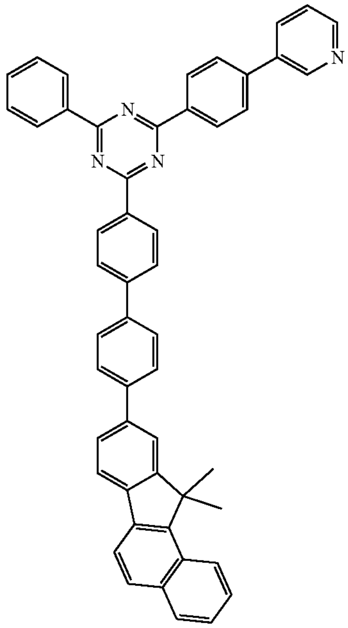
336
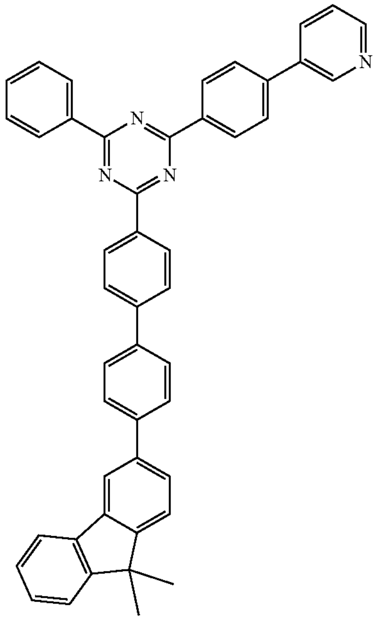

-continued
337
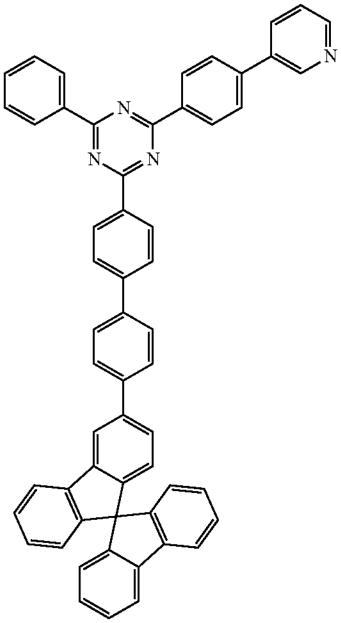
338
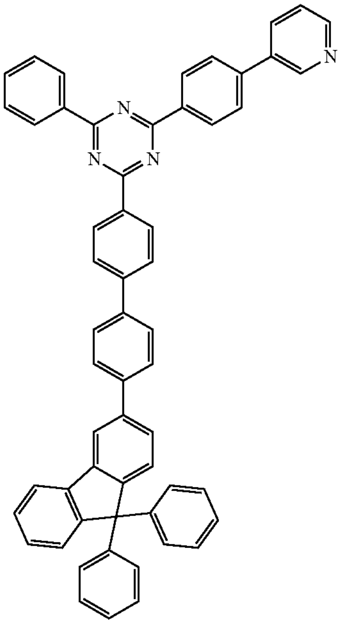
-continued
339
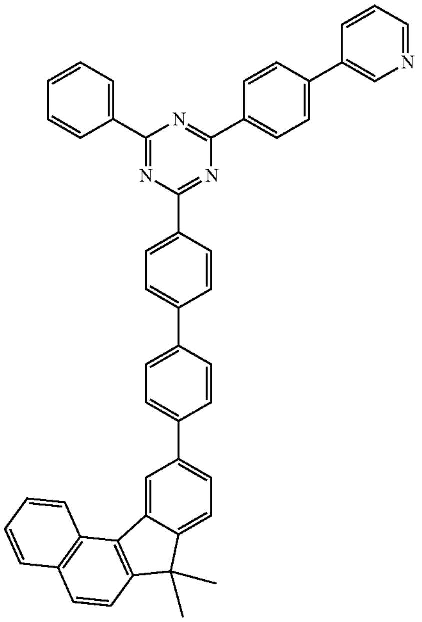
340
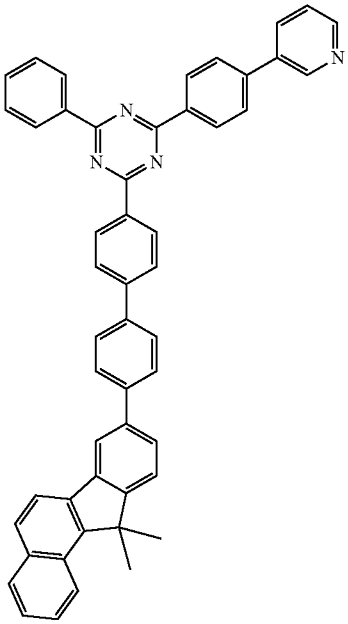

-continued
341
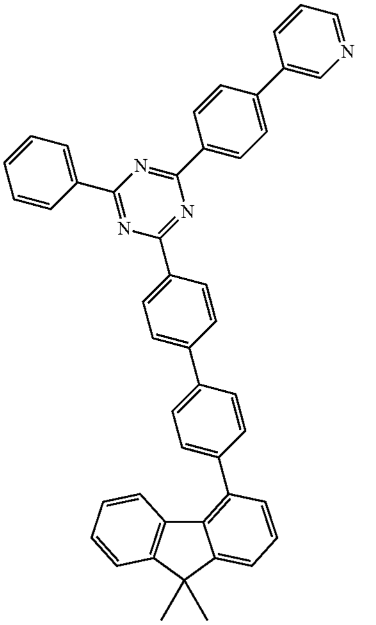
342
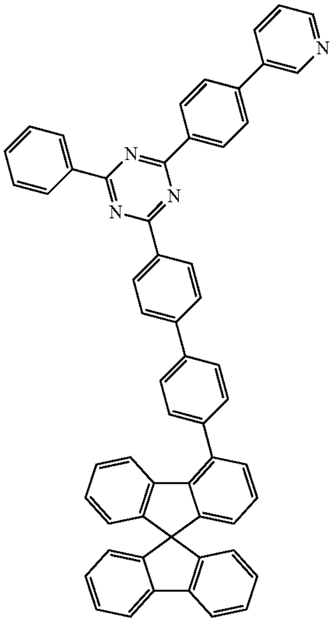
-continued
343
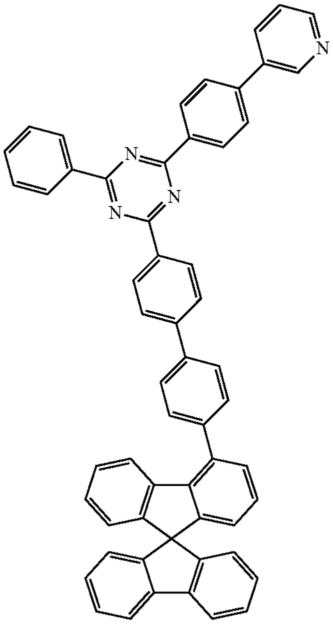
344
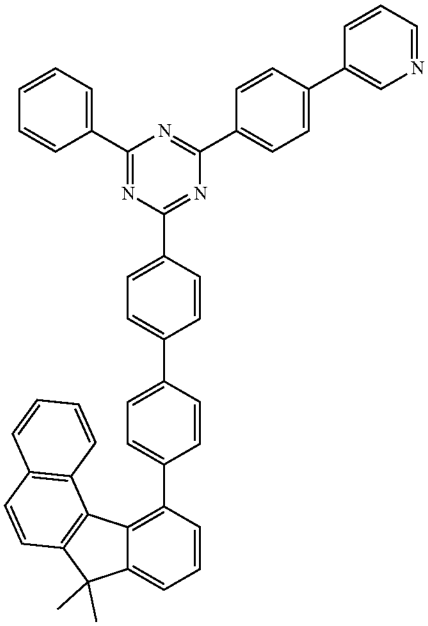

-continued
345
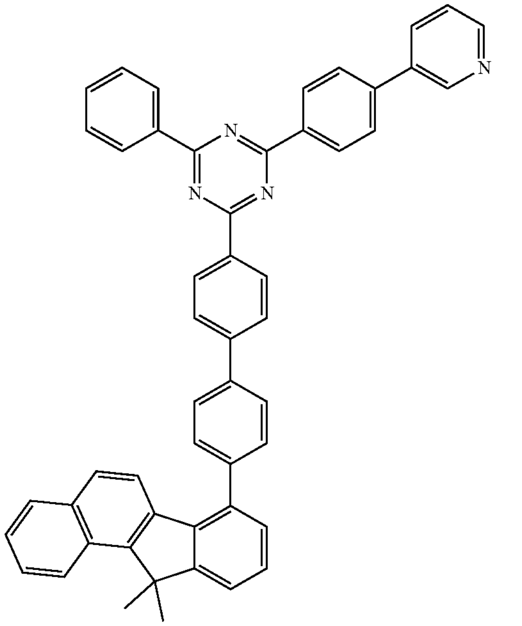
-continued
347
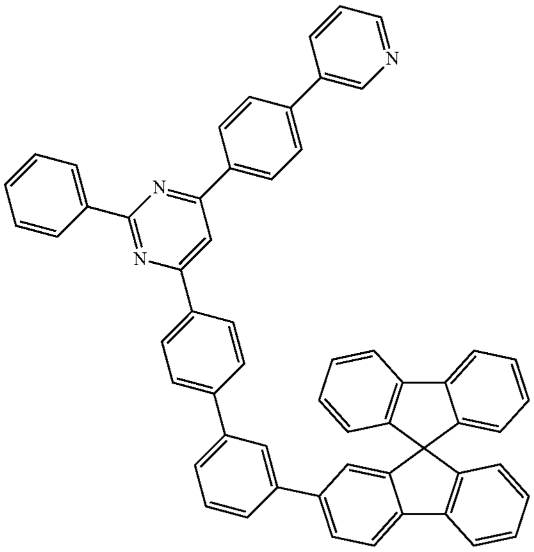
346
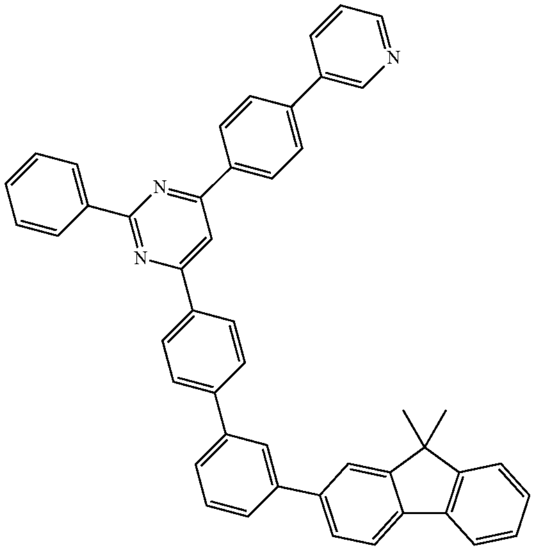
348
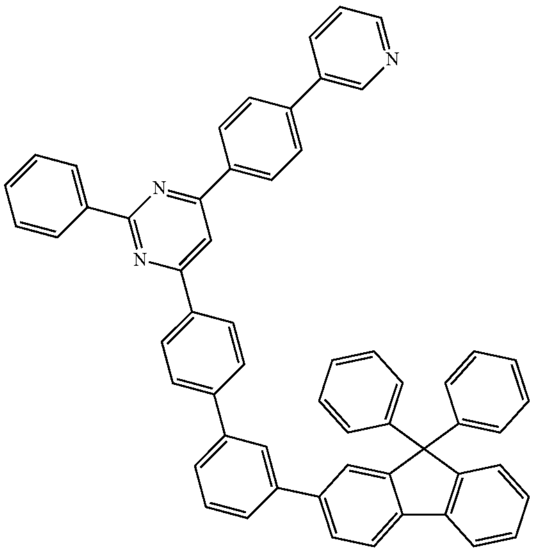

-continued
349
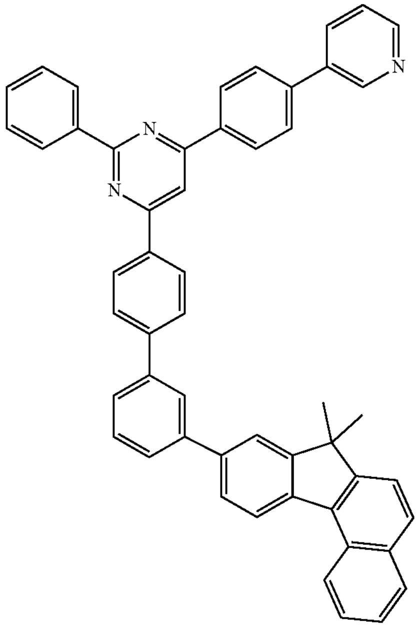
350
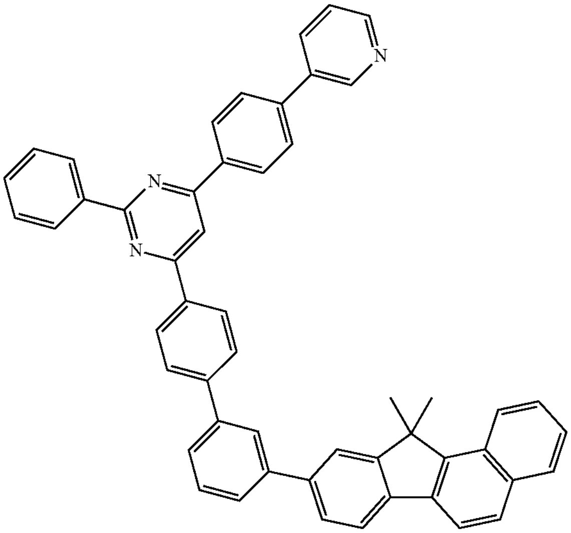
-continued
351
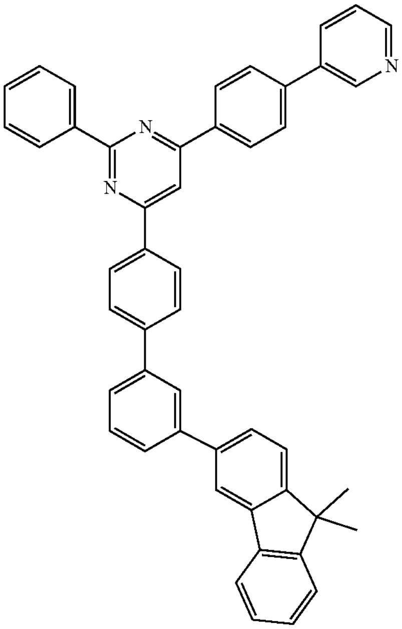
352
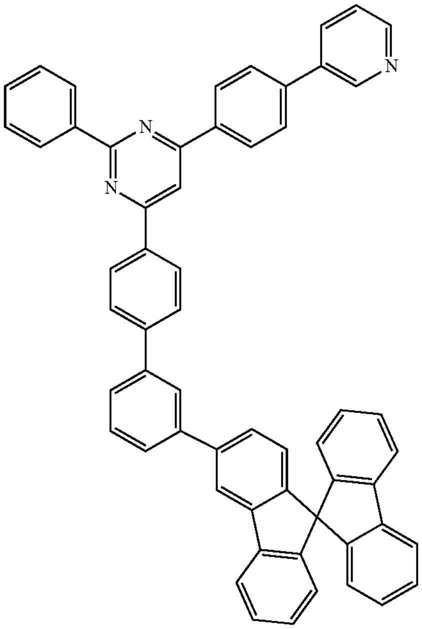

-continued
353
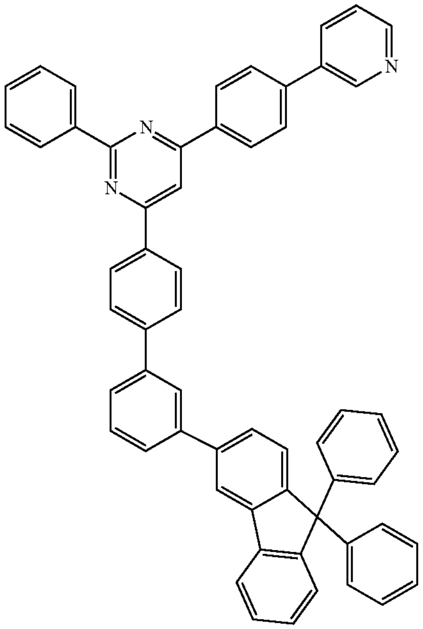
354
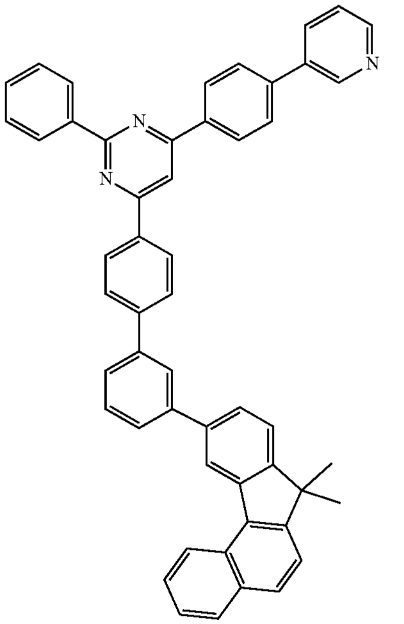
-continued
355
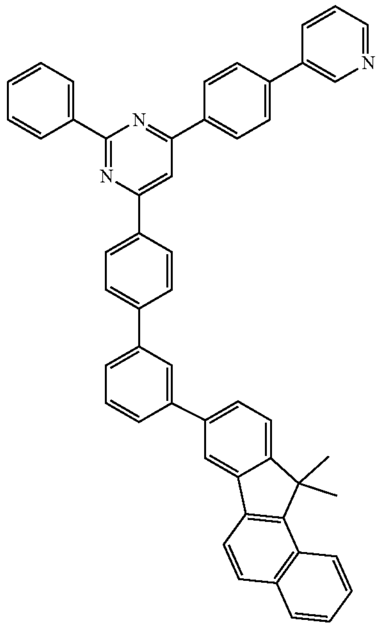
356
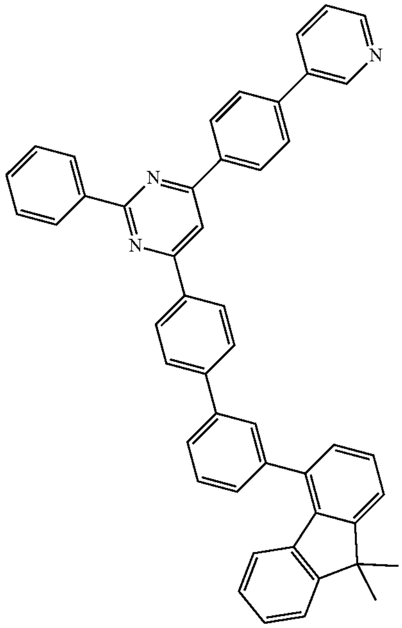

-continued
357
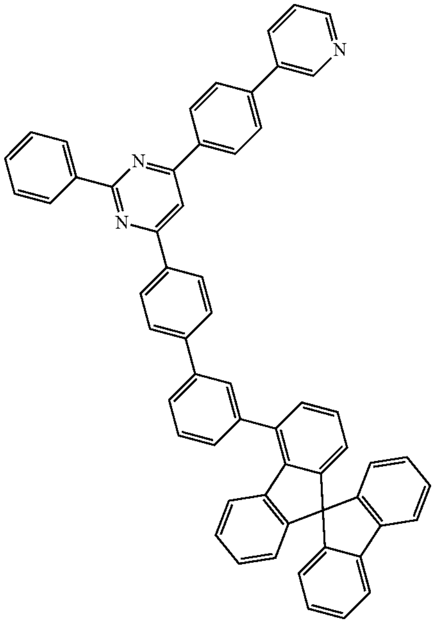
358
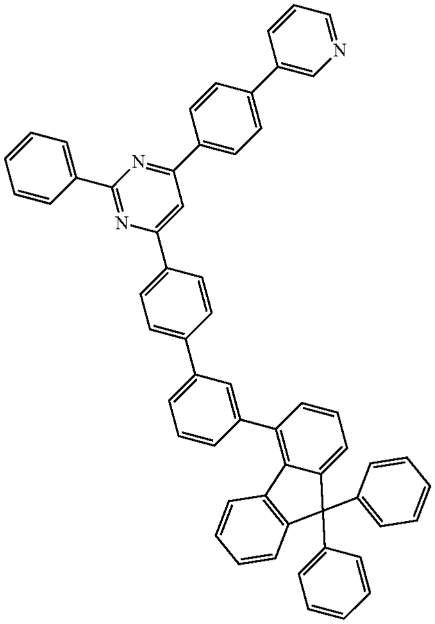
-continued
359
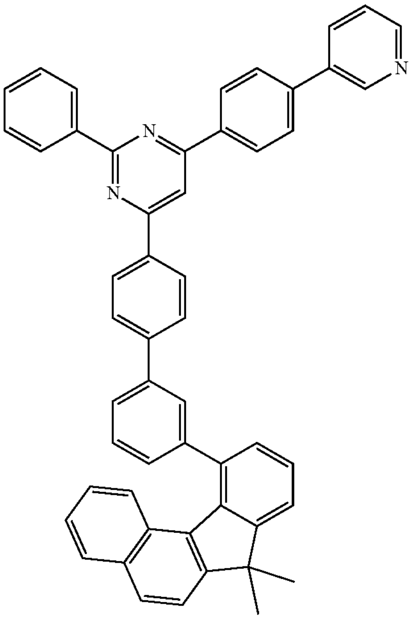
360
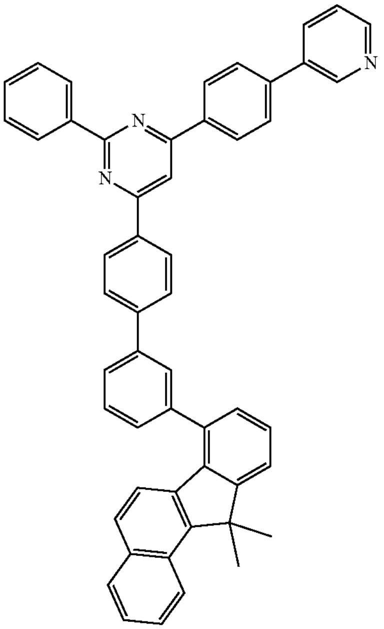

-continued
361
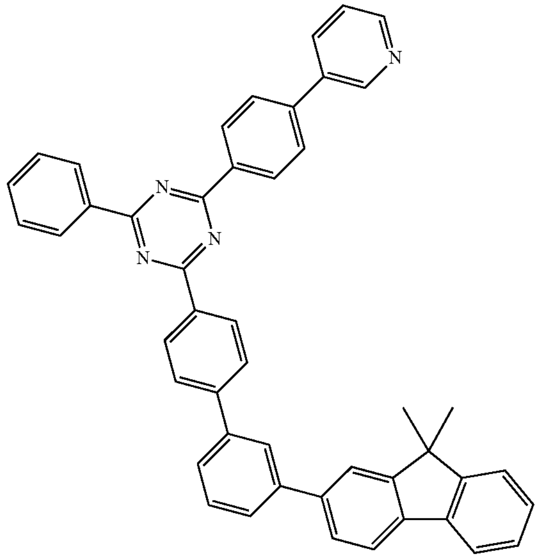
362
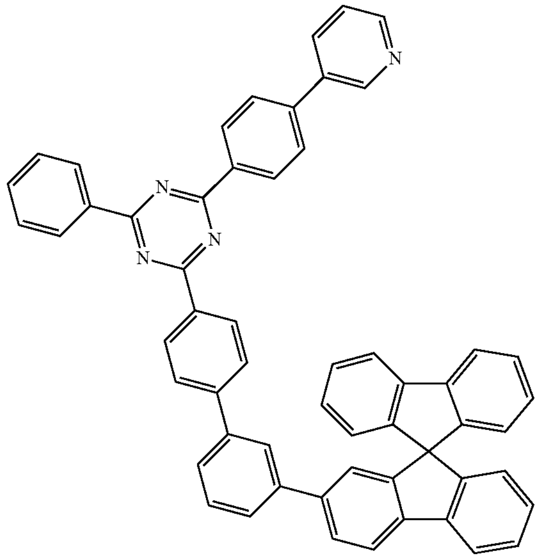
-continued
363
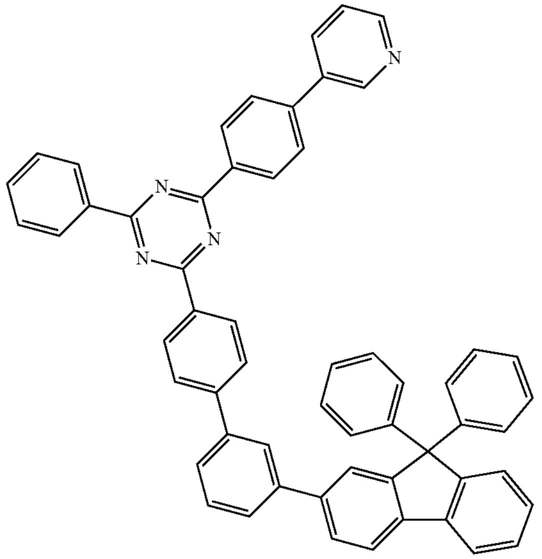
364
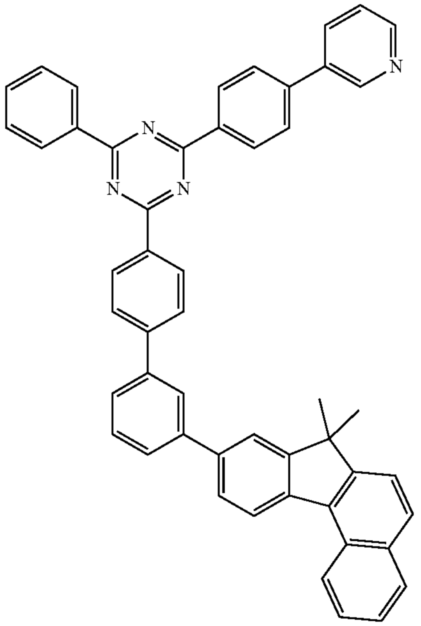

-continued
365
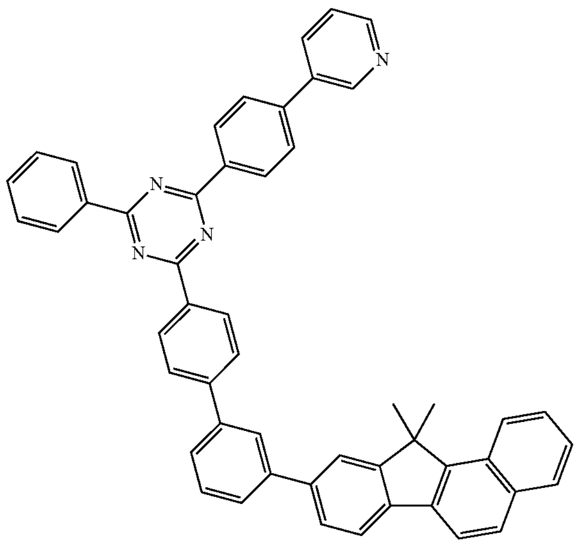
366
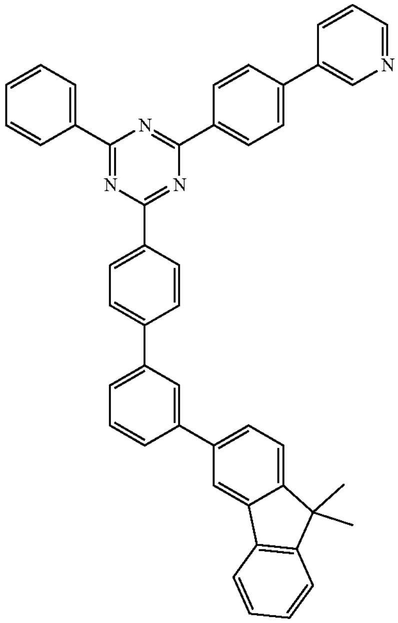
-continued
367
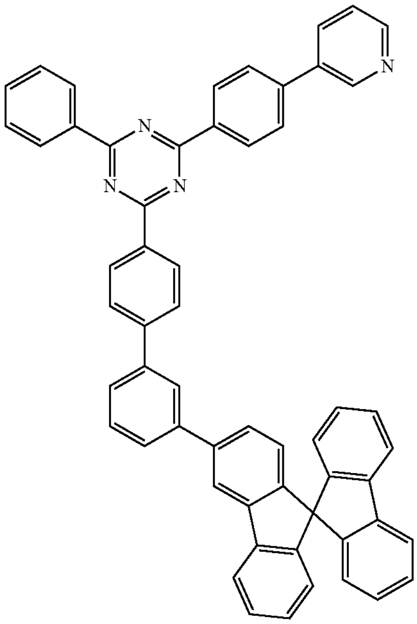
368
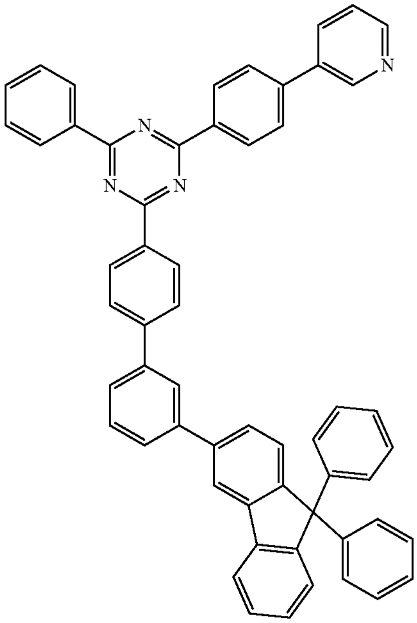

369
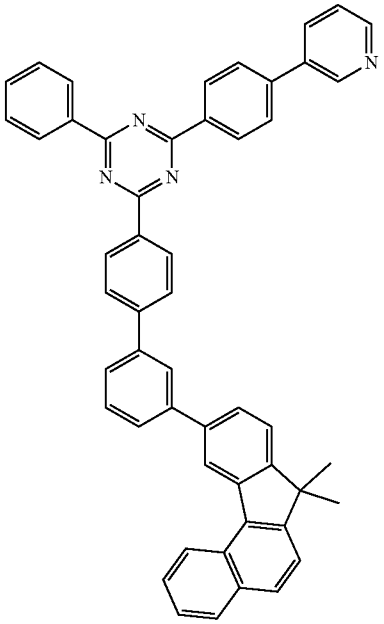
370
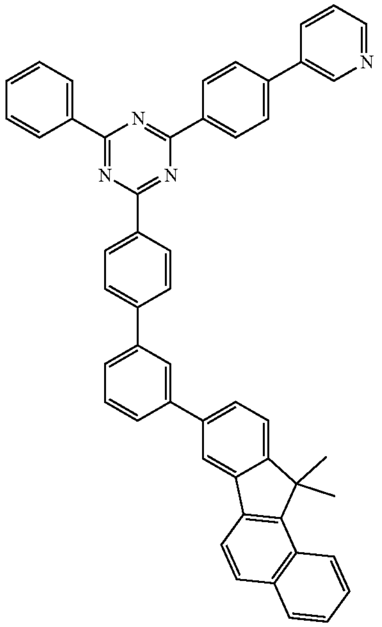
371
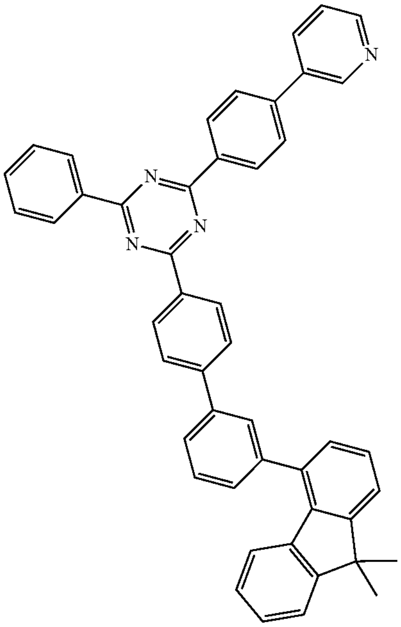
372
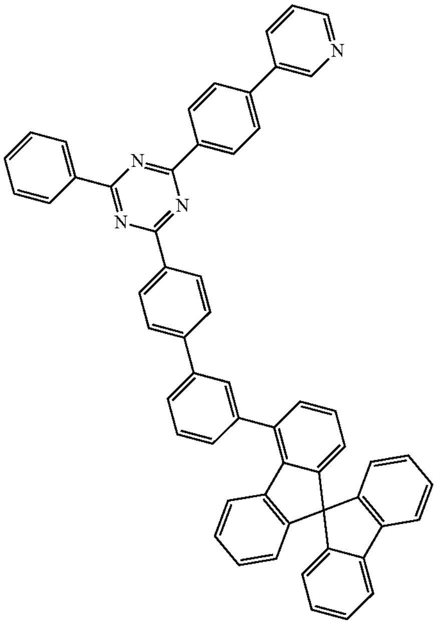

-continued
373
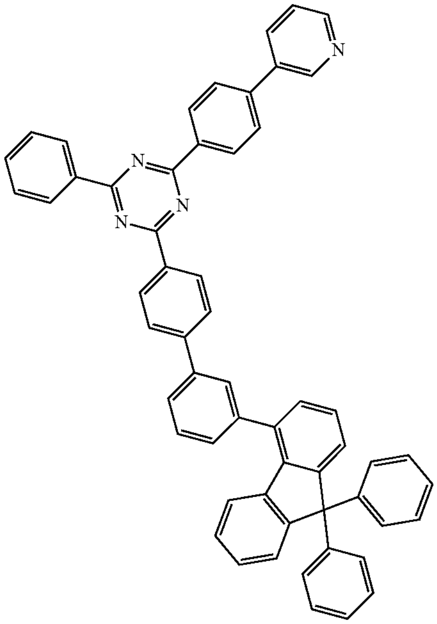
374
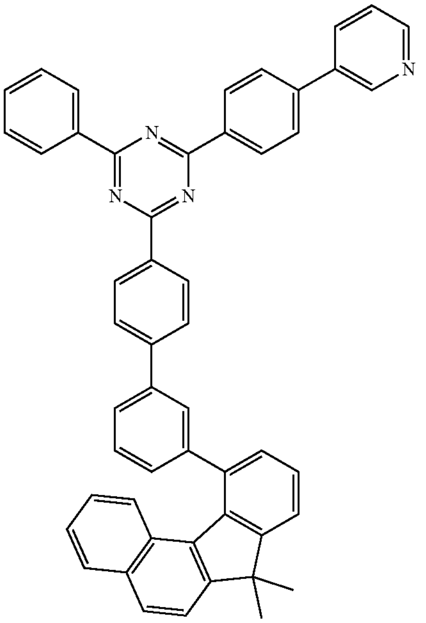
-continued
375
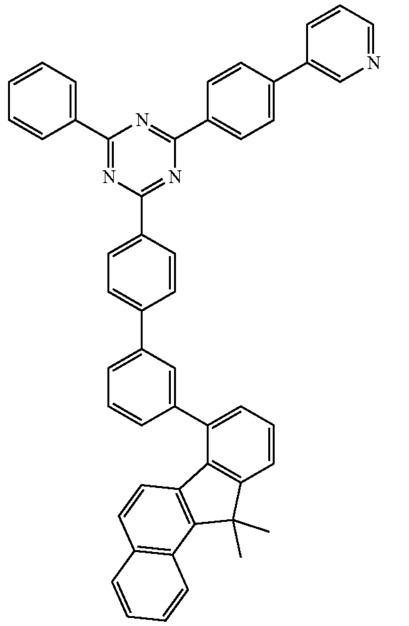
376
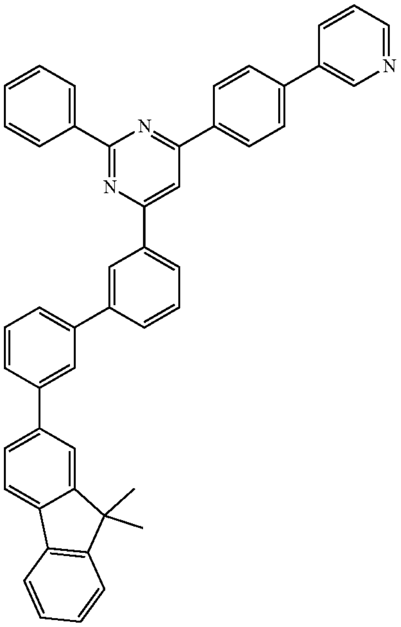

-continued
377
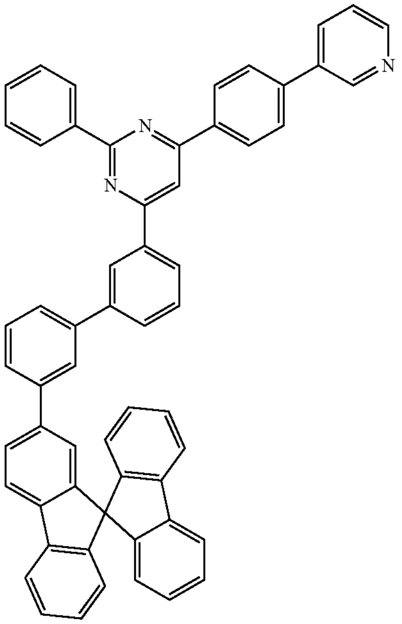
378
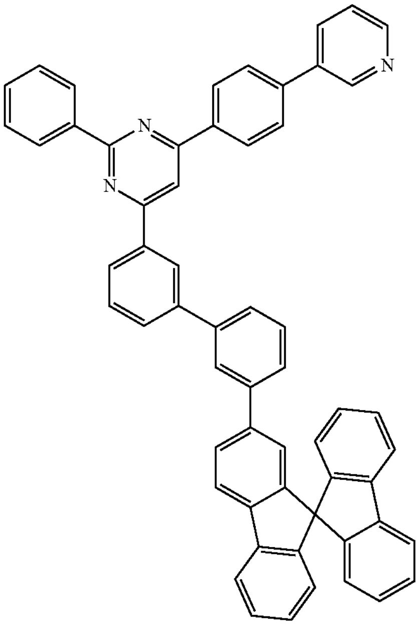
-continued
379
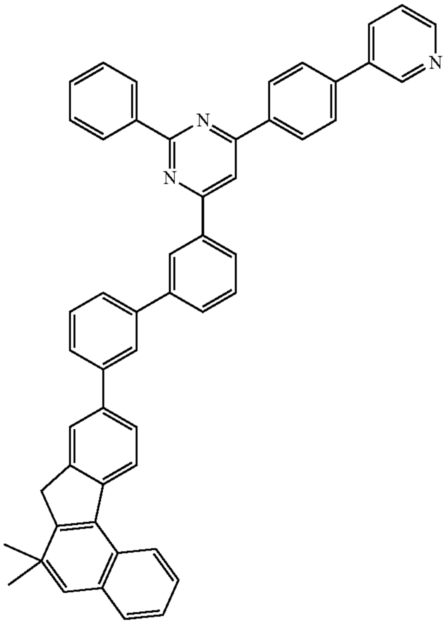
380
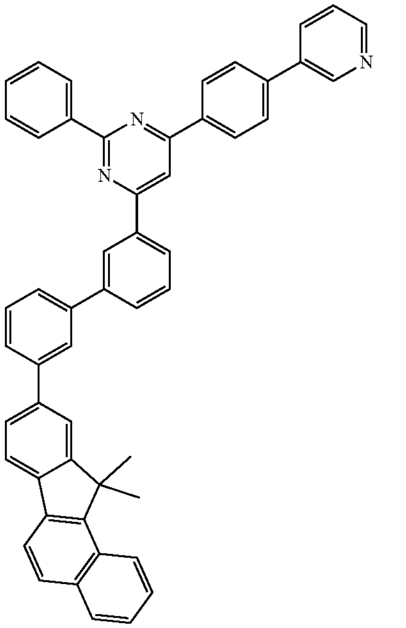

-continued
381
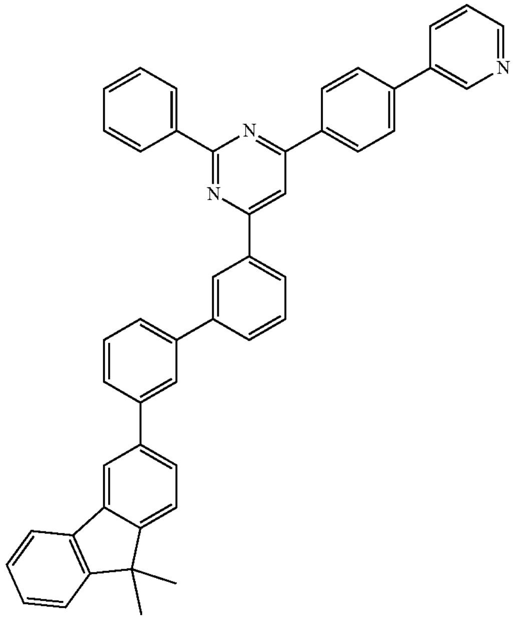
382
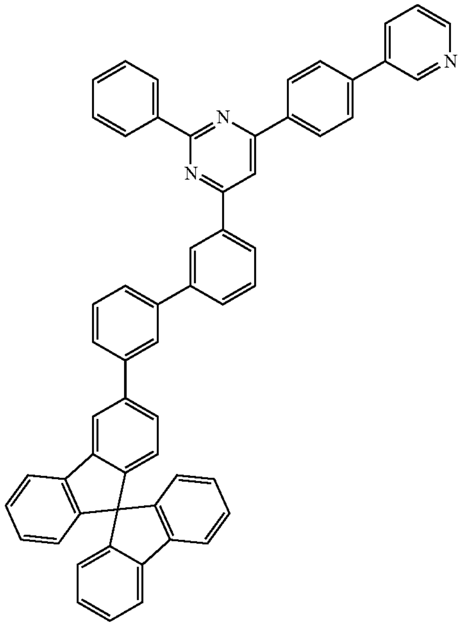
-continued
383
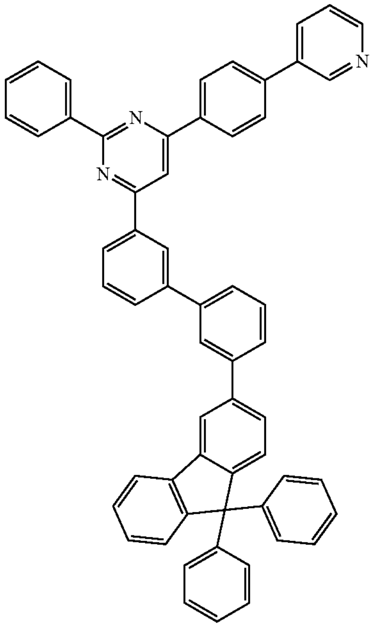
384
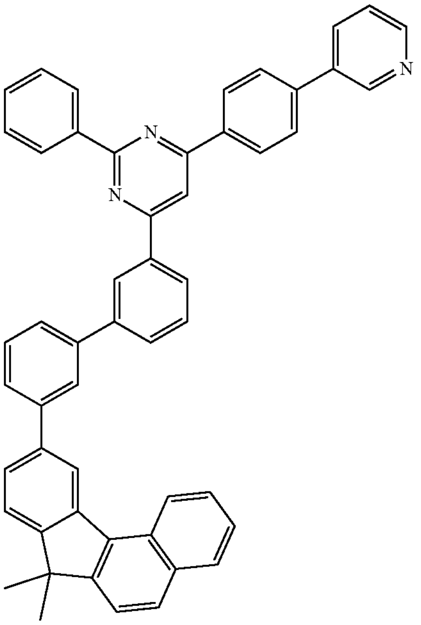

-continued
385
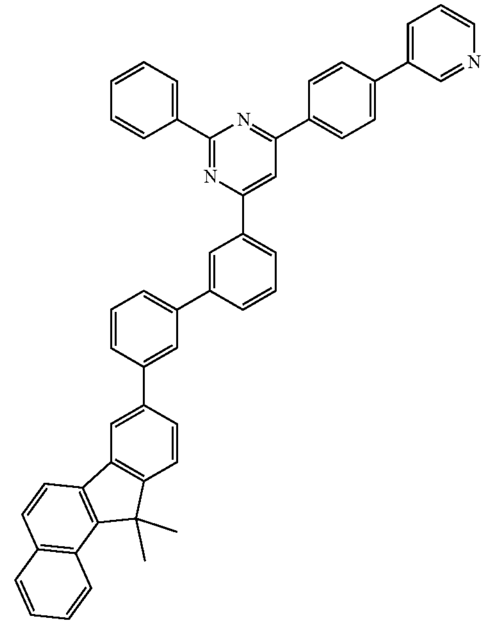
386
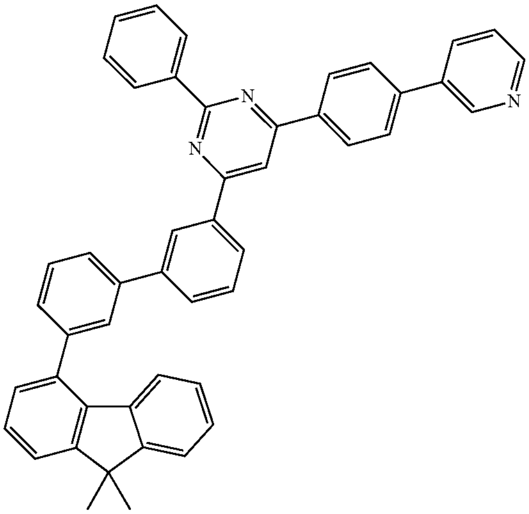
-continued
387
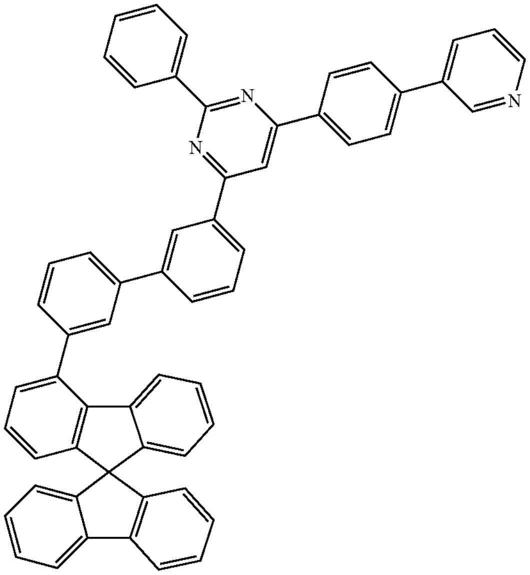
388
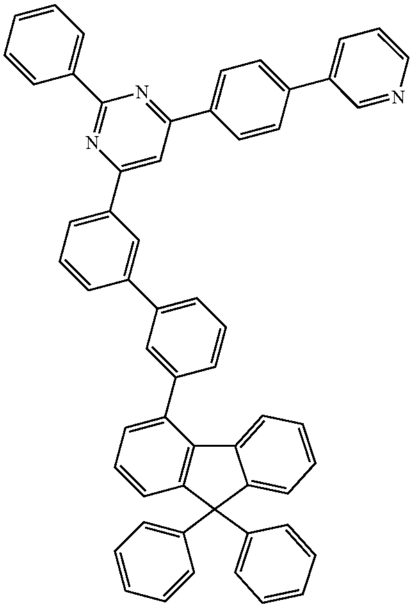

-continued
389
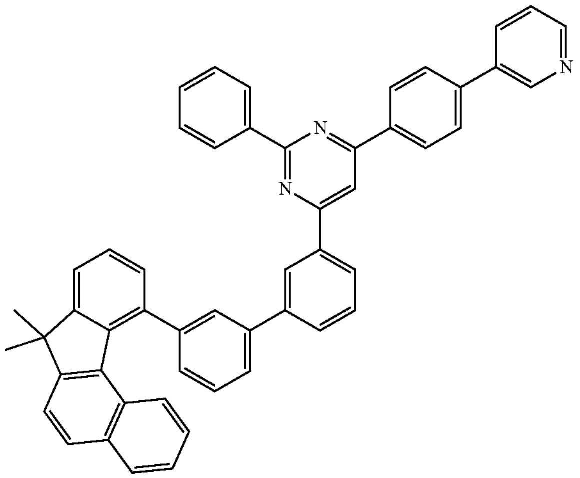
390
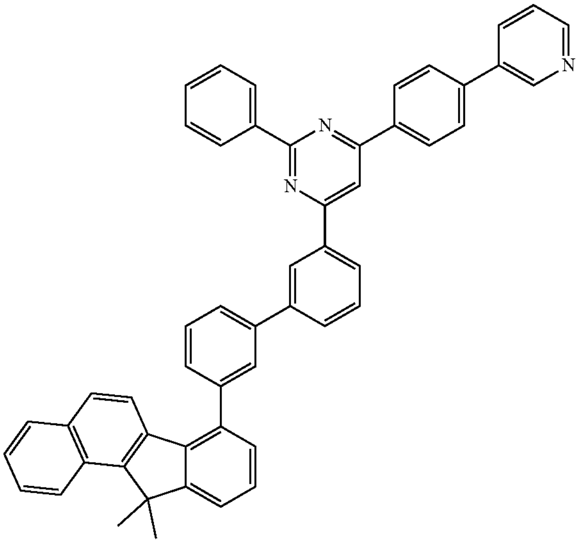
391
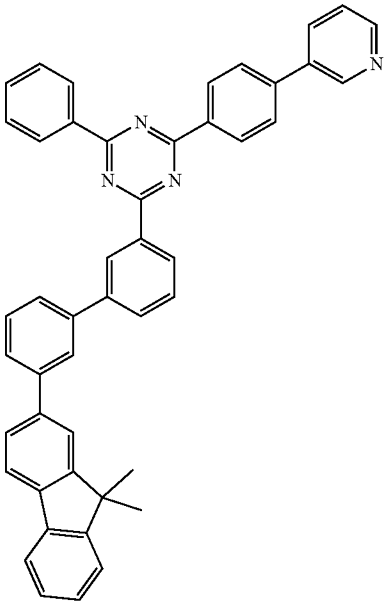
-continued
392
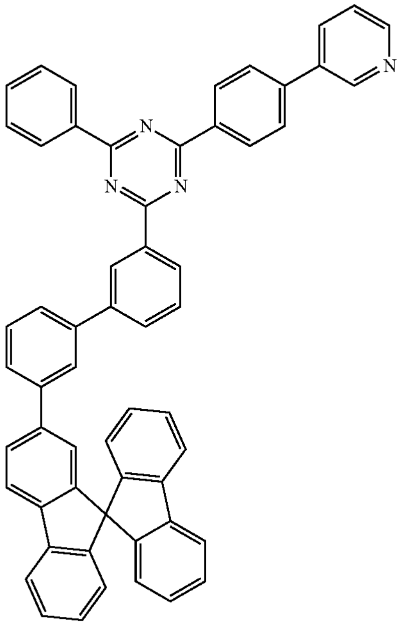
393
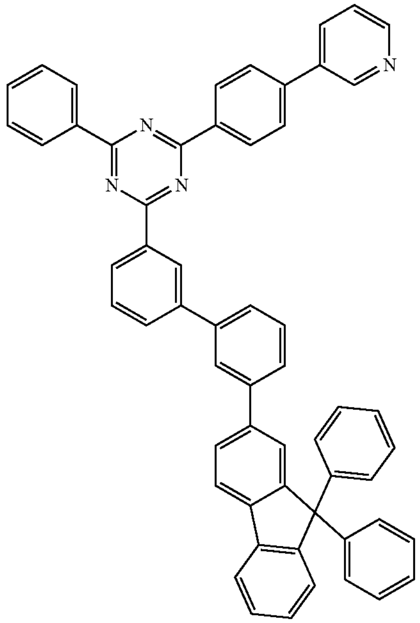

-continued
394
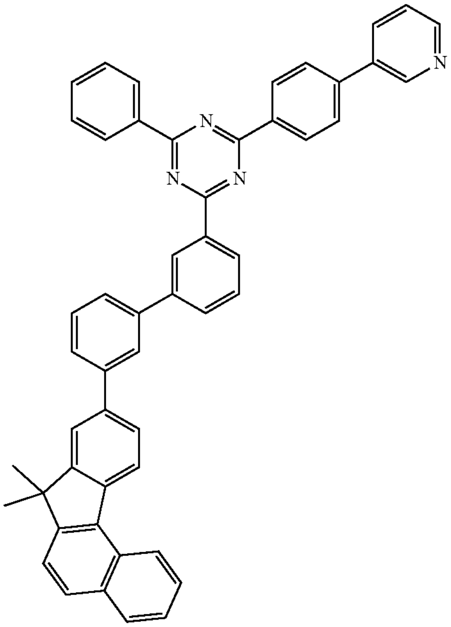
395
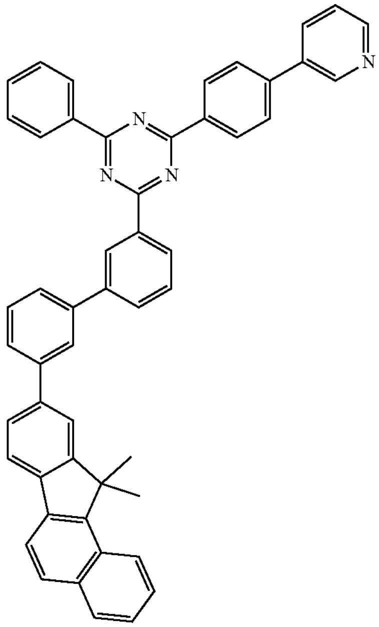
-continued
396
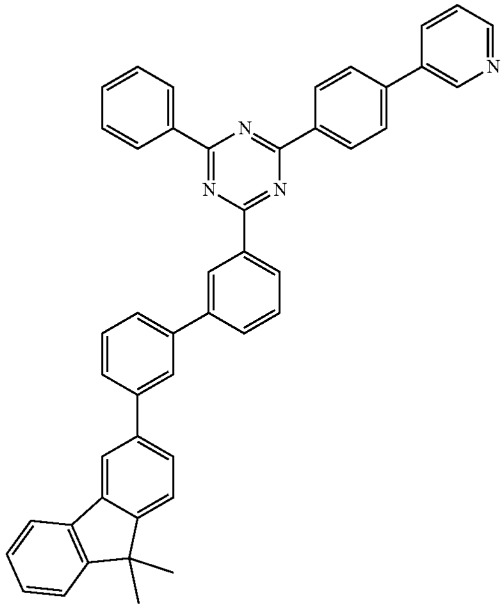
397
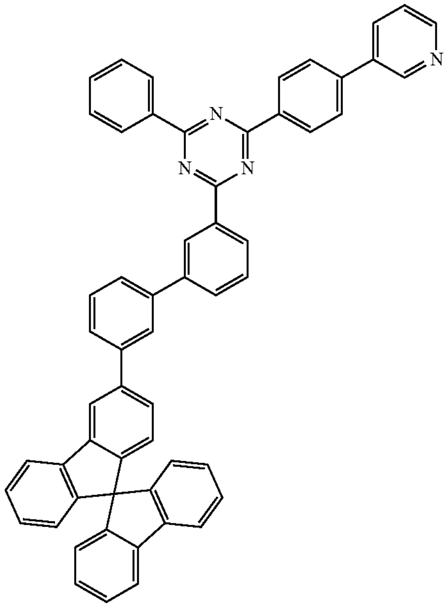

-continued
398
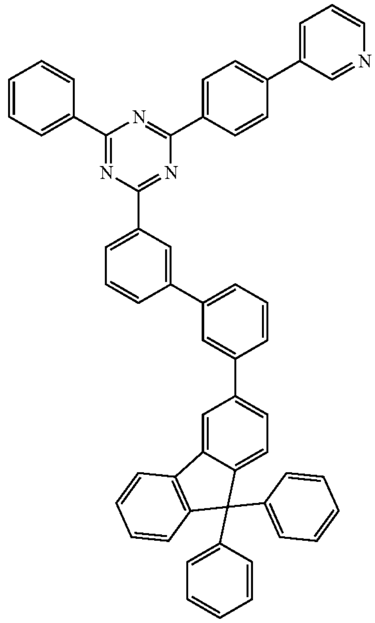
399
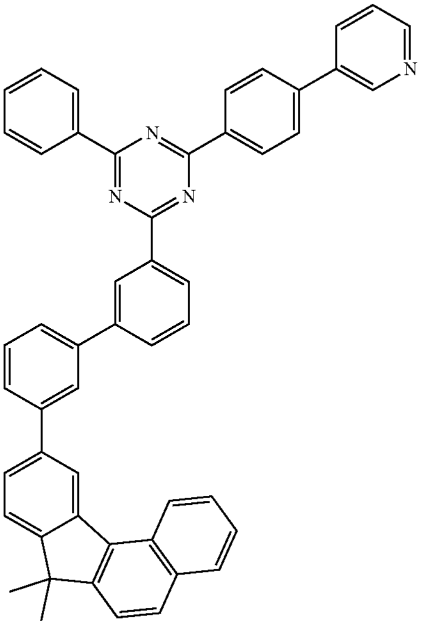
-continued
400
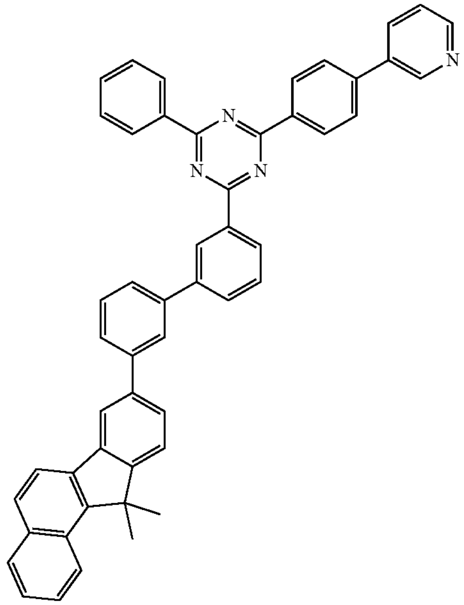
401
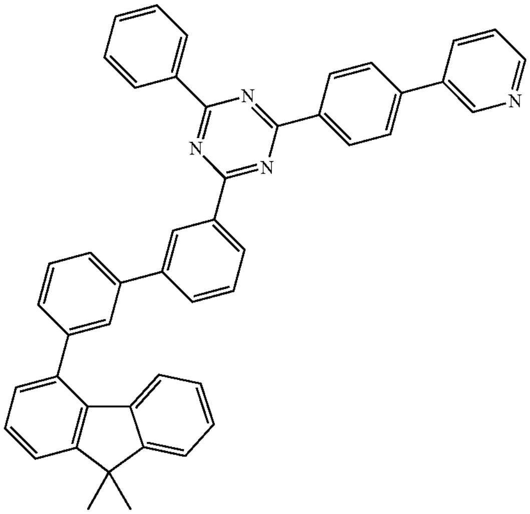

-continued
402
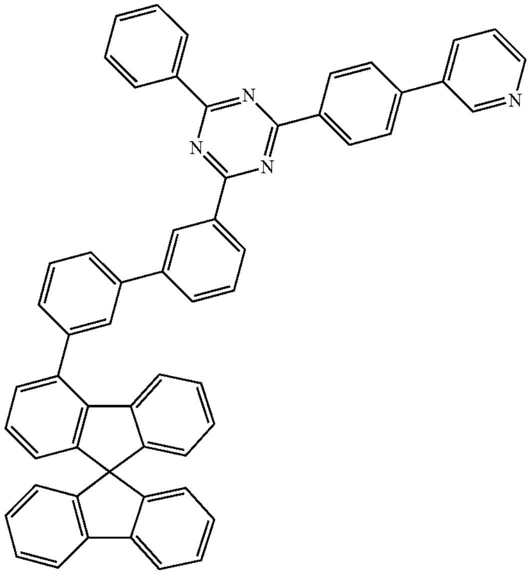
403
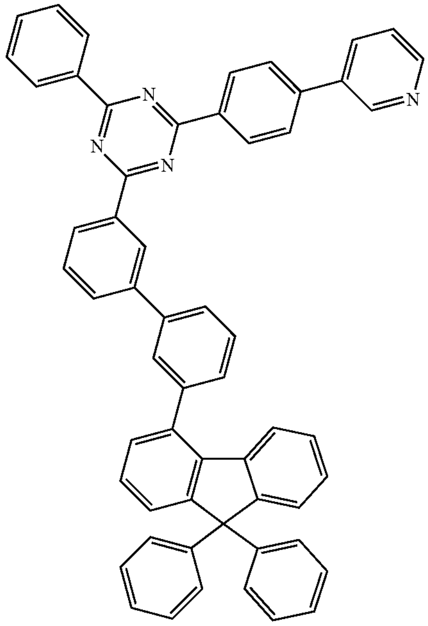
-continued
404
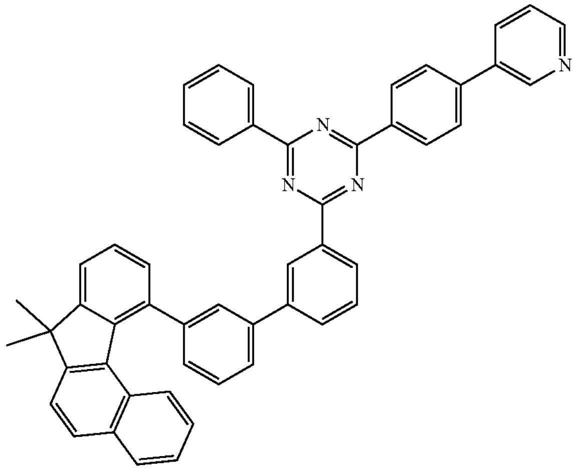
405
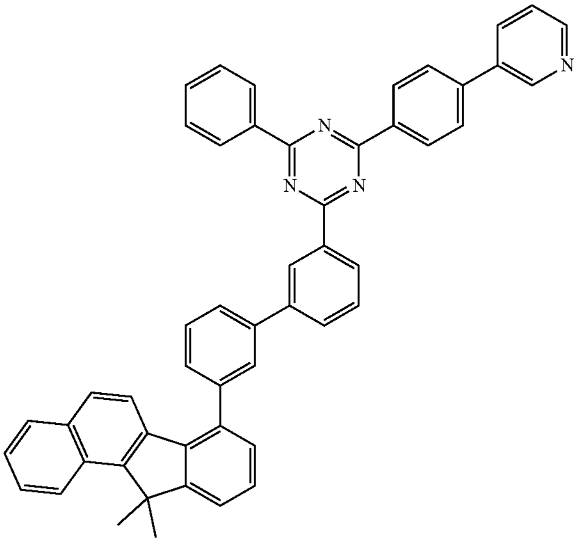

-continued
406
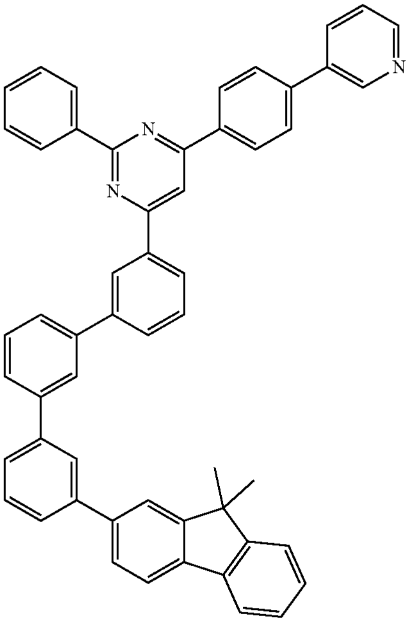
407
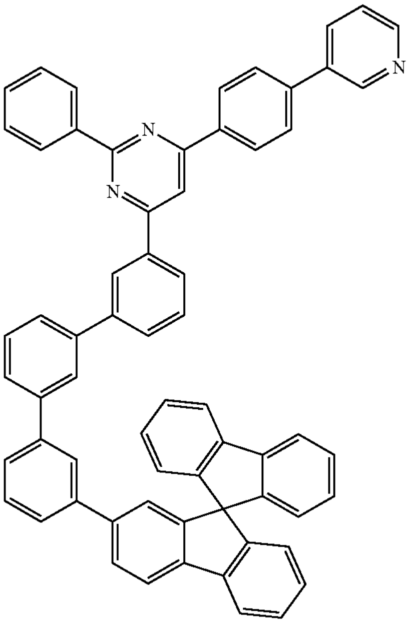
-continued
408
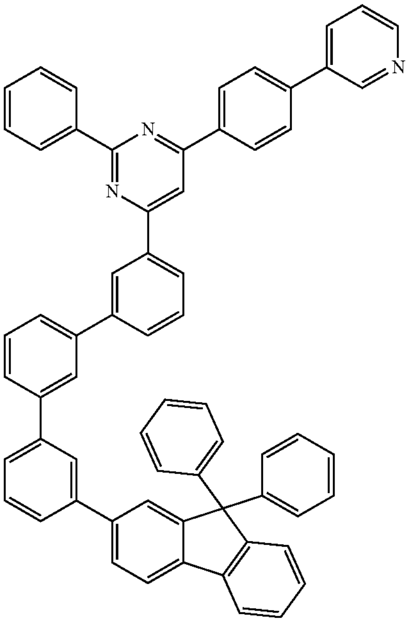
409
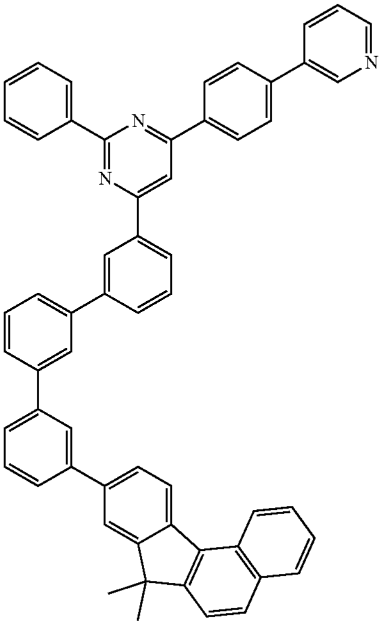

-continued
410
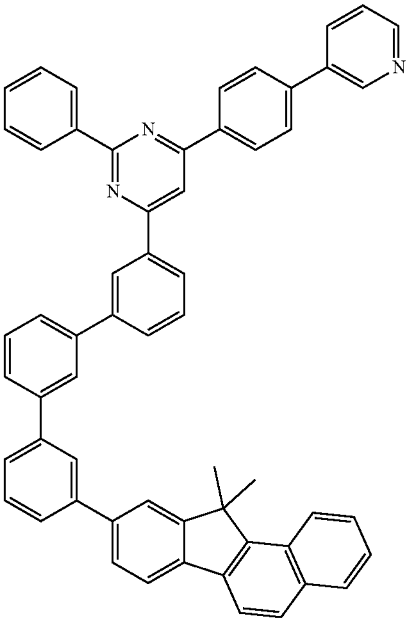
411
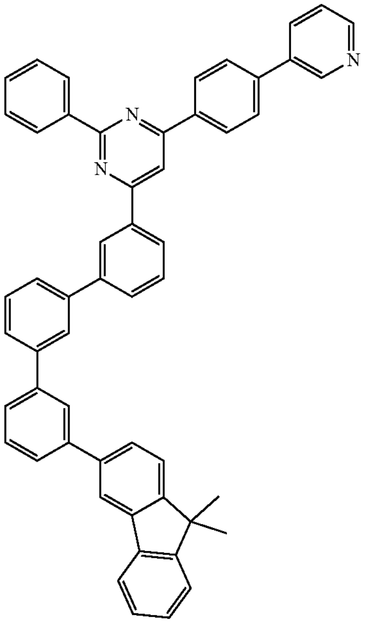
-continued
412
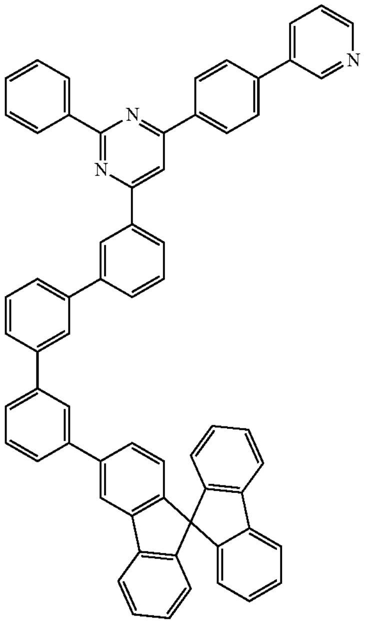
413
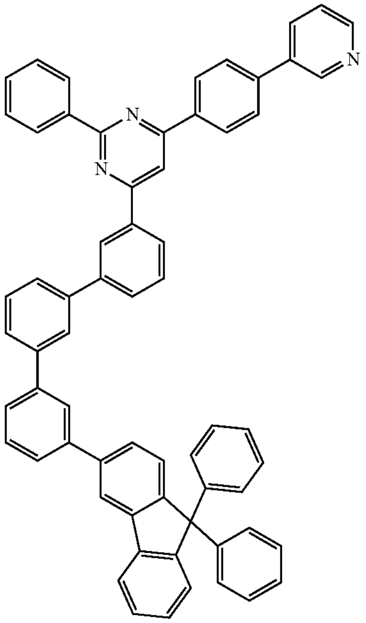

-continued
414
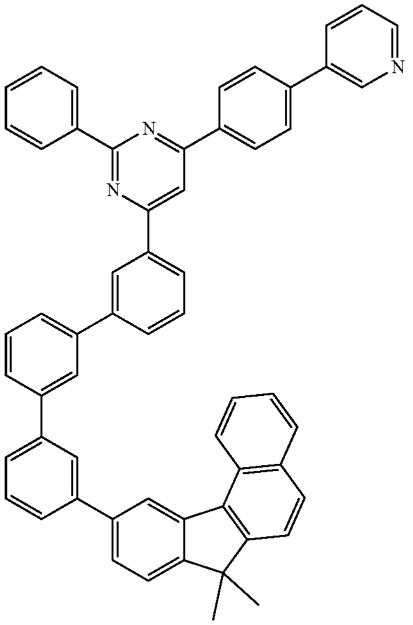
415
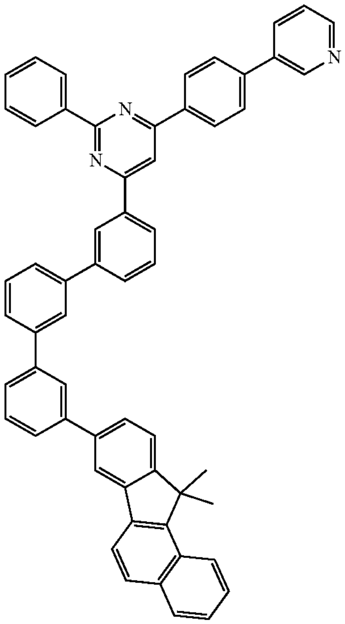
-continued
416
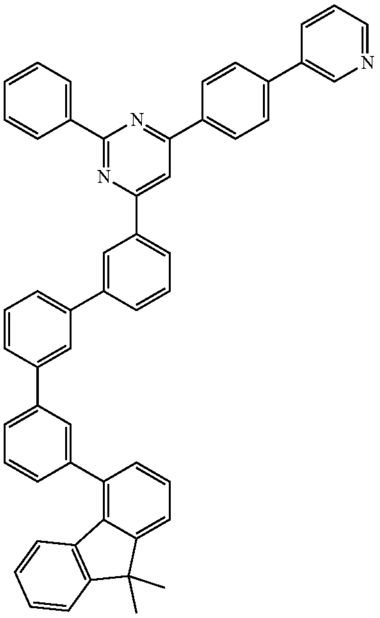
417
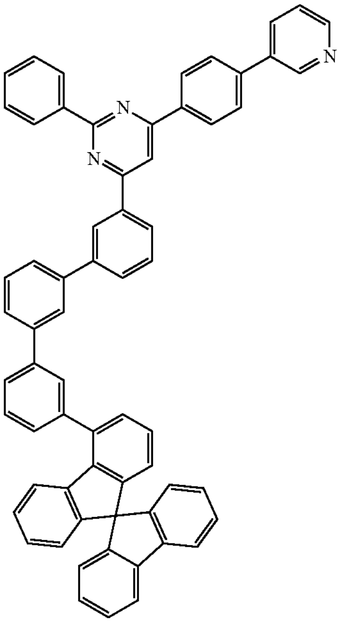

-continued
418
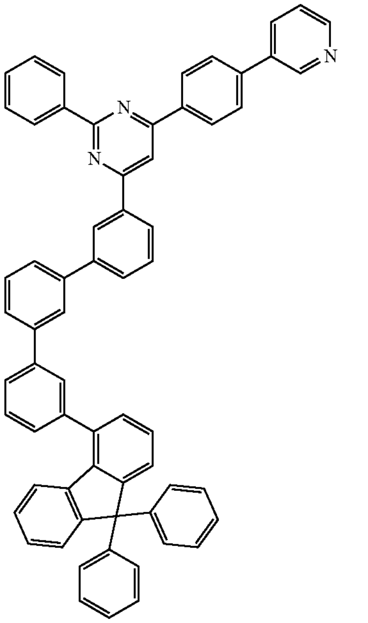
419
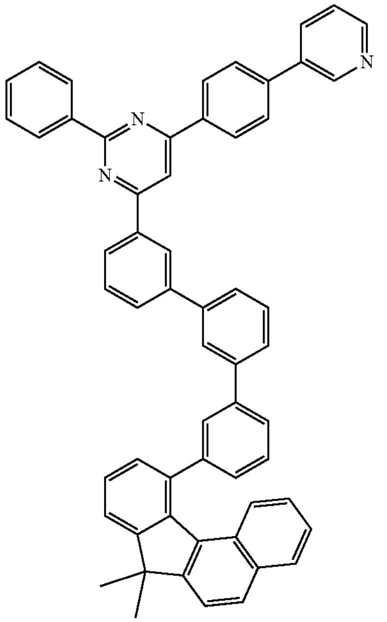
-continued
420
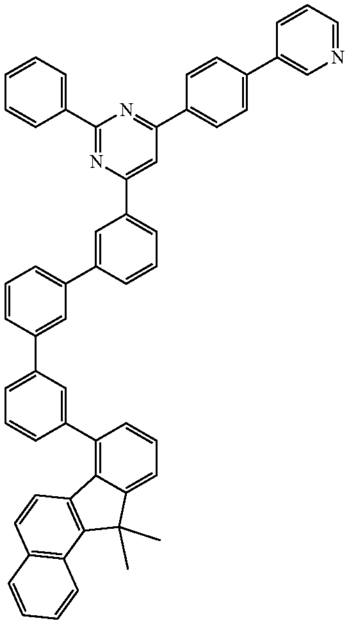
421
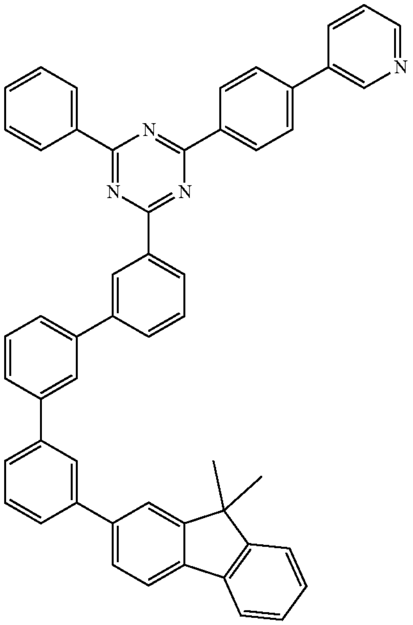

-continued
422
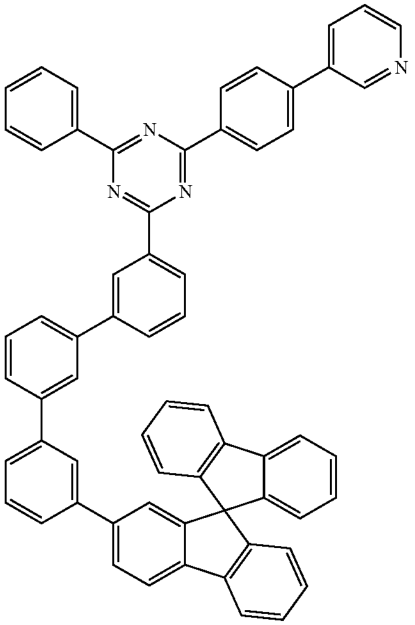
423
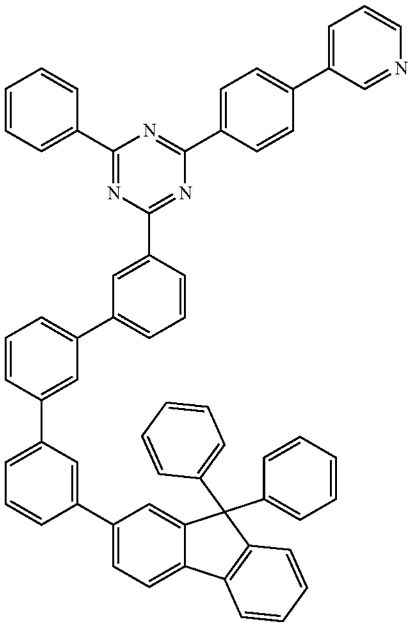
-continued
424
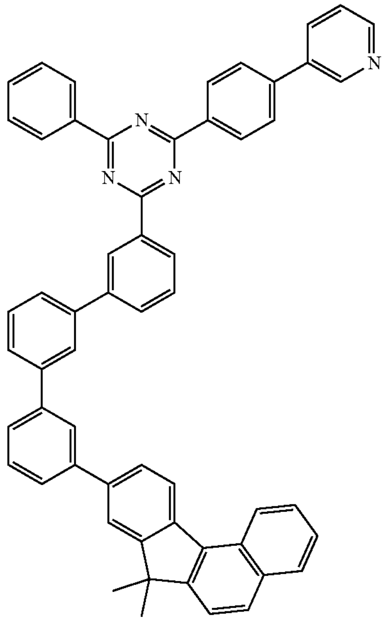
425
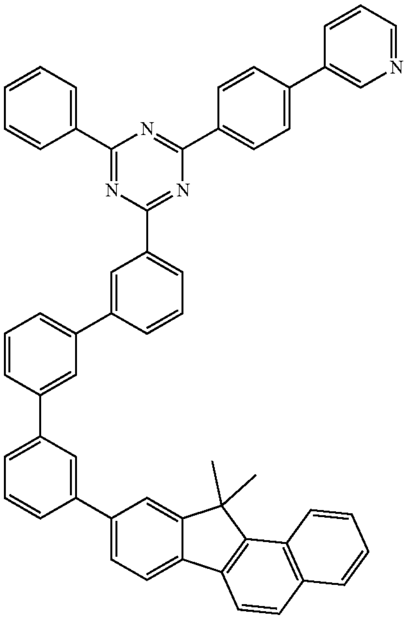

-continued
426
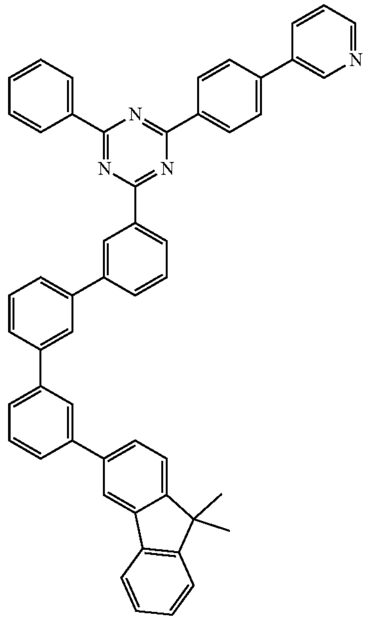
427
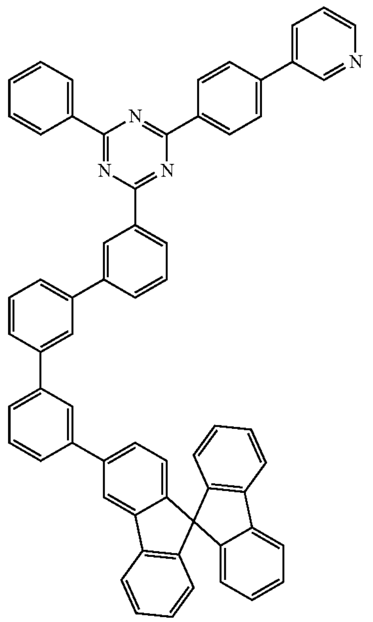
-continued
428
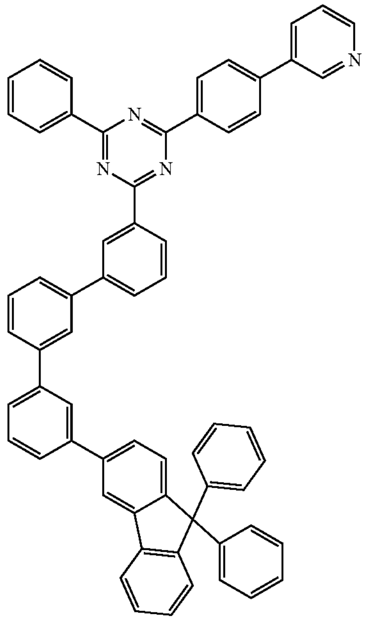
429
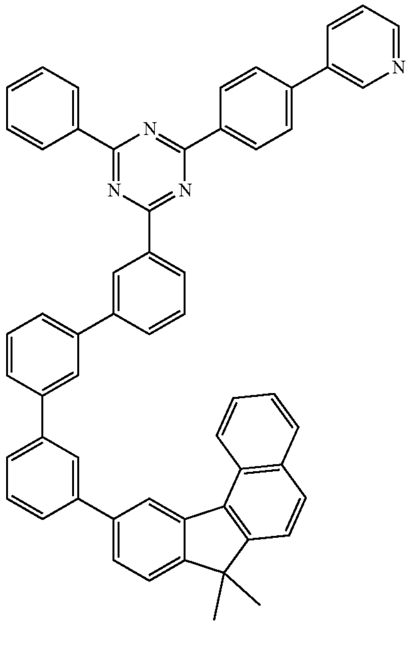

-continued
430
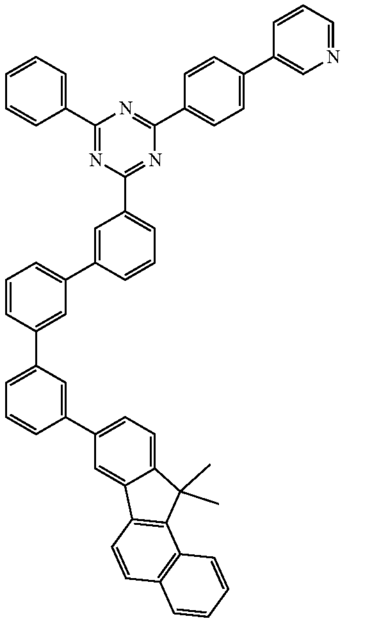
431
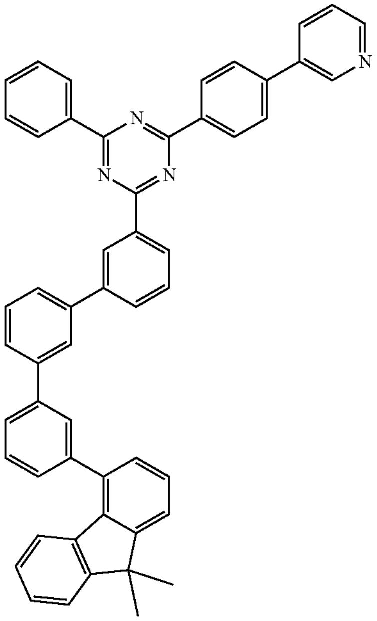
-continued
432
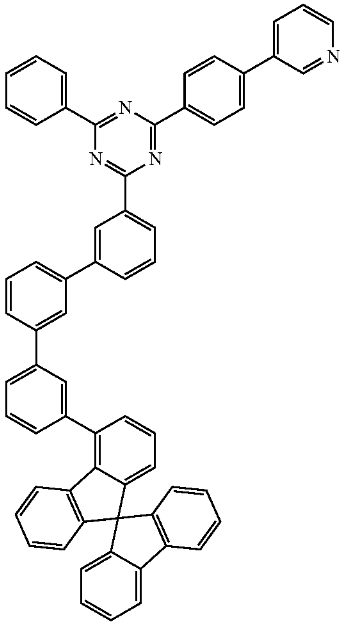
433
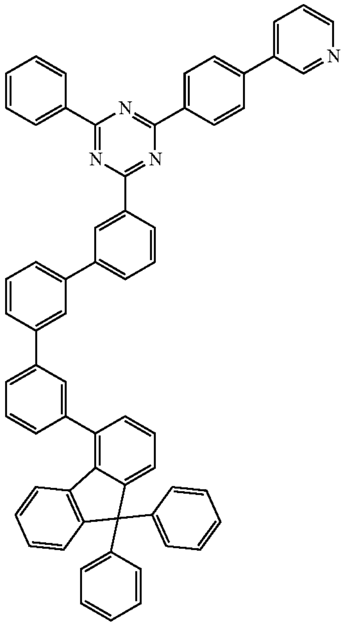

-continued
434
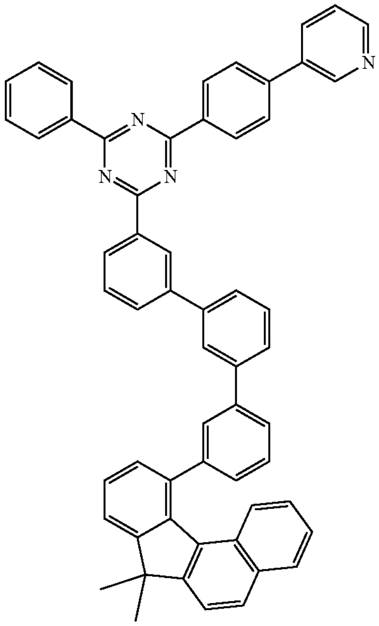
435
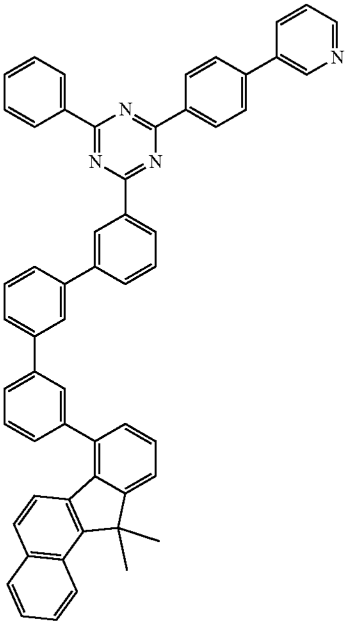
-continued
436
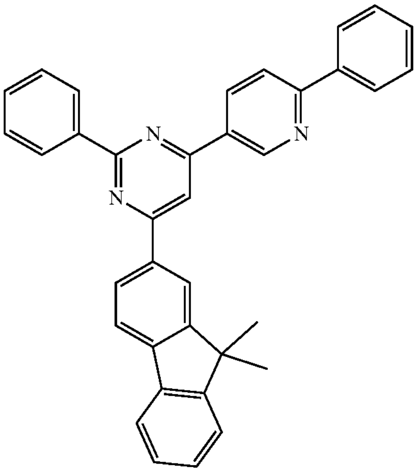
437
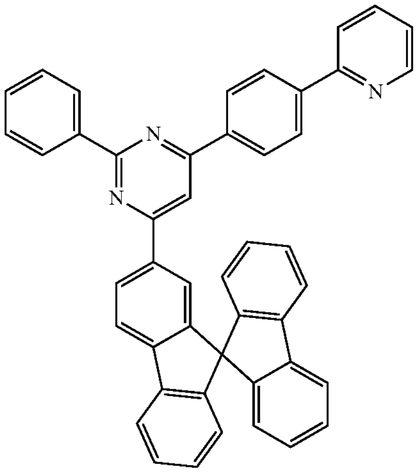
438
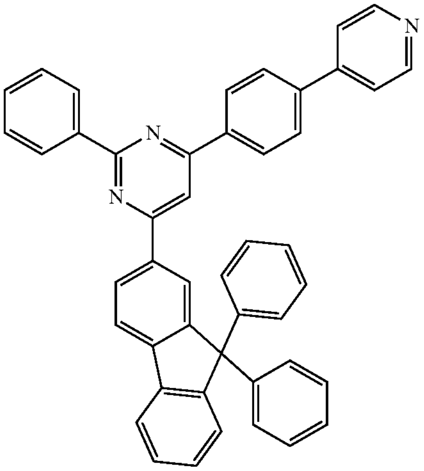

-continued
439
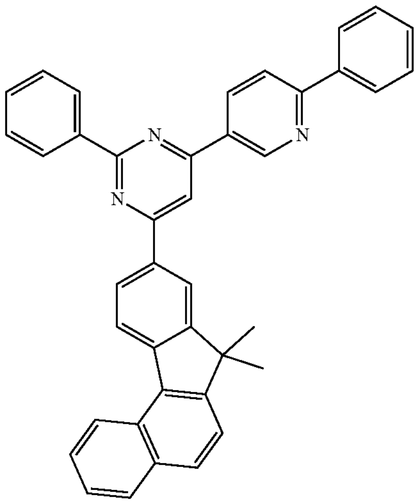
440
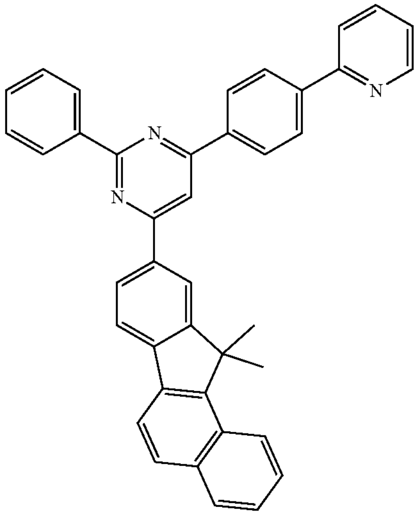
441
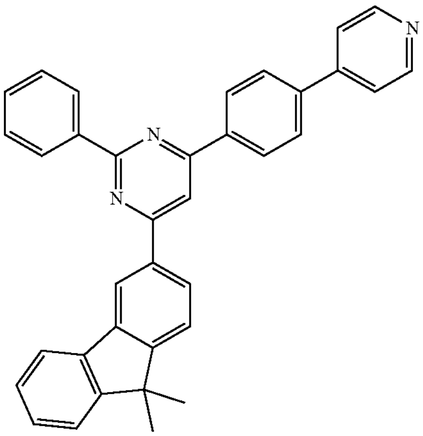
-continued
442
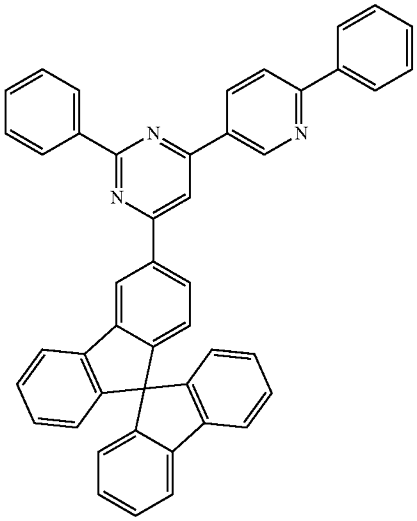
443
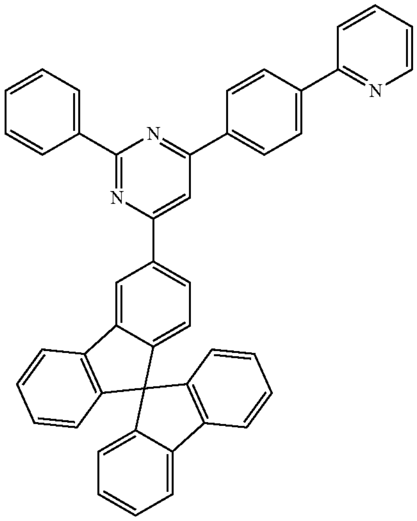
444
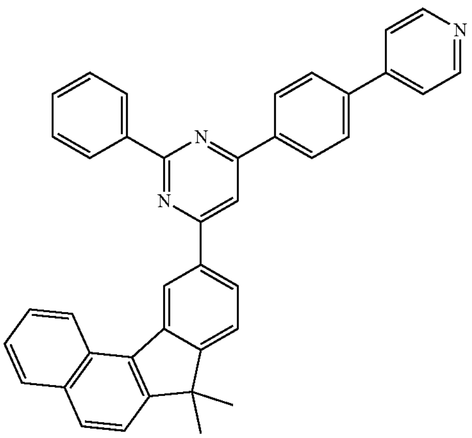

-continued
445
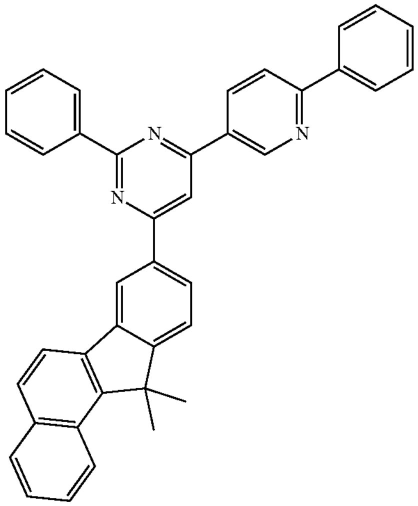
446
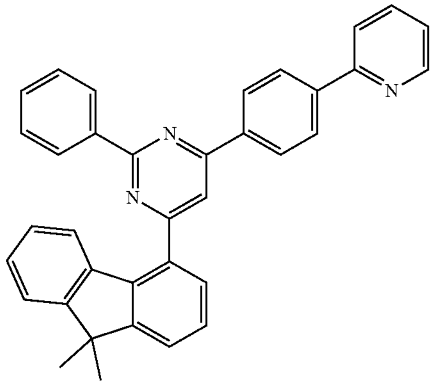
447
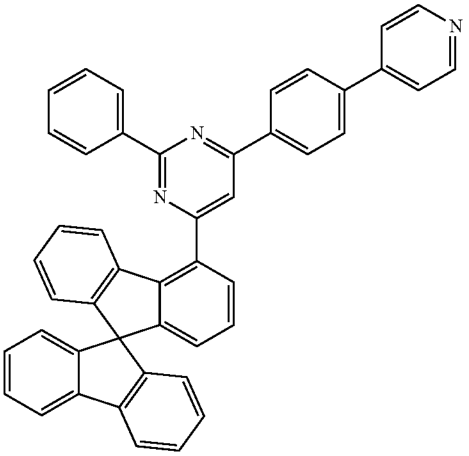
-continued
448
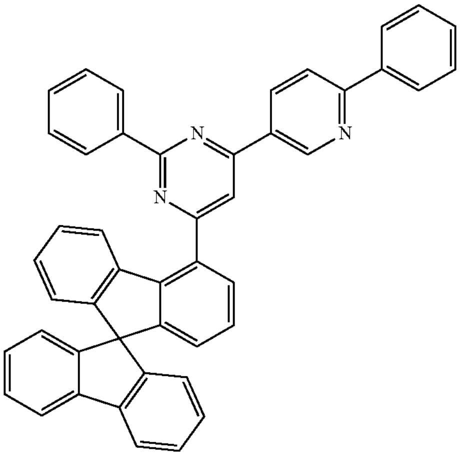
449
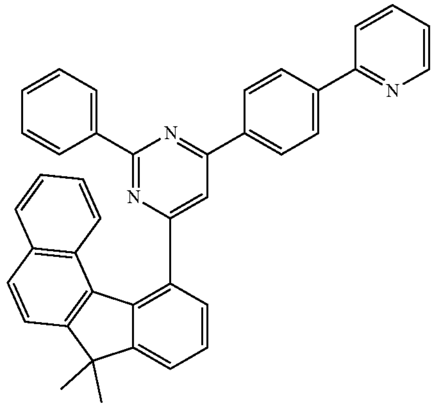
450
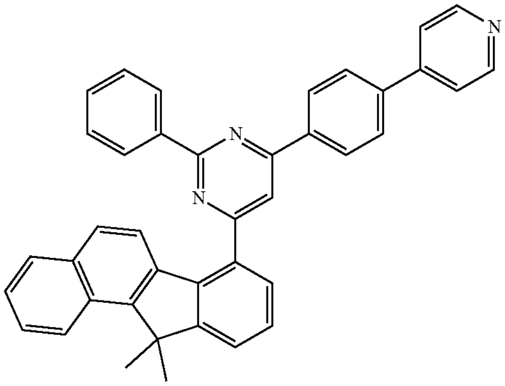

-continued
451
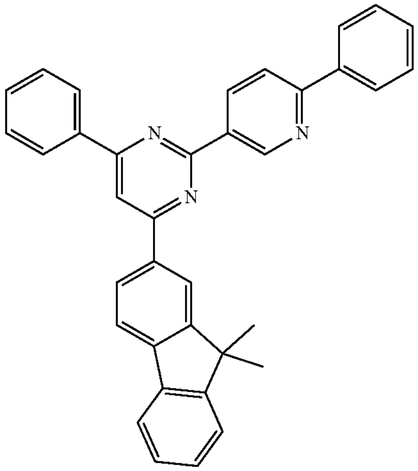
452
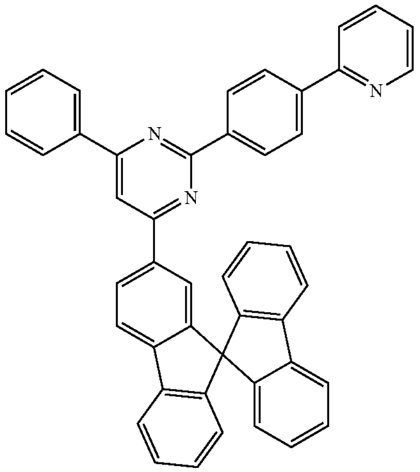
453
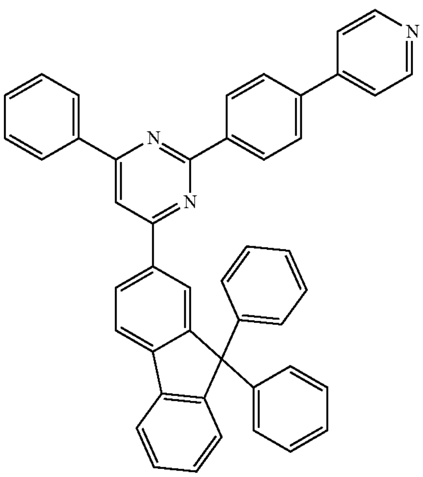
-continued
454
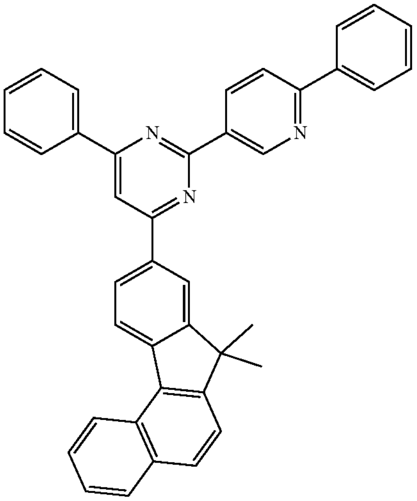
455
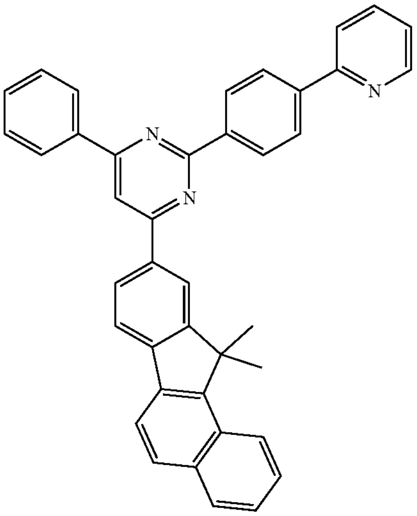
556
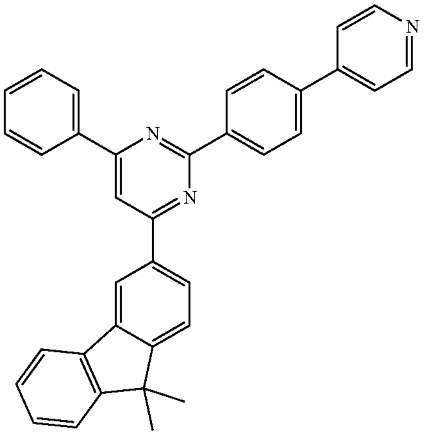

557
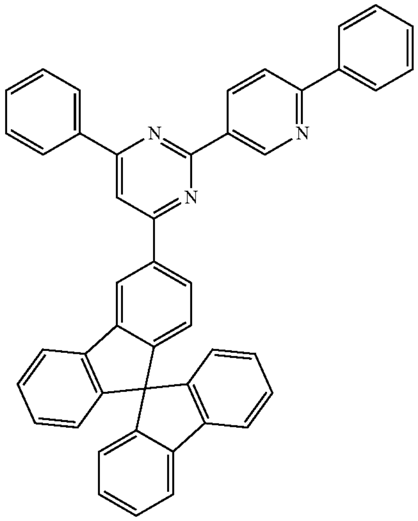
558
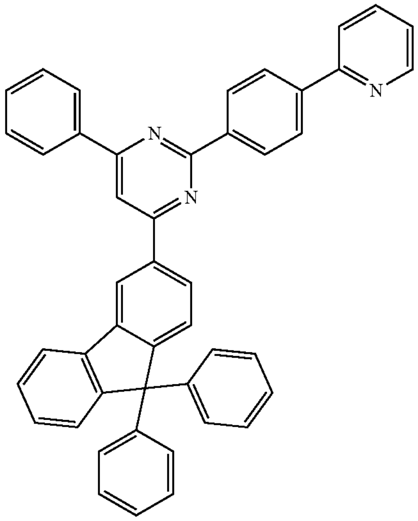
459
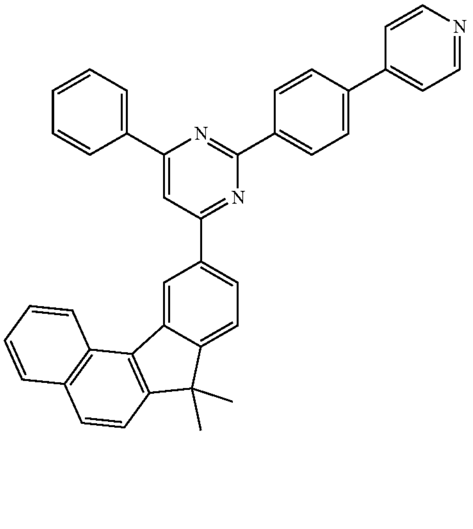
460
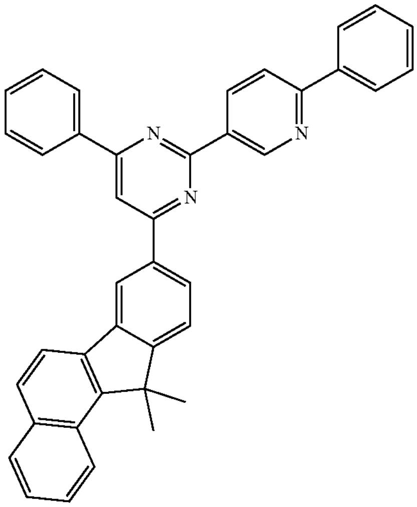
461
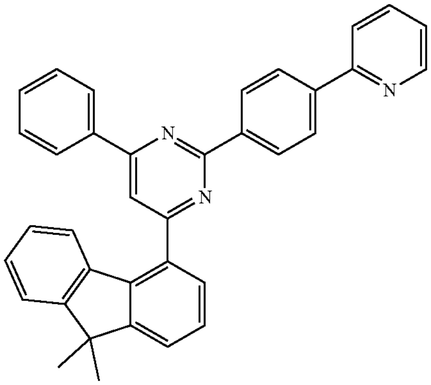
462
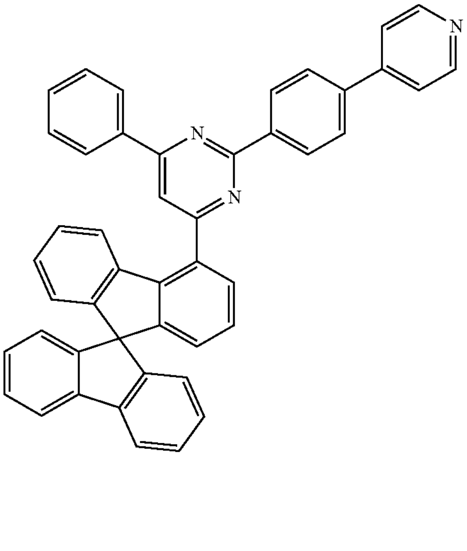

-continued
463
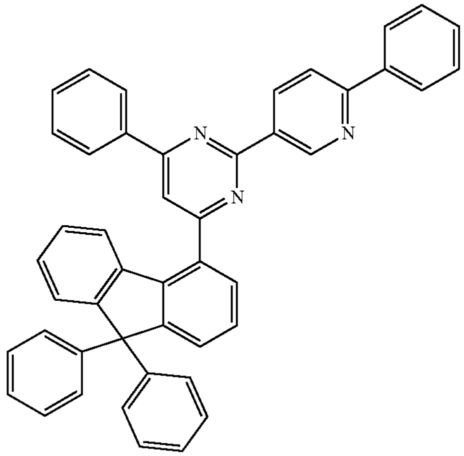
464
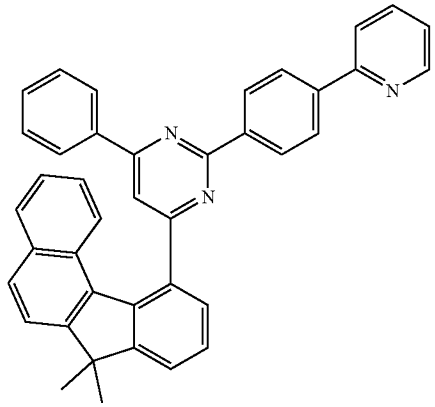
465
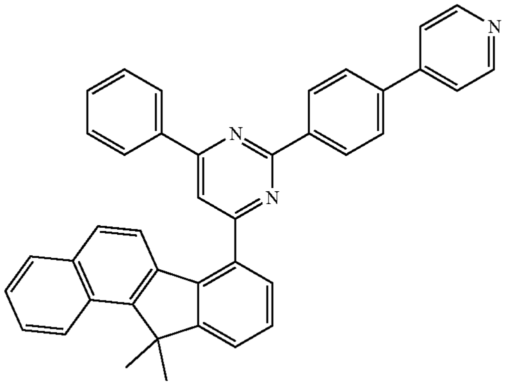
-continued
466
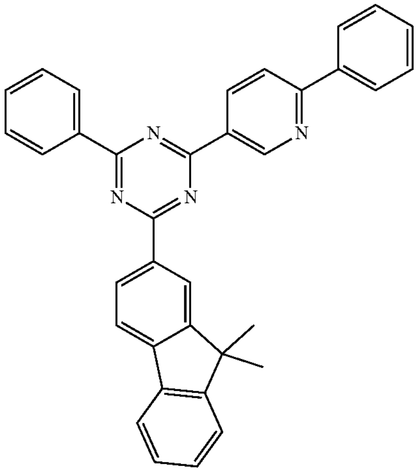
467
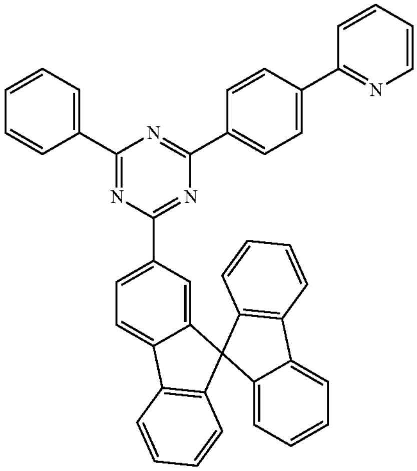
468
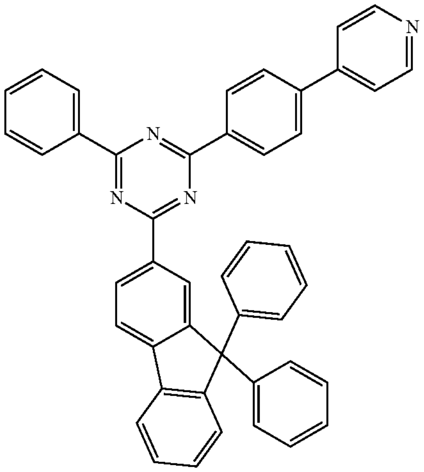

-continued
469
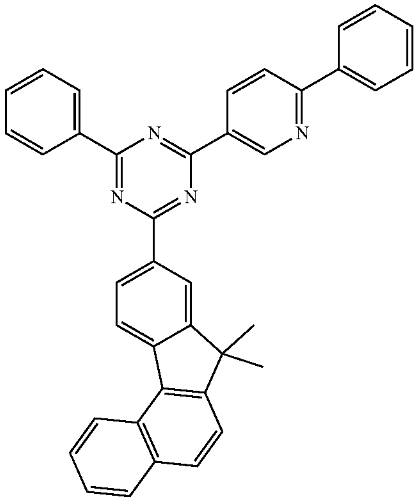
470
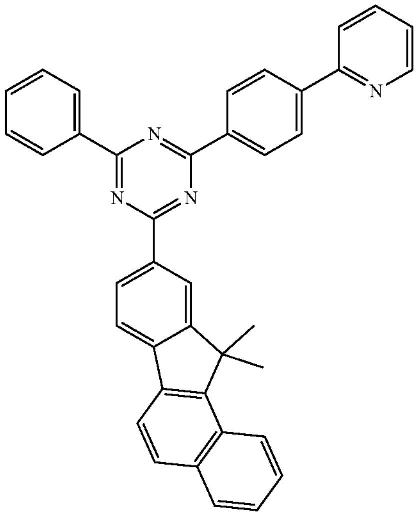
471
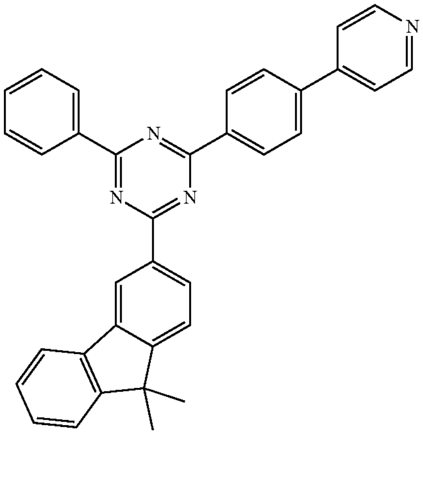
-continued
472
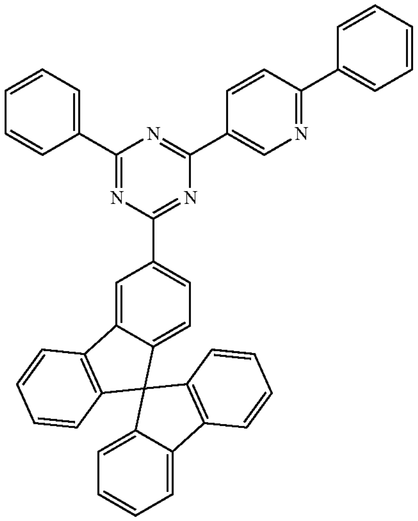
473
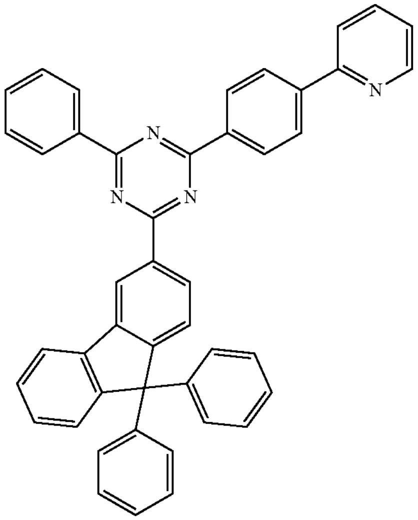
474
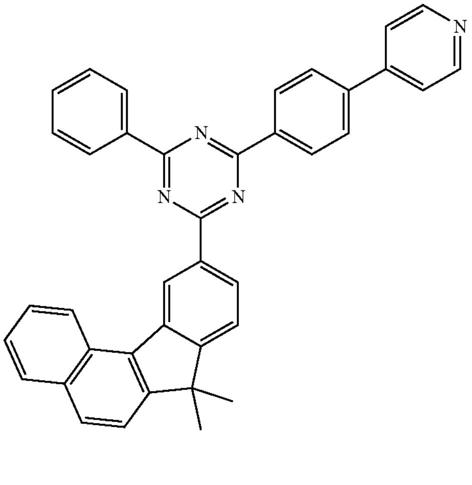

-continued
475
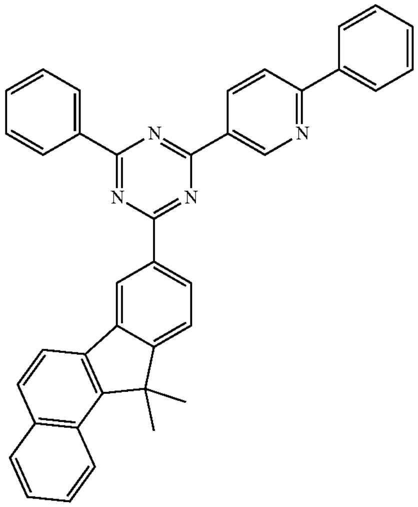
476
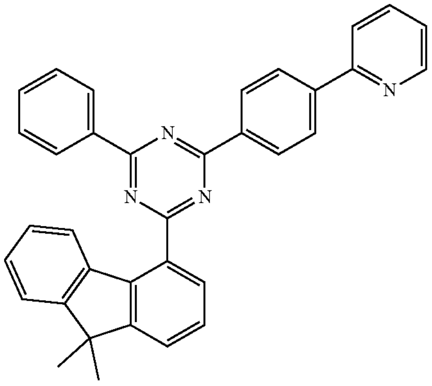
477
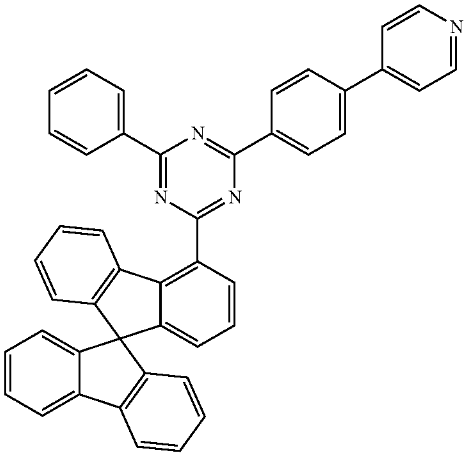
-continued
478
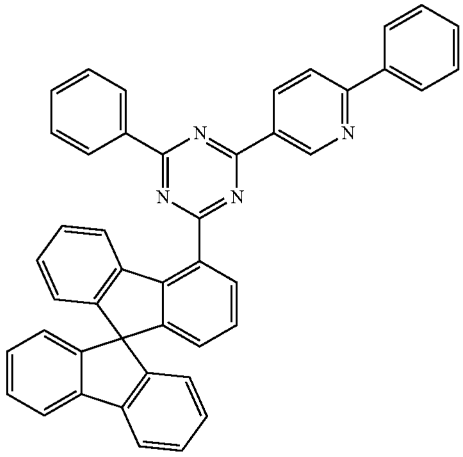
479
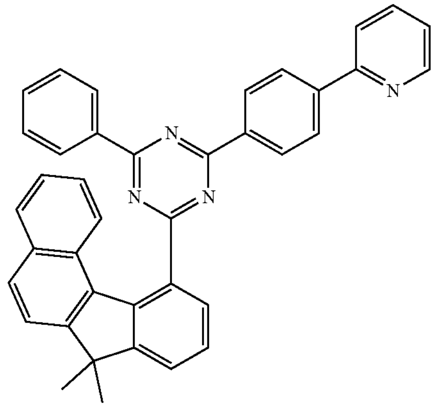
480
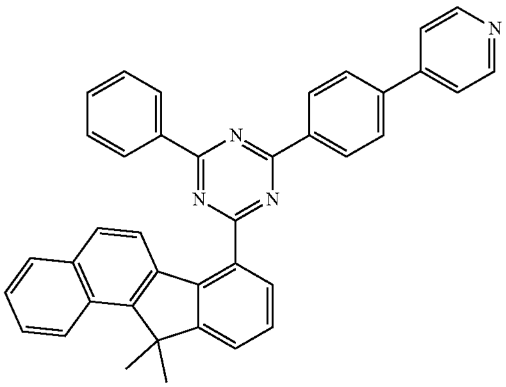

-continued
481
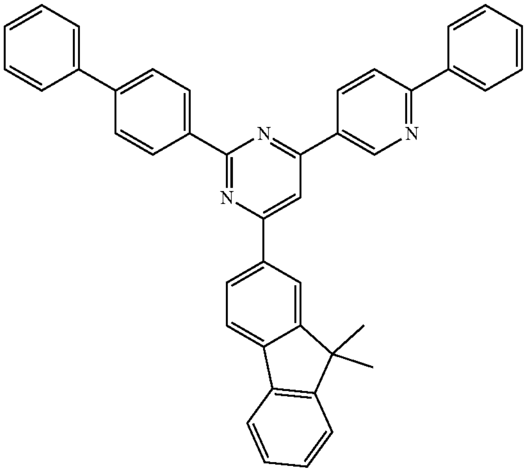
482
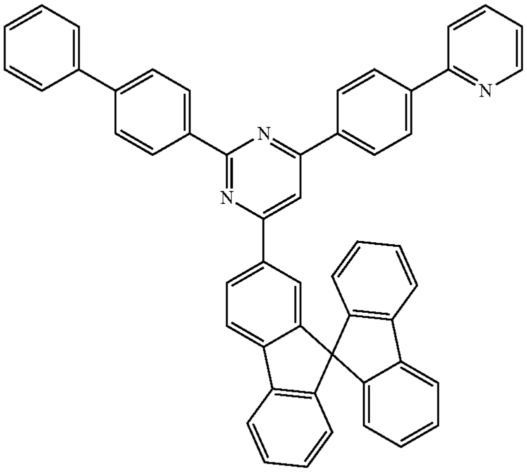
483
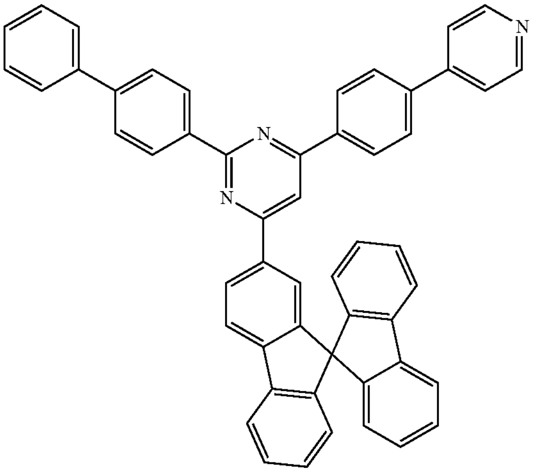
-continued
484
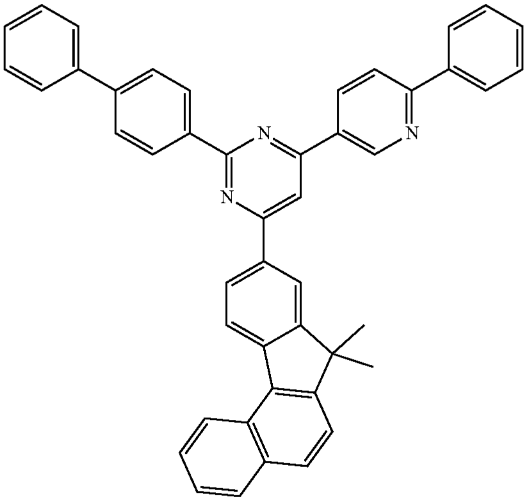
485
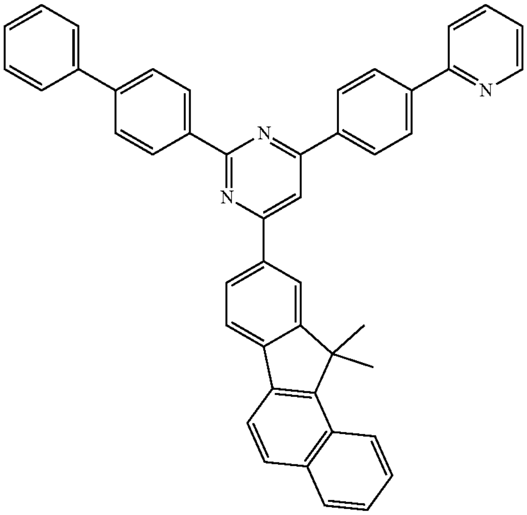
486
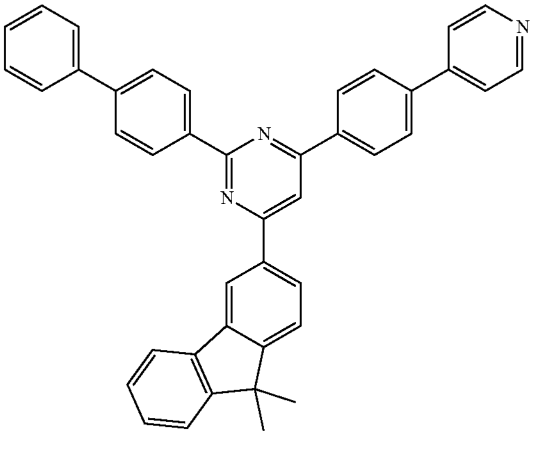

-continued
487
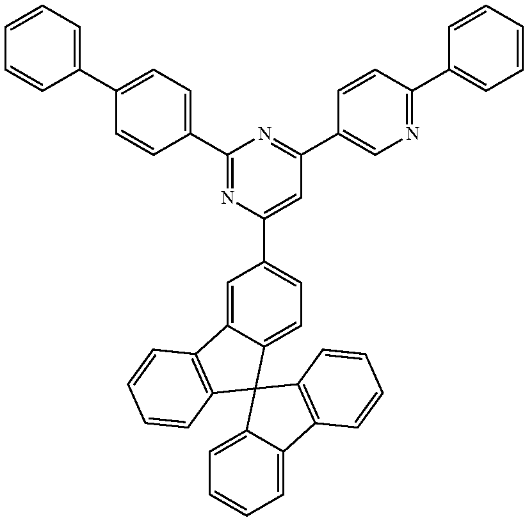
488
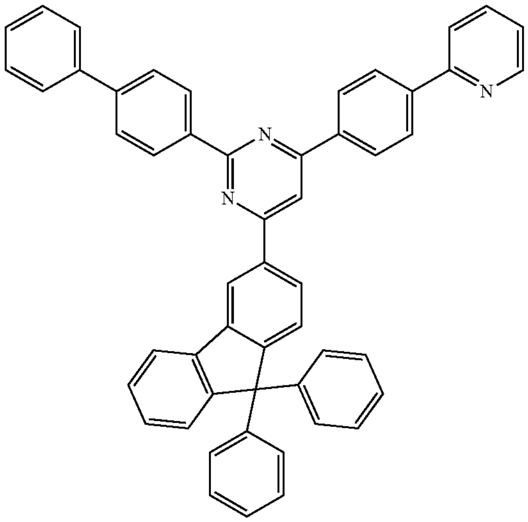
489
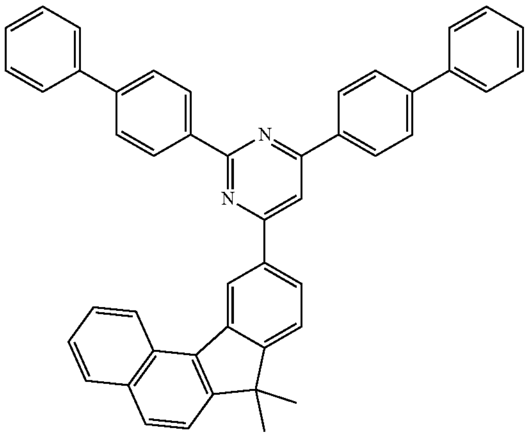
-continued
490
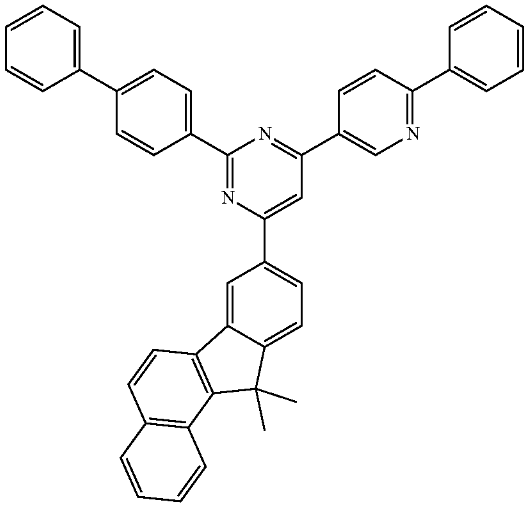
491
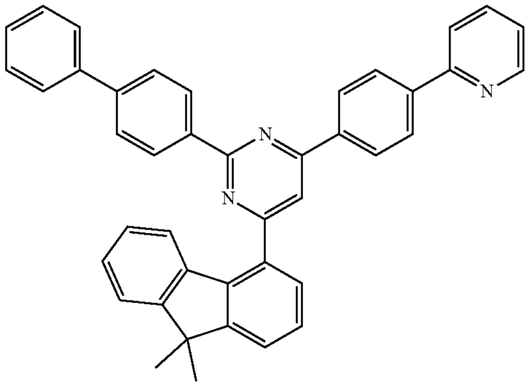
492
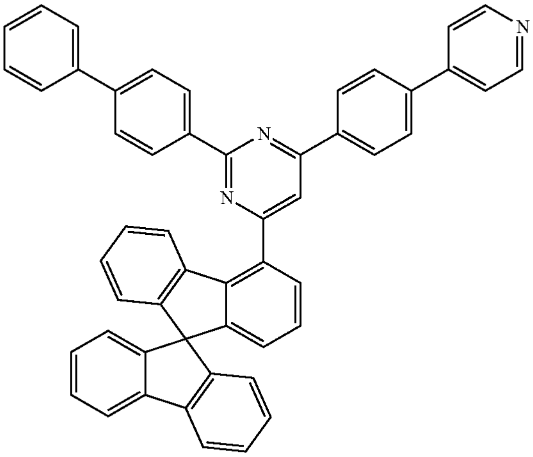

-continued
493
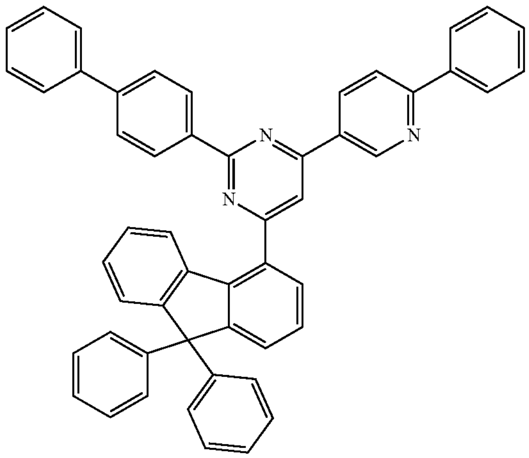
494
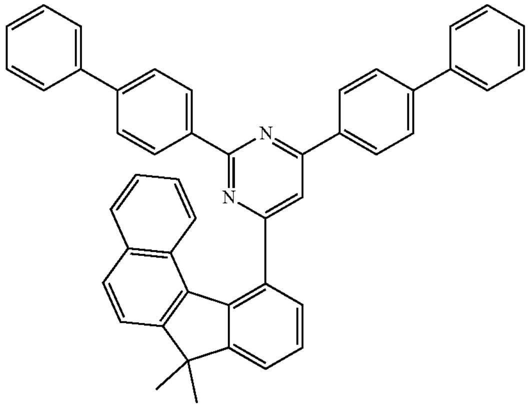
495
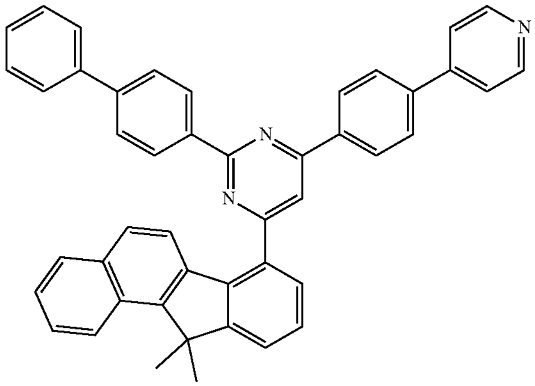
-continued
496
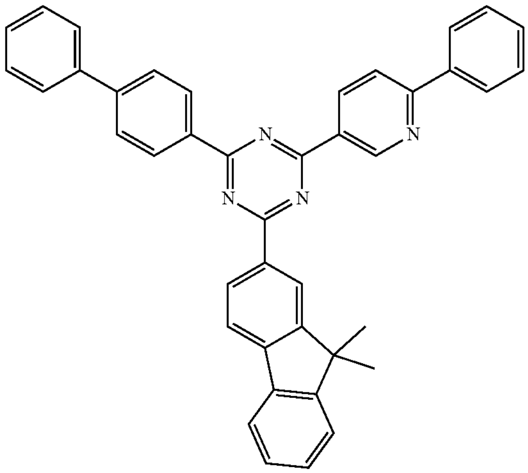
497
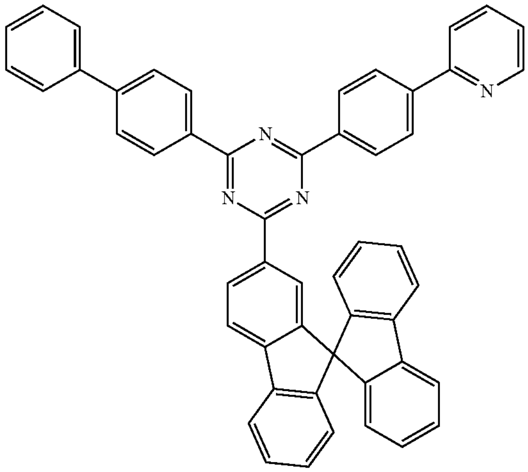
498
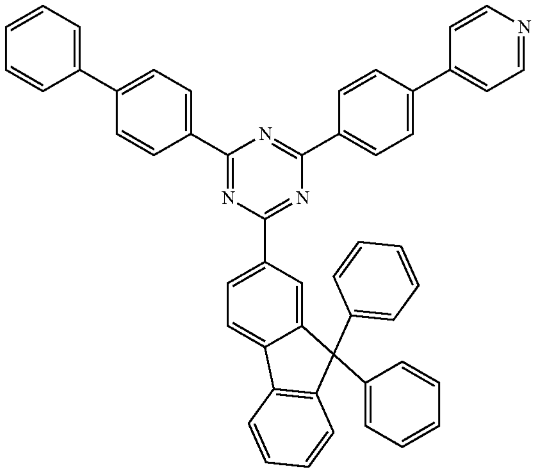

-continued
499
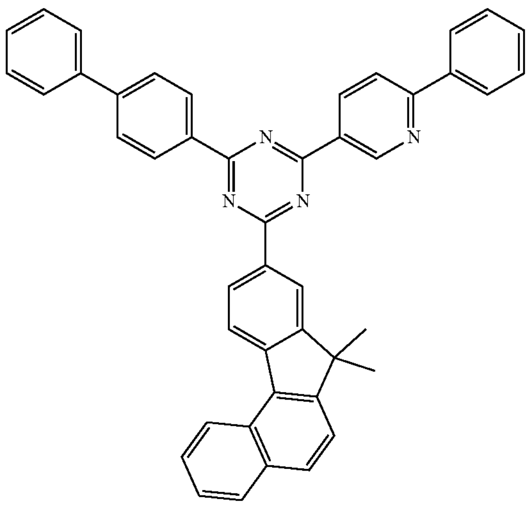
500
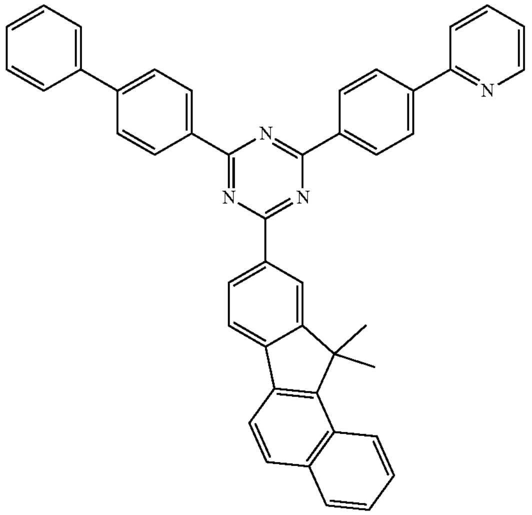
501
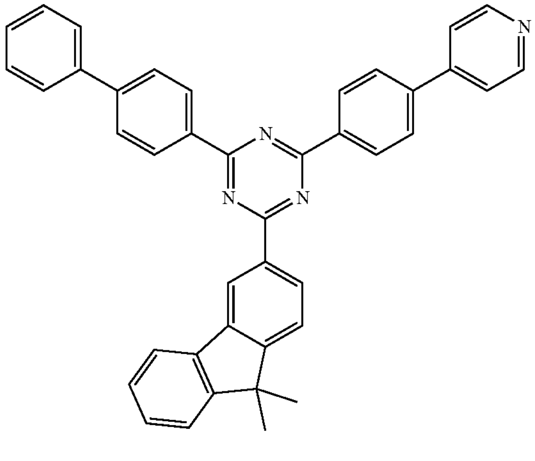
-continued
502
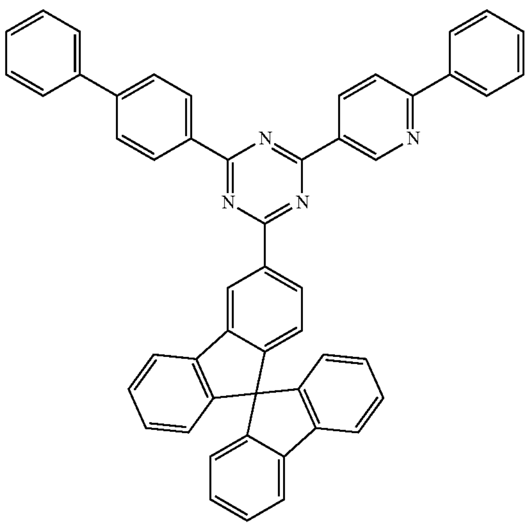
503
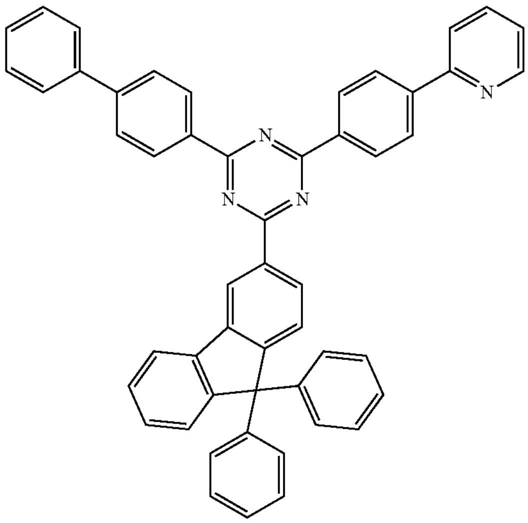
504
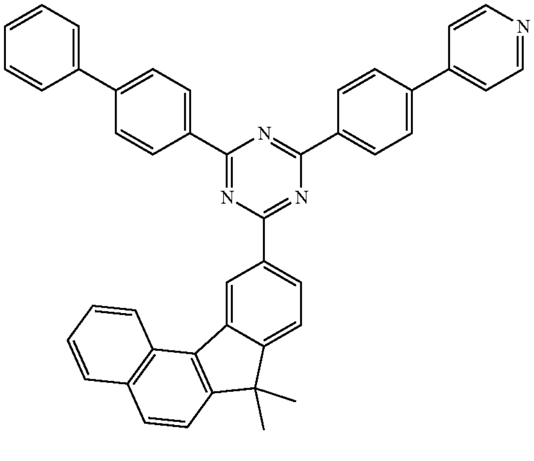

-continued
505
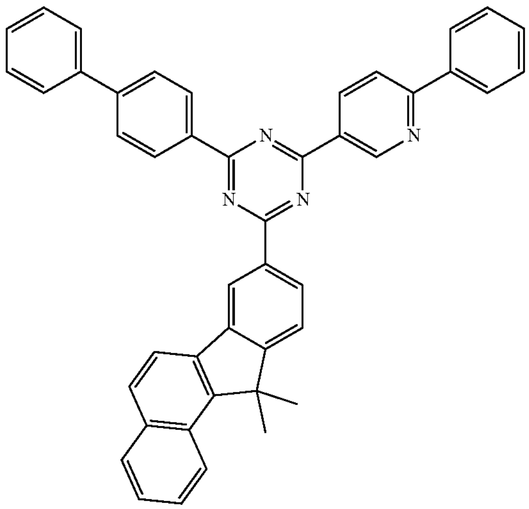
506
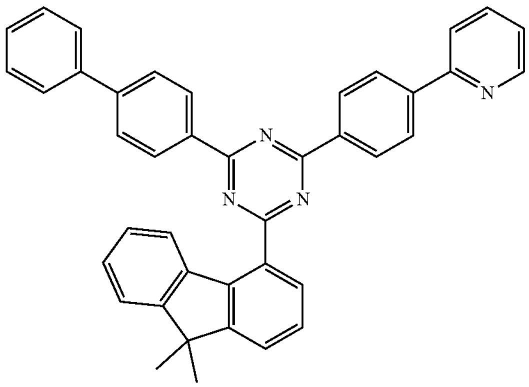
507
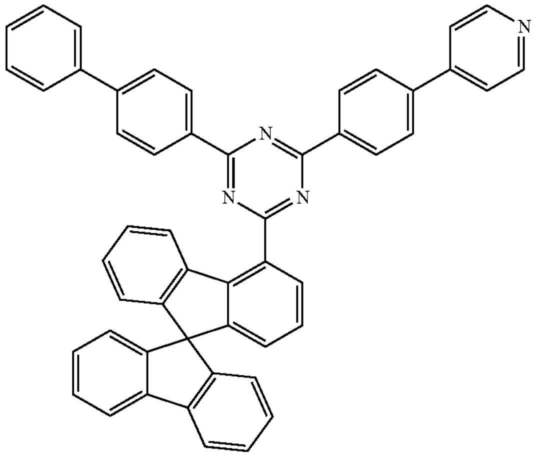
-continued
508
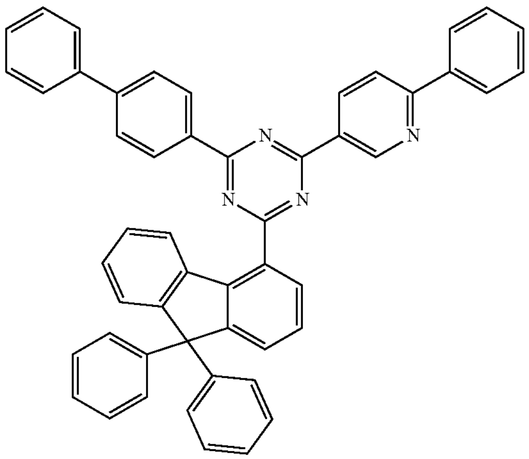
509
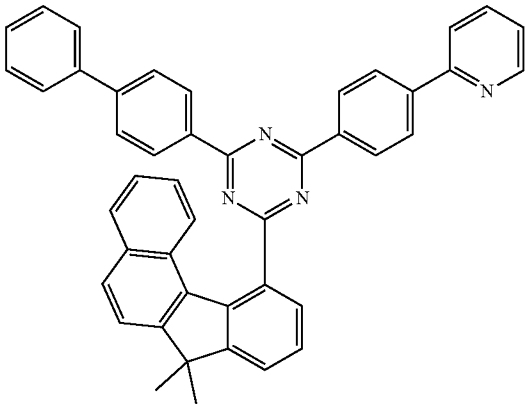
510
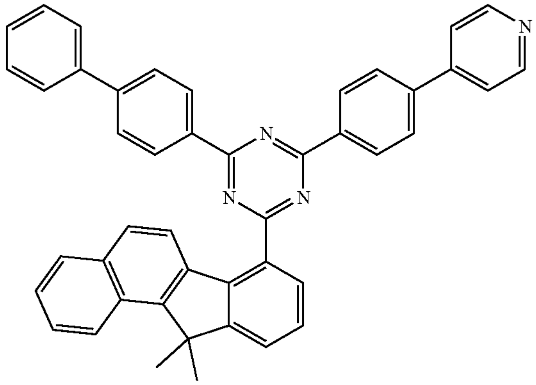

511
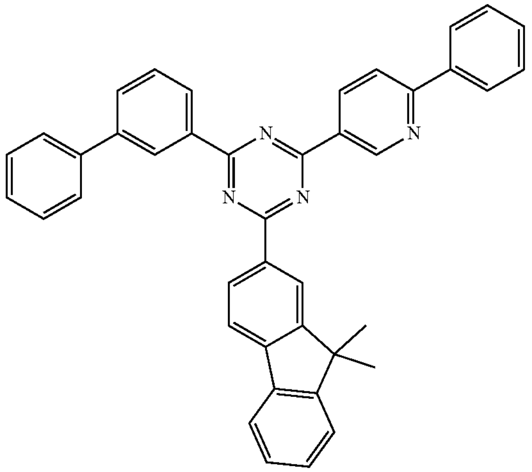
512
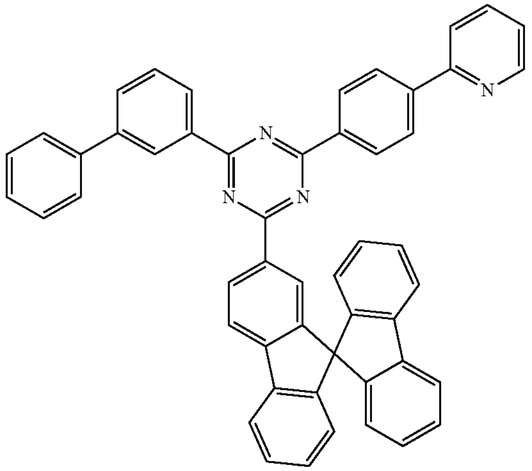
513
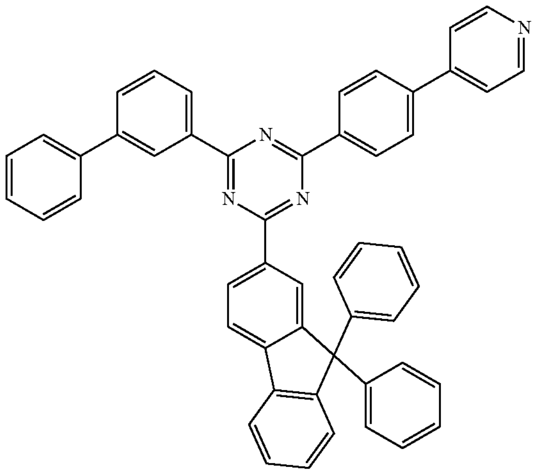
514
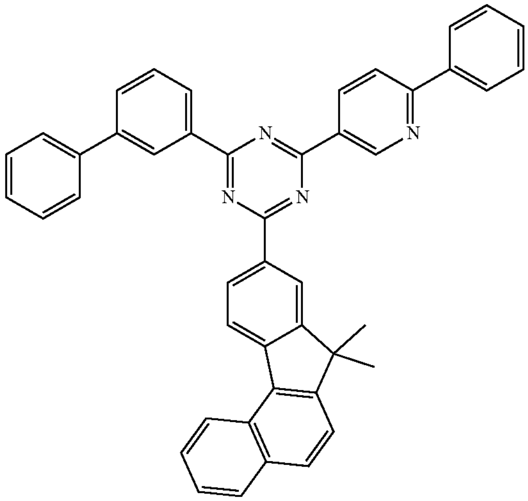
515
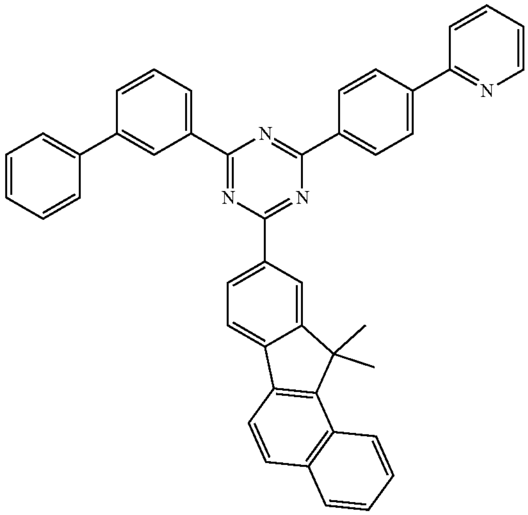
516
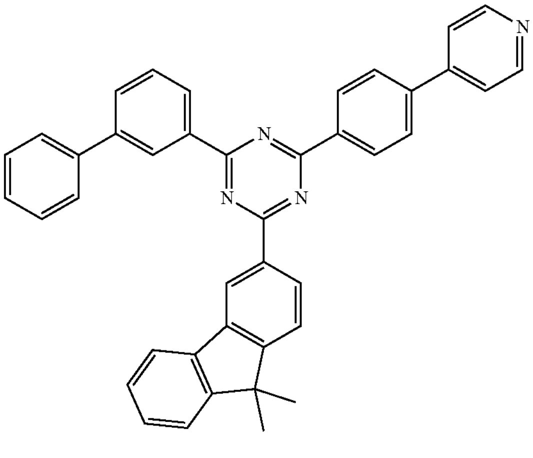

-continued
517
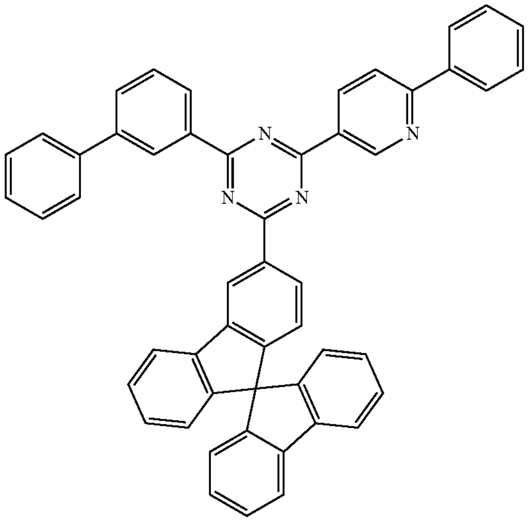
518
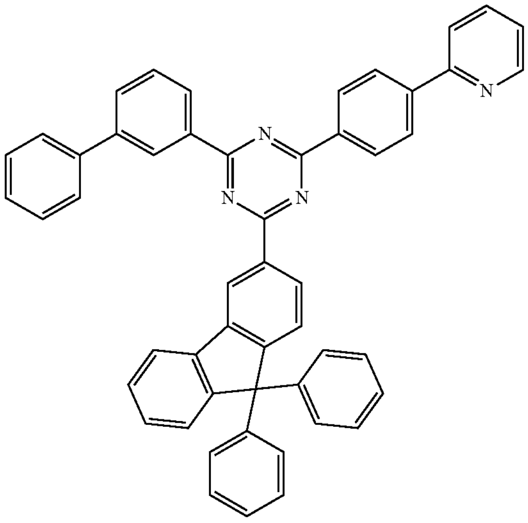
519
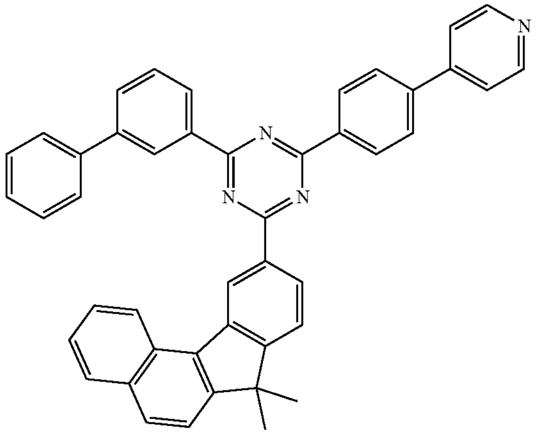
-continued
520
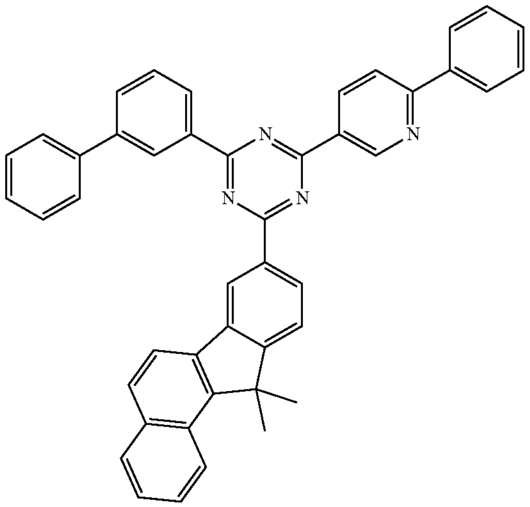
521
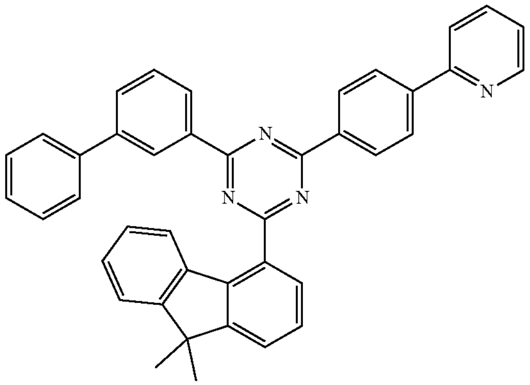
522
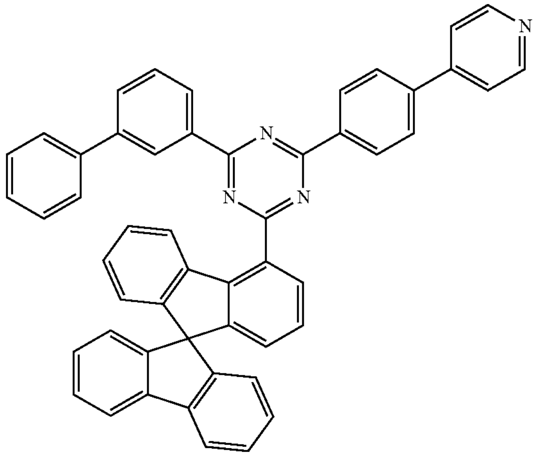

-continued
523
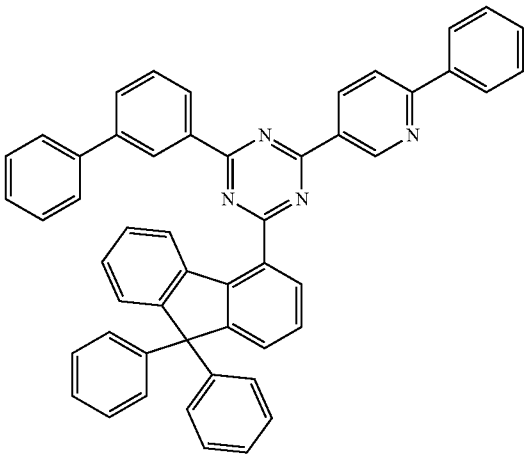
524
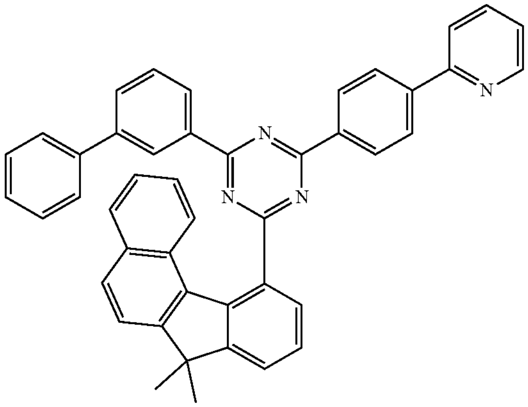
525
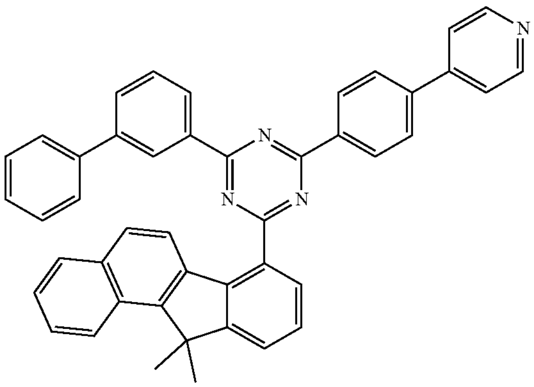
-continued
526
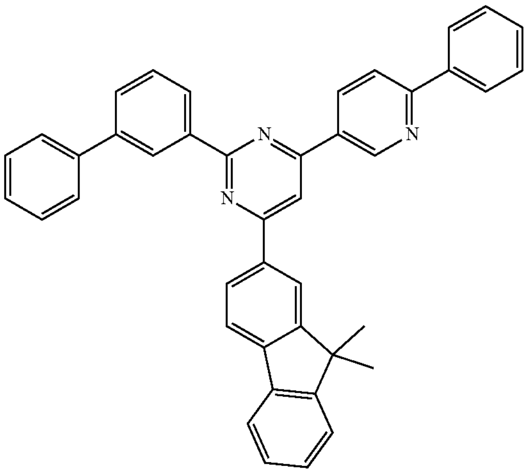
527
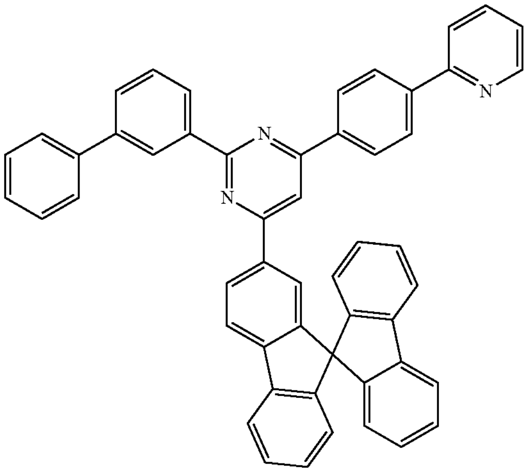
528
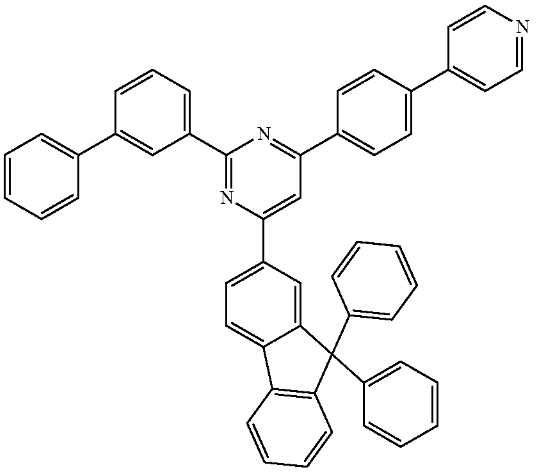

-continued
529
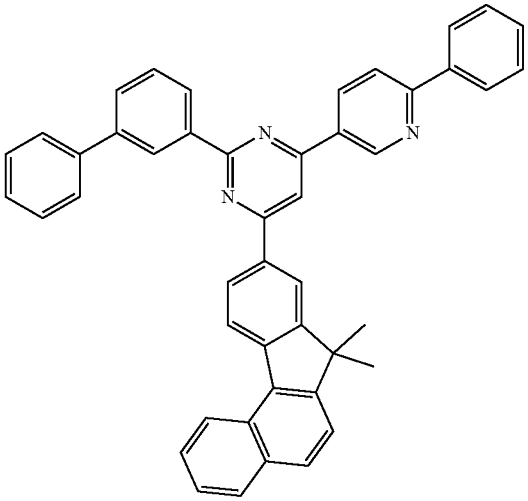
530
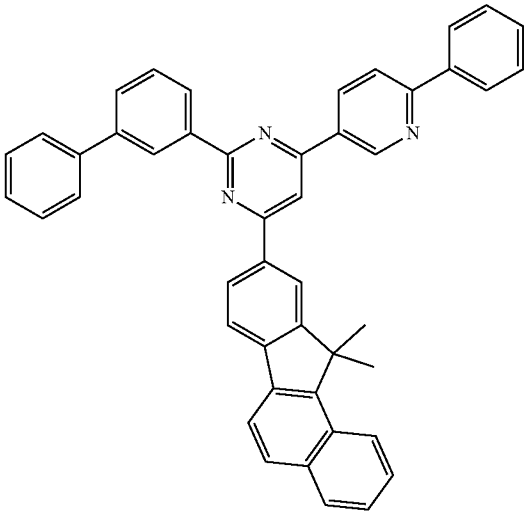
531
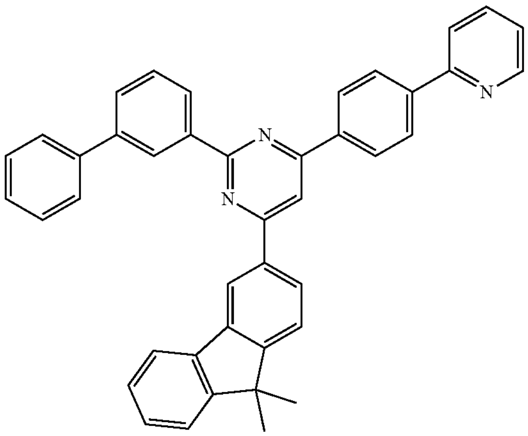
-continued
532
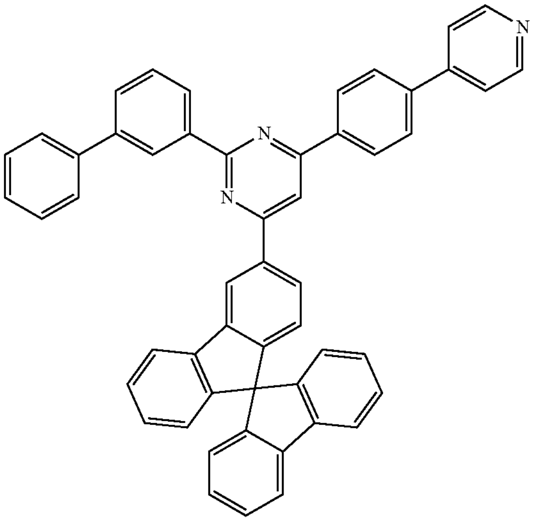
533
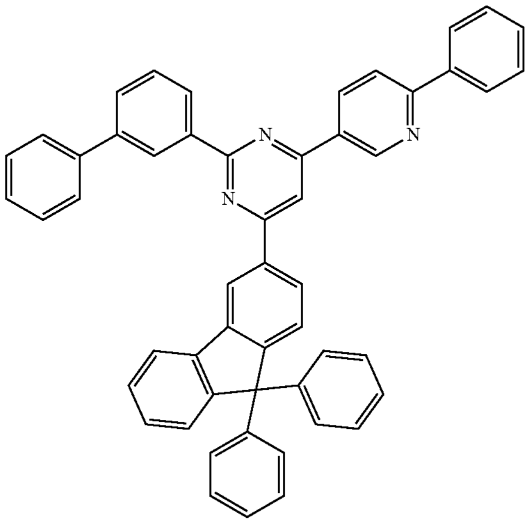
534
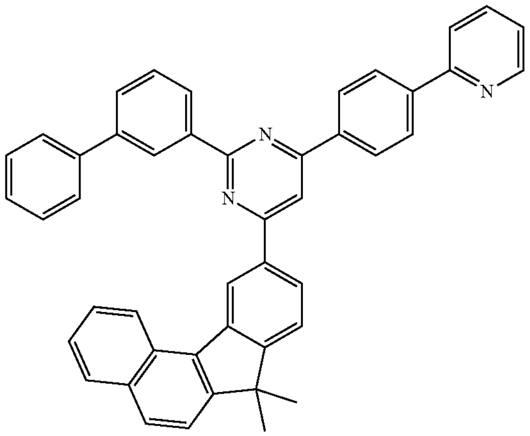

-continued
535
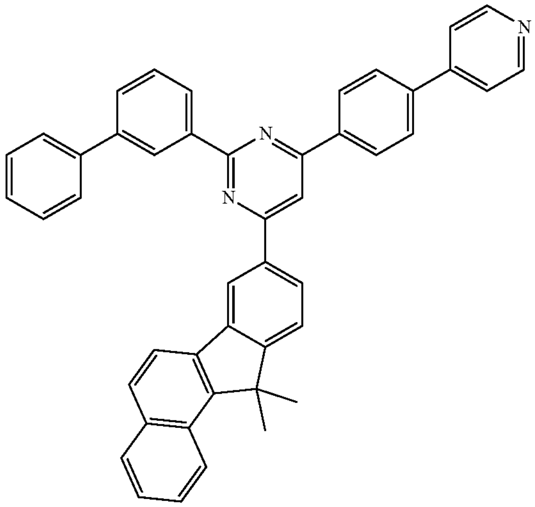
536
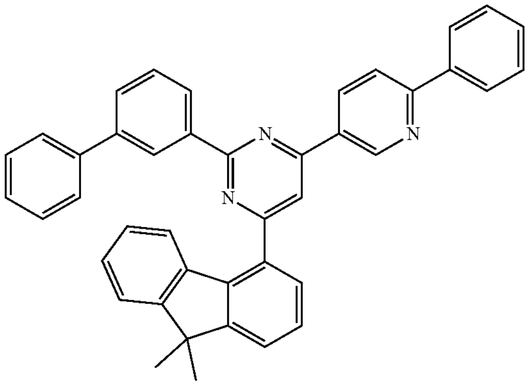
537
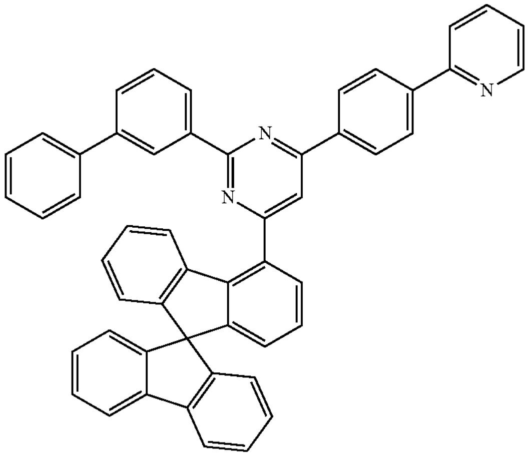
-continued
538
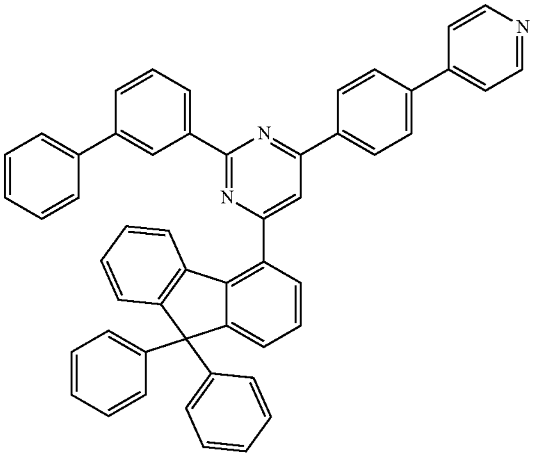
539
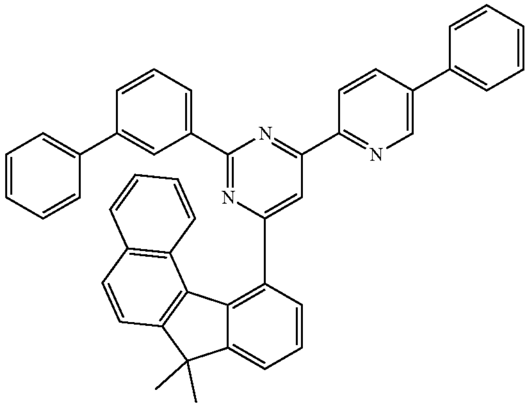
540
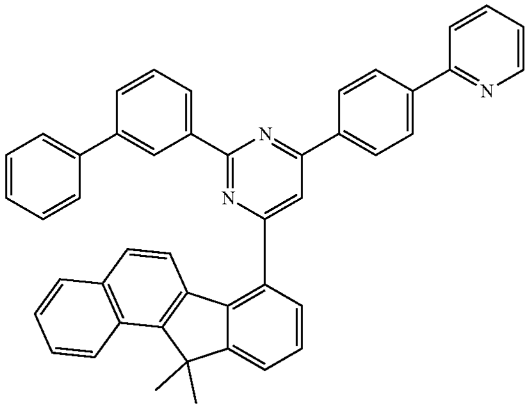

541
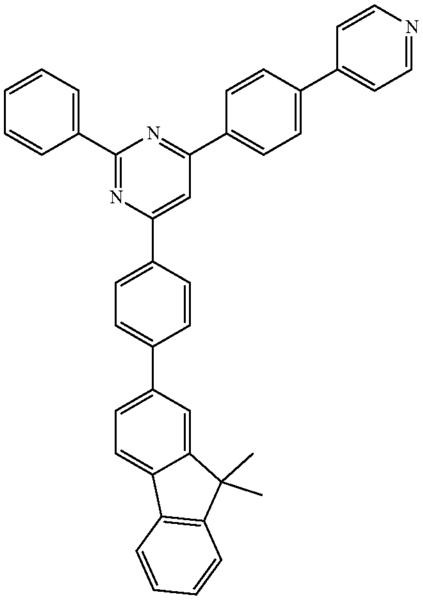
542
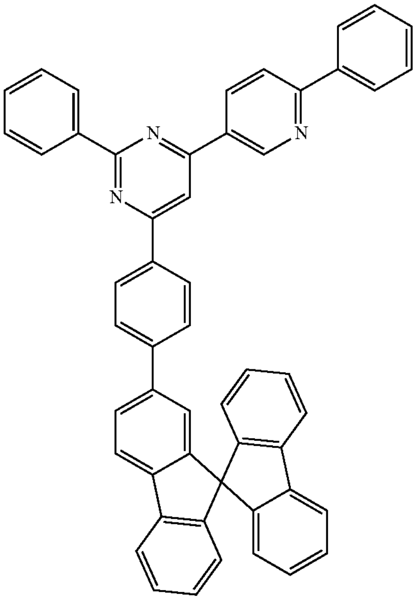
543
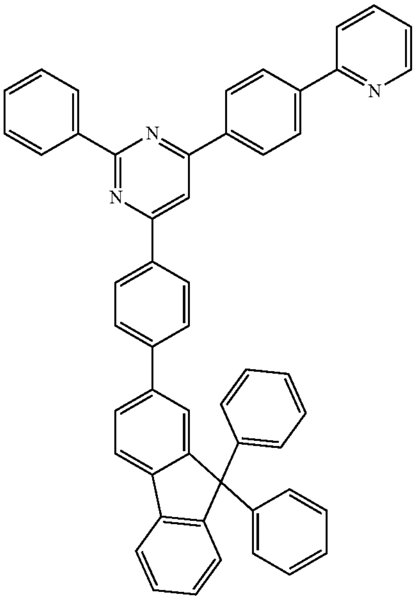
544
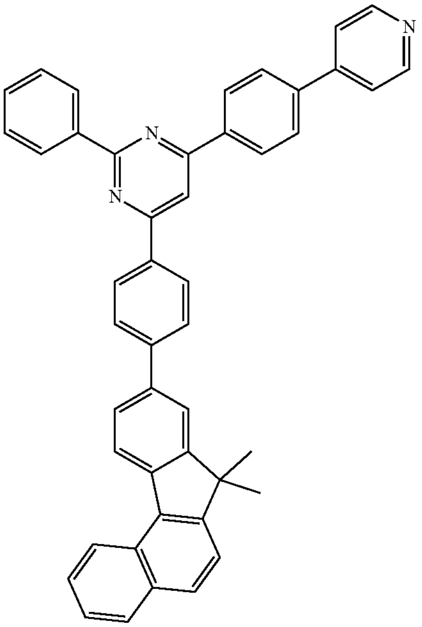

545
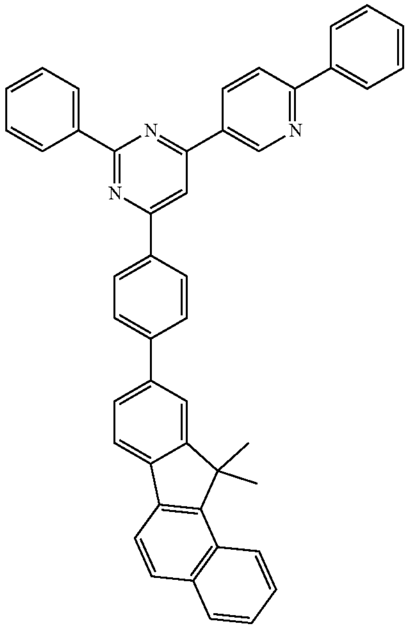
546
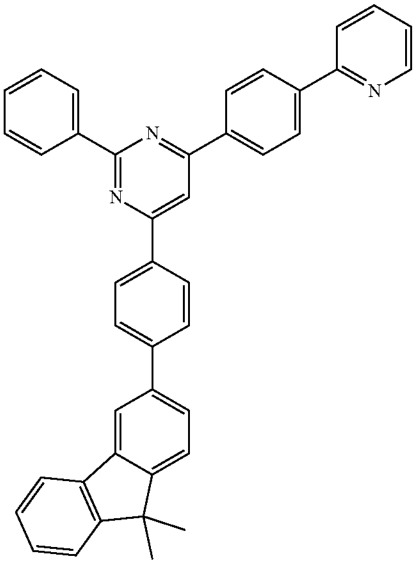
547
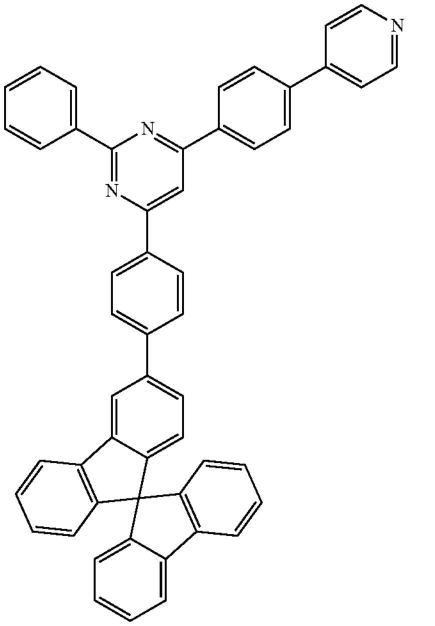
548
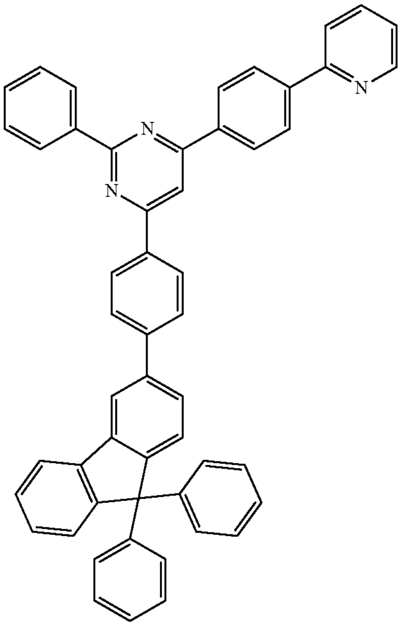

549
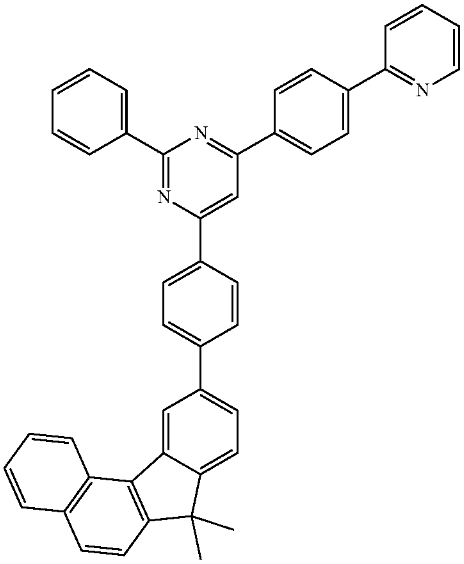
550
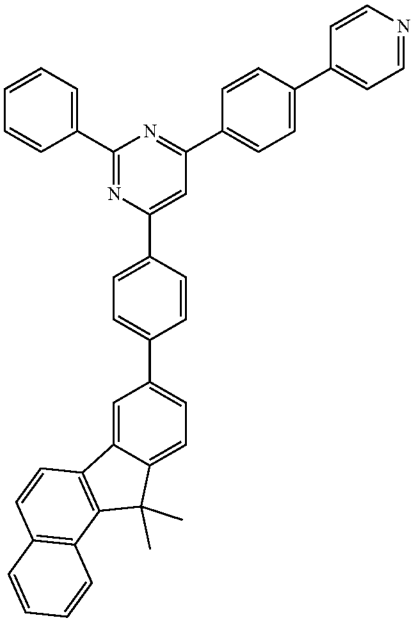
551
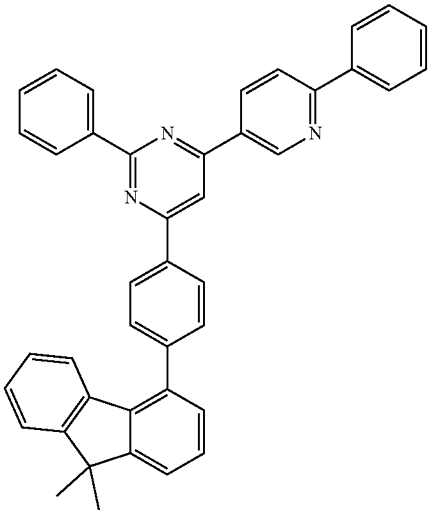
552
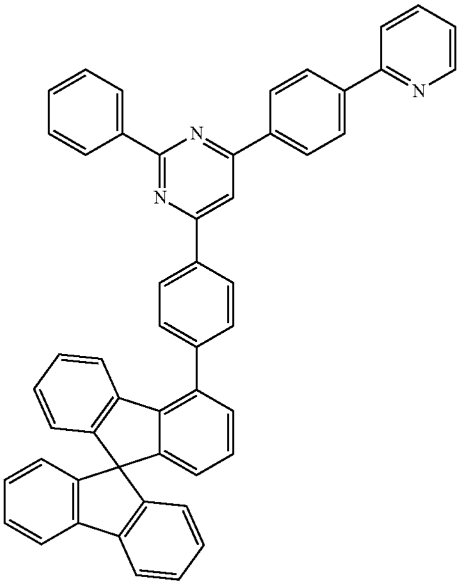

-continued
553
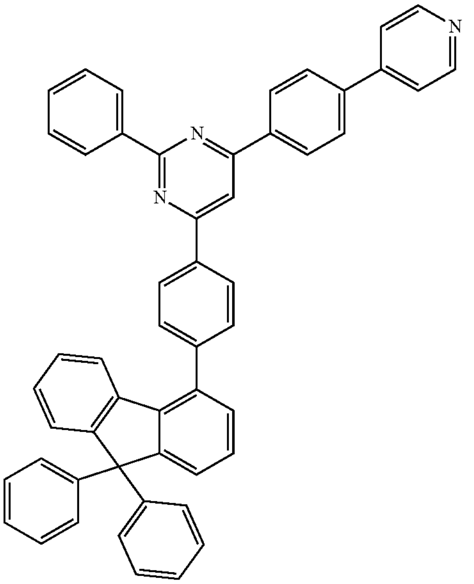
554
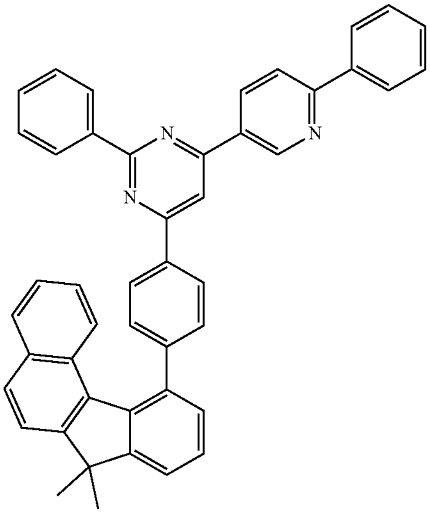
555
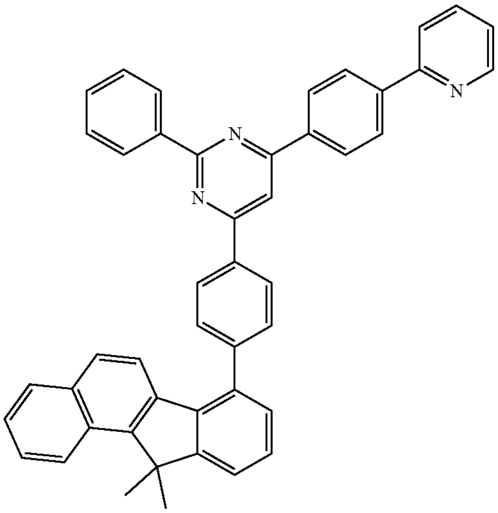
-continued
556
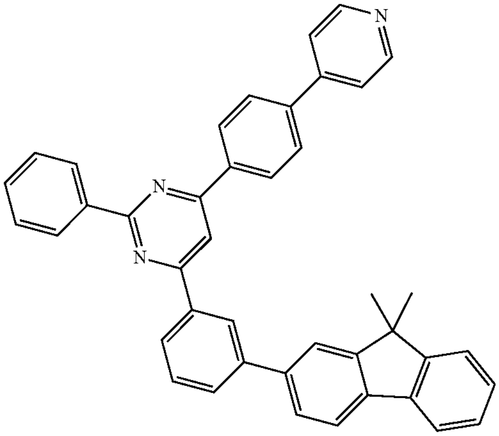
557
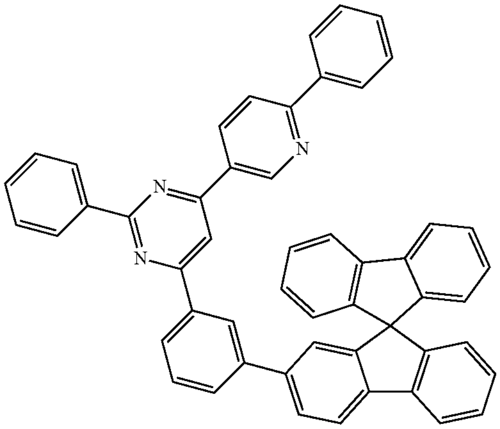
558
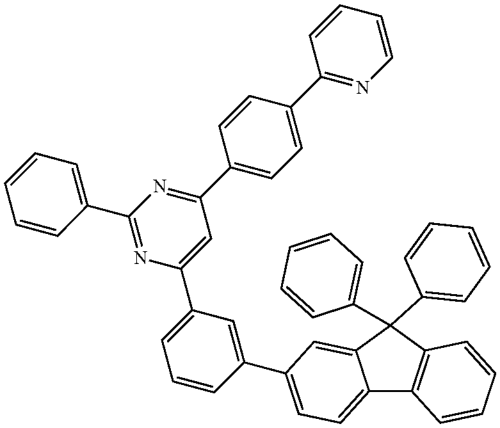

-continued
559
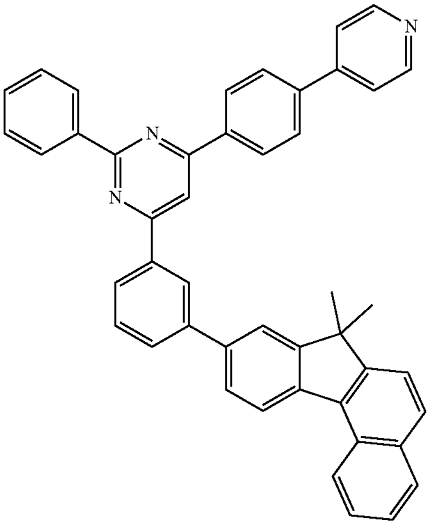
560
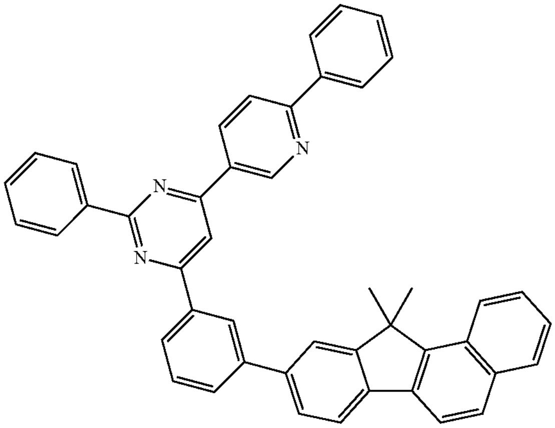
561
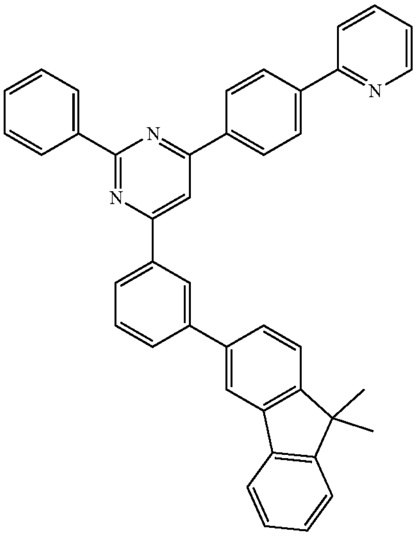
562
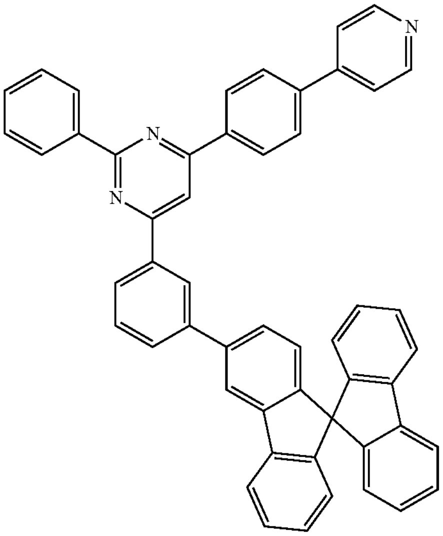
563
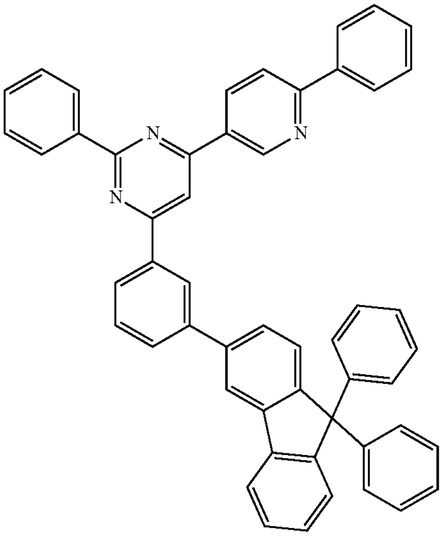
564
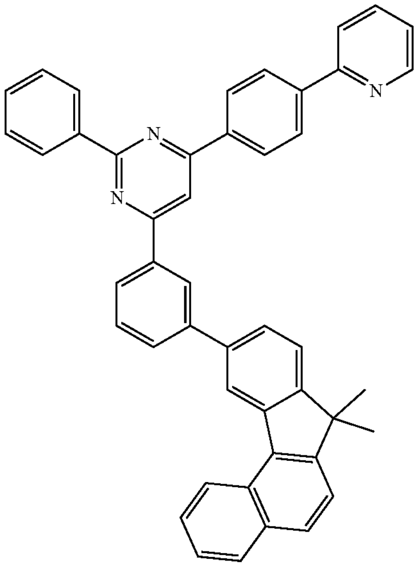

-continued
565
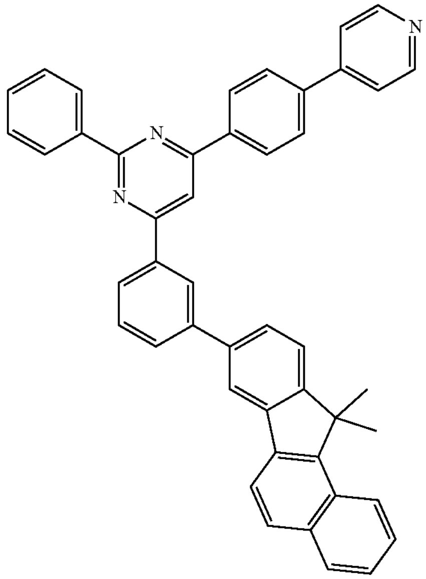
566
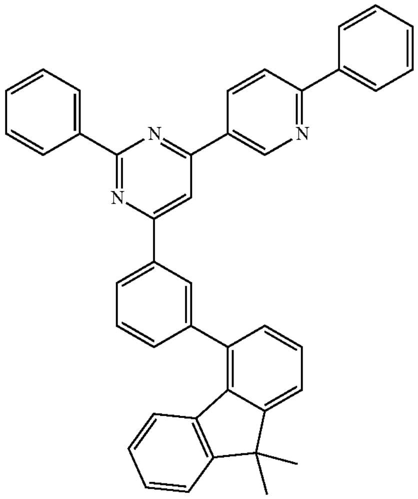
-continued
567
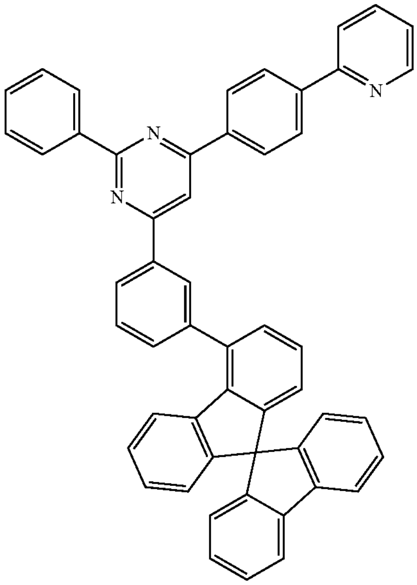
568
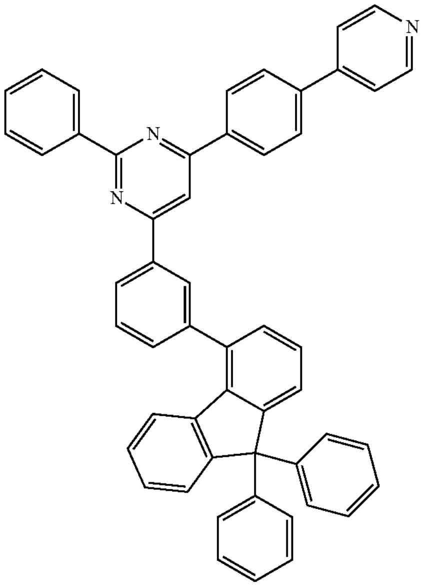
569
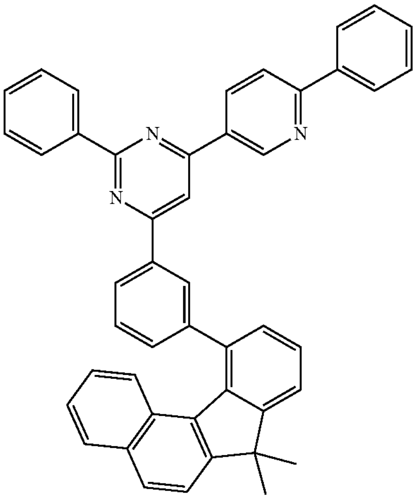

-continued
570
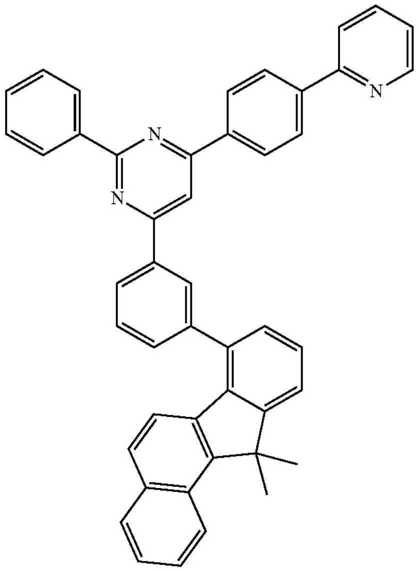
571
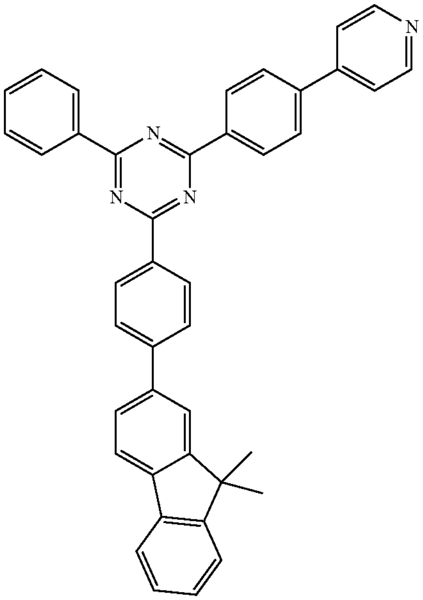
-continued
572
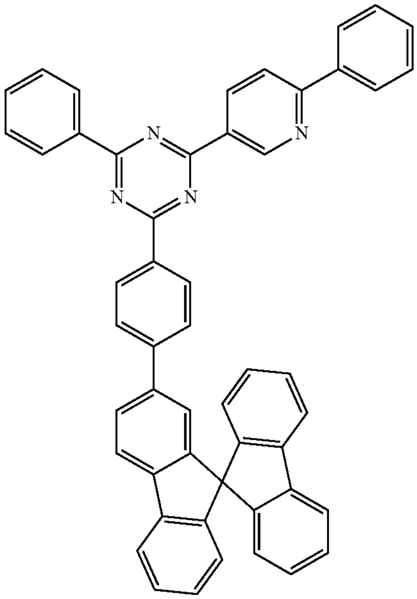
573
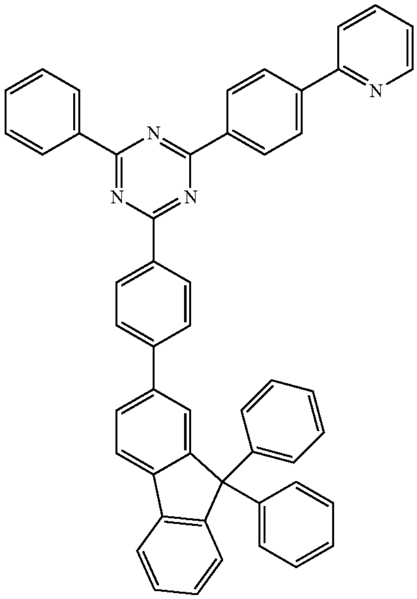

-continued
574
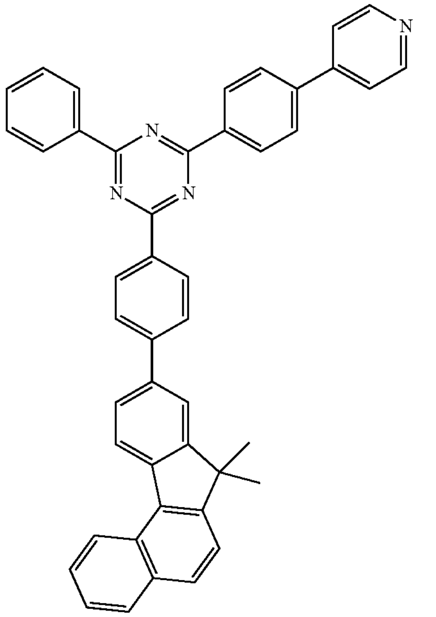
575
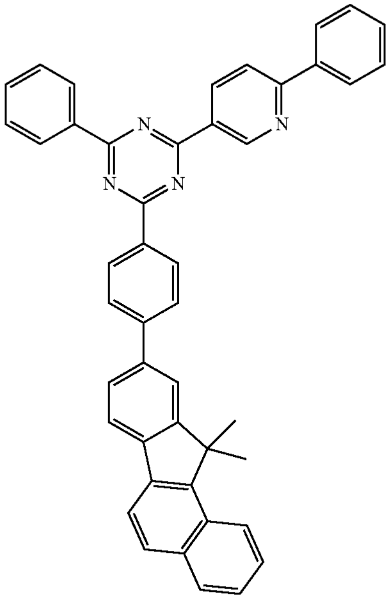
-continued
576
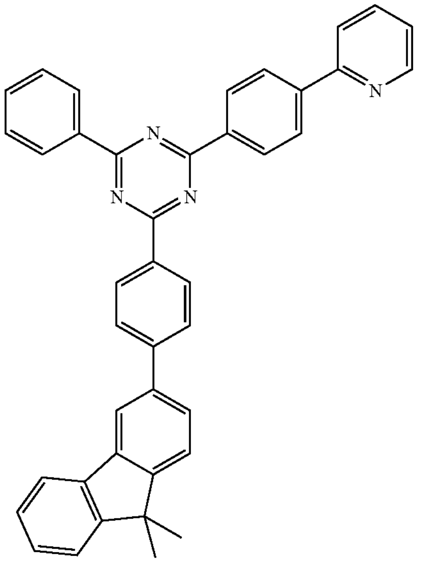
577
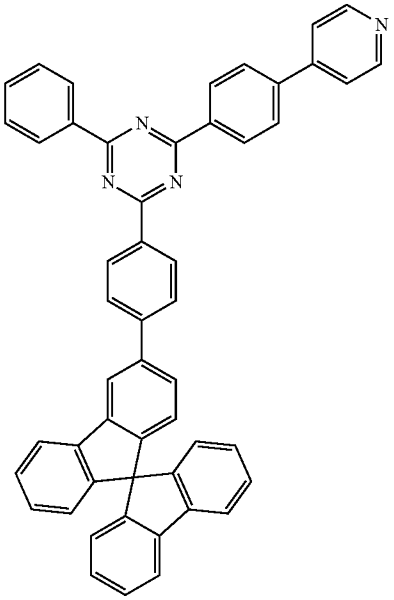

-continued
578
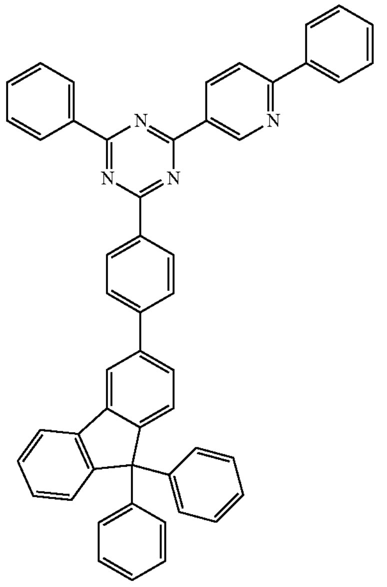
579
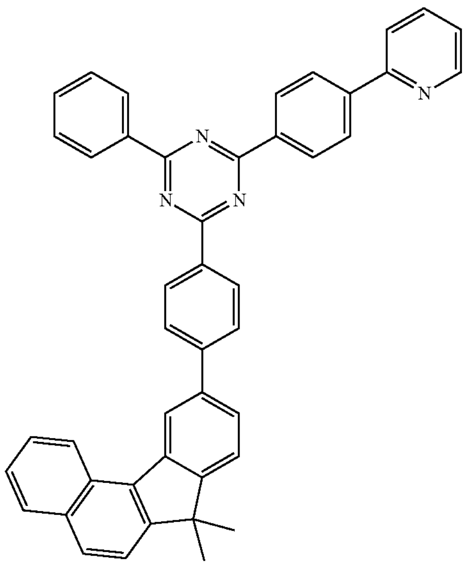
-continued
580
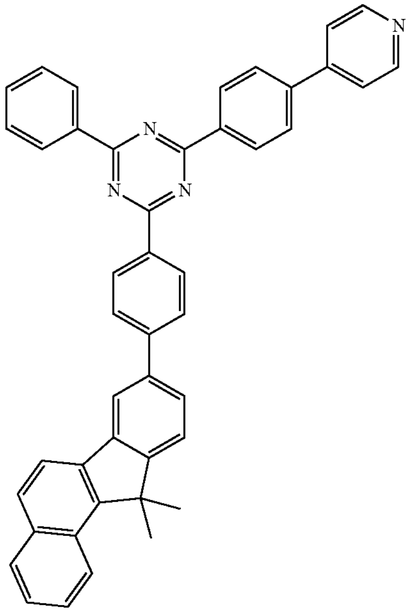
581
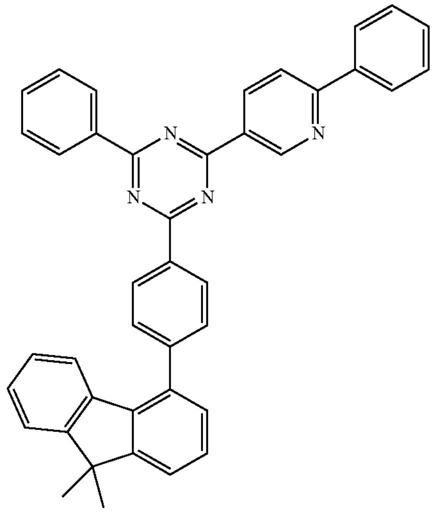

-continued
582
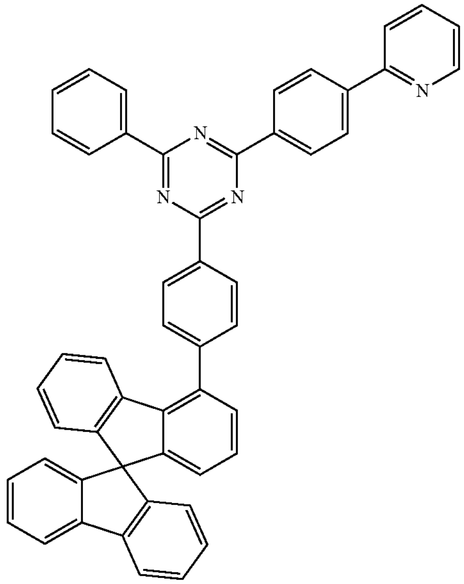
583
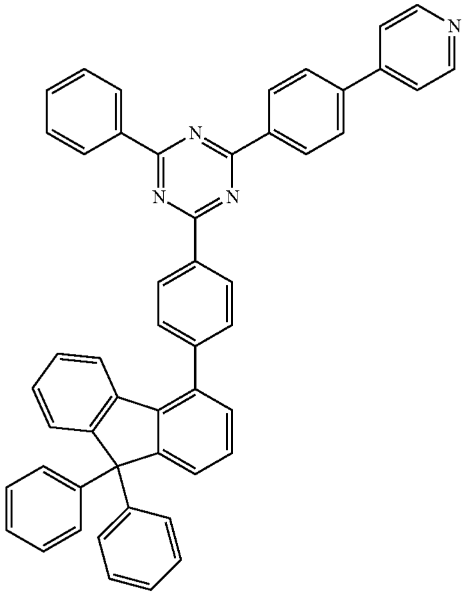
-continued
584
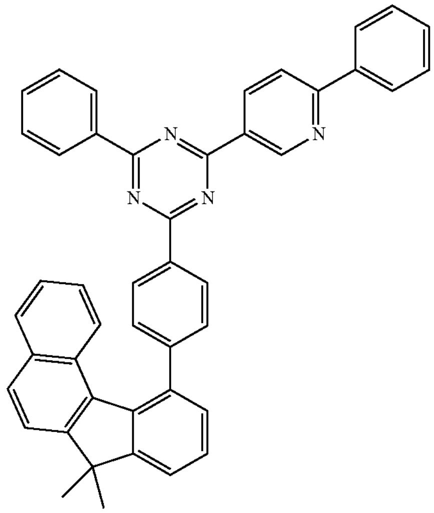
585
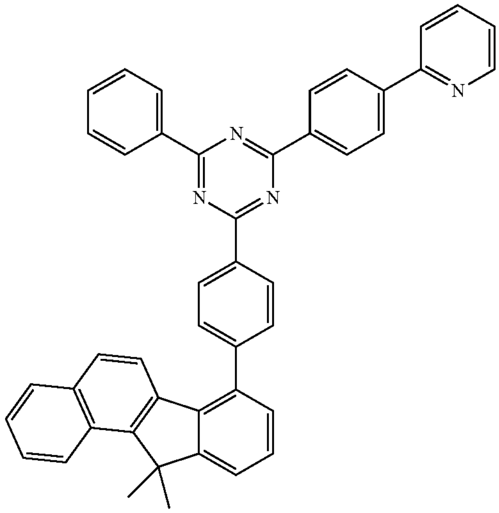
586
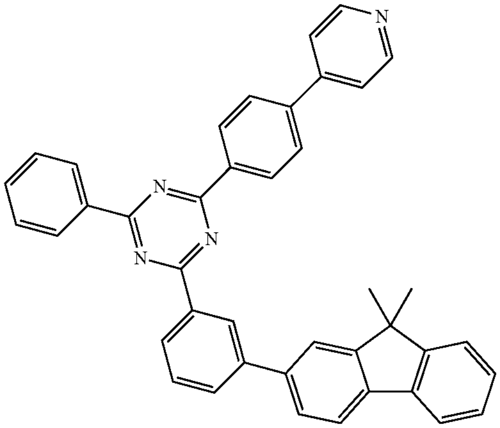

-continued
587
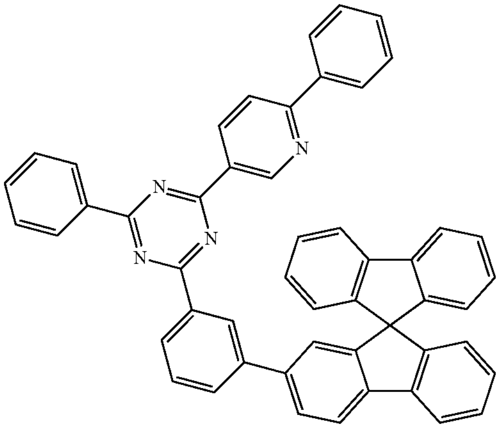
588
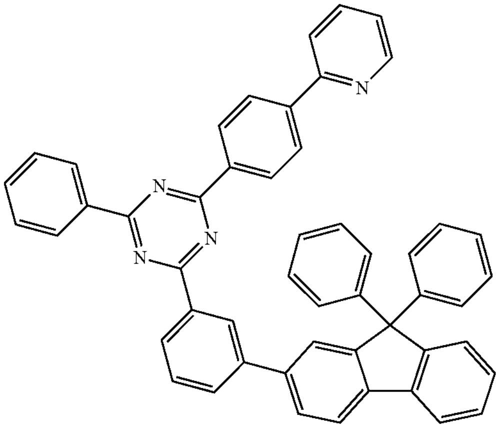
589
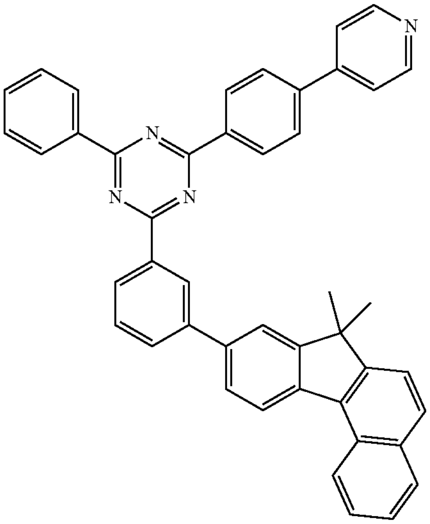
-continued
590
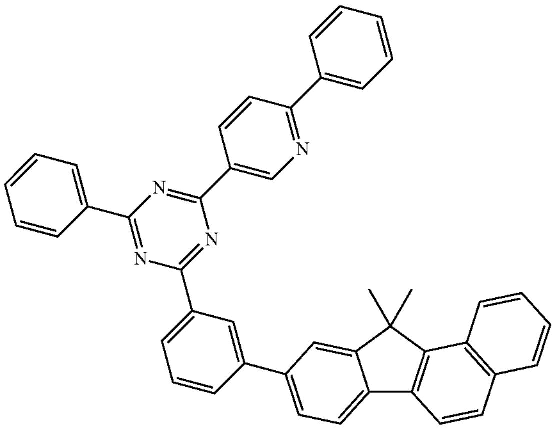
591
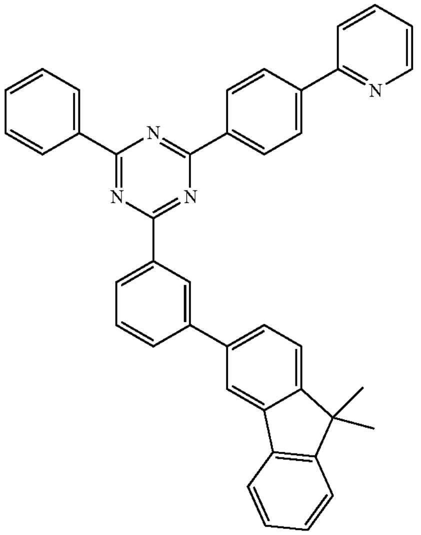
592
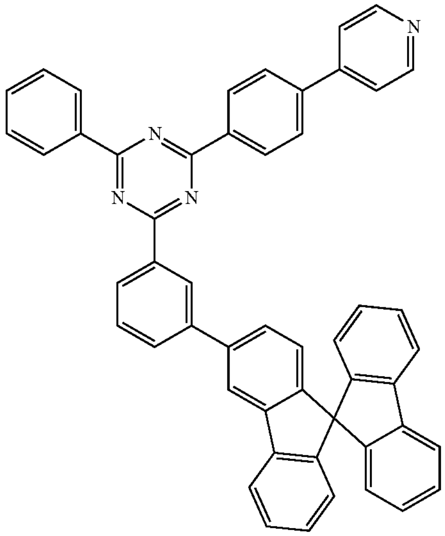

-continued
593
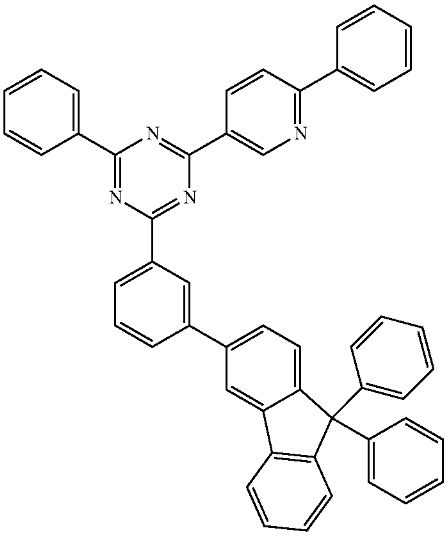
594
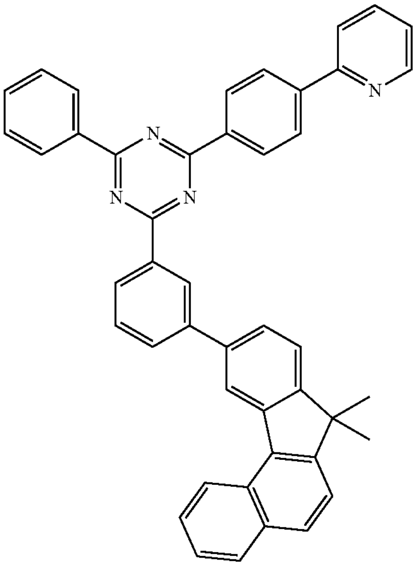
-continued
595
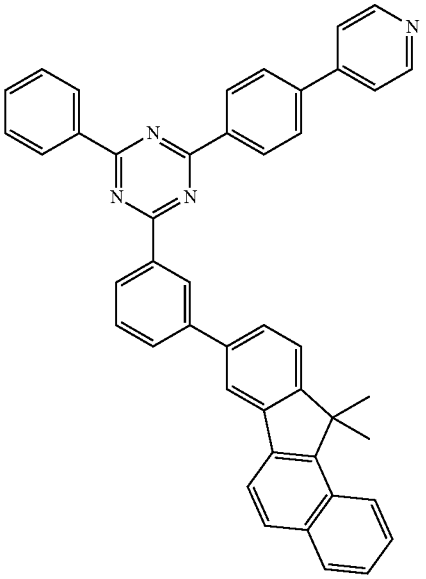
596
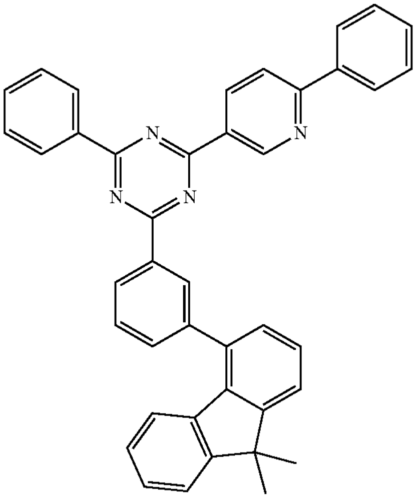
597
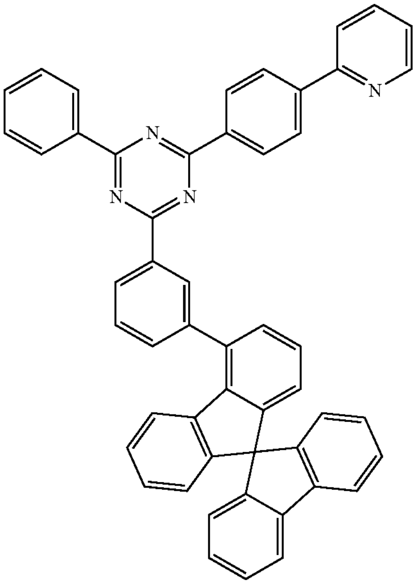

-continued
598
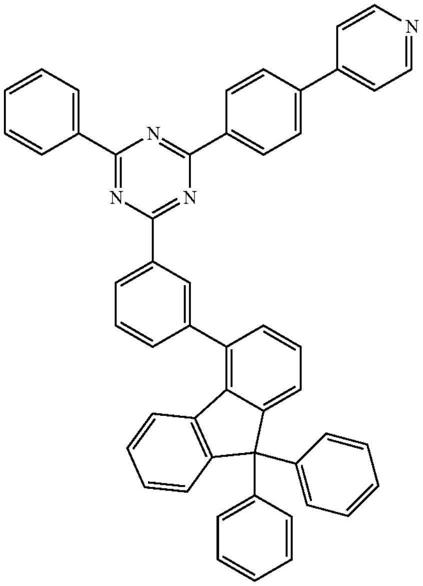
599
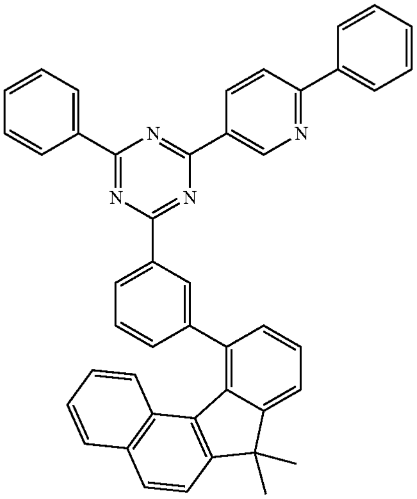
600
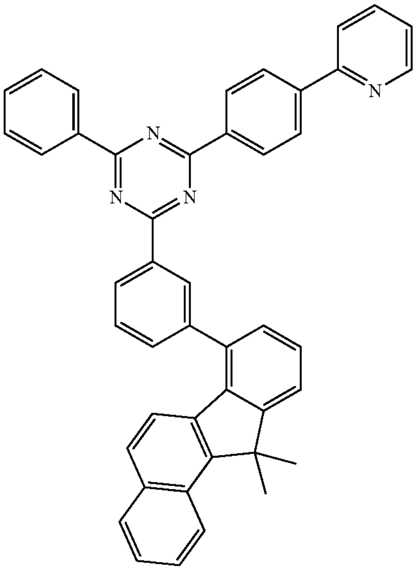
-continued
601
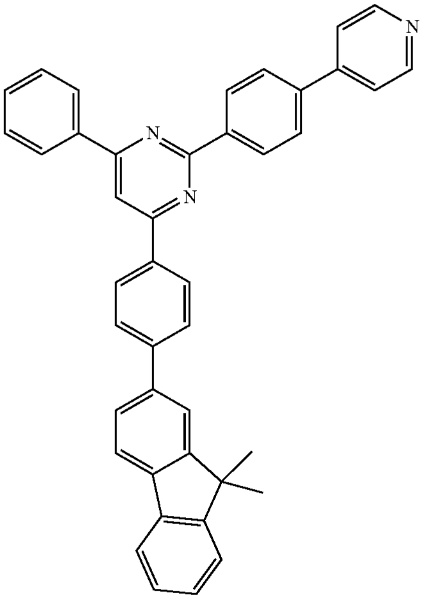
602
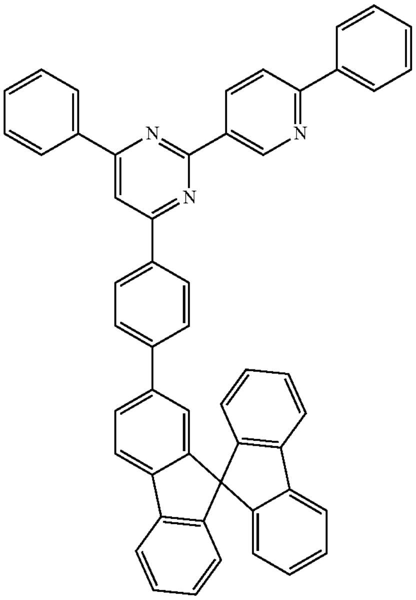

603
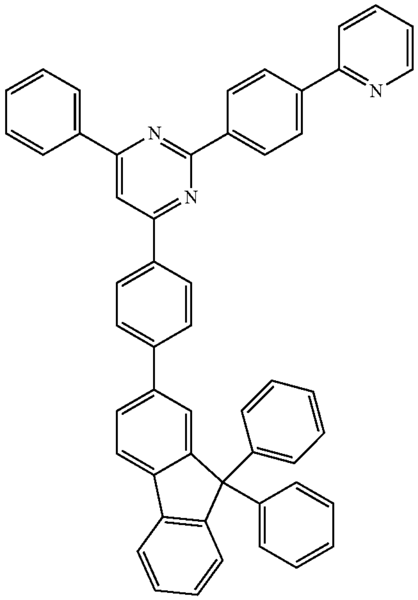
604
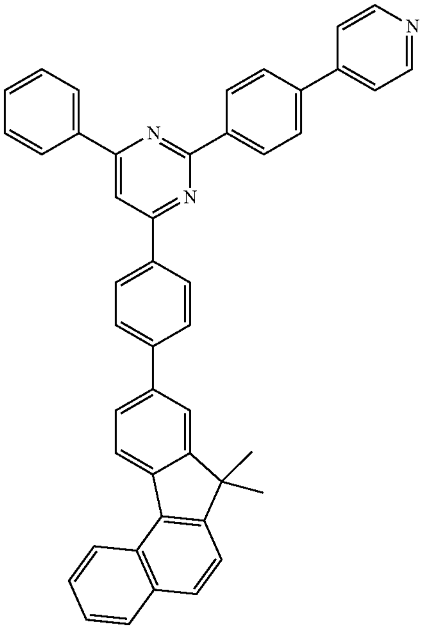
605
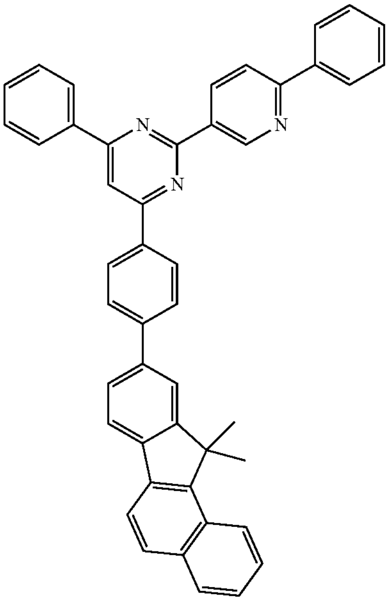
606
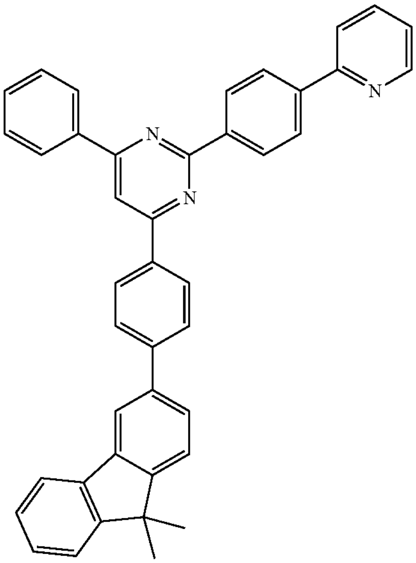

-continued
607
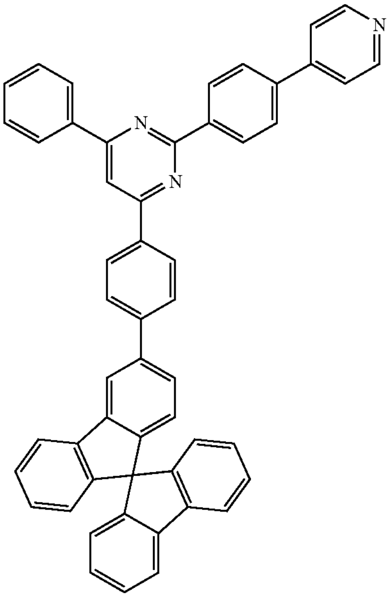
608
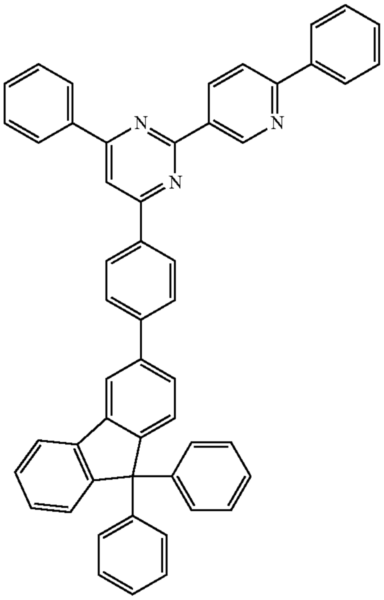
-continued
609
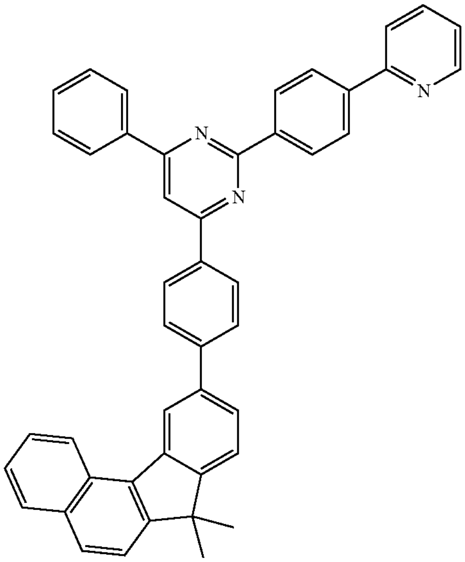
610
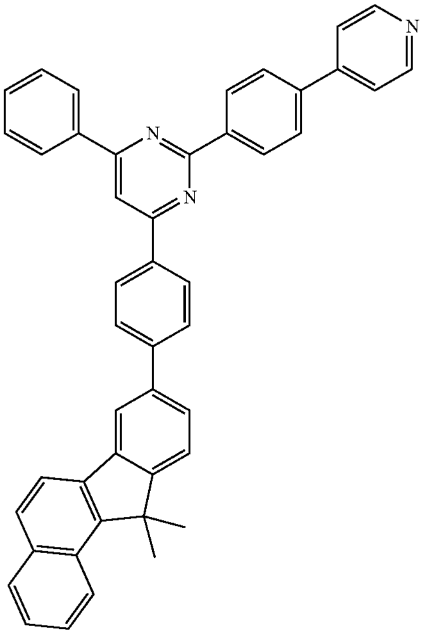

-continued
611
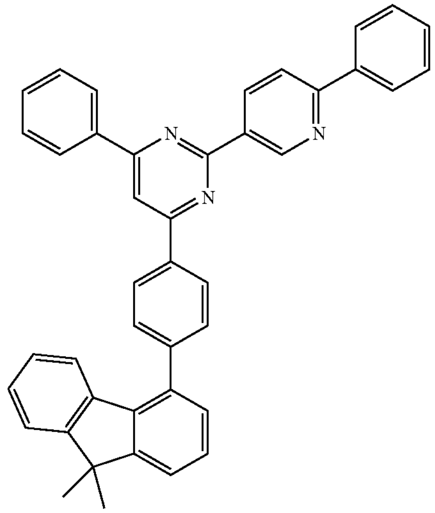
612
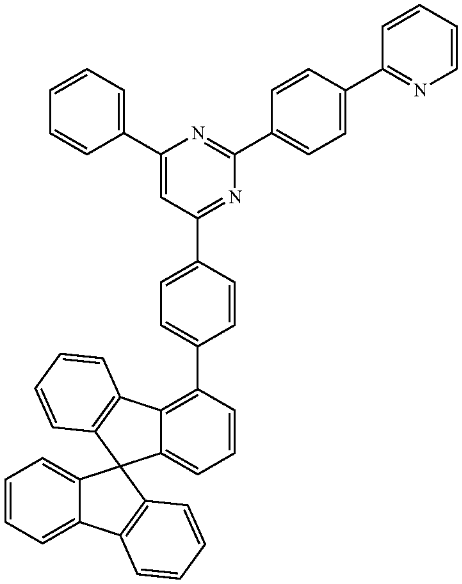
-continued
613
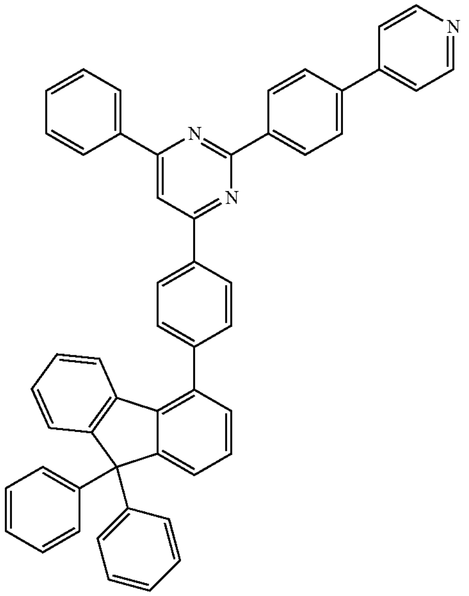
614
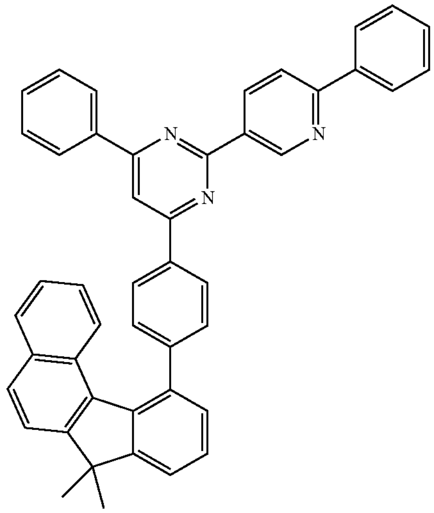
615
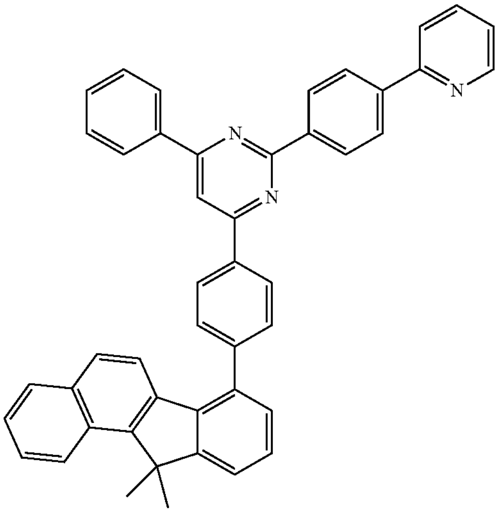

-continued
616
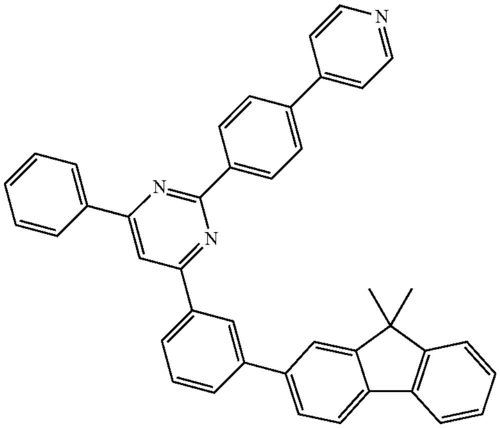
617
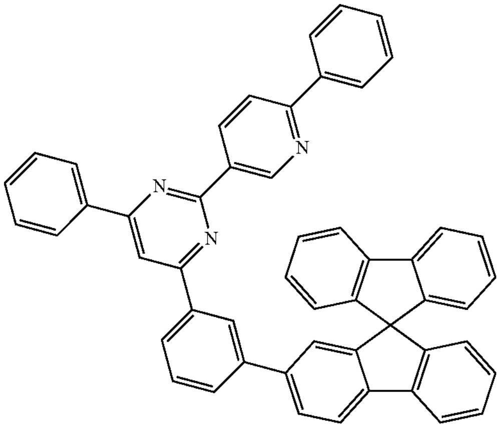
618
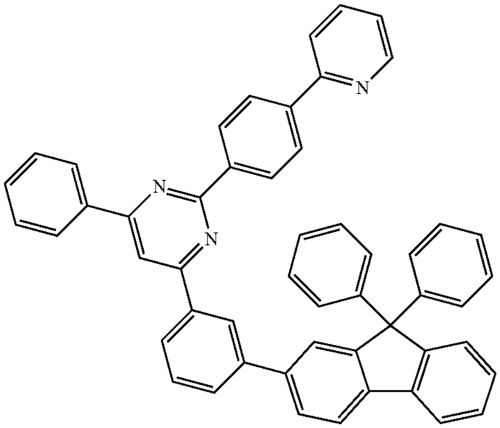
-continued
619
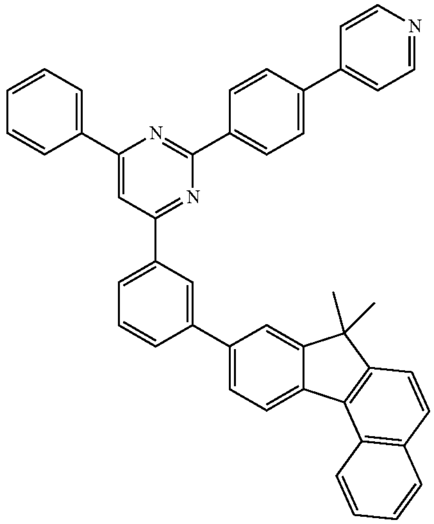
620
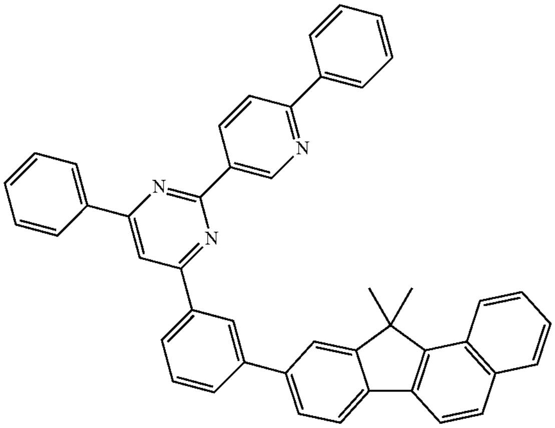
621
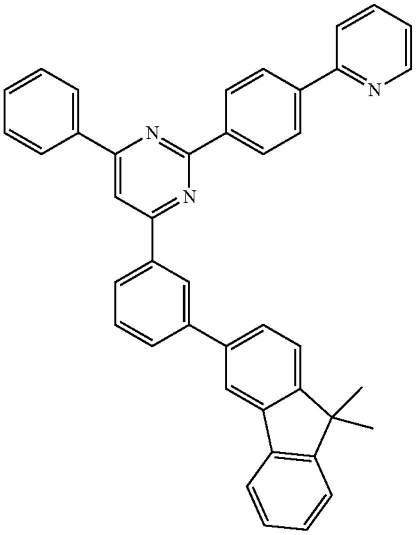

-continued
622
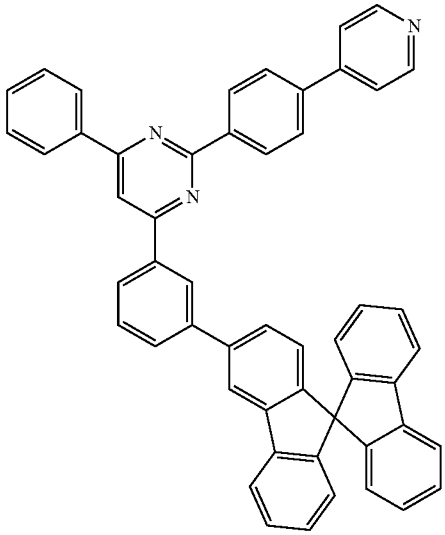
623
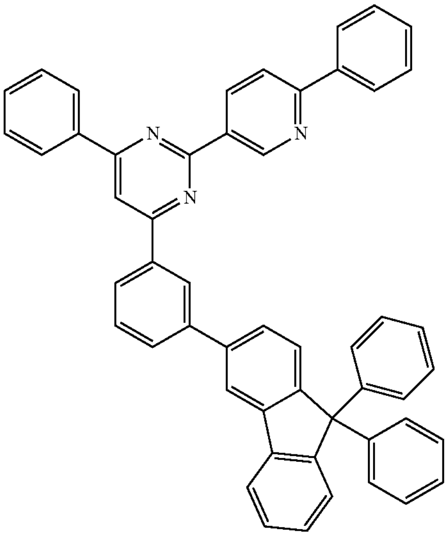
624
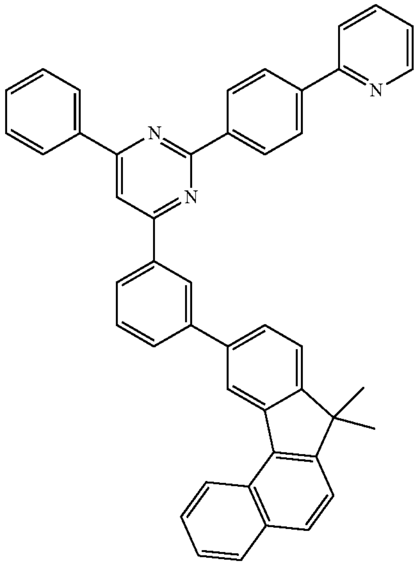
-continued
625
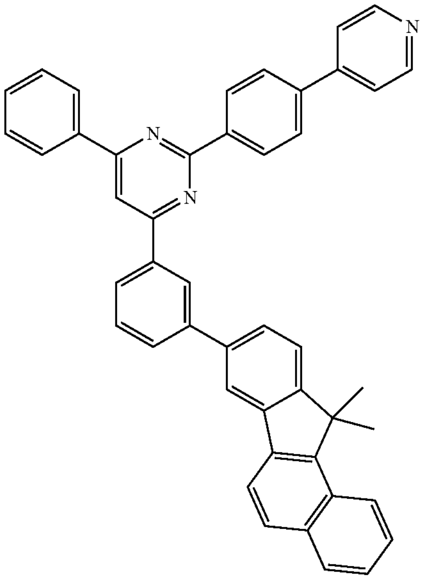
626
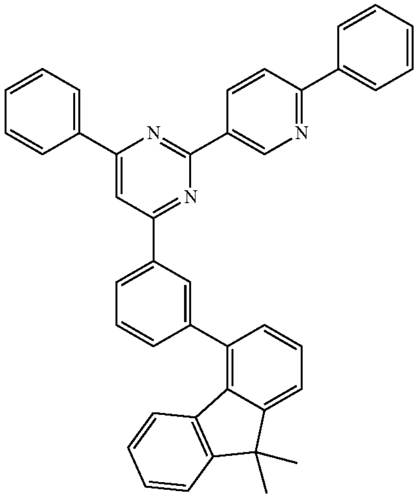
627
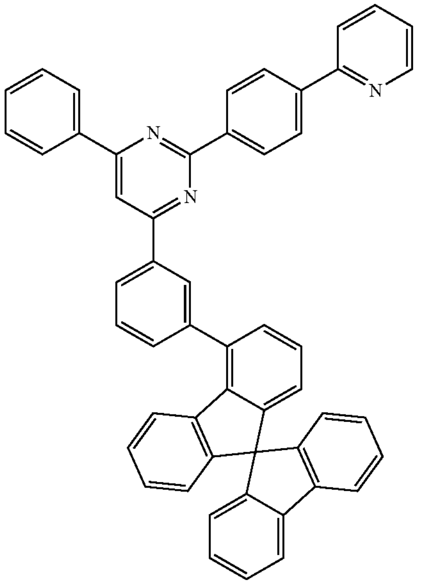

-continued
628
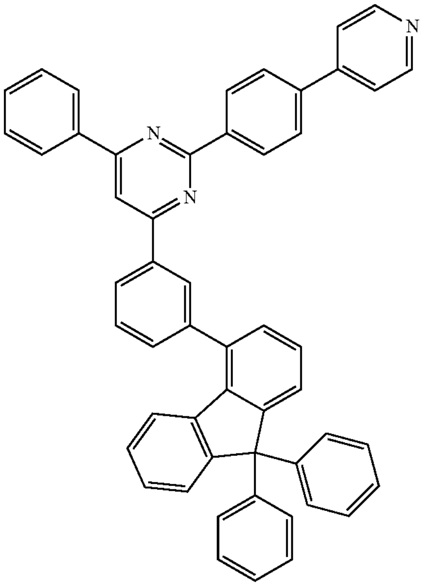
629
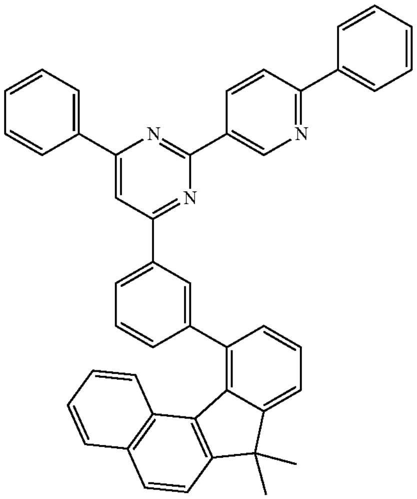
630
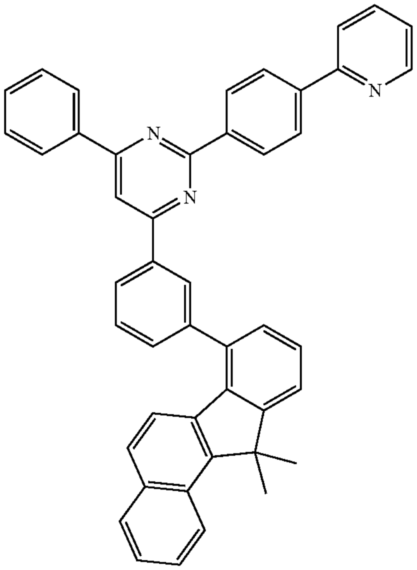
-continued
631
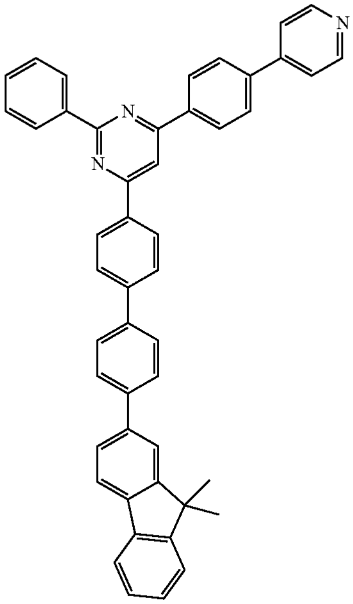
632
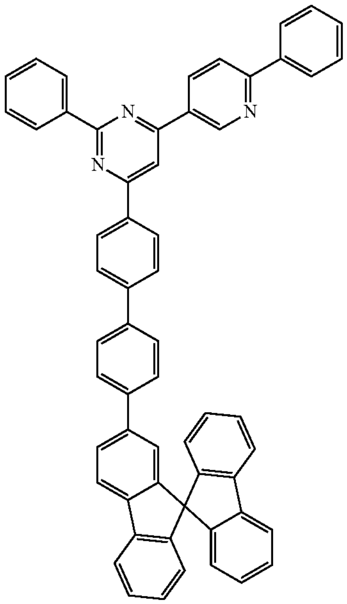

-continued
633
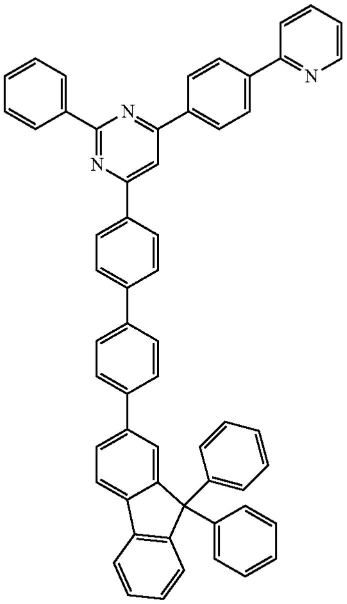
634
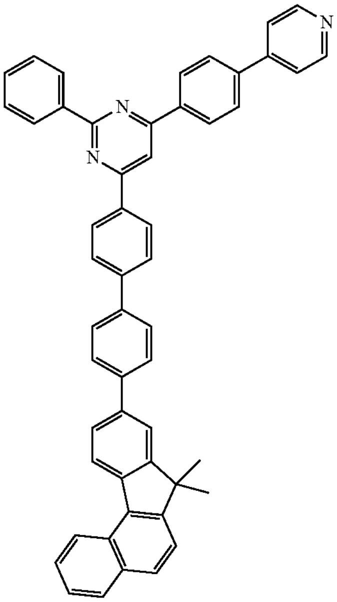
-continued
635
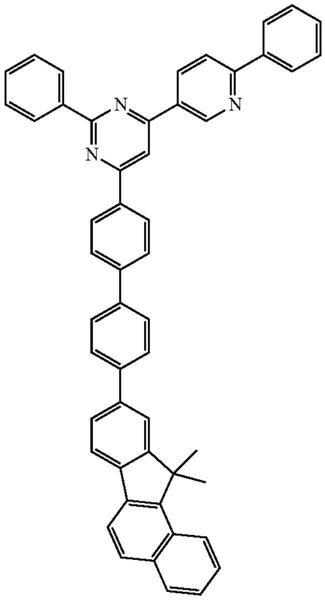
636
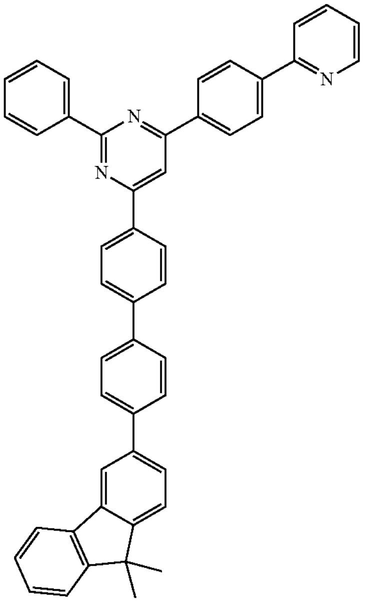

637
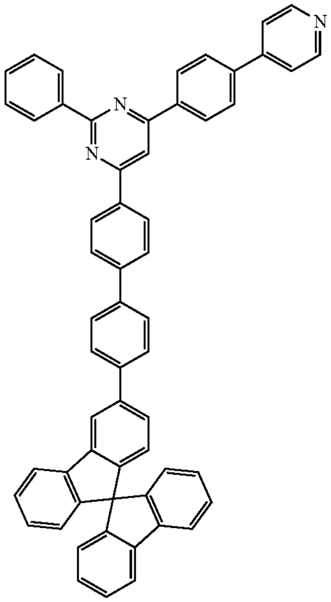
638
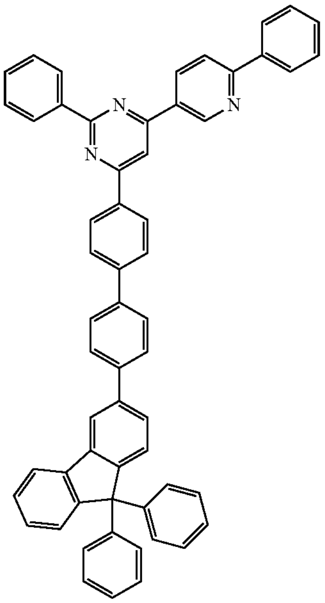
639
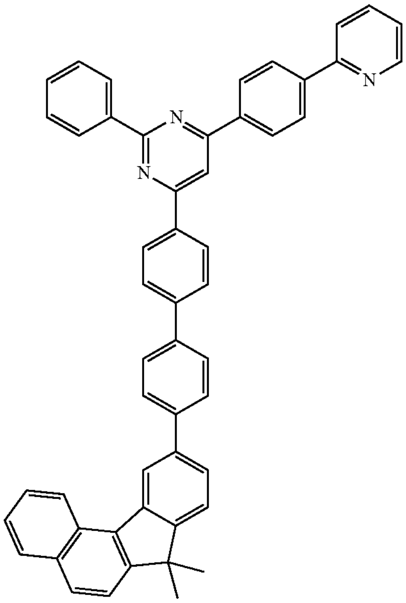
640
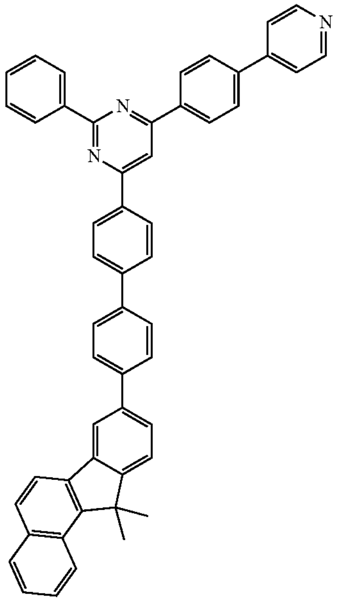

-continued
641
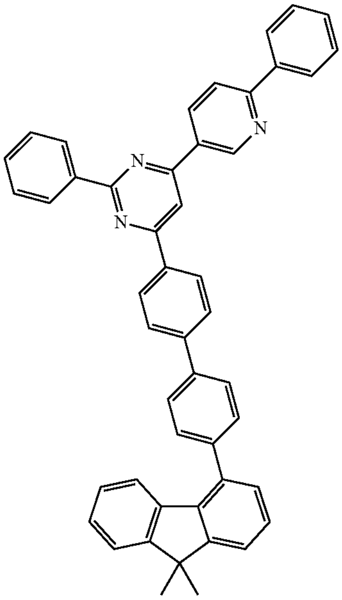
642
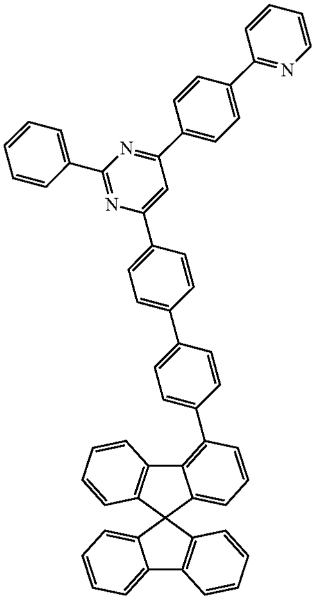
-continued
643
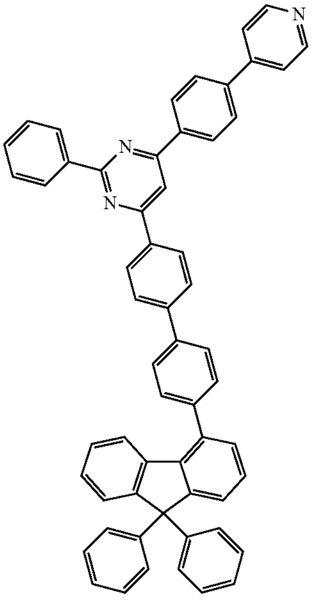
644
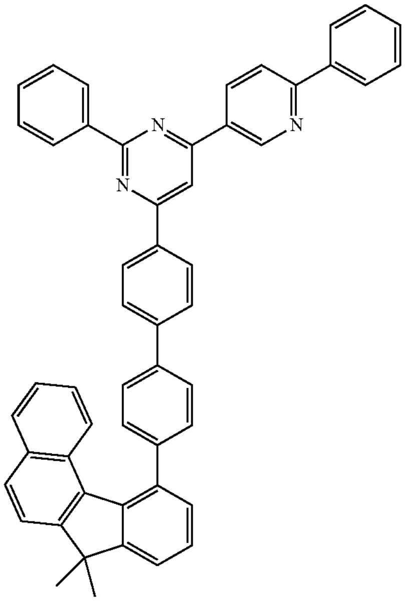

-continued
645
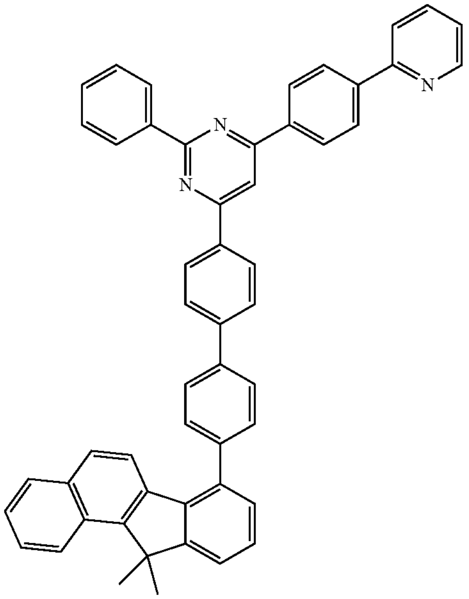
646
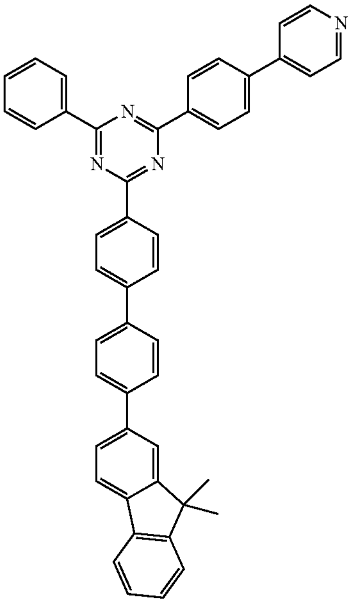
-continued
647
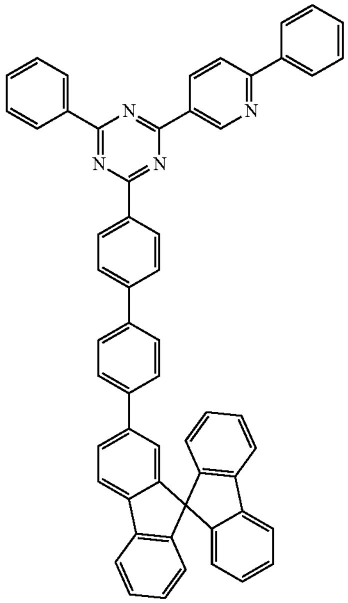
648
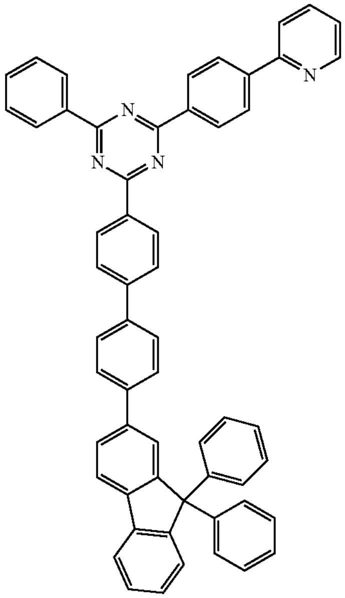

-continued
649
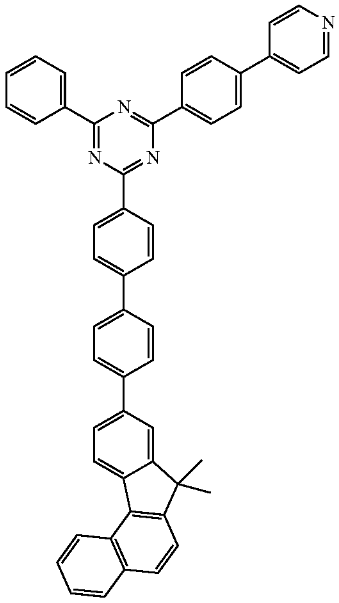
650
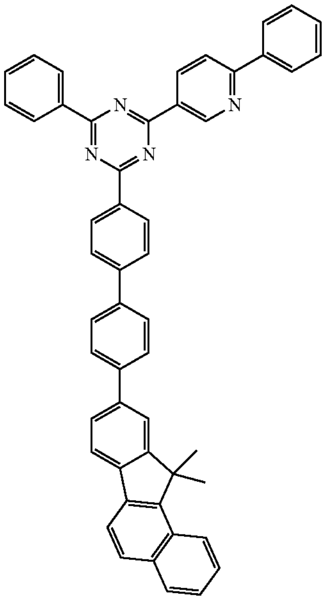
-continued
651
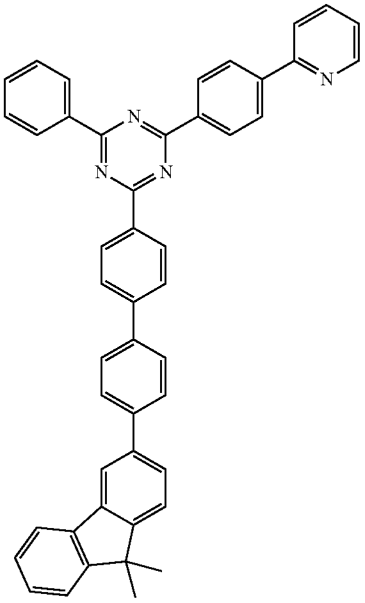
652
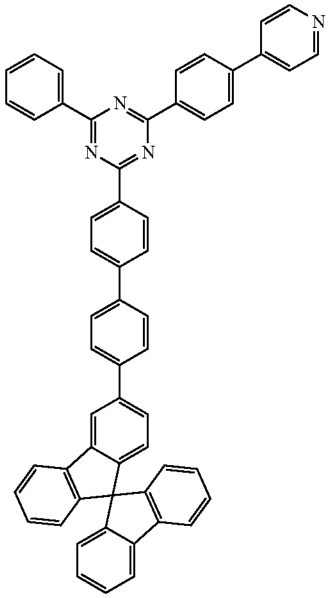

-continued
653
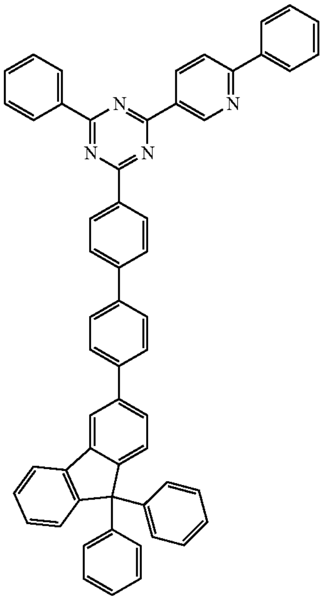
654
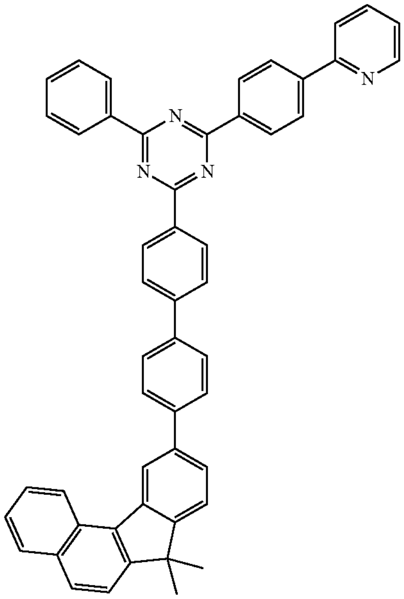
-continued
655
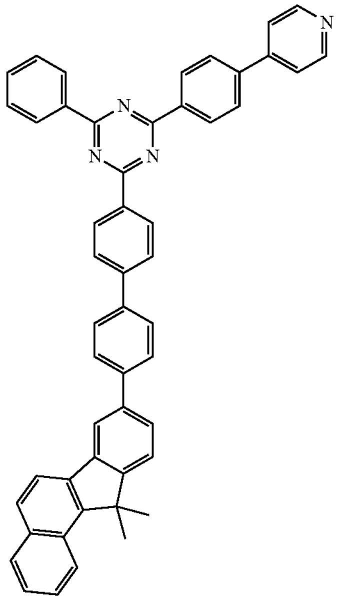
656
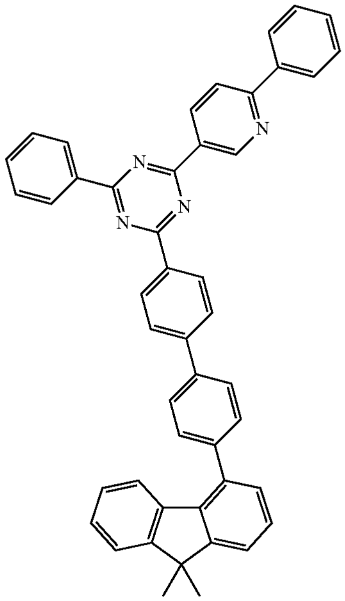

-continued
657
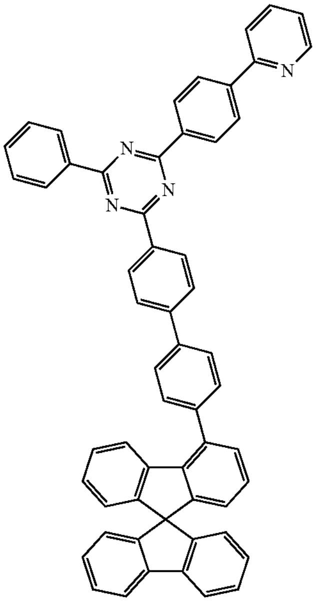
658
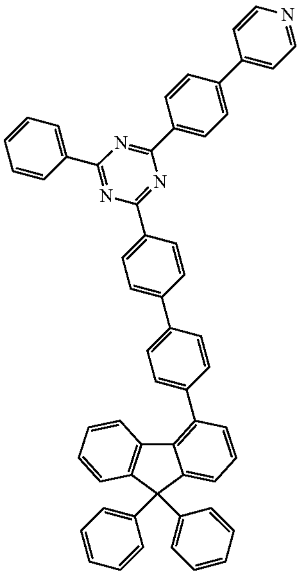
-continued
659
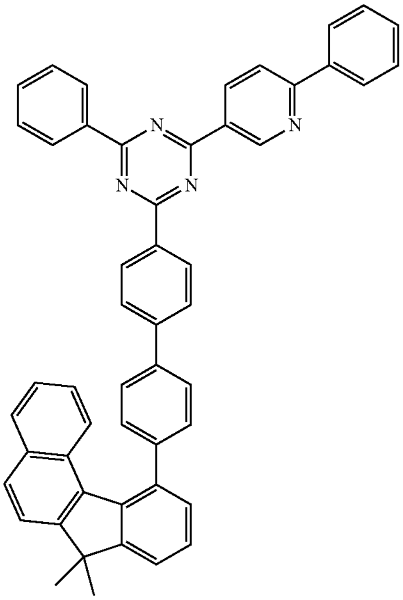
660
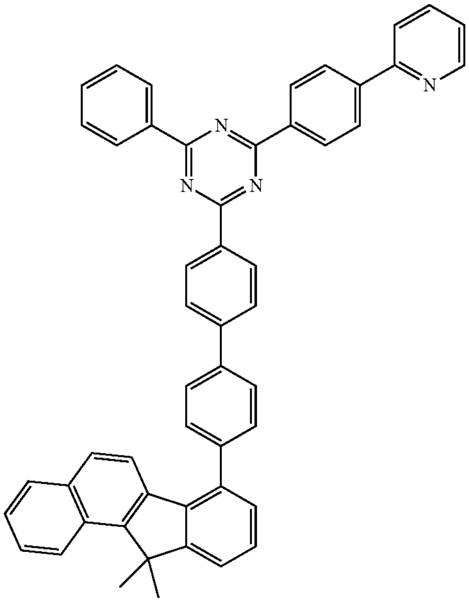

-continued
661
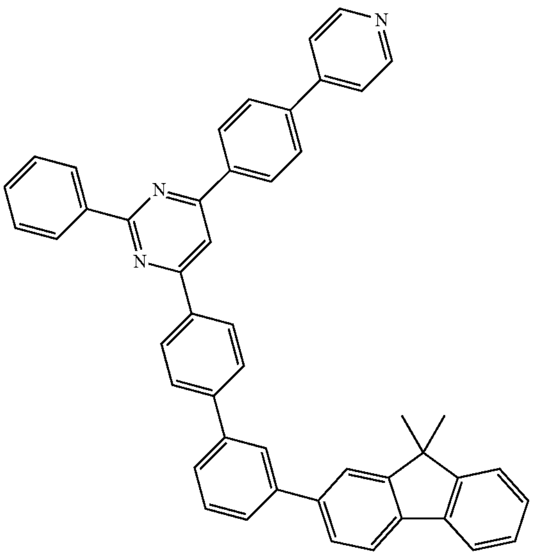
662
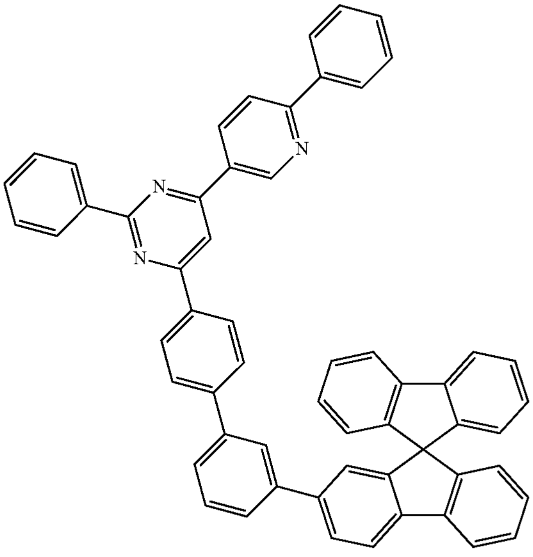
-continued
663
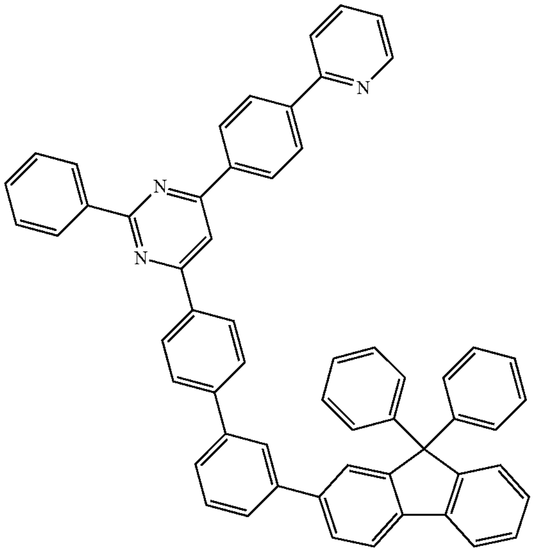
664
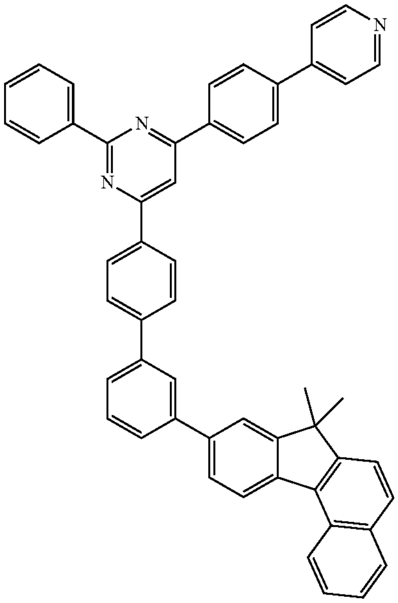

-continued
665
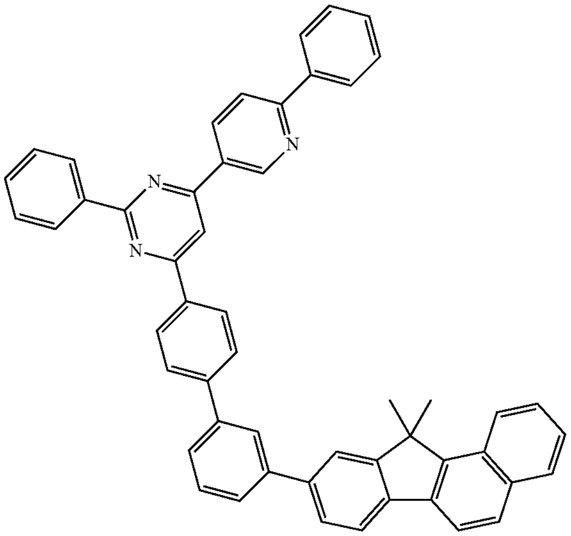
666
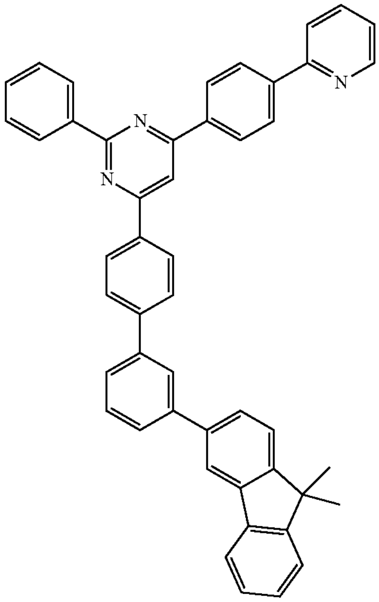
-continued
667
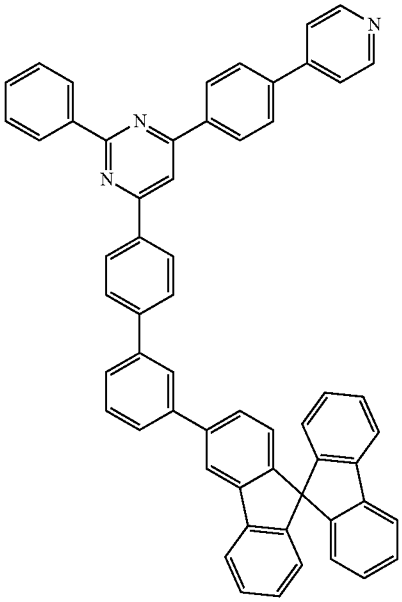
668
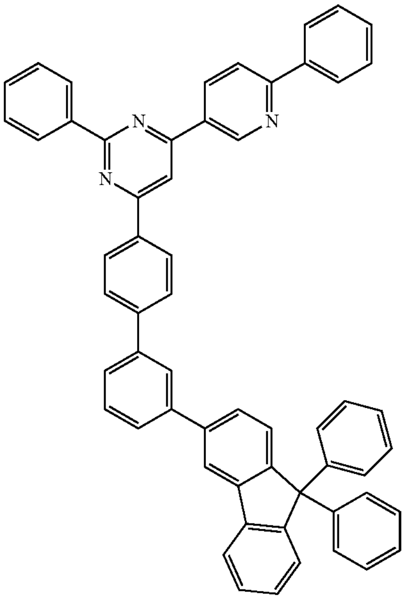

-continued
669
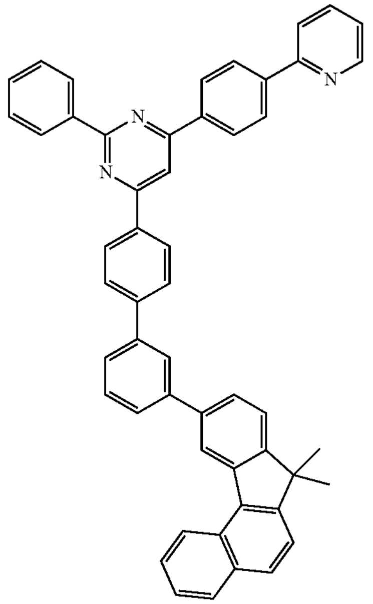
670
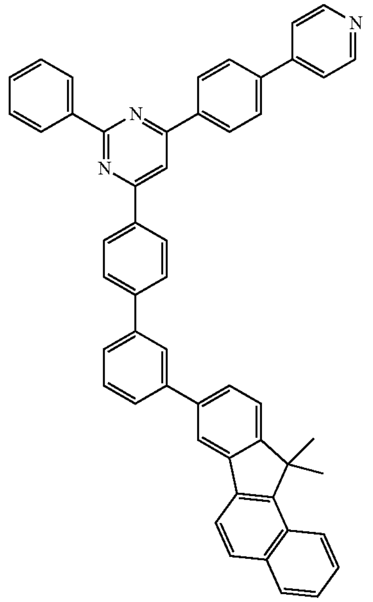
-continued
671
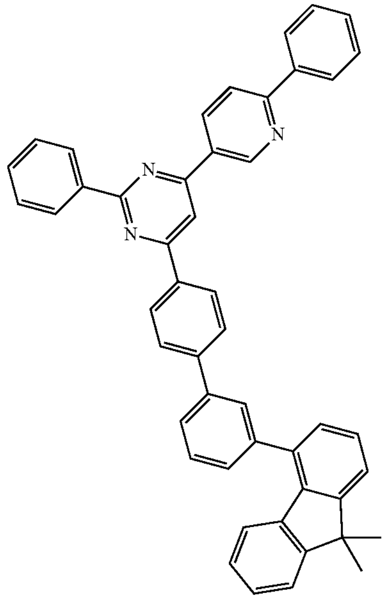
672
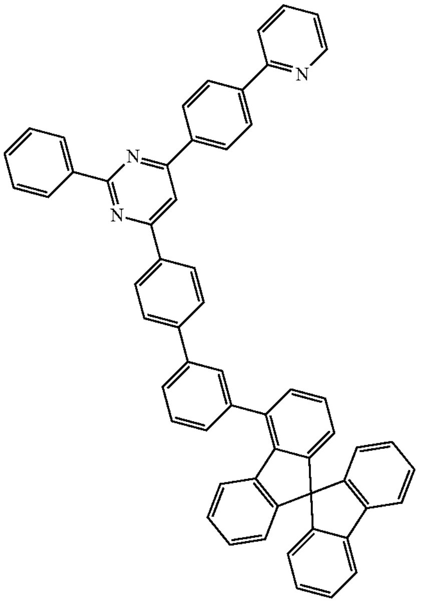

-continued
673
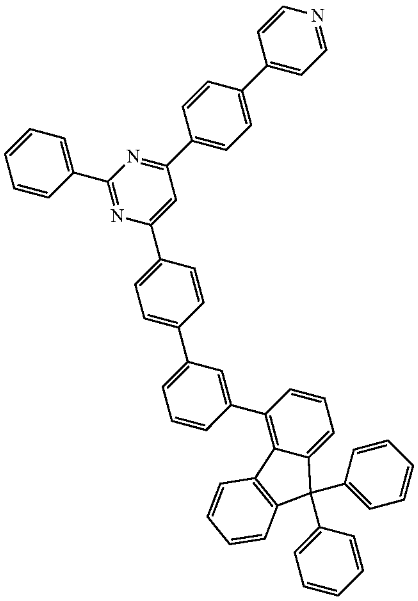
674
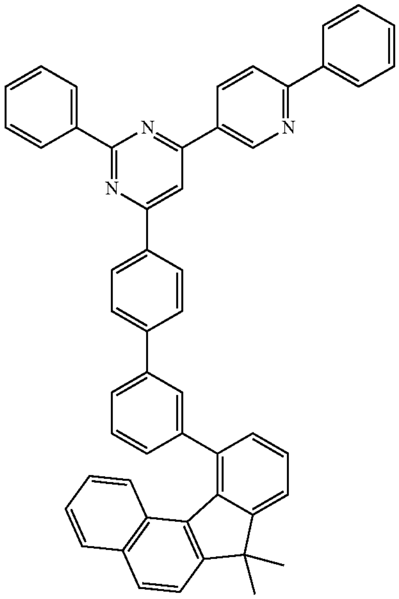
-continued
675
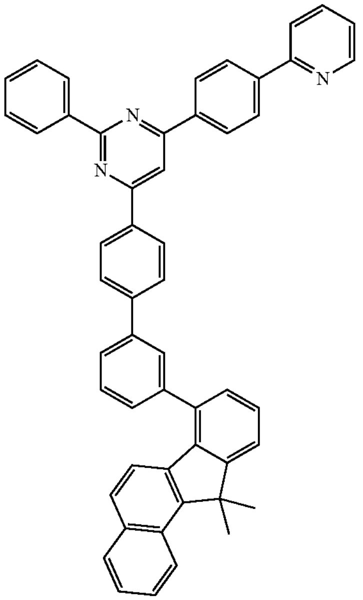
676
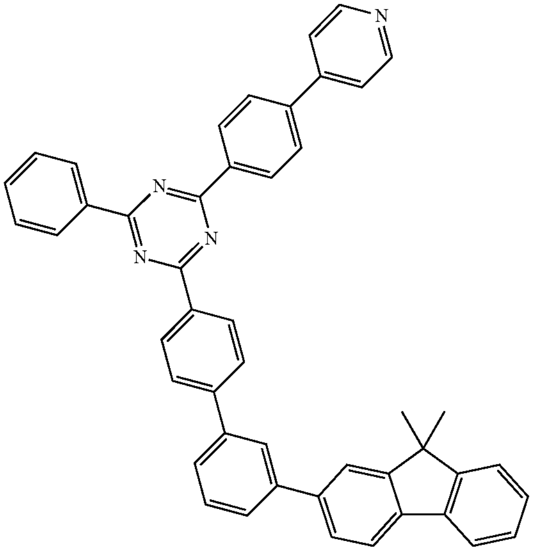

-continued
677
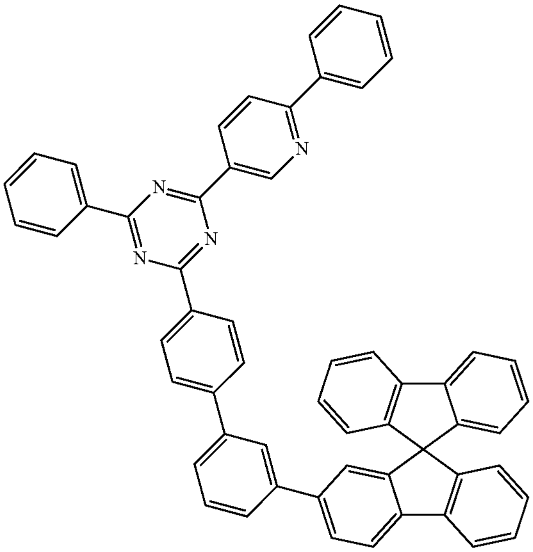
678
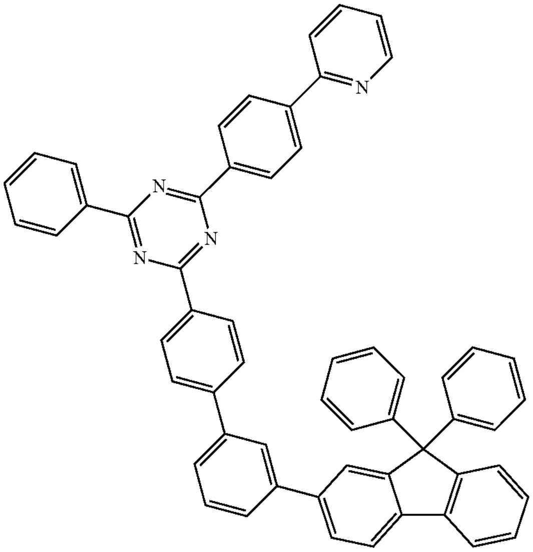
-continued
679
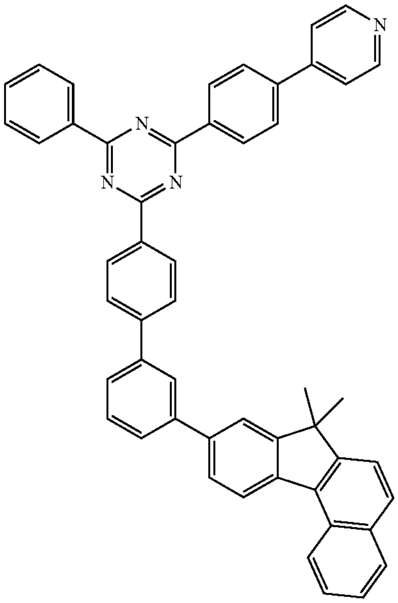
680
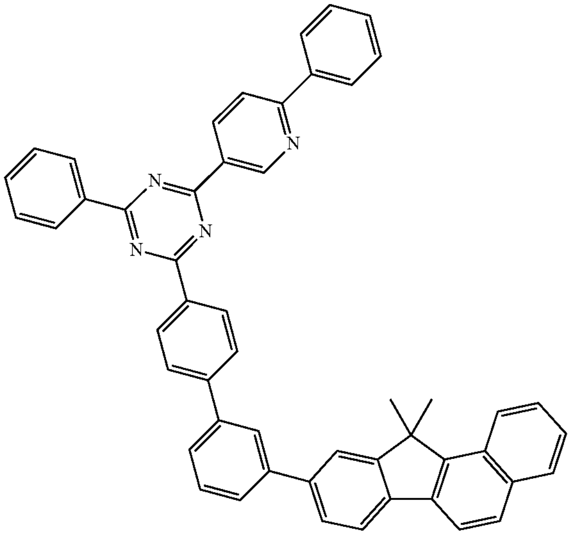

-continued
681
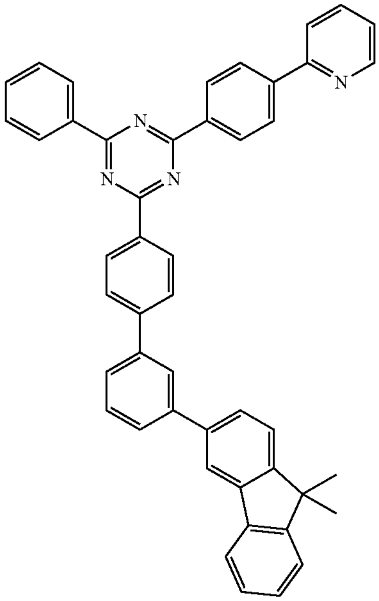
682
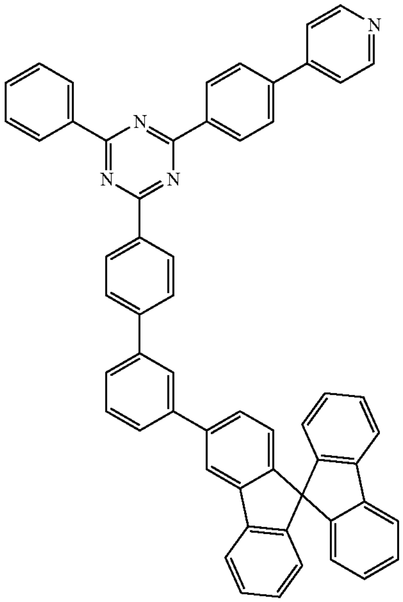
-continued
683
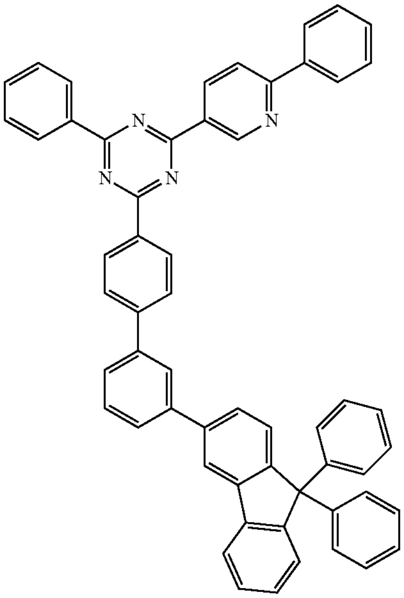
684
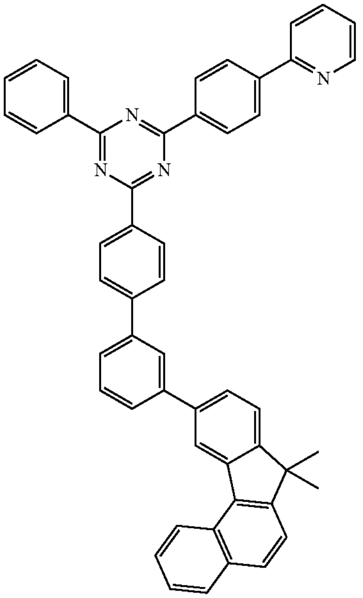

-continued
685
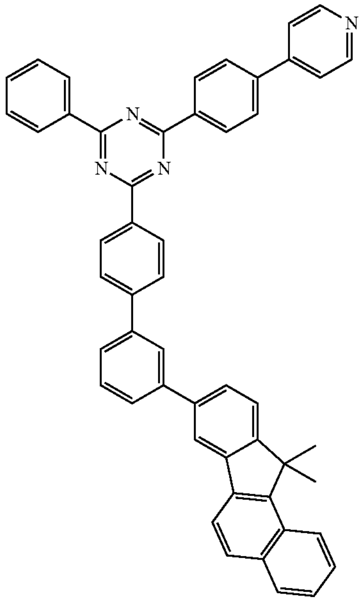
686
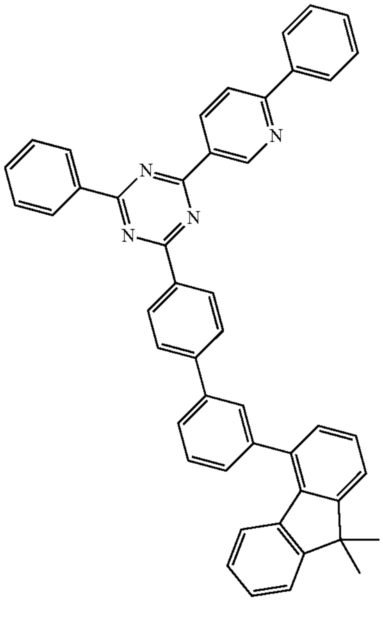
-continued
687
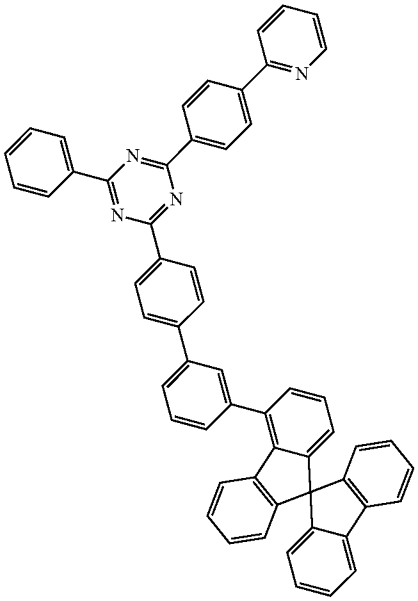
688
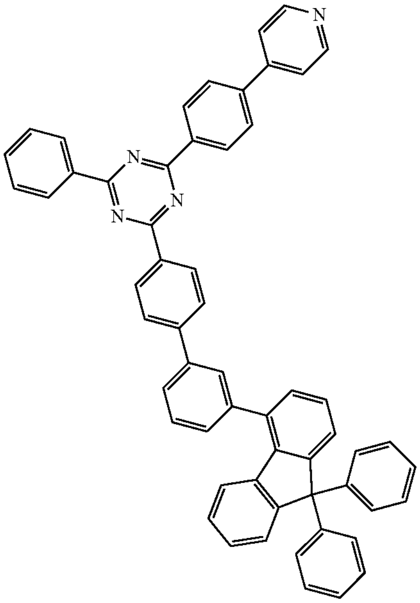

-continued
689
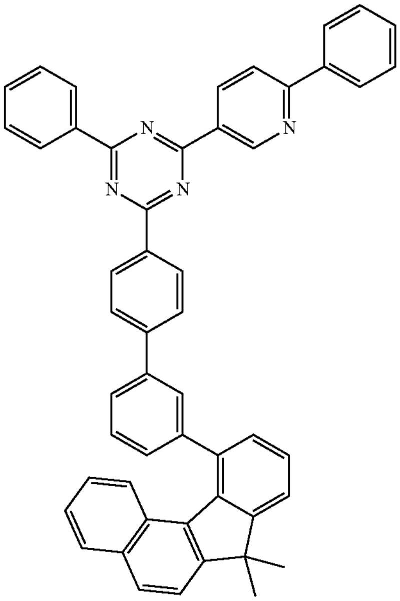
690
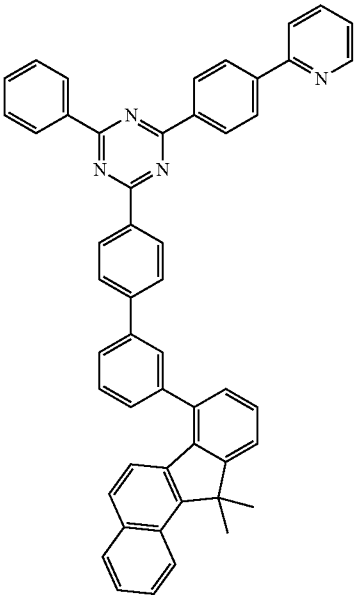
-continued
691
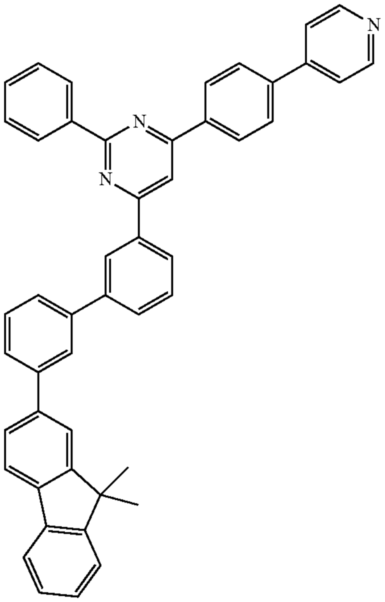
692
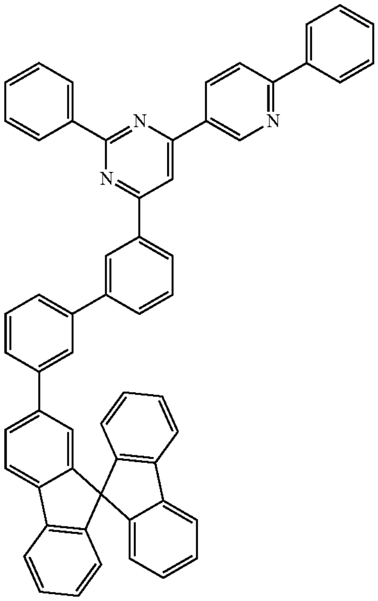

-continued
693
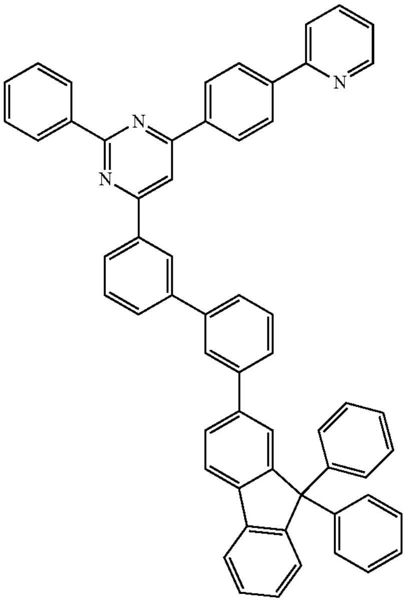
694
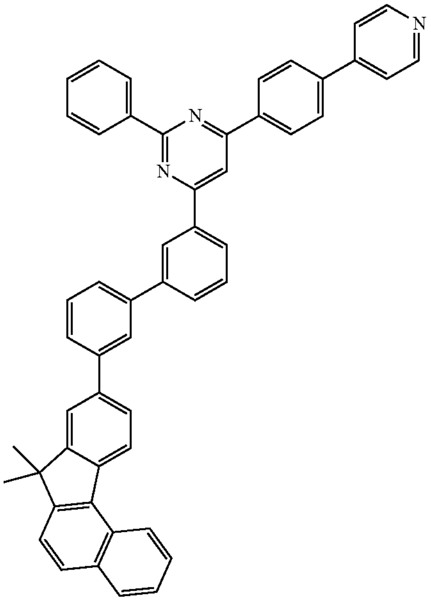
-continued
695
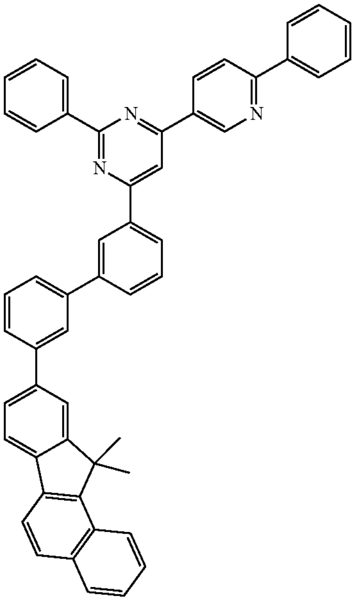
696
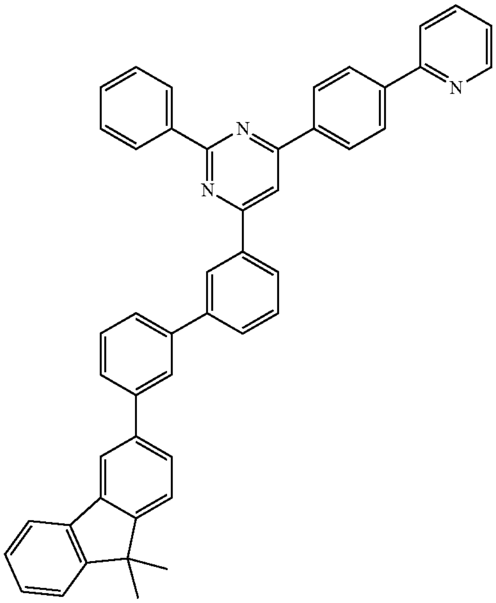

697
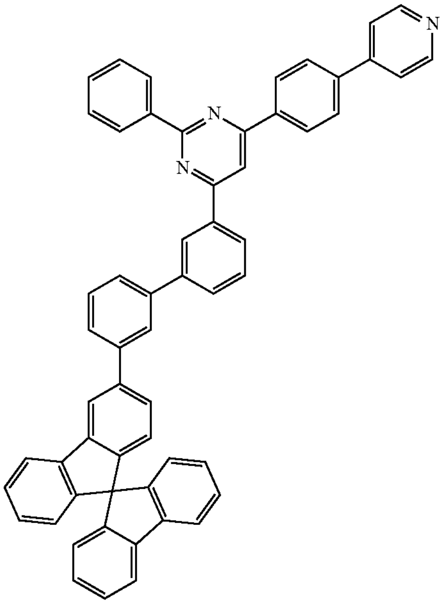
699
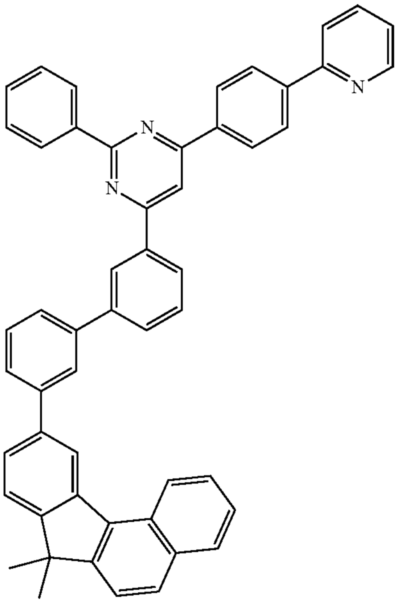
698
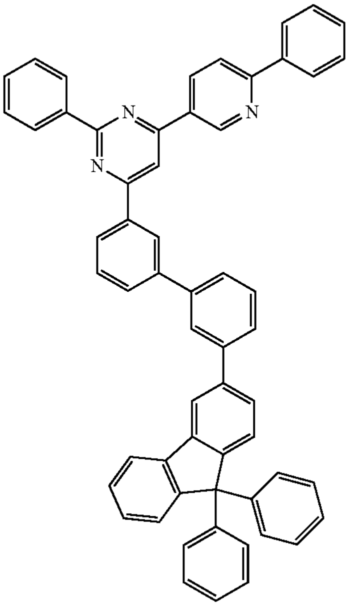
700
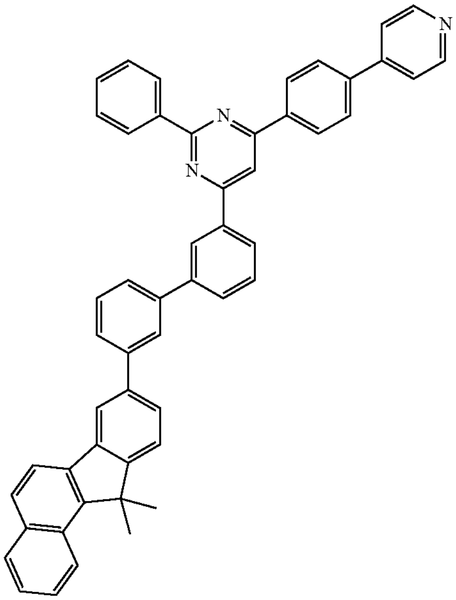

-continued
701
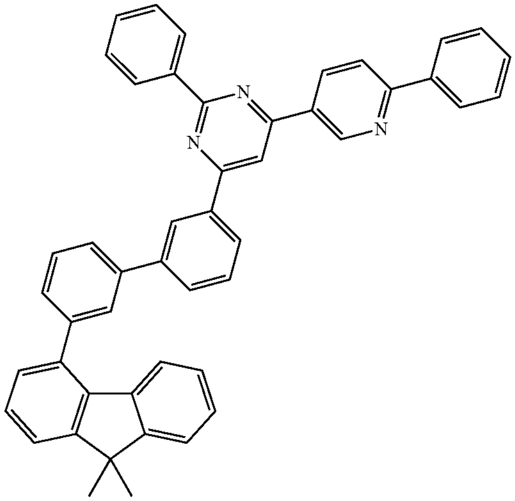
702
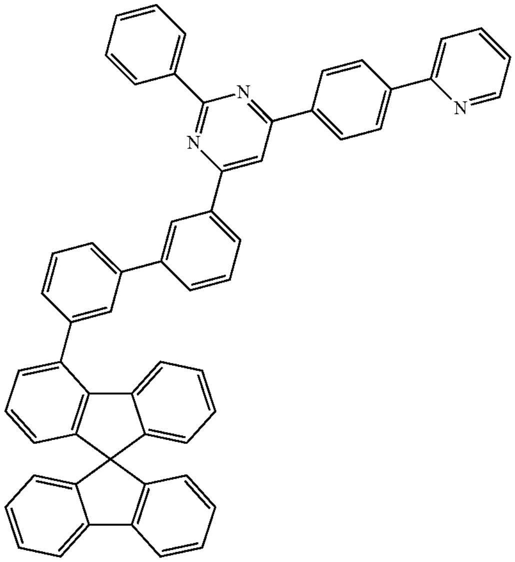
-continued
703
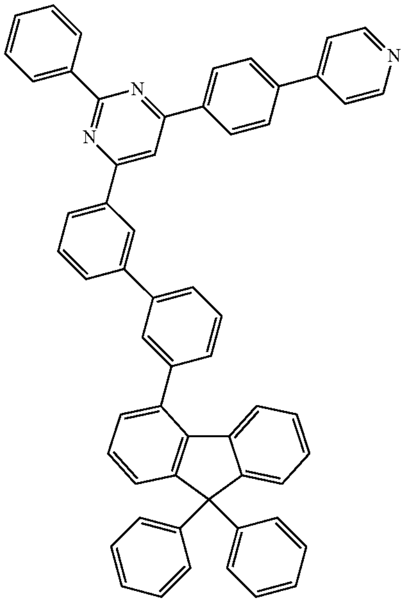
704
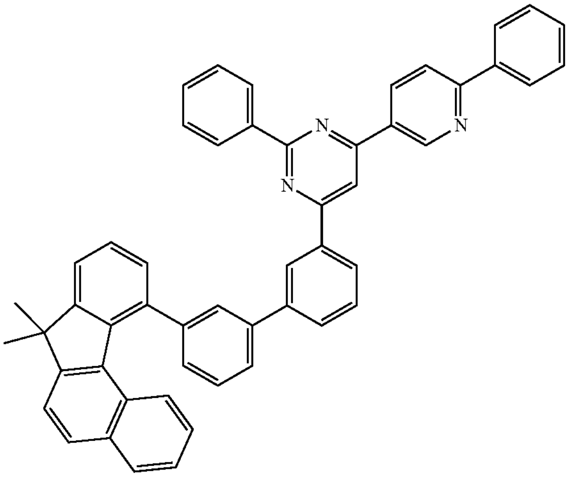
705
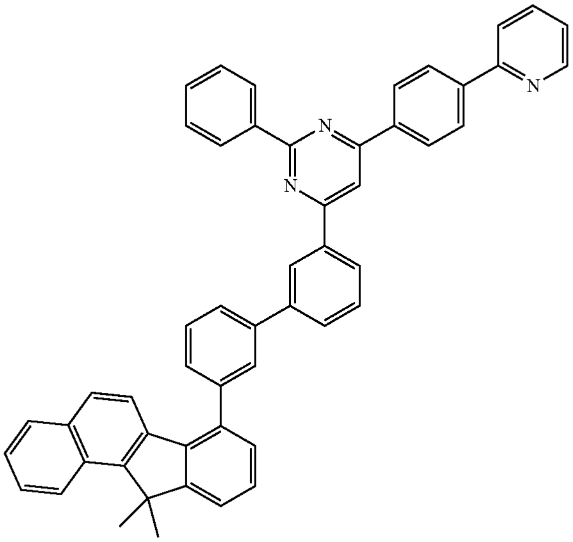

-continued
706
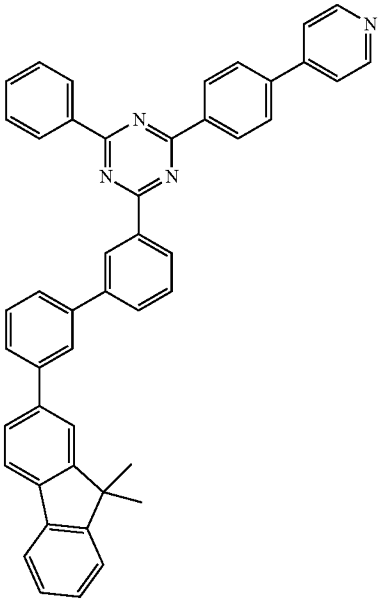
707
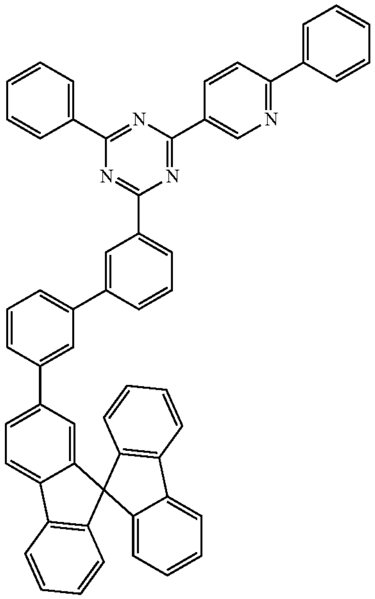
-continued
708
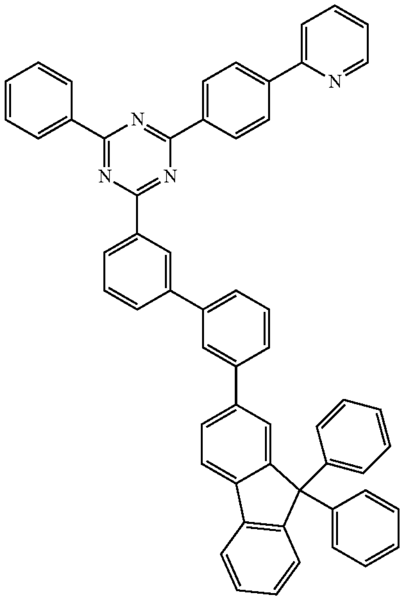
709
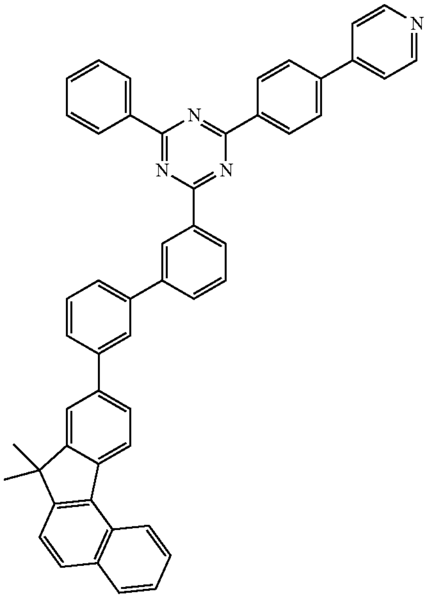

-continued
710
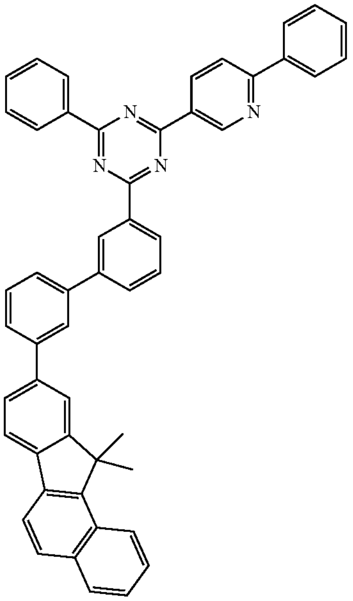
711
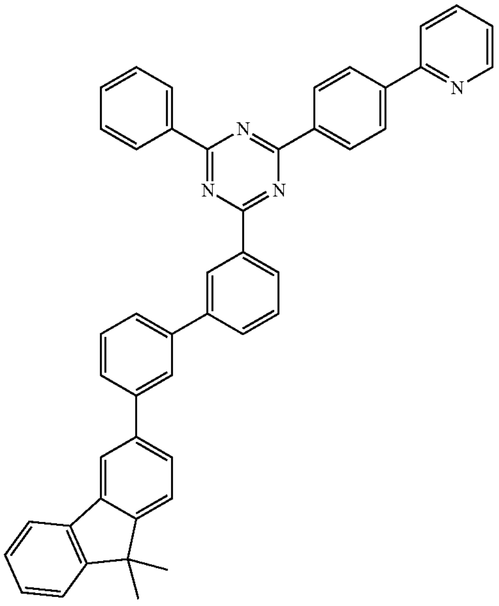
-continued
712
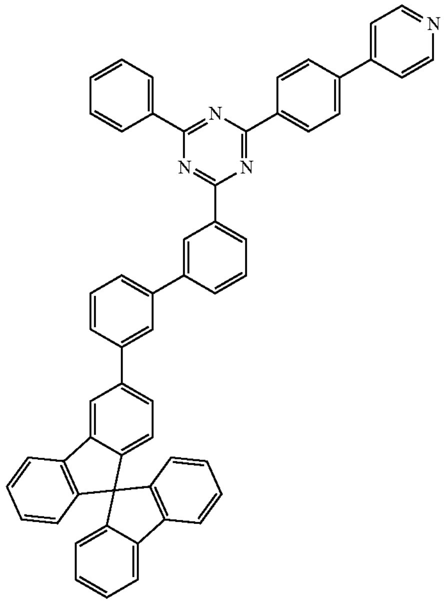
713
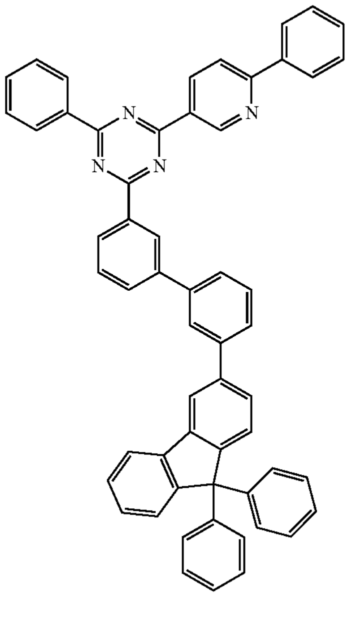

-continued
714
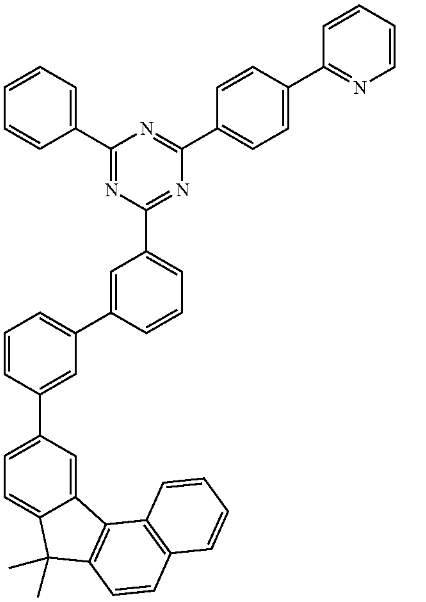
715
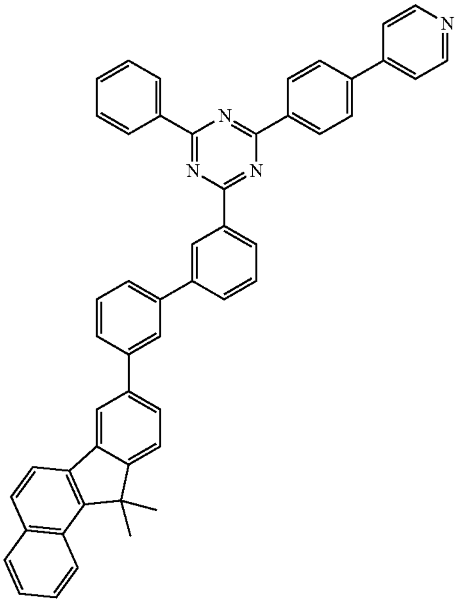
-continued
716
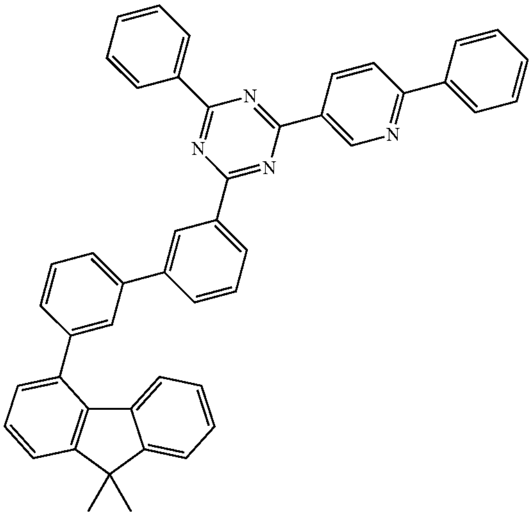
717
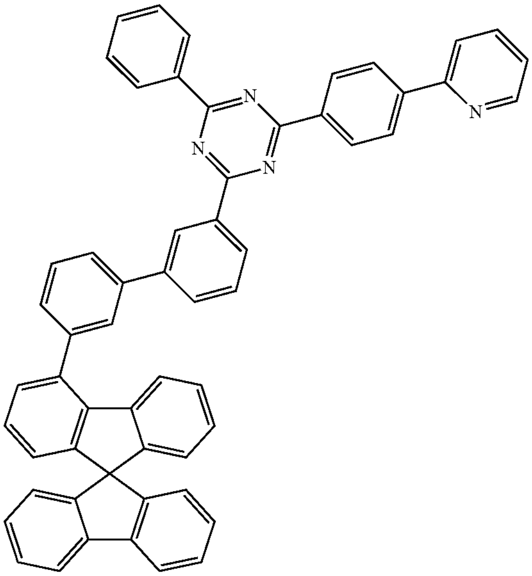

-continued
718
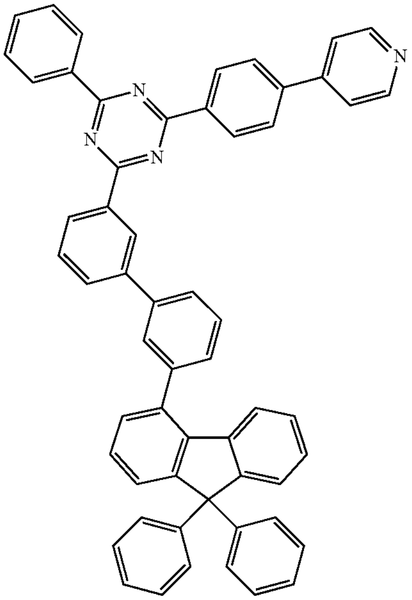
719
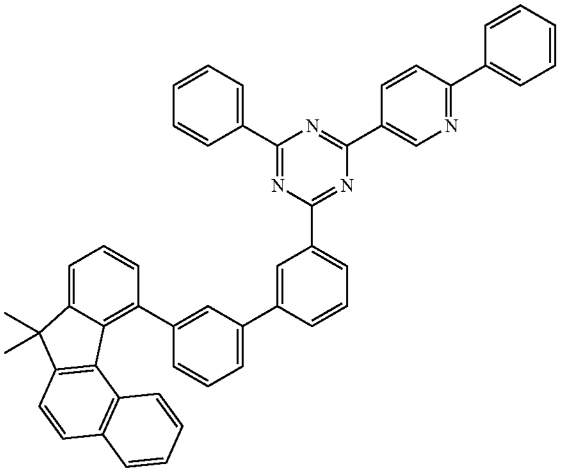
720
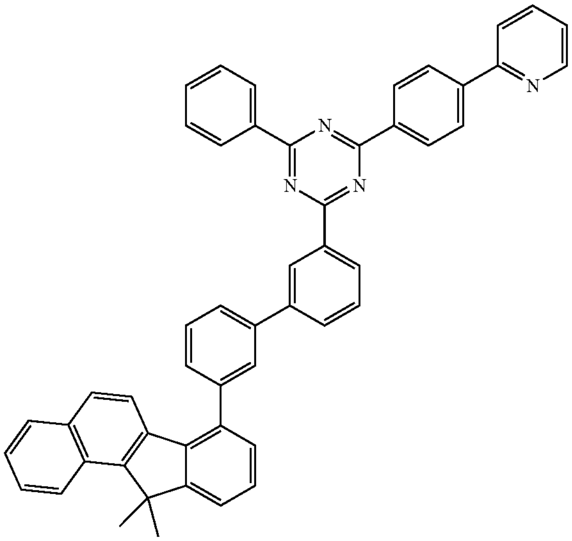
-continued
721
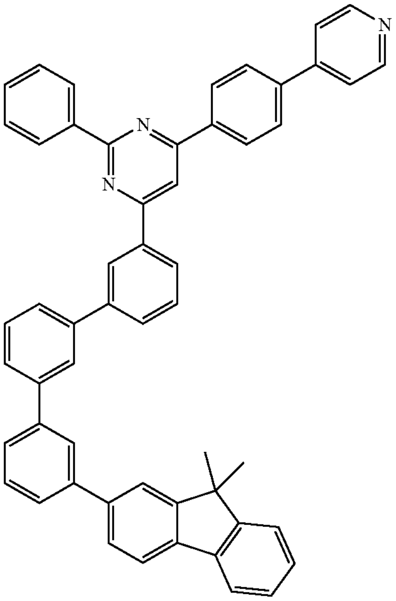
722
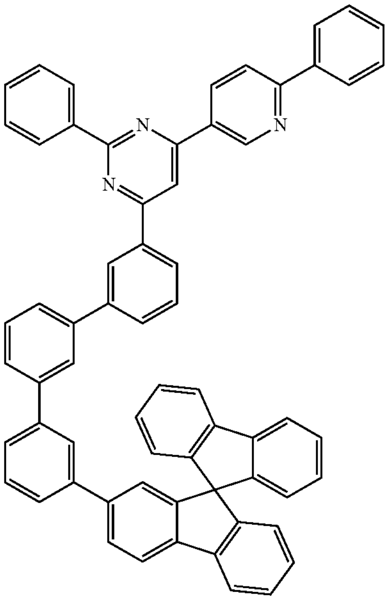

723
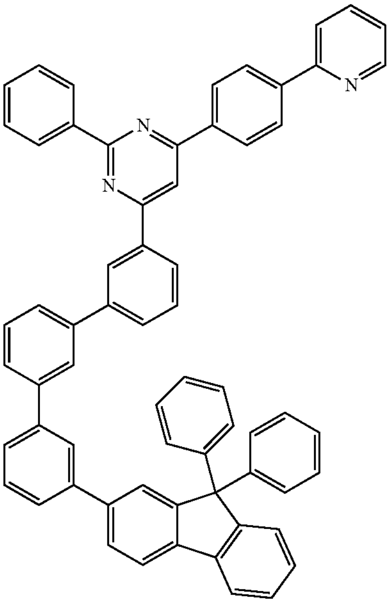
724
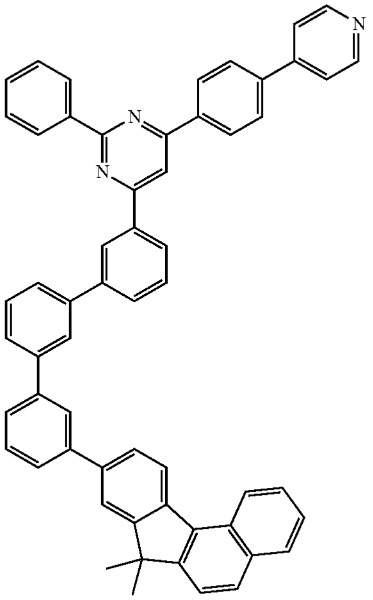
725
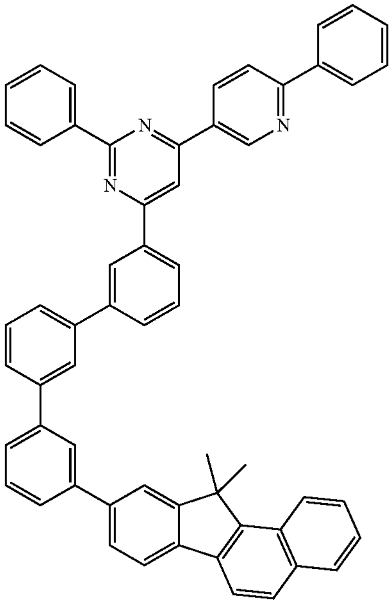
726
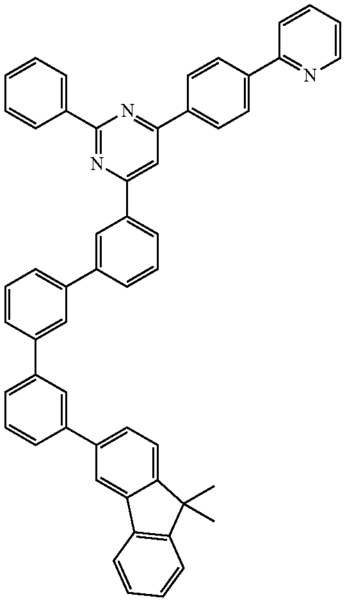

-continued
727
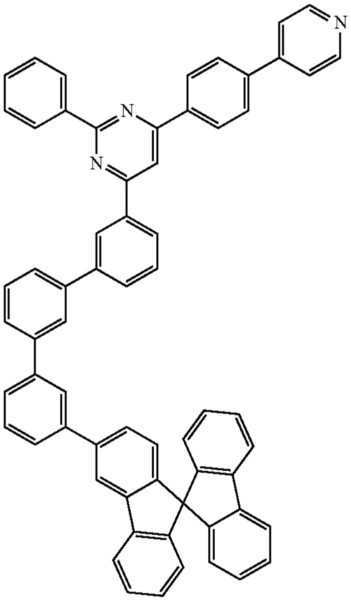
728
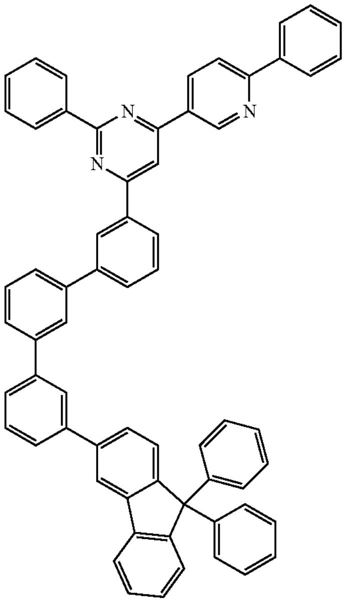
-continued
729
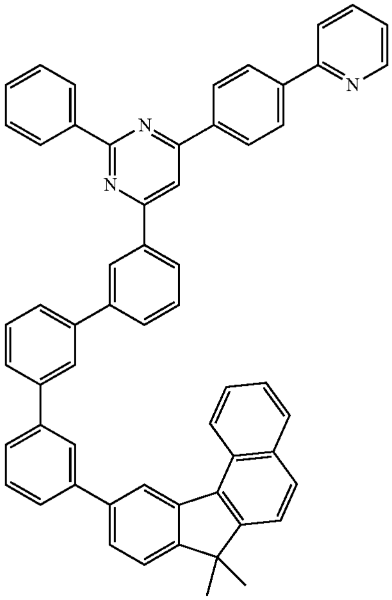
730
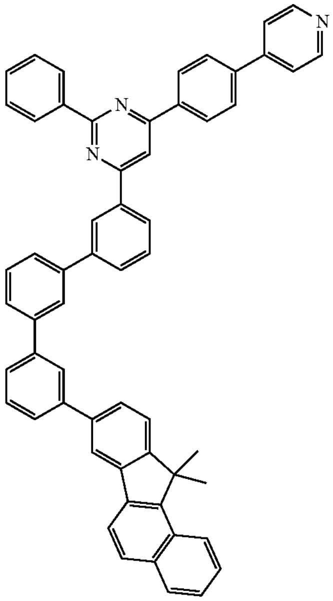

-continued
731
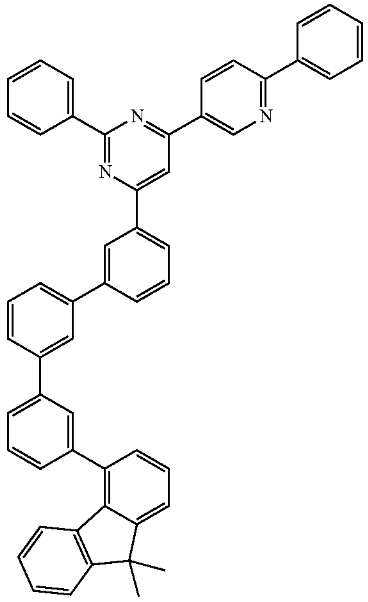
733
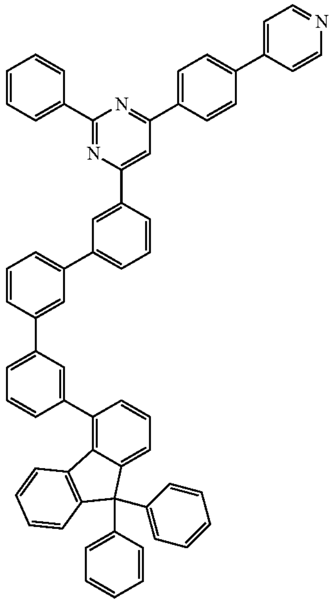
732
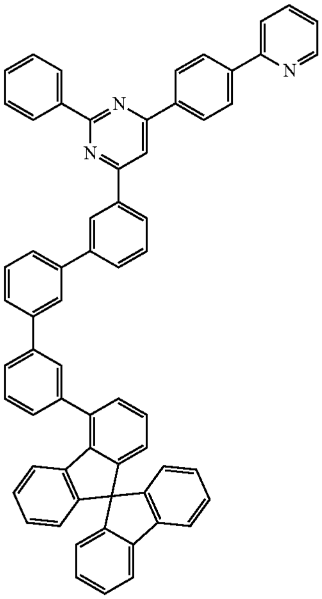
734
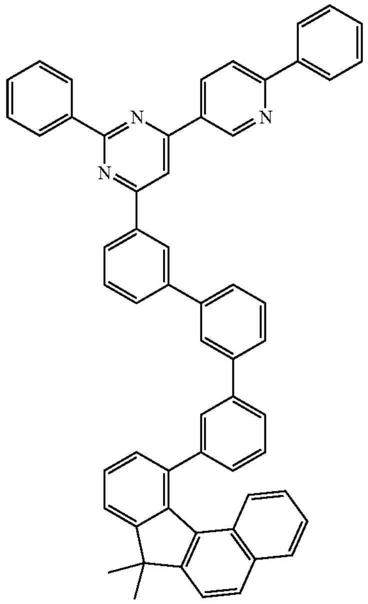

-continued
735
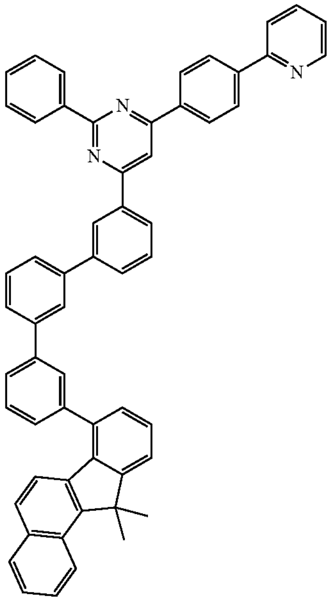
736
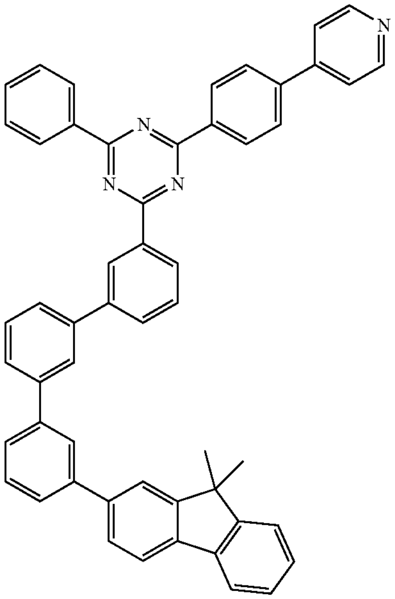
-continued
737
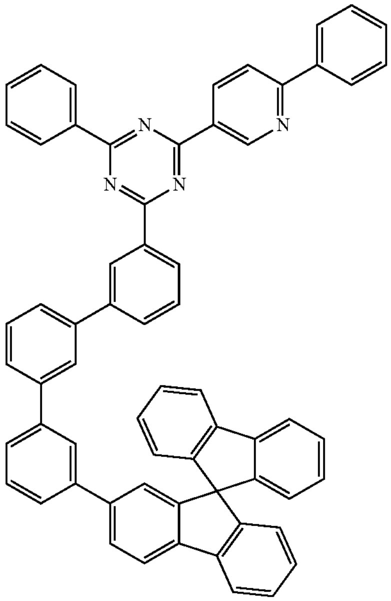
738
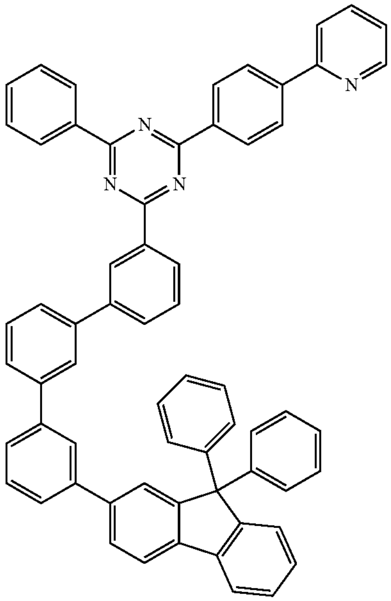

-continued
739
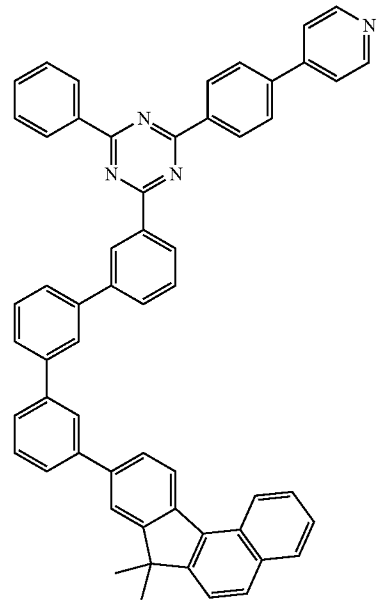
740
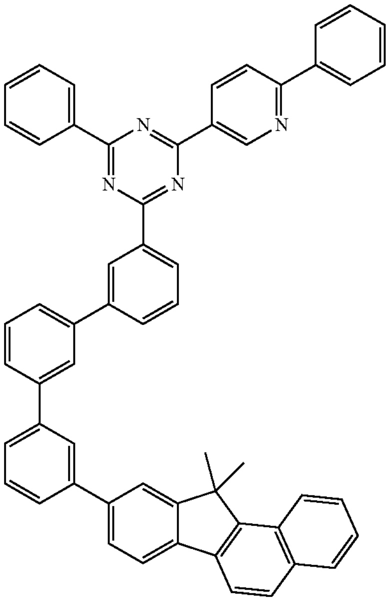
-continued
741
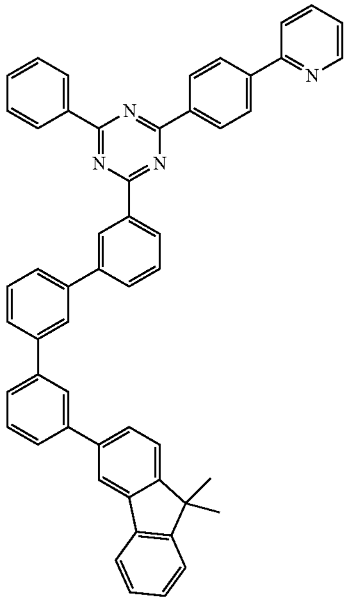
742
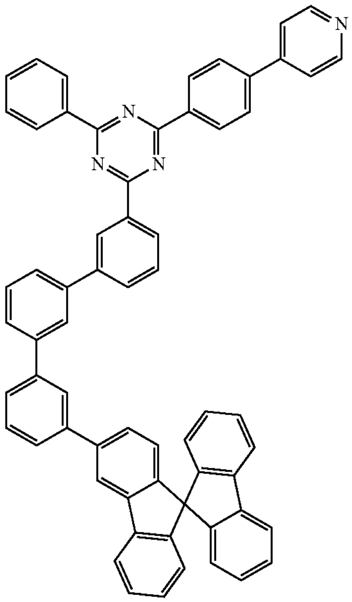

-continued
743
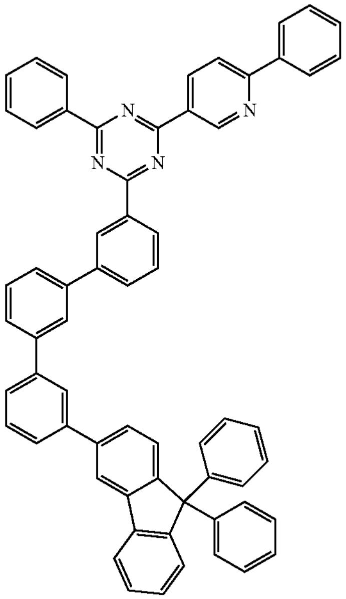
745
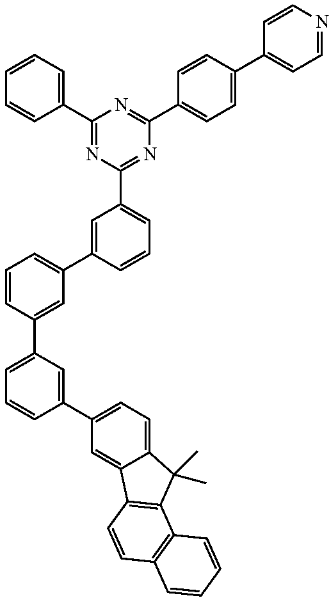
744
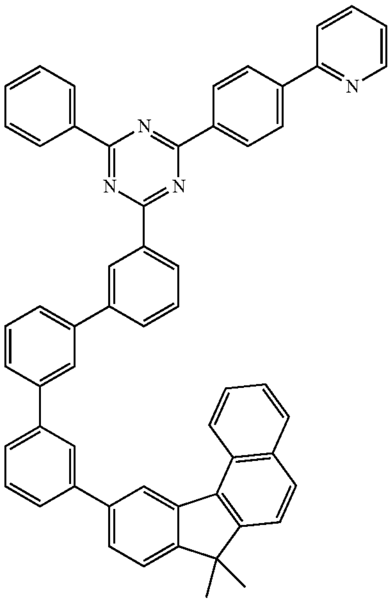
746
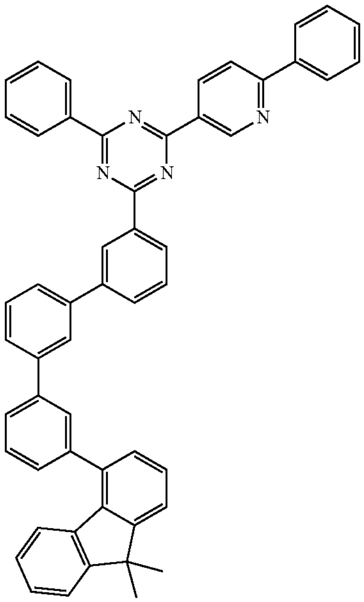

-continued

747

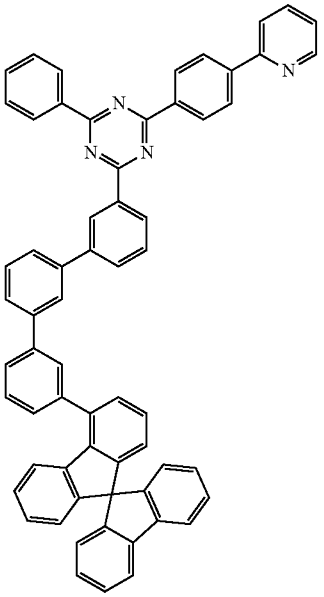

748

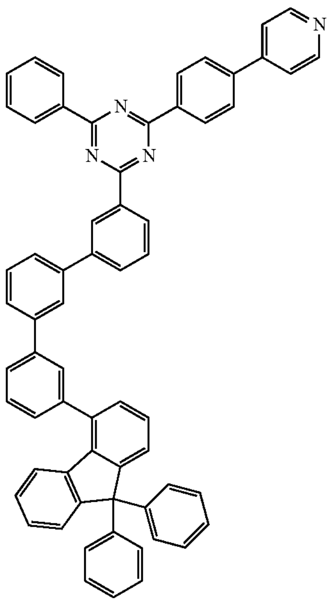

-continued

749

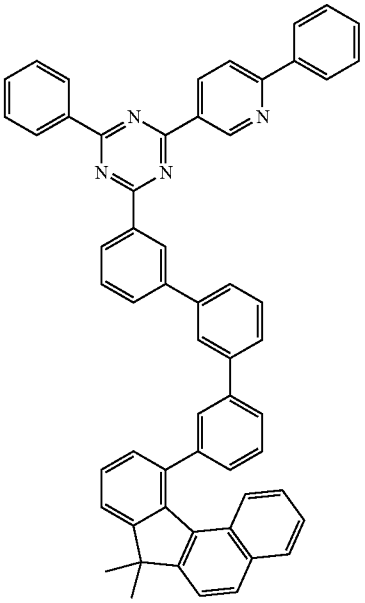

750

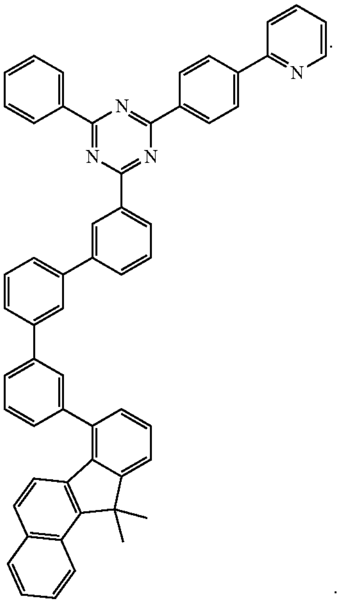

As used herein, “alkyl” refers to a monovalent functional group obtained by removing a hydrogen atom from a saturated, linear or branched hydrocarbon having 1 to 40 carbon atoms. Examples of such alkyl may include, but are not limited to, methyl, ethyl, propyl, isobutyl, sec-butyl, pentyl, iso-amyl, hexyl or the like.

As used herein, “alkenyl” refers to a monovalent substituent derived from an unsaturated, linear or branched hydrocarbon having 2 to 40 carbon atoms, having at least one carbon-carbon double bond. Examples of such alkenyl may include, but are not limited to, vinyl, allyl, isopropenyl, 2-butenyl or the like.

As used herein, “alkynyl” refers to a monovalent substituent derived from an unsaturated, linear or branched hydrocarbon having 2 to 40 carbon atoms, having at least one carbon-carbon triple bond. Examples of such alkynyl may include, but are not limited to, ethynyl, 2-propynyl or the like.

As used herein, “aryl” refers to a monovalent substituent derived from an aromatic hydrocarbon having 6 to 60 carbon atoms, which is in a structure with a single ring or two or more rings combined with each other. In addition, a form in which two or more rings are pendant (e.g., simply attached) to or fused with each other may also be included. Examples of such aryl may include, but are not limited to, phenyl, naphthyl, phenanthryl, anthryl or the like.

As used herein, “heteroaryl” refers to a monovalent substituent derived from a monoheterocyclic or polyheterocyclic aromatic hydrocarbon having 5 to 60 nuclear atoms. In such a case, one or more carbons in the ring, preferably one to three carbons, are substituted with a heteroatom such as N, O, S or Se. In addition, a form in which two or more rings are pendant to or fused with each other may be included, and a form fused with an aryl group may also be included. Examples of such heteroaryl may include, but are not limited to, a 6-membered monocyclic ring such as pyridyl, pyrazinyl, pyrimidinyl, pyridazinyl and triazinyl; a polycyclic ring such as phenoxathienyl, indolizinyl, indolyl, purinyl, quinolyl, benzothiazole and carbazolyl; 2-furanyl; N-imidazolyl; 2-isoxazolyl; 2-pyridinyl; 2-pyrimidinyl or the like.

As used herein, “aryloxy” refers to a monovalent functional group represented by R"O—, where R" is aryl having 6 to 60 carbon atoms. Examples of such aryloxy may include, but are not limited to, phenyloxy, naphthyloxy, diphenyloxy or the like.

As used herein, “alkyloxy” refers to a monovalent functional group represented by R'O—, where R' is alkyl having 1 to 40 carbon atoms. Such alkyloxy may include a linear, branched or cyclic structure. Examples of such alkyloxy may include, but are not limited to, methoxy, ethoxy, n-propoxy, 1-propoxy, t-butoxy, n-butoxy, pentoxy or the like.

As used herein, “cycloalkyl” refers to a monovalent functional group obtained by removing a hydrogen atom from a monocyclic or polycyclic non-aromatic hydrocarbon (saturated cyclic hydrocarbon) having 3 to 40 carbon atoms. Examples of such cycloalkyl may include, but are not limited to, cyclopropyl, cyclopentyl, cyclohexyl, norbornyl, adamantine or the like.

As used herein, “heterocycloalkyl” refers to a monovalent functional group obtained by removing a hydrogen atom from a non-aromatic hydrocarbon (saturated cyclic hydrocarbon) having 3 to 40 nuclear atoms, where one or more carbons in the ring, preferably one to three carbons, are substituted with a heteroatom such as N, O, or S. Examples of such heterocycloalkyl may include, but are not limited to, morpholine, piperazine or the like.

As used herein, “alkylsilyl” refers to silyl substituted with alkyl having 1 to 40 carbon atoms, “arylsilyl” refers to silyl substituted with aryl having 6 to 60 carbon atoms, “alkylboron group” refers to a boron group substituted with alkyl having 1 to 40 carbon atoms, “arylboron group” refers to a boron group substituted with aryl having 6 to 60 carbon atoms, “arylphosphine group” refers to a phosphine group substituted with aryl having 6 to 60 carbon atoms, and “arylamine” refers to amine substituted with aryl having 6 to 60 carbon atoms.

As used herein, the term “fused (e.g., condensed) ring” refers to a fused aliphatic ring, a fused aromatic ring, a fused heteroaliphatic ring, a fused heteroaromatic ring, or a combination thereof.

Such a compound represented by Chemical Formula 1 of the present disclosure may be synthesized in various manners with reference to the synthesis process of embodiments described below. The detailed synthesis process will be described below in synthesis embodiments.

<Organic Electroluminescent Device>

The present disclosure provides an organic electroluminescent device (“EL device”) including the compound represented by Chemical Formula 1.

More specifically, the organic EL device according to the present disclosure includes an anode, a cathode, and one or more organic layers disposed (e.g., interposed) between the anode and the cathode, and at least one of the one or more organic layers include the compound represented by Chemical Formula 1. In such a case, the compound may be used solely or as a combination of two or more kinds thereof.

The one or more organic layers may be any one or more of a hole injection layer, a hole transporting layer, a light emitting auxiliary layer, a light emitting layer, an electron transport auxiliary layer, an electron transporting layer, and an electron injection layer, and at least one of the organic layers may include the compound represented by Chemical Formula 1. Specifically, the organic layer including the compound represented by Chemical Formula 1 may preferably be a light emitting layer, an electron transport auxiliary layer, and/or an electron transporting layer.

The light emitting layer of the organic EL device of the present disclosure may include a host material (preferably, a phosphorescent host material). In addition, the light emitting layer of the organic EL device of the present disclosure may include, as a host, a compound other than the compound represented by Chemical Formula 1.

A structure of the organic EL device of the present disclosure is not particularly limited, but a non-limiting example thereof may have a structure in which a substrate, an anode, a hole injection layer, a hole transporting layer, a light emitting auxiliary layer, a light emitting layer, an electron transporting layer and a cathode are sequentially laminated. In such a case, at least one of the hole injection layer, the hole transporting layer, the light emitting auxiliary layer, the light emitting layer, and the electron transporting layer may include the compound represented by Chemical Formula 1, and preferably, the light emitting layer or the electron transporting layer may include the compound represented by Chemical Formula 1. In such a case, an electron injection layer may further be laminated on the electron transporting layer. In addition, the structure of the organic EL device of the present disclosure may have a structure in which an electron transport auxiliary layer is provided in addition to the electrodes and the organic layers described above. In such an embodiment, one or more of the hole injection layer, the hole transporting layer, the light emitting auxiliary layer, the light emitting layer, the electron transport auxiliary layer and the electron transporting layer may include the compound represented by Chemical Formula 1, and preferably, the light emitting layer, the electron transport auxiliary layer or the electron transporting layer may include the compound represented by Chemical Formula 1.

Meanwhile, the organic EL device of the present disclosure may be manufactured by forming organic layers and electrodes with conventional materials and through conventional methods known in the art, except that one or more of the aforementioned organic layers include the compound represented by Chemical Formula 1.

The organic layers may be formed by a vacuum deposition method or a solution coating method. Examples of the solution coating method may include, but are not limited to, spin coating, dip coating, doctor blading, inkjet printing, thermal transfer or the like.

The substrate used for manufacturing the organic EL device of the present disclosure is not particularly limited, but silicon wafers, quartz, glass plates, metal plates, plastic films, sheets or the like may be used.

In addition, a material of the anode may include, but not limited to, a metal such as vanadium, chromium, copper, zinc and gold or an alloy thereof; a metal oxide such as zinc oxide, indium oxide, indium tin oxide (ITO) and indium zinc oxide (IZO); a combination of oxide with metal such as ZnO:Al or $SnO_2$:Sb; a conductive polymer such as polythiophene, poly(3-methylthiophene), poly[3,4-(ethylene-1,2-dioxy)thiophene] (PEDT), polypyrrole or polyaniline; carbon black or the like.

In addition, a material of the cathode may include, but not limited to, a metal such as magnesium, calcium, sodium, potassium, titanium, indium, yttrium, lithium, gadolinium, aluminum, silver, tin and lead or an alloy thereof; a multi-layered material such as LiF/Al and $LiO_2$/Al or the like.

In addition, materials of the hole injection layer, the hole transporting layer and the light emitting auxiliary layer are not particularly limited and conventional materials known in the art may be used.

Hereinafter, the present disclosure will be described in detail through exemplary embodiments. However, the following embodiments are merely to illustrate the invention, and the present disclosure is not limited by the following embodiments.

[Preparation Example 1] Synthesis of PPY-1

<Step 1> Synthesis of PPY-1

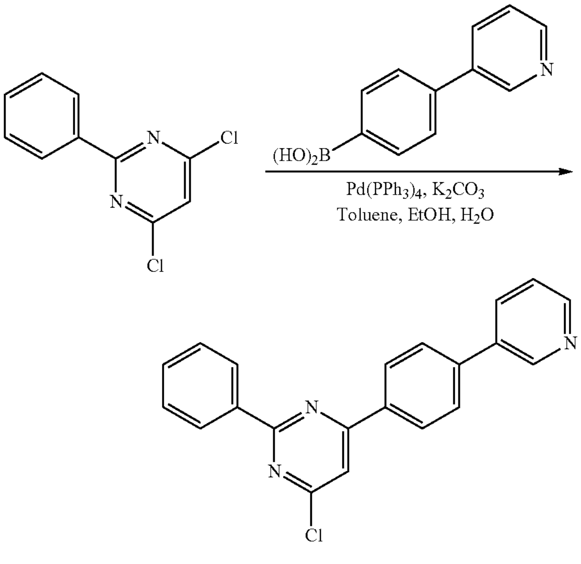

PPY-1

45.0 g of 4,6-dichloro-2-phenylpyrimidine and 40.0 g of (4-(pyridin-3-yl)phenyl) boronic acid, 6.0 g of tetrakis(phenylphosphine) palladium (0), and 42 g of $K_2CO_3$ were added to 800 ml of toluene, 200 ml of ethanol, and 200 ml of water, and the mixture was stirred and heated under reflux for 2 hours. After the reaction was completed, the solution was inactivated with a sufficient amount of water, and transferred to a separatory funnel, followed by extraction with methylene chloride. An organic layer was dried over magnesium sulfate, concentrated and purified by column chromatography, thereby obtaining 39.8 g (yield 58%) of PPY-1.

1H-NMR: δ 9.24 (s, 1H), 8.70 (d, 1H), 8.42-8.30 (m, 5H), 7.57-7.50 (m, 4H), 7.25 (d, 2H) 7.03 (s, 1H)

Mass: [(M+H)+]: 344

[Preparation Example 2] Synthesis of PPY-2 and 3

<Step 1> Synthesis of (E)-1-(4-bromophenyl)-3-(4-pyridin-3-yl)phenyl) prop-2-ene-1-one

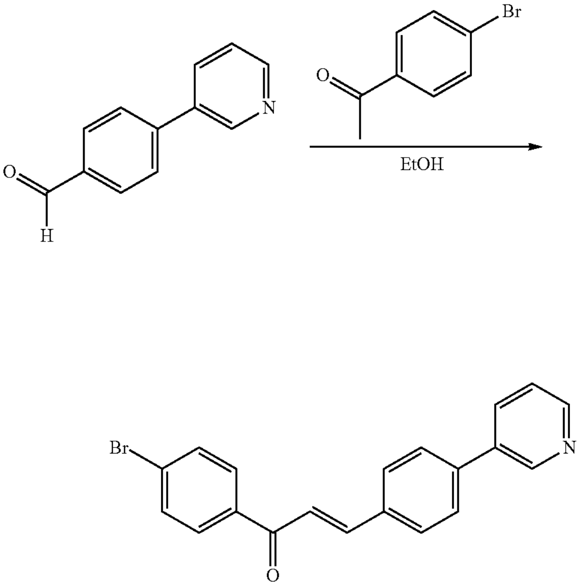

50.0 g of 4-(pyridin-3-yl)benzaldehyde, 49.1 g of 1-(4-bromophenyl) ethan-1-one, and 18.2 g of sodium methoxide were added to 800 ml of ethanol, and the mixture was stirred for 8 hours. After the reaction was completed, the mixture was stirred at room temperature for 1 hour, followed by extraction with ethyl acetate. An organic layer was dried over magnesium sulfate, concentrated and purified by column chromatography, thereby obtaining 36.4 g (yield 72%) of (E)-1-(4-bromophenyl)-3-(4-pyridin-3-yl)phenyl) prop-2-ene-1-one.

1H-NMR: δ 9.24 (s, 1H), 8.50 (d, 1H), 8.38 (d, 1H), 8.08-8.01 (m, 3H), 7.75 (d, 2H), 7.60-7.45 (m, 6H)

Mass: [(M+H)+]: 364

<Step 2> Synthesis of PPY-2

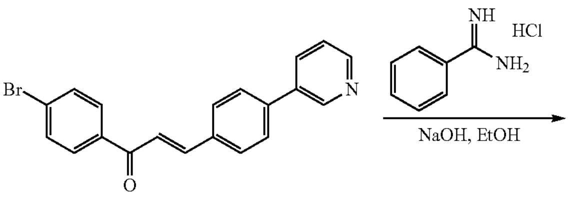

-continued

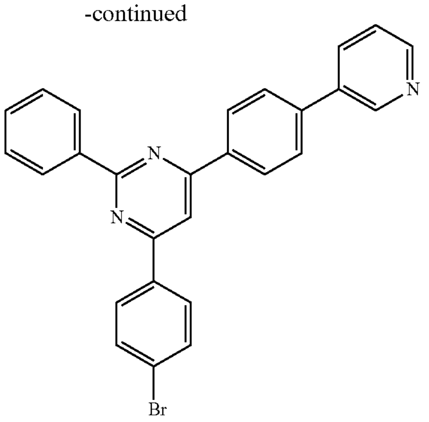

PPY-2

36.4 g of (E)-1-(4-bromophenyl)-3-(4-pyridin-3-yl)phenyl) prop-2-ene-1-one, 24.1 g of benzimidamide hydrochloride, 14.2 g of sodium hydroxide were added to 500 ml of ethanol, and the mixture was stirred and heated under reflux for 4 hours. After the reaction was completed, the reaction product was concentrated under reduced pressure to 250 ml, inactivated with a sufficient amount of water, and then transferred to a separatory funnel, followed by extraction with methylene chloride. An organic layer was dried over magnesium sulfate, concentrated, and purified by column chromatography, thereby obtaining 36.2 g (yield 79%) of PPY-2.

1H-NMR: δ 9.21 (s, 1H), 8.70 (d, 1H), 8.42-8.30 (m, 6H), 7.76 (d, 2H), 7.59-7.55 (m, 6H), 7.25 (d, 2H)

Mass: [(M+H)+]: 464

<Step 3> Synthesis of PPY-3

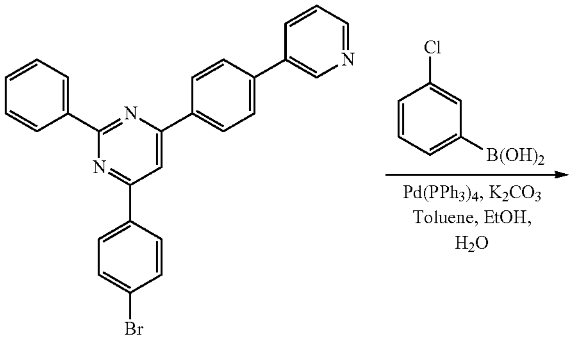

PPY-2

-continued

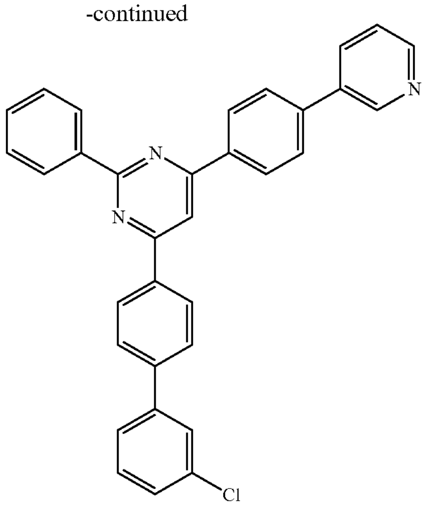

PPY-3

15.0 g of PPY-2, 6.1 g of (3-chlorophenyl) boronic acid, 0.9 g of tetrakis(phenylphosphine) palladium (0), and 7.0 g of $K_2CO_3$ were added to 300 ml of toluene, 60 ml of ethanol, and 60 ml of water, and the mixture was stirred and heated under reflux for 2 hours. After the reaction was completed, the solution was inactivated with a sufficient amount of water, and transferred to a separatory funnel, followed by extraction with methylene chloride. An organic layer was dried over magnesium sulfate, concentrated and purified by column chromatography, thereby obtaining 10.9 g (yield 68%) of PPY-3.

1H-NMR: δ9.21 (s, 1H), 8.70 (d, 1H), 8.42-8.30 (m, 6H), 7.97 (s, 1H), 7.76 (d, 2H), 7.59-7.55 (m, 6H), 7.48 (m, 2H), 7.39 (d, 1H), 7.25 (d, 2H)

Mass: [(M+H)+]: 496

[Preparation Example 3] Synthesis of PPY-4 to 6

<Step 1> Synthesis of (E)-1-(3-bromophenyl)-3-(4-pyridin-3-yl)phenyl) prop-2-ene-1-one

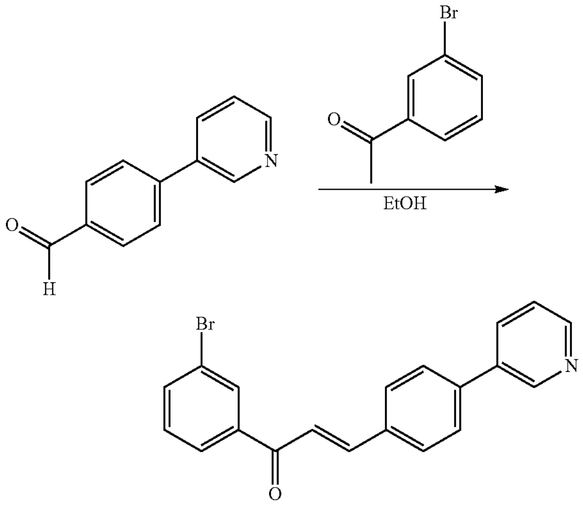

50.0 g of 4-(pyridin-3-yl)benzaldehyde, 49.1 g of 1-(3-bromophenyl) ethan-1-one, and 18.2 g of sodium methoxide were added to 800 ml of ethanol, and the mixture was stirred for 8 hours. After the reaction was completed, the mixture was stirred at room temperature for 1 hour, followed by extraction with ethyl acetate. An organic layer was dried over magnesium sulfate, concentrated and purified by column chromatography, thereby obtaining 38.2 g (yield 74%) of (E)-1-(3-bromophenyl)-3-(4-pyridin-3-yl)phenyl) prop-2-ene-1-one.

1H-NMR: δ 9.24 (s, 1H), 8.50 (d, 1H), 8.38 (d, 1H), 8.08-8.01 (m, 3H), 7.82 (d, 1H), 7.60-7.45 (m, 7H)

Mass: [(M+H)+]: 364

<Step 2> Synthesis of PPY-4

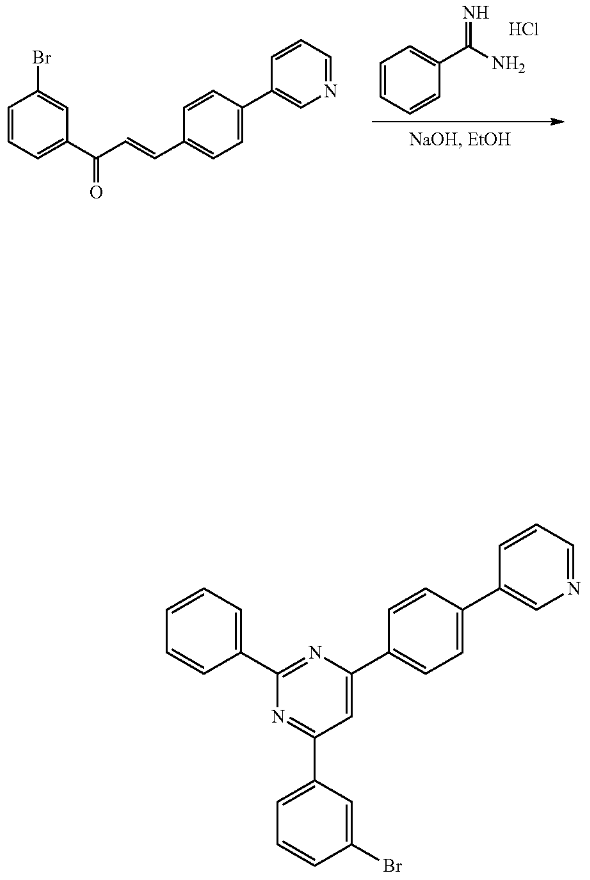

PPY-4

38.2 g of (E)-1-(3-bromophenyl)-3-(4-pyridin-3-yl)phenyl) prop-2-ene-1-one, 25.0 g of benzimidamide hydrochloride, and 14.8 g of sodium hydroxide were added to 500 ml of ethanol, and the mixture was stirred and heated under reflux for 4 hours. After the reaction was completed, the reaction product was concentrated under reduced pressure to 250 ml, inactivated with a sufficient amount of water, and then transferred to a separatory funnel, followed by extraction with methylene chloride. An organic layer was dried over magnesium sulfate, concentrated, and purified by column chromatography, thereby obtaining 34.2 g (yield 75%) of PPY-4.

1H-NMR: δ 9.24 (s, 1H), 8.70 (d, 1H), 8.42-8.30 (m, 6H), 7.78 (d, 1H), 7.67 (d, 1H) 7.50-7.43 (m, 6H), 7.25 (d, 2H)

Mass: [(M+H)+]: 464

<Step 3> Synthesis of PPY-5

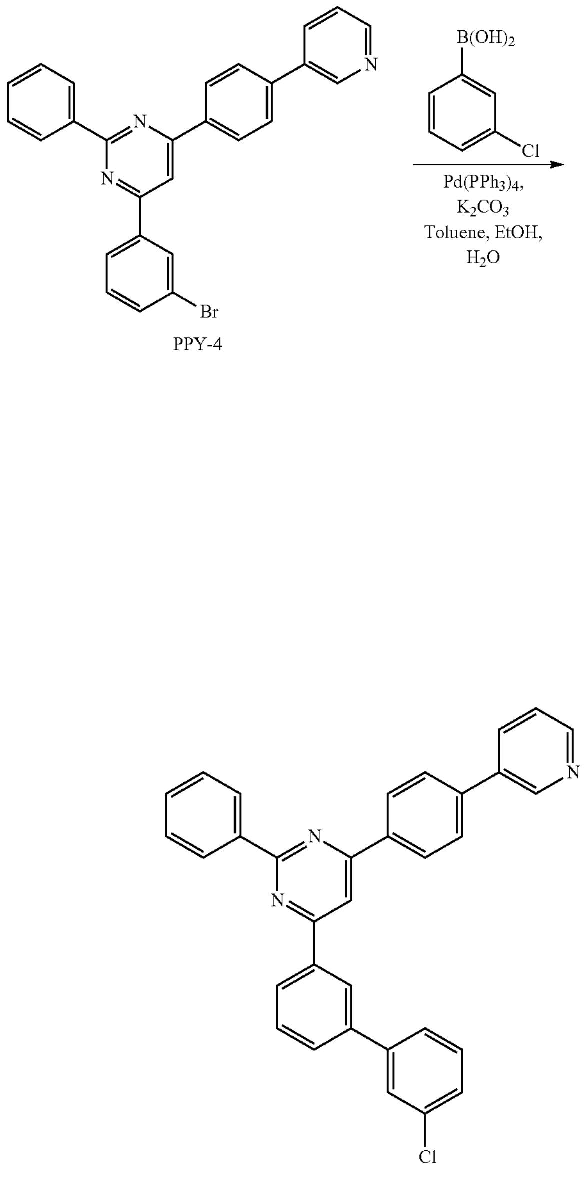

PPY-4

PPY-5

15.0 g of PPY-4, 6.1 g of (3-chlorophenyl) boronic acid, 0.9 g of tetrakis(phenylphosphine) palladium (0), and 7.0 g of of $K_2CO_3$ were added to 300 ml of toluene, 60 ml of ethanol, and 60 ml of water, and the mixture was stirred and heated under reflux for 2 hours. After the reaction was completed, the solution was inactivated with a sufficient amount of water, and transferred to a separatory funnel, followed by extraction with methylene chloride. An organic layer was dried over magnesium sulfate, concentrated and purified by column chromatography, thereby obtaining 10.1 g (yield 67%) of PPY-5.

1H-NMR: δ 9.24 (s, 1H), 8.70 (d, 1H), 8.42-8.30 (m, 6H), 7.97 (s, 1H), 7.78 (d, 1H), 7.67 (d, 1H) 7.50-7.43 (m, 8H), 7.35 (d, 1H), 7.25 (d, 2H)

Mass: [(M+H)+]: 496

<Step 4> Synthesis of PPY-6

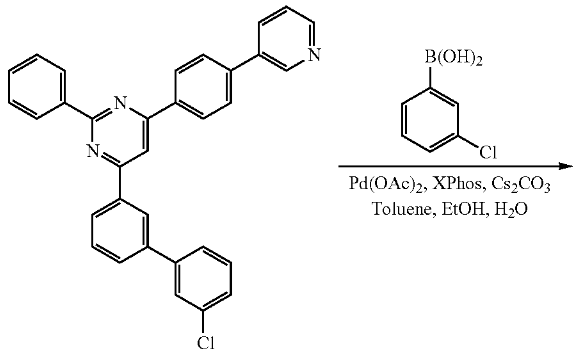

PPY-5

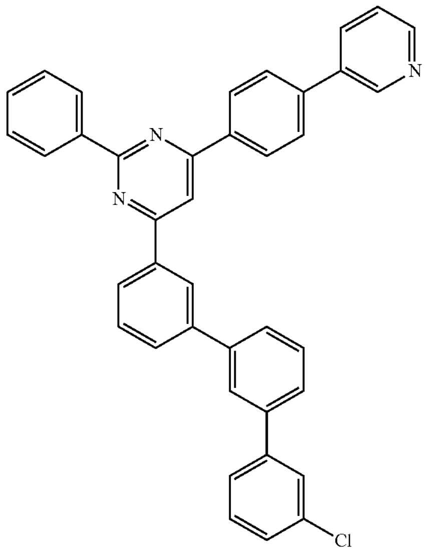

PPY-6

10.0 g of PPY-5, 4.1 g of (3-chlorophenyl) boronic acid, 0.1 g of Pd(OAc) 2, 0.4 g of Xphos, and 4.5 g of $Cs_2CO_3$ were added to 200 ml of toluene, 40 ml of ethanol, and 40 ml of water, and the mixture was stirred and heated under reflux for 2 hours. After the reaction was completed, the solution was inactivated with a sufficient amount of water, and transferred to a separatory funnel, followed by extraction with methylene chloride. An organic layer was dried over magnesium sulfate, concentrated and purified by column chromatography, thereby obtaining 6.7 g (yield 66%) of PPY-6.

1H-NMR: δ9.24 (s, 1H), 8.70 (d, 1H), 8.42-8.30 (m, 6H), 7.97 (s, 1H), 7.90 (s, 1H), 7.78 10 (d, 1H), 7.67 (d, 1H) 7.50-7.40 (m, 10H), 7.35 (d, 2H), 7.25 (d, 2H)

Mass: [(M+H)+]: 572

[Preparation Example 4] Synthesis of PPY-7 and 8

<Step 1> Synthesis of PPY-7

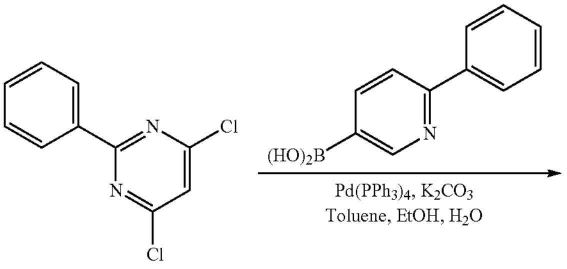

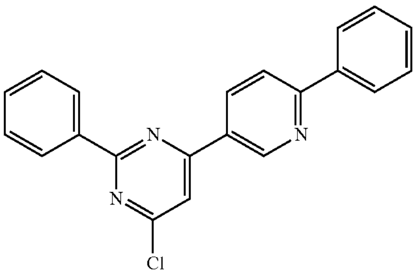

PPY-7

45.0 g of 4,6-dichloro-2-phenylpyrimidine, 38.7 g of (6-phenylpyridin-3-yl) boronic acid, 6.0 g of tetrakis(phenylphosphine) palladium (0), and 42 g of $K_2CO_3$ were added to 800 ml of toluene, 200 ml of ethanol, and 200 ml of water, and the mixture was stirred and heated under reflux for 2 hours. After the reaction was completed, the solution was inactivated with a sufficient amount of water, and transferred to a separatory funnel, followed by extraction with methylene chloride. An organic layer was dried over magnesium sulfate, concentrated and purified by column chromatography, thereby obtaining 40.7 g (yield 61%) of PPY-7.

1H-NMR: δ 9.23 (s, 1H), 8.62 (d, 1H), 8.42-8.30 (m, 3H), 7.96 (d, 2H), 7.73 (s, 1H), 7.54-7.48 (m, 4H), 7.31 (d, 2H)

Mass: [(M+H)+]: 344

<Step 2> Synthesis of PPY-8

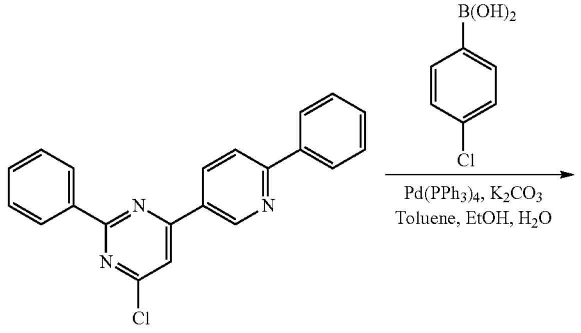

PPY-7

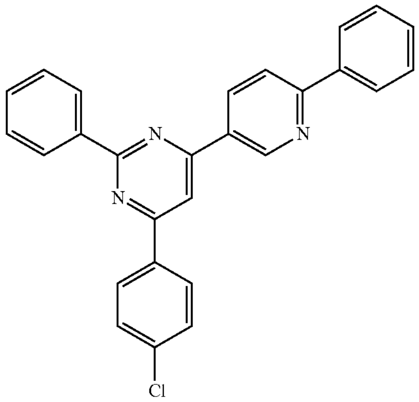

PPY-8

15.0 g of PPY-7, 6.1 g of (3-chlorophenyl) boronic acid, 0.9 g of tetrakis(phenylphosphine) palladium (0), and 7.1 g of $K_2CO_3$ were added to 300 ml of toluene, 60 ml of ethanol, and 60 ml of water, and the mixture was stirred and heated under reflux for 2 hours. After the reaction was completed, the solution was inactivated with a sufficient amount of water, and transferred to a separatory funnel, followed by extraction with methylene chloride. An organic layer was dried over magnesium sulfate, concentrated and purified by column chromatography, thereby obtaining 13.7 g (yield 72%) of PPY-8.

1H-NMR: δ 9.15 (s, 1H), 8.73 (d, 1H), 8.43-8.12 (m, 4H), 8.13 (s, 1H), 7.99-7.97 (m, 3H), 7.52-7.41 (m, 6H), 7.11 (d, 2H)

Mass: [(M+H)+]: 420

[Preparation Example 5] Synthesis of PPY-1 and 2

<Step 1> Synthesis of PTZ-1

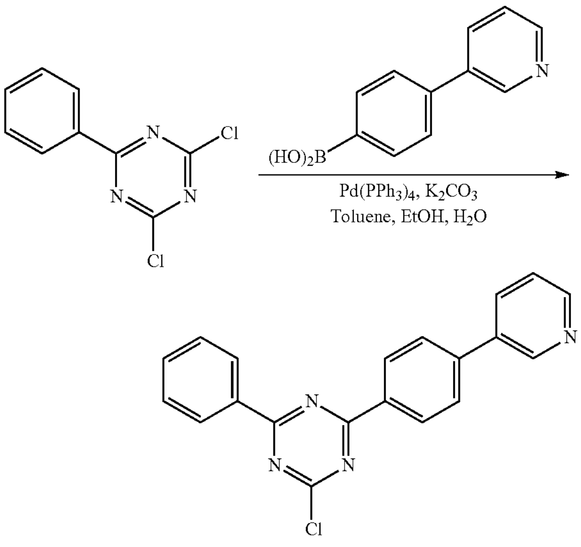

PTZ-1

45.0 g of 2,4-dichloro-6-phenyl-1,3,5-triazine, 39.2 g of (4-(pyridin-3-yl)phenyl) boronic acid, 6.0 g of tetrakis(phenylphosphine) palladium (0), and 42 g of $K_2CO_3$ were added to 800 ml of toluene, 200 ml of ethanol, and 200 ml of water, and the mixture was stirred and heated under reflux for 2 hours. After the reaction was completed, the solution was inactivated with a sufficient amount of water, and transferred to a separatory funnel, followed by extraction with methylene chloride. An organic layer was dried over magnesium sulfate, concentrated and purified by column chromatography, thereby obtaining 36.2 g (yield 53%) of PTZ-1.

1H-NMR: δ 9.24 (s, 1H), 8.70 (d, 1H), 8.42-8.30 (m, 3H), 7.96 (d, 2H), 7.57-7.50 (m, 4H), 7.25 (d, 2H)

Mass: [(M+H)+]: 345

<Step 2> Synthesis of PTZ-2

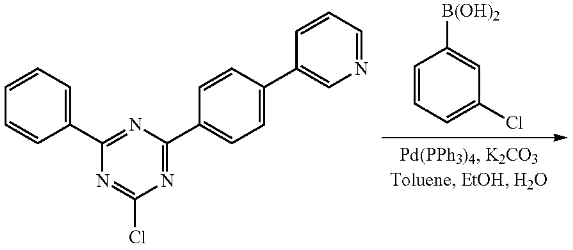

PTZ-1

-continued

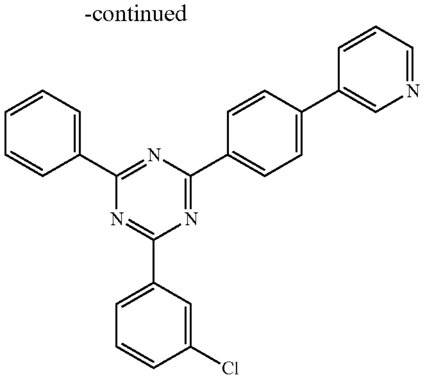

PTZ-2

10.0 g of PTZ-1, 4.1 g of (3-chlorophenyl) boronic acid, 0.6 g of tetrakis(phenylphosphine) palladium (0), and 4.7 g of $K_2CO_3$ were added to 200 ml of toluene, 40 ml of ethanol, and 40 ml of water, and the mixture was stirred and heated under reflux for 2 hours. After the reaction was completed, the solution was inactivated with a sufficient amount of water, and transferred to a separatory funnel, followed by extraction with methylene chloride. An organic layer was dried over magnesium sulfate, concentrated and purified by column chromatography, thereby obtaining 8.7 g (yield 71%) of PTZ-2.

1H-NMR: δ 9.24 (s, 1H), 8.70 (d, 1H), 8.42-8.30 (m, 3H), 8.16 (s, 1H), 7.96-7.95 (m, 3H), 7.50-7.43 (m, 6H), 7.25 (d, 2H)

Mass: [(M+H)+]: 421

[Preparation Example 6] Synthesis of PTZ-3

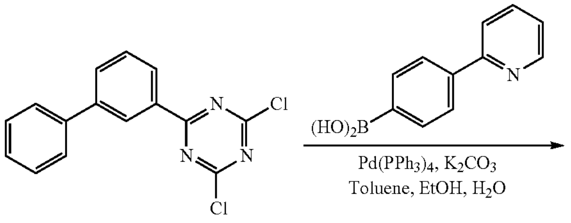

-continued

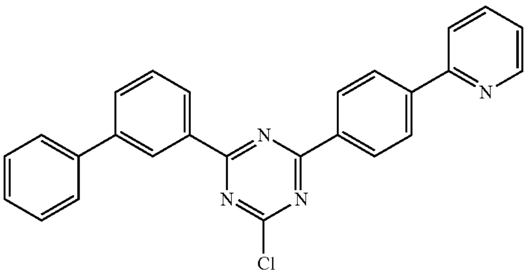

PTZ-3

45.0 g of 2-([1,1'-biphenyl]-3-yl)-4,6-dichloro-1,3,5-triazine, 38.1 g of (4-(pyridin-2-yl)phenyl) boronic acid, 6.0 g of tetrakis(phenylphosphine) palladium (0), and 42 g of $K_2CO_3$ were added to 800 ml of toluene, 200 ml of ethanol, and 200 ml of water, and the mixture was stirred and heated under reflux for 2 hours. After the reaction was completed, the solution was inactivated with a sufficient amount of water, and transferred to a separatory funnel, followed by extraction with methylene chloride. An organic layer was dried over magnesium sulfate, concentrated and purified by column chromatography, thereby obtaining 40.4 g (yield 65%) of PTZ-3.

1H-NMR: δ 9.23 (s, 1H), 8.70 (d, 1H), 8.42-8.30 (m, 3H), 7.96 (d, 2H), 7.75 (d, 2H) 7.67-7.43 (m, 7H), 7.23 (d, 2H)

Mass: [(M+H)+]: 421

[Synthesis Example 1] Synthesis of Compound 1

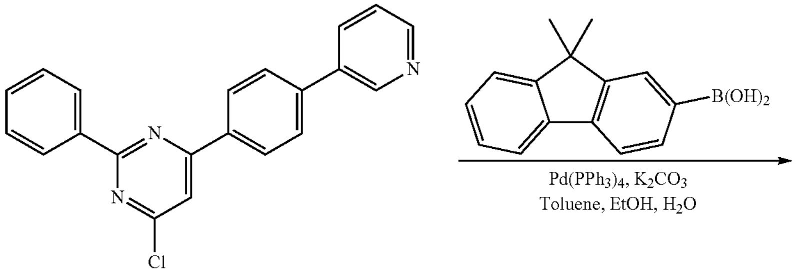

PPY-1

-continued

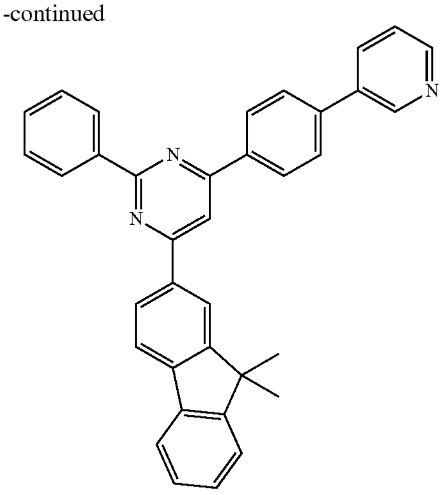

1

3.0 g of PPY-1, 4.3 g of (9,9-dimethyl-9H-fluoren-2-yl) boronic acid, and 3.3 g of $K_2CO_3$ were mixed, 60 ml of toluene, 12 ml of ethanol, and 12 ml of water were added thereto, 500 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:Hex=2:1 was performed, thereby obtaining 2.8 g (yield 55%) of Compound 1 in a white solid state.

Mass: [(M+H)+]: 502

[Synthesis Example 2] Synthesis of Compound 2

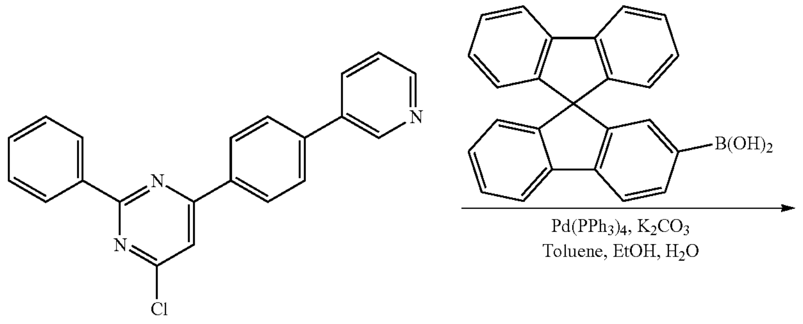

PPY-1

-continued

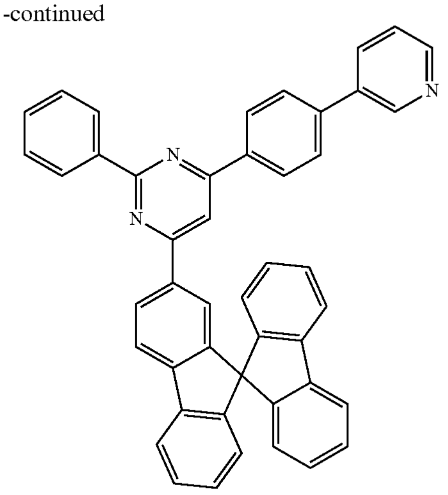

2

3.0 g of PPY-1, 5.1 g of 9,9'-spirobi[fluorene]-2-yl boronic acid, and 3.3 g of $K_2CO_3$ were mixed, 60 ml of toluene, 12 ml of ethanol, and 12 ml of water were added thereto, 500 mg of 5 tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:Hex=2:1 was performed, thereby obtaining 3.2 g (yield 58%) of Compound 2 in a white solid state.

Mass: [(M+H)+]: 624

[Synthesis Example 3] Synthesis of Compound 4

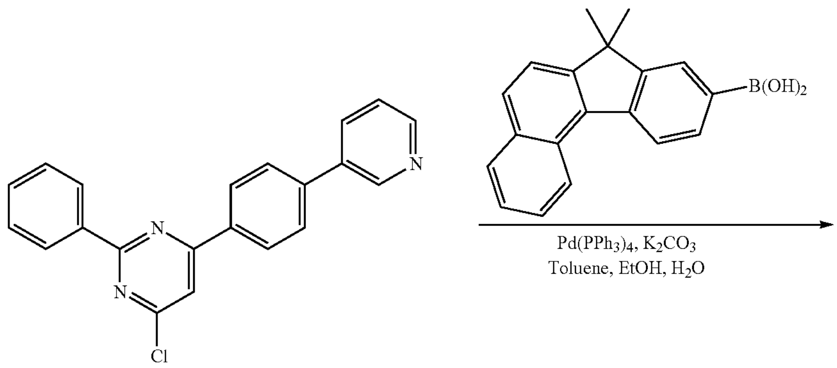

PPY-1

-continued

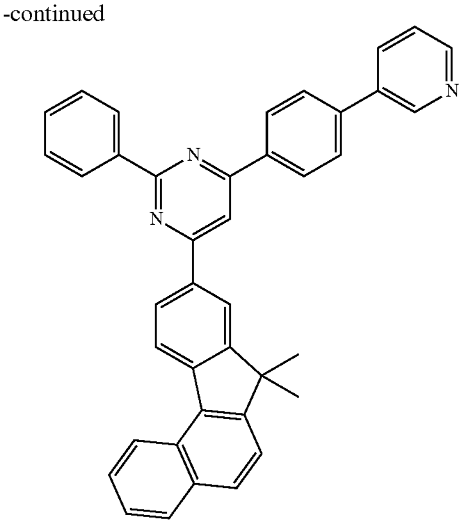

4

3.1 g of PPY-1, 4.8 g of (7,7-dimethyl-7H-benzo[c]fluoren-9-yl) boronic acid, and 3.3 g of $K_2CO_3$ were mixed, 60 ml of toluene, 12 ml of ethanol, and 12 ml of water were added thereto, 500 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:Hex=2:1 was performed, thereby obtaining 3.5 g (yield 56%) of Compound 4 in a white solid state.

Mass: [(M+H)+]: 551

[Synthesis Example 4] Synthesis of Compound 42

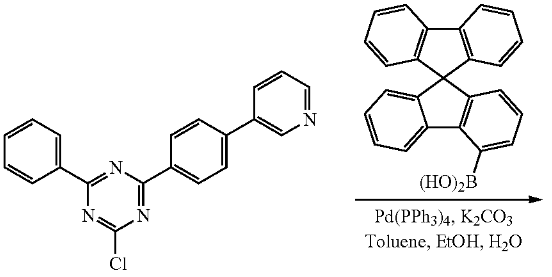

PTZ-1

-continued

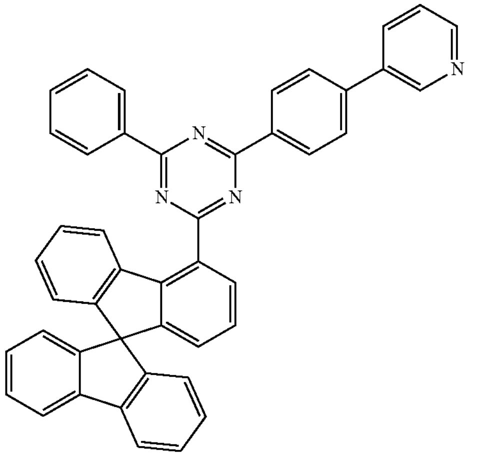

42

3.0 g of PTZ-1, 5.1 g of 9,9'-spirobi[fluorene]-4-yl boronic acid, and 3.3 g of $K_2CO_3$ were mixed, 60 ml of toluene, 12 ml of ethanol, and 12 ml of water were added thereto, 500 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, the resultant solid was filtered out, the resultant solid was dissolved in a sufficient amount of MC and concentrated under reduced pressure, and column chromatography with MC:Hex=2:1 was performed, thereby obtaining 4.1 g (yield 75%) of Compound 42 in a white solid state.

Mass: [(M+H)+]: 625

[Synthesis Example 5] Synthesis of Compound 45

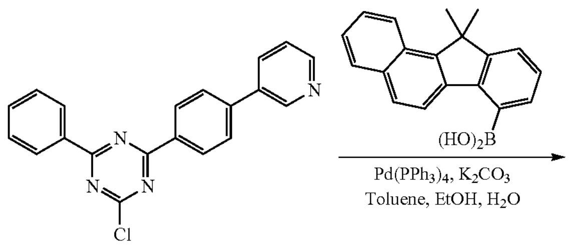

PTZ-1

-continued

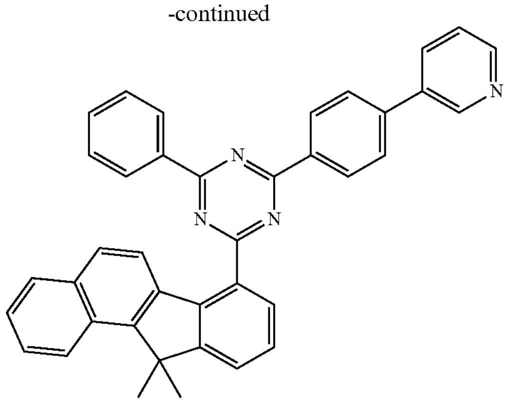

45

3.2 g of PTZ-1, 4.9 g of (7,7-dimethyl-7H-benzo[c]fluoren-7-yl) boronic acid, and 3.3 g of $K_2CO_3$ were mixed, 60 ml of toluene, 12 ml of ethanol, and 12 ml of water were added thereto, 520 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:Hex=2:1 was 10 performed, thereby obtaining 3.8 g (yield 57%) of Compound 45 in a white solid state.

Mass: [(M+H)+]: 553

[Synthesis Example 6] Synthesis of Compound 111

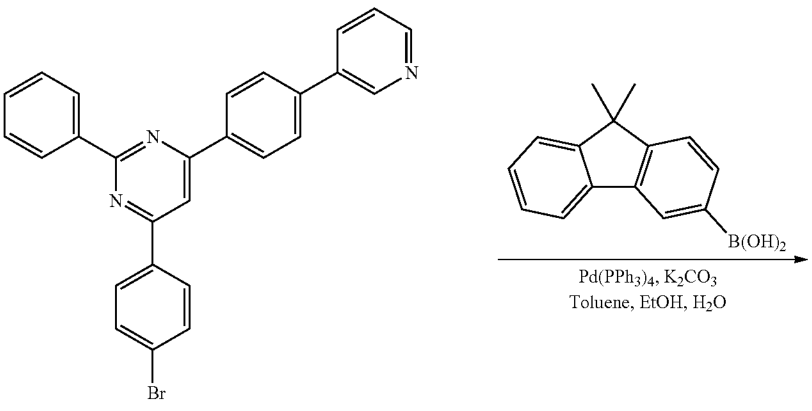

PPY-2

-continued

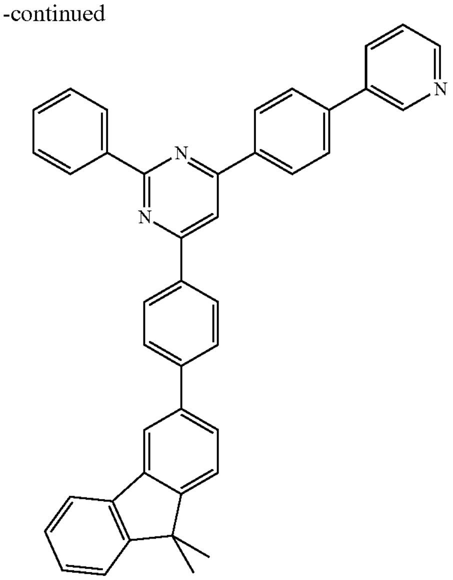

111

2.0 g of PPY-2, 2.1 g of (9,9-dimethyl-9H-fluoren-3-yl) boronic acid, and 1.8 g of $K_2CO_3$ were mixed, 50 ml of toluene, 10 ml of ethanol, and 10 ml of water were added thereto, 200 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC was performed, thereby obtaining 1.8 g (yield 76%) of Compound 111 in a white solid state.

Mass: $[(M+H)^+]$: 578

[Synthesis Example 7] Synthesis of Compound 112

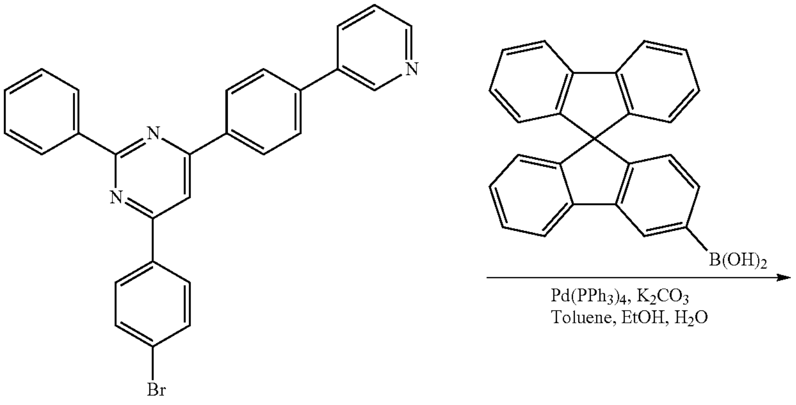

PPY-2

-continued

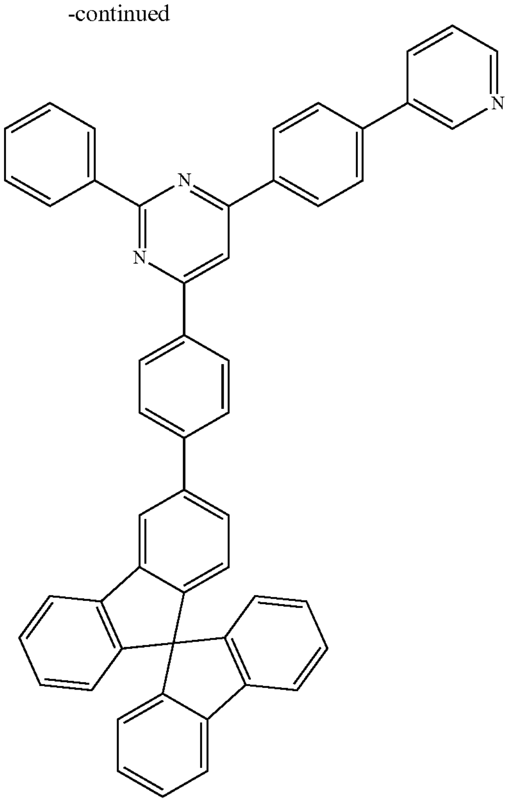

112

2.0 g of PPY-2, 2.5 g of 9,9'-spirobi[fluorene]-3-yl boronic acid, and 2.0 g of $K_2CO_3$ were mixed, 50 ml of toluene, 12 ml of ethanol, and 12 ml of water were added thereto, 200 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with THF:Hex=1:5 was performed, thereby obtaining 1.5 g (yield 55%) of Compound 112 in a white solid state.

Mass: $[(M+H)^+]$: 700

[Synthesis Example 8] Synthesis of Compound 121

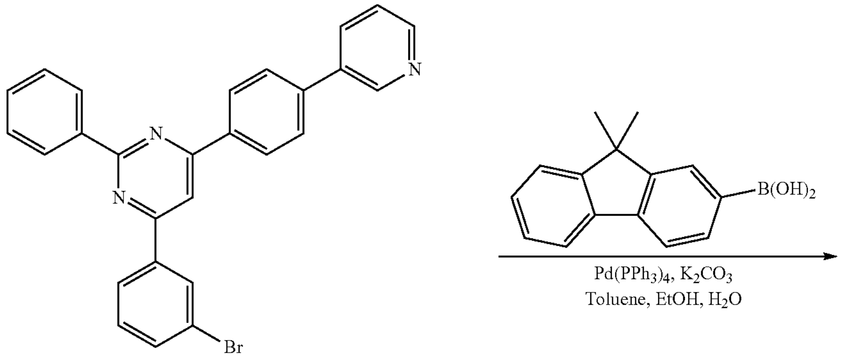

PPY-4

-continued

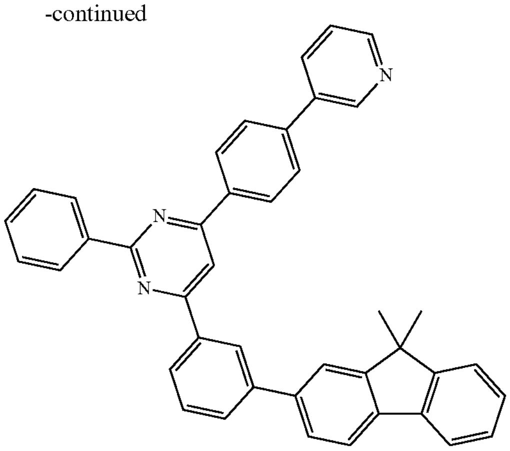

121

2.1 g of PPY-4, 2.2 g of (9,9-dimethyl-9H-fluoren-2-yl) boronic acid, and 1.9 g of $K_2CO_3$ were mixed, 50 ml of toluene, 10 ml of ethanol, and 10 ml of water were added thereto, 220 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC was performed, thereby obtaining 1.6 g (yield 72%) of Compound 121 in a white solid state.

Mass: [(M+H)+]: 578

[Synthesis Example 9] Synthesis of Compound 133

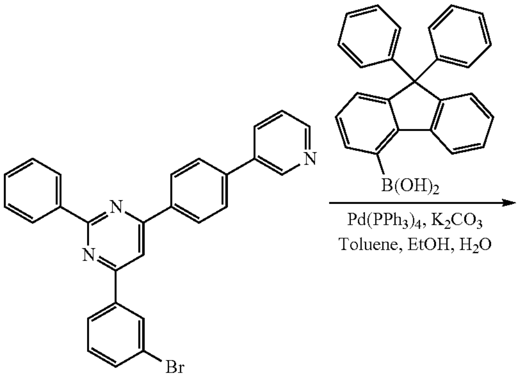

PPY-4

-continued

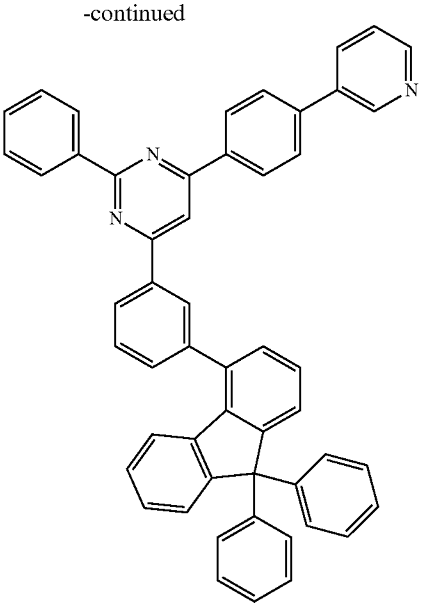

133

2.1 g of PPY-4, 2.7 g of (9,9-diphenyl-9H-fluoren-4-yl) boronic acid, and 2.1 g of $K_2CO_3$ were mixed, 50 ml of toluene, 12 ml of ethanol, and 12 ml of water were added thereto, 210 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC added with some pyridine was performed, thereby obtaining 2.1 g (yield 68%) of Compound 133 in a white solid state.

Mass: [(M+H)+]: 702

[Synthesis Example 10] Synthesis of Compound 151

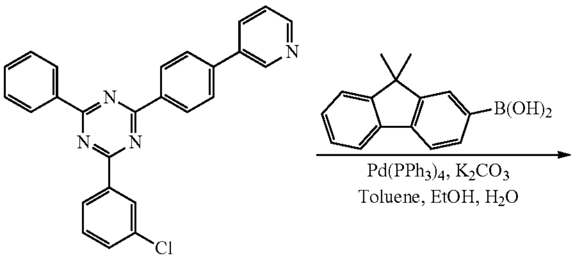

PTZ-2

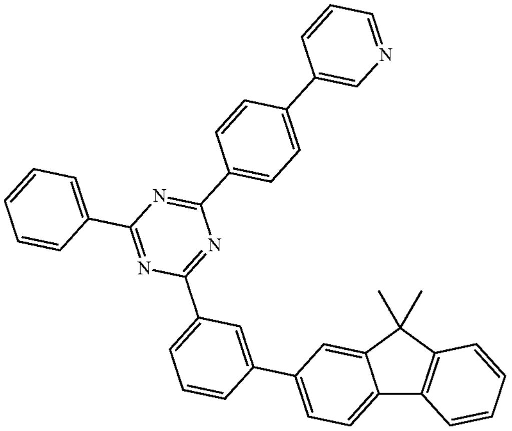

151

2.3 g of PTZ-2, 2.3 g of (9,9-dimethyl-9H-fluoren-2-yl) boronic acid, and 3.0 g of $Cs_2CO_3$ were mixed, 60 ml of toluene, 12 ml of ethanol, and 12 ml of water were added thereto, 50 mg of Pd(OAc) 2 and 230 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC was performed, thereby obtaining 2.2 g (yield 75%) of Compound 151 in a white solid state.

Mass: [(M+H)+]: 579

[Synthesis Example 11] Synthesis of Compound 156

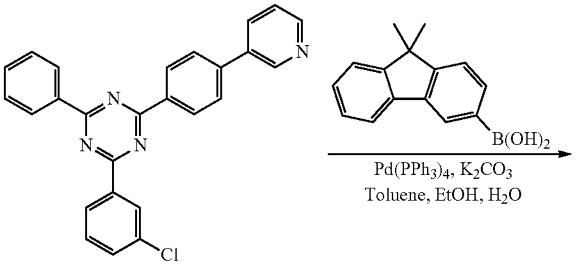

PTZ-2

-continued

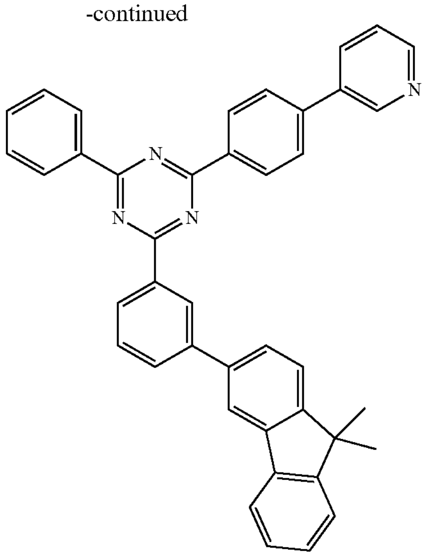

156

2.1 g of PTZ-2, 2.2 g of (9,9-dimethyl-9H-fluoren-3-yl) boronic acid, and 2.8 g of $Cs_2CO_3$ were mixed, 60 ml of toluene, 12 ml of ethanol, and 12 ml of water were added thereto, 48 mg of Pd(OAc) 2 and 200 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC was performed, thereby obtaining 2.0 g (yield 71%) of Compound 156 in a white solid state.

Mass: [(M+H)+]: 579

[Synthesis Example 12] Synthesis of Compound 346

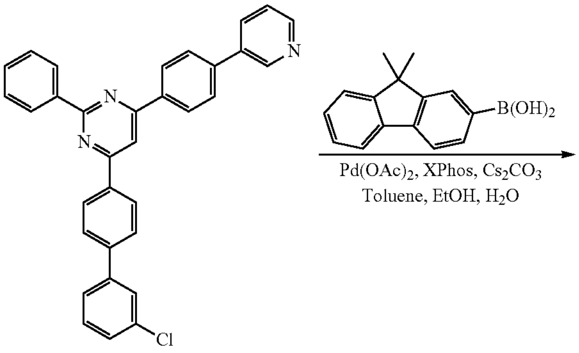

PPY-3

-continued

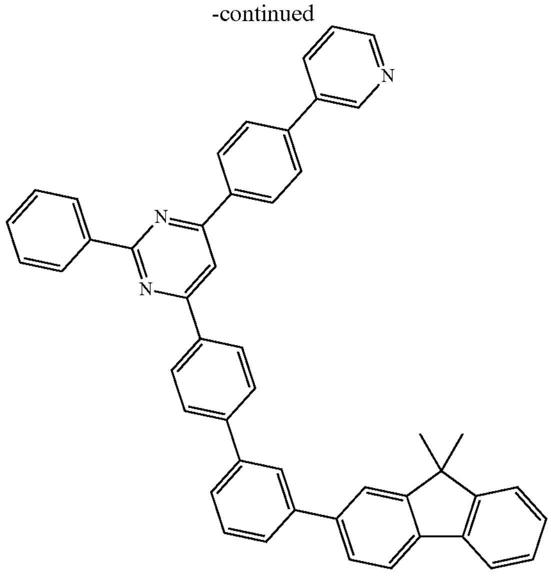

346

2.5 g of PPY-3, 2.4 g of (9,9-dimethyl-9H-fluoren-2-yl) boronic acid, and 3.3 g of $Cs_2CO_3$ were mixed, 60 ml of toluene, 12 ml of ethanol, and 12 ml of water were added thereto, 57 mg of Pd(OAc) 2 and 250 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC was performed, thereby obtaining 2.3 g 10 (yield 70%) of Compound 346 in a white solid state.

Mass: [(M+H)+]: 654

[Synthesis Example 13] Synthesis of Compound 350

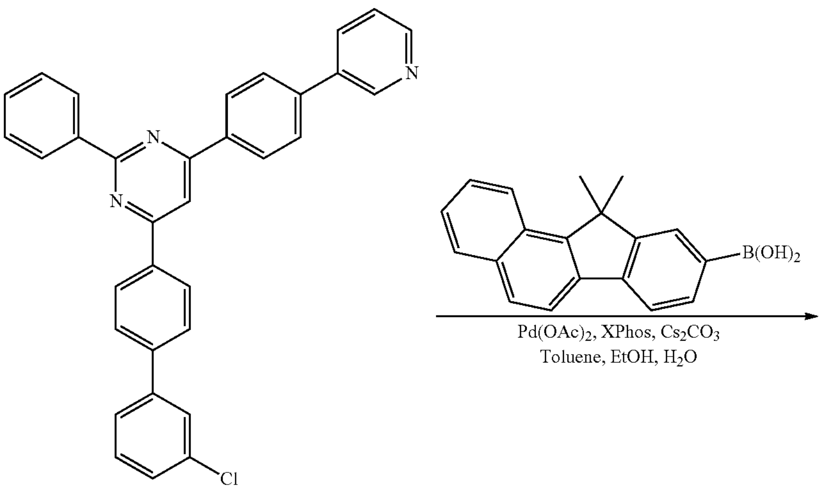

PPY-3

-continued

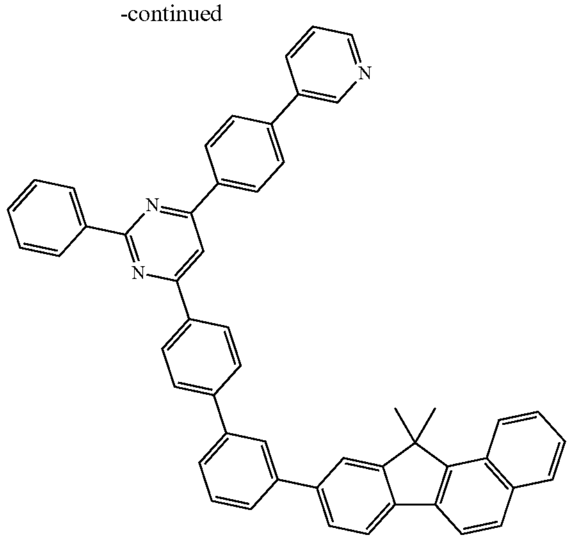

350

2.5 g of PPY-3, 2.8 g of (7,7-dimethyl-7H-benzo[c]fluoren-9-yl) boronic acid, and 3.3 g of $Cs_2CO_3$ were mixed, 60 ml of toluene, 12 ml of ethanol, and 12 ml of water were added thereto, 57 mg of Pd(OAc) 2 and 250 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC was performed, thereby obtaining 2.5 g (yield 71%) of Compound 350 in a white solid state.

Mass: [(M+H)+]: 704

[Synthesis Example 14] Synthesis of Compound 376

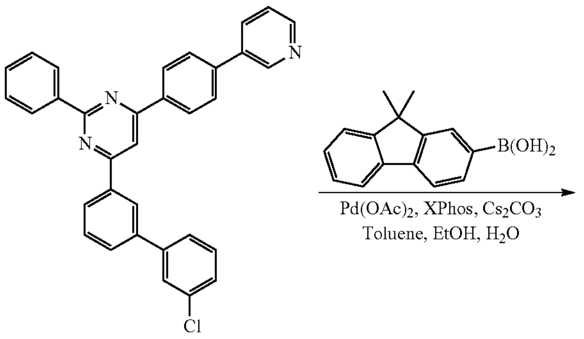

PPY-5

-continued

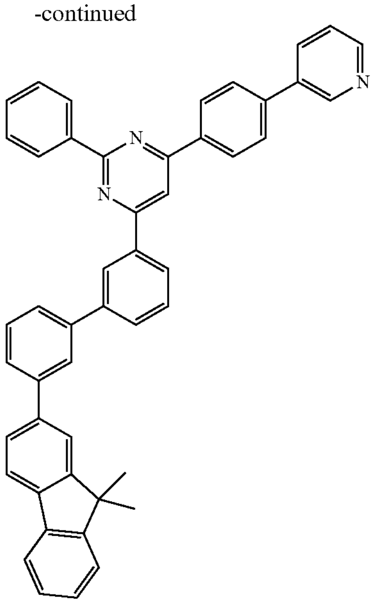

376

2.2 g of PPY-5, 2.3 g of (9,9-dimethyl-9H-fluoren-2-yl) boronic acid, and 3.0 g of $Cs_2CO_3$ were mixed, 60 ml of toluene, 12 ml of ethanol, and 12 ml of water were added thereto, 50 mg of Pd(OAc) 2 and 230 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC was performed, thereby obtaining 2.0 g (yield 66%) of Compound 376 in a white solid state.

Mass: [(M+H)+]: 654

[Synthesis Example 15] Synthesis of Compound 377

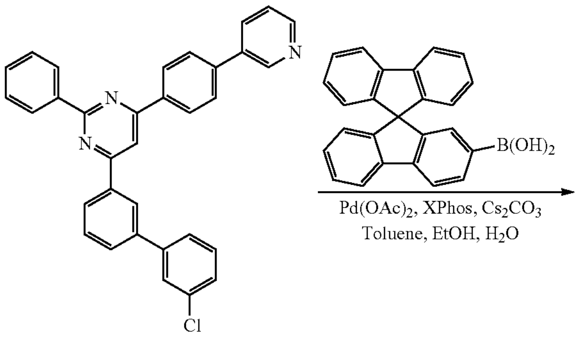

PPY-5

-continued

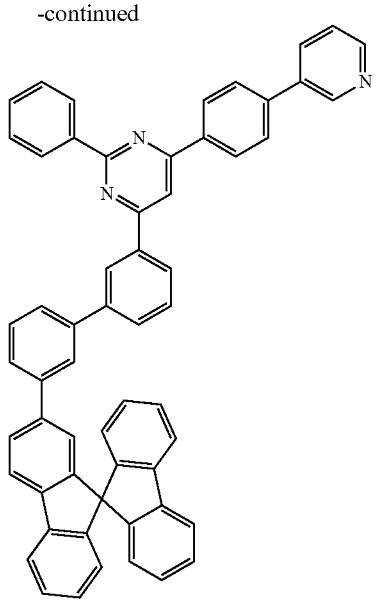

377

2.0 g of PPY-5, 2.5 g of (9,9-dimethyl-9H-fluoren-2-yl) boronic acid, and 3.0 g of $Cs_2CO_3$ were mixed, 60 ml of toluene, 12 ml of ethanol, and 12 ml of water were added thereto, 50 mg of Pd(OAc) 2 and 230 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with THF:Hex=1:2 was performed, thereby obtaining 2.3 g (yield 66%) of Compound 377 in a white solid state.

Mass: [(M+H)+]: 776

[Synthesis Example 16] Synthesis of Compound 380

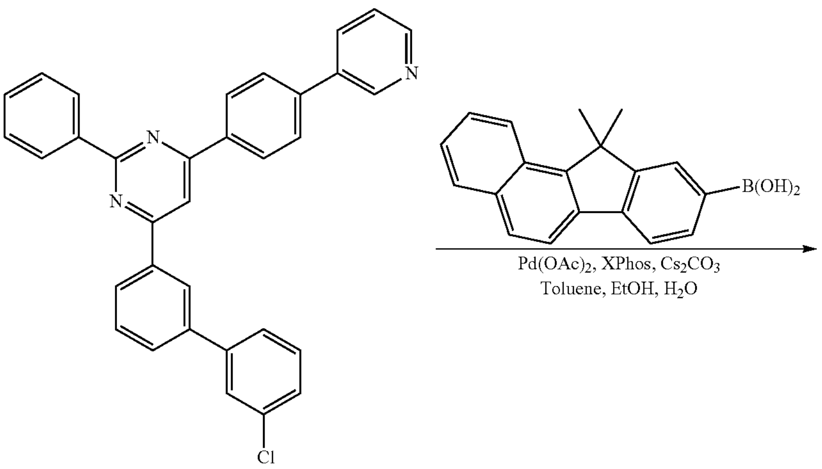

PPY-5

-continued

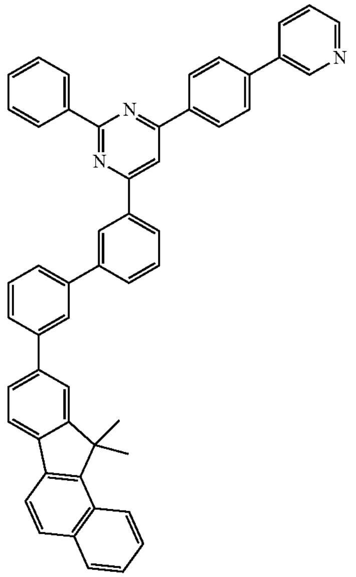

380

2.1 g of PPY-5, 2.4 g of (11,11-dimethyl-11H-benzo[a]fluoren-9-yl) boronic acid, and 2.9 g of $Cs_2CO_3$ were mixed, 60 ml of toluene, 12 ml of ethanol, and 12 ml of water were added thereto, 53 mg of Pd(OAc) 2 and 240 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC was performed, thereby obtaining 1.9 g (yield 63%) of Compound 380 in a white solid state.

Mass: [(M+H)+]: 704

[Synthesis Example 17] Synthesis of Compound 409

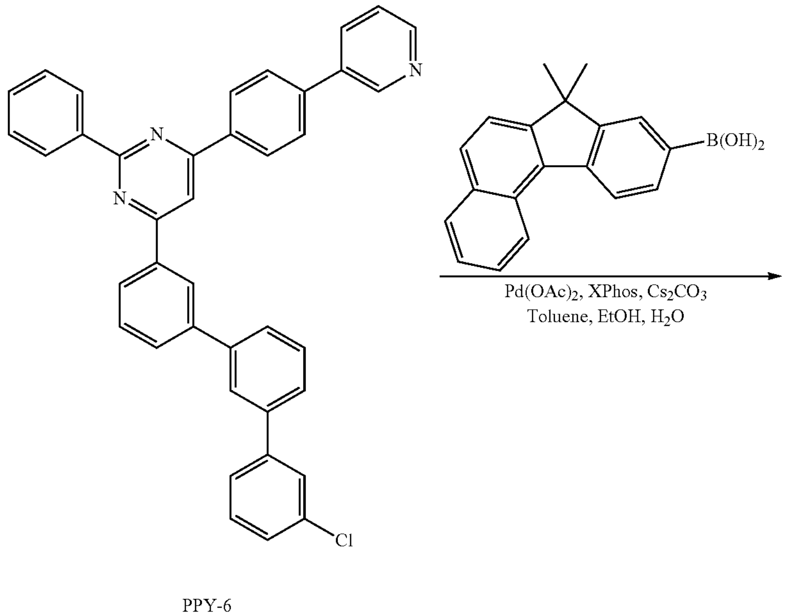

PPY-6

-continued

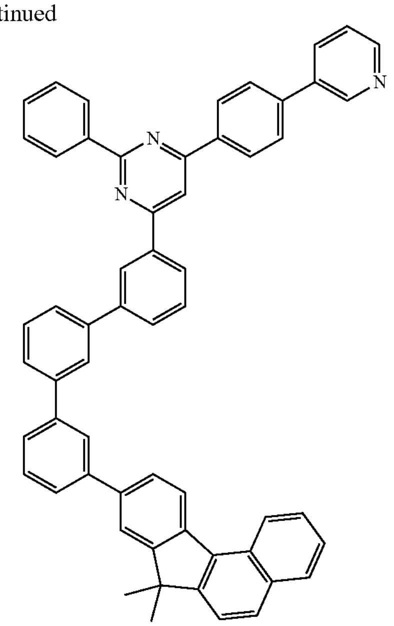

409

2.0 g of PPY-6, 2.1 g of (7,7-dimethyl-7H-benzo[c]fluoren-9-yl) boronic acid, and 2.5 g of $Cs_2CO_3$ were mixed, 60 ml of toluene, 12 ml of ethanol, and 12 ml of water were added thereto, 48 mg of Pd(OAc) 2 and 210 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:MeOH=100:1 was performed, thereby obtaining 2.1 g (yield 66%) of Compound 409 in a white solid state.

Mass: [(M+H)+]: 780

[Synthesis Example 18] Synthesis of Compound 411

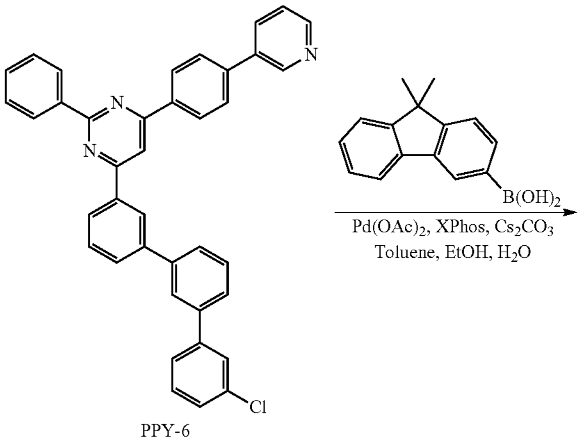

PPY-6

-continued

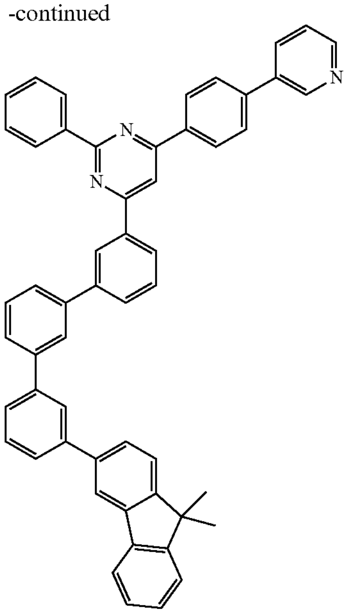

411

2.0 g of PPY-6, 2.0 g of (9,9-dimethyl-9H-fluoren-3-yl) boronic acid, and 2.5 g of $Cs_2CO_3$ were mixed, 60 ml of toluene, 12 ml of ethanol, and 12 ml of water were added thereto, 48 mg of Pd(OAc) 2 and 210 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:MeOH=100:1 was performed, thereby obtaining 1.6 g (yield 59%) of Compound 411 in a white solid state.

Mass: [(M+H)+]: 730

[Synthesis Example 19] Synthesis of Compound 436

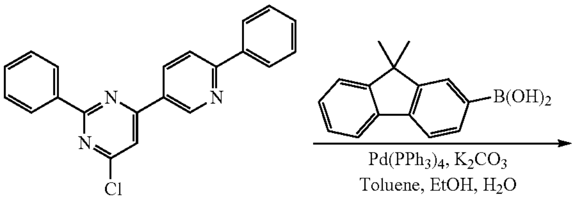

PPY-7

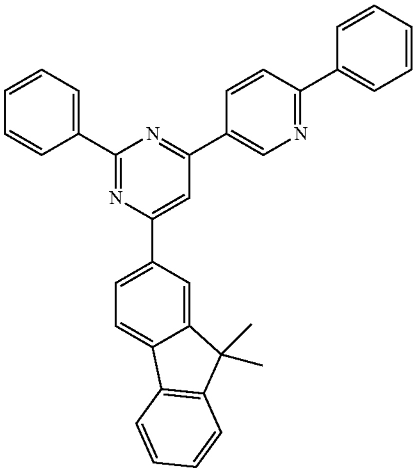

436

3.0 g of PPY-7, 4.6 g of (9,9'-dimethyl-9H-fluoren-2-yl) boronic acid, and 3.2 g of $K_2CO_3$ were mixed, 60 ml of toluene, 12 ml of ethanol, and 12 ml of water were added thereto, 500 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:Hex=2:1 was performed, thereby obtaining 3.0 g (yield 65%) of Compound 436 in a white solid state.

Mass: [(M+H)+]: 502

[Synthesis Example 20] Synthesis of Compound 448

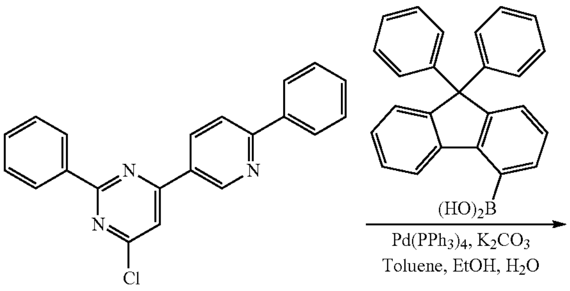

PPY-7

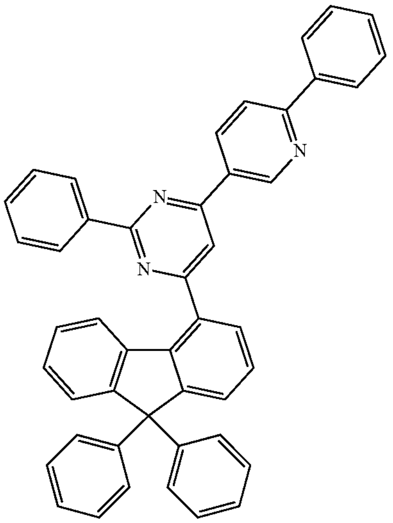

448

2.9 g of PPY-7, 5.0 g of (9,9-diphenyl-9H-fluoren-4-yl) boronic acid, and 3.1 g of $K_2CO_3$ were mixed, 60 ml of toluene, 12 ml of ethanol, and 12 ml of water were added thereto, 500 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:Hex=2:1 was performed, thereby obtaining 3.9 g (yield 62%) of Compound 448 in a white solid state.

Mass: [(M+H)+]: 626

[Synthesis Example 21] Synthesis of Compound 518

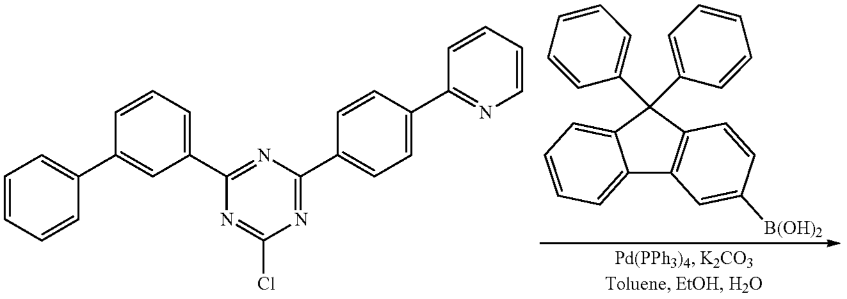

PTZ-3

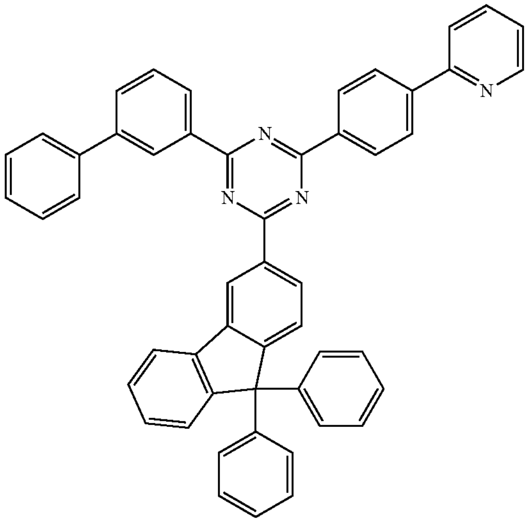

518

2.6 g of PTZ-3, 4.6 g of (9,9'-diphenyl-9H-fluoren-3-yl) boronic acid, and 3.3 g of $K_2CO_3$ were mixed, 60 ml of toluene, 12 ml of ethanol, and 12 ml of water were added thereto, 480 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:Hex=2:1 was performed, thereby obtaining 4.2 g (yield 72%) of Compound 518 in a white solid state.

Mass: [(M+H)+]: 703

[Synthesis Example 22] Synthesis of Compound 524

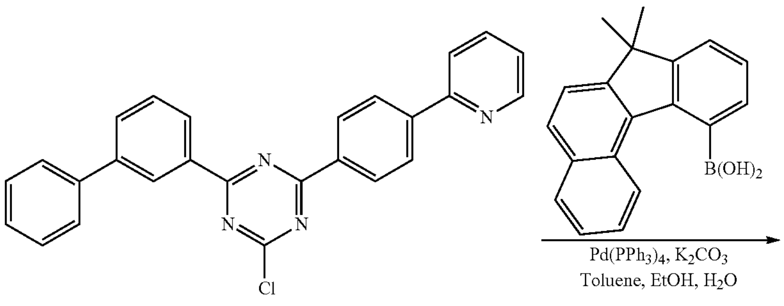

PTZ-3

-continued

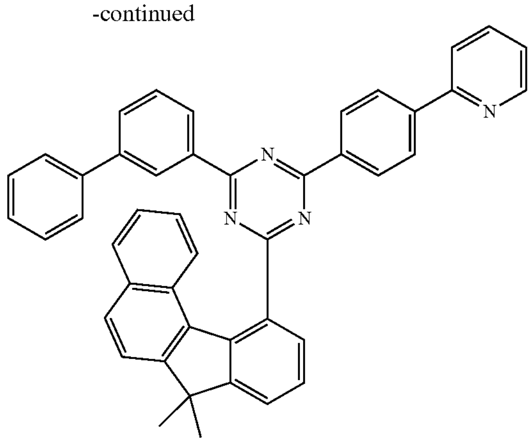

524

2.0 g of PTZ-3, 3.6 g of (7,7-dimethyl-7H-benzo[c]fluoren-11-yl) boronic acid, and 2.3 g of $K_2CO_3$ were mixed, 50 ml of toluene, 10 ml of ethanol, and 10 ml of water were added thereto, 400 mg of tetrakis(phenylphosphine) palladium (0) was further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC:Hex=2:1 was 10 performed, thereby obtaining 4.2 g (yield 72%) of Compound 524 in a white solid state.

Mass: [(M+H)+]: 629

[Synthesis Example 23] Synthesis of Compound 542

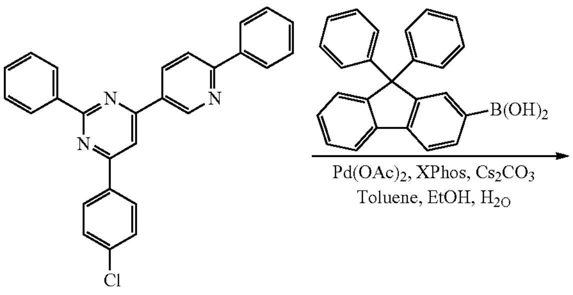

PPY-8

-continued

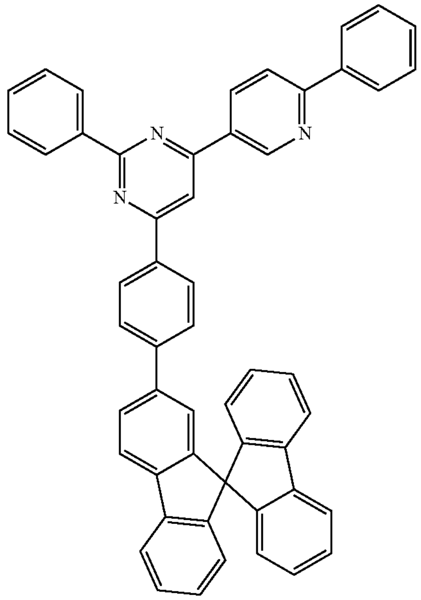

542

2.2 g of PPY-8, 2.6 g of 9,9'-spirobi[fluorene]-2-yl boronic acid, and 2.9 g of $Cs_2CO_3$ were mixed, 60 ml of toluene, 12 ml of ethanol, and 12 ml of water were added thereto, 50 mg of Pd(OAc) 2 and 230 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with MC was performed, thereby obtaining 2.1 g (yield 53%) of Compound 542 in a white solid state.

Mass: [(M+H)+]: 700

[Synthesis Example 24] Synthesis of Compound 545

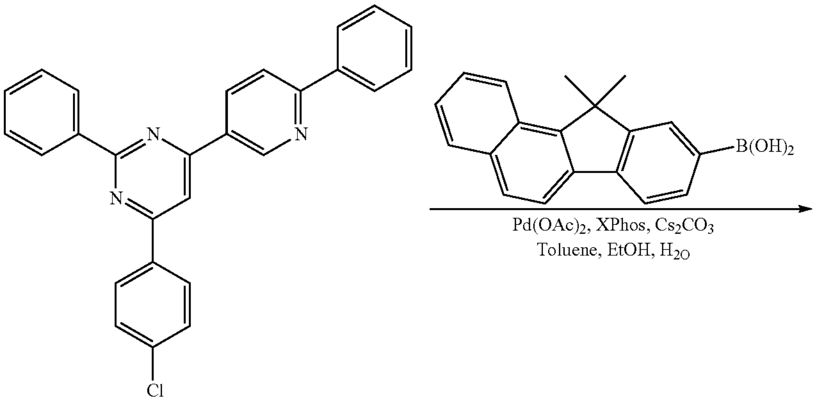

PPY-8

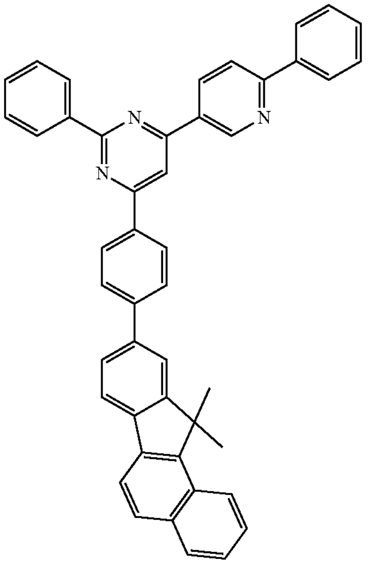

545

2.3 g of PPY-8, 2.4 g of (11,11-dimethyl-11H-benzo[a]fluoren-9-yl) boronic acid, and 3.0 g of $Cs_2CO_3$ were mixed, 60 ml of toluene, 12 ml of ethanol, and 12 ml of water were added thereto, 55 mg of Pd(OAc) 2 and 250 mg of Xphos were further added thereto, and the mixture was stirred and heated for 4 hours. After the reaction was completed, the temperature was lowered to room temperature, and the reaction product was filtered. The filtrate was poured into water, followed by extraction with chloroform. An organic layer was dried over $MgSO_4$ and concentrated under reduced pressure, and column chromatography with THF:Hex=1:3 was performed, thereby obtaining 2.6 g (yield 63%) of Compound 545 in a white solid state.

Mass: [(M+H)+]: 628

[Embodiments 1 to 13] Manufacturing of Blue Organic Electroluminescent Device

Compounds 1, 2, 4, 42, 45, 111, 112, 121, 133, 151, 156, 346, and 350 synthesized in the above Synthesis Examples were subjected to high purity sublimation purification by a commonly known method and then blue organic EL devices were manufactured as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics CO., LTD., 80 nm)/NPB (15 nm)/ADN+5% DS-405 (Doosan Electronics CO., LTD., 30 nm)/respective Compounds 1, 2, 4, 42, 45, 111, 112, 121, 133, 151, 156, 346, and 350 (30 nm)/LiF (1 nm)/Al (200 nm) were laminated in the order listed, thereby manufacturing organic EL devices.

[Comparative Example 1] Manufacturing of Blue Organic EL Device

A blue organic EL device was manufactured in the same manner as in Embodiment 1, except that $Alq_3$, instead of Compound 1, was used as the material of the electron transporting layer.

[Comparative Example 2] Manufacturing of Blue Organic EL Device

A blue organic EL device was manufactured in the same manner as in Embodiment 1, except that Compound 1 was not used as the material of the electron transporting layer.

The structures of NPB, ADN, and $Alq_3$ used in Embodiments 1 to 13 and Comparative Examples 1 and 2 are as follows.

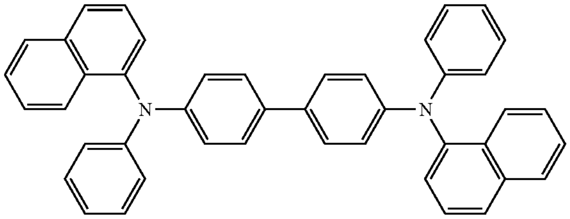

NPB

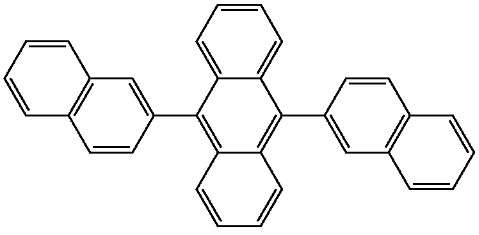

ADN

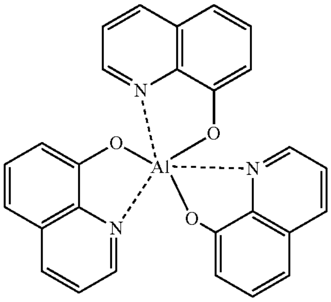

$Alq_3$

Evaluation Example 1

For each of the blue organic EL devices manufactured in Embodiments 1 to 13 and Comparative Examples 1 and 2, a driving voltage, a current efficiency and a light emission peak at a current density of 10 mA/cm$^2$ were measured and the results are shown in Table 1 below.

TABLE 1

| Sample | Electron transporting layer | Driving voltage (V) | Emission peak (nm) | Current efficiency (cd/A) |
|---|---|---|---|---|
| Embodiment 1 | Compound 1 | 3.6 | 455 | 8.1 |
| Embodiment 2 | Compound 2 | 3.8 | 451 | 8.6 |
| Embodiment 3 | Compound 4 | 3.8 | 452 | 9.1 |
| Embodiment 4 | Compound 42 | 3.6 | 452 | 8.5 |
| Embodiment 5 | Compound 45 | 3.7 | 453 | 8.6 |
| Embodiment 6 | Compound 111 | 3.6 | 451 | 8.8 |
| Embodiment 7 | Compound 112 | 3.9 | 451 | 9.1 |
| Embodiment 8 | Compound 121 | 3.4 | 453 | 7.7 |
| Embodiment 9 | Compound 133 | 3.3 | 452 | 7.6 |
| Embodiment 10 | Compound 151 | 3.1 | 451 | 7.1 |
| Embodiment 11 | Compound 156 | 3.2 | 450 | 7.3 |
| Embodiment 12 | Compound 346 | 4.3 | 451 | 8.9 |
| Embodiment 13 | Compound 350 | 4.4 | 453 | 9.0 |
| Comparative example 1 | $Alq_3$ | 4.8 | 457 | 5.6 |
| Comparative example 2 | — | 4.7 | 459 | 6.1 |

As shown in Table 1, it was appreciated that the blue organic EL devices (Embodiments 1 to 13) in which Compounds 1 1, 2, 4, 42, 45, 111, 112, 121, 133, 151, 156, 346 and 350 of the present disclosure, synthesized in the above Synthesis Examples, were used in the electron transporting layer exhibited excellent performance in terms of the driving voltage, the emission peak and the current efficiency, as compared with a conventional blue organic EL device (Comparative Example 1) in which $Alq_3$ was used in the electron transporting layer and a conventional blue organic EL device (Comparative Example 2) in which the electron transporting layer is absent.

[Embodiments 14 to 24] Manufacturing of Blue Organic Electroluminescent Device

Compounds 376, 377, 380, 409, 411, 436, 448, 518, 524, 542, and 545 synthesized in the above Synthesis Examples were subjected to high purity sublimation purification by a commonly known method and then blue organic EL devices were manufactured as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics CO., LTD., 80 nm)/NPB (15 nm)/ADN+5% DS-405 (Doosan Electronics CO., LTD., 30 nm)/respective Compounds 376, 377, 380, 409, 411, 436, 448, 518, 524, 542, and 545 (5 nm)/$Alq_3$ (25 nm)/LiF (1 nm)/Al (200 nm) were laminated in the order listed, thereby manufacturing organic EL devices.

[Comparative Example 3] Manufacturing of Blue Organic EL Device

A blue organic EL device was manufactured in the same manner as in Embodiment 14, except that Compound 376 was not used as a material of an electron transport auxiliary layer and that $Alq_3$, which is a material for the electron transporting layer, was laminated to 30 nm rather than 25 nm.

Evaluation Example 2

For each of the blue organic EL devices manufactured in Embodiments 14 to 24 and Comparative Example 3, a driving voltage, a current efficiency and a light emission peak at a current density of 10 $mA/cm^2$ were measured and the results are shown in Table 2 below.

TABLE 2

| Sample | Electron transporting auxiliary layer | Driving voltage (V) | Emission peak (nm) | Current efficiency (cd/A) |
|---|---|---|---|---|
| Embodiment 14 | Compound 376 | 3.7 | 456 | 9.0 |
| Embodiment 15 | Compound 377 | 3.6 | 455 | 8.8 |
| Embodiment 16 | Compound 380 | 3.5 | 456 | 8.6 |
| Embodiment 17 | Compound 409 | 3.9 | 455 | 8.5 |
| Embodiment 18 | Compound 411 | 3.4 | 456 | 9.1 |
| Embodiment 19 | Compound 436 | 3.3 | 457 | 8.8 |
| Embodiment 20 | Compound 448 | 3.6 | 455 | 9.1 |
| Embodiment 21 | Compound 518 | 3.4 | 454 | 8.4 |
| Embodiment 22 | Compound 524 | 3.7 | 455 | 8.6 |
| Embodiment 23 | Compound 542 | 3.4 | 456 | 8.8 |
| Embodiment 24 | Compound 545 | 3.6 | 455 | 9.3 |
| Comparative example 3 | — | 4.7 | 459 | 6.1 |

As shown in Table 2, it was appreciated that the blue organic EL devices (Embodiments 14 to 24) in which the compounds of the present disclosure, synthesized in the above Synthesis Examples, were used in the electron transporting auxiliary layer exhibited excellent performance in terms of the driving voltage, the emission peak and the current efficiency, as compared with conventional blue organic EL device (Comparative Example 3) in which the electron transporting auxiliary layer is absent.

Although the preferred embodiments of the present disclosure have been described above, the present disclosure is not limited thereto, and various modifications and changes may be made within the scope of the claims and the detailed description of the invention, which also fall within the scope of the invention.

The invention claimed is:

1. A compound represented by the following Chemical Formula 1:

[Chemical Formula 1]

[Chemical Formula 1]

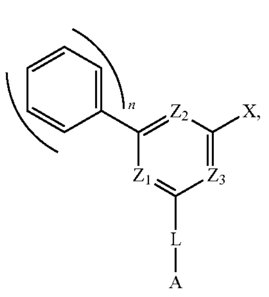

where in Chemical Formula 1, $Z_2$ is nitrogen, and one of $Z_1$ and $Z_3$ is nitrogen and the other is CH, X is represented by the following Chemical Formula 2,

[Chemical Formula 2]

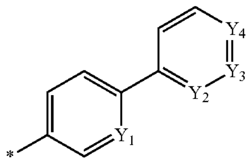

in Chemical Formula 2, one of $Y_1$ to $Y_4$ is nitrogen and the others are CH,

* means a site where a bond with Chemical Formula 1 is made, n is an integer 1,

L is a $C_6$ to $C_{18}$ arylene group, and

A is represented by the following Chemical Formula 4,

[Chemical Formula 4]

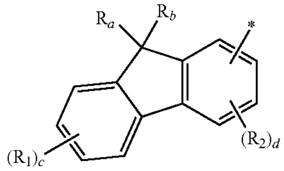

in Chemical Formula 4, $R_a$ and $R_b$ are the same as or different from each other, each independently a $C_1$ alkyl group or $C_6$ aryl group, $R_1$ and $R_2$ are independently hydrogen, or $R_1$ is bound with an adjacent group to form a fused ring represented by the following formula A-4, A-5, or A-6,

A-4

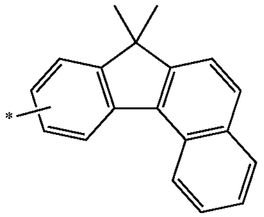

A-5

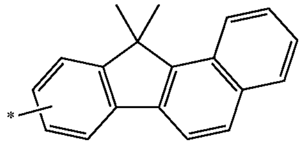

A-6

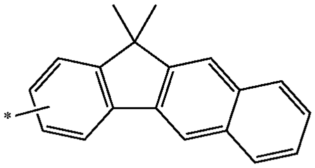

c is an integer ranging from 1 to 4, d is an integer of 3,

* means a site where a bond with Chemical Formula 1 is made.

2. The compound of claim 1, wherein the compound represented by Chemical Formula 1 is a compound represented by the following Chemical Formula 5 or Chemical Formula 6:

[Chemical Formula 5]

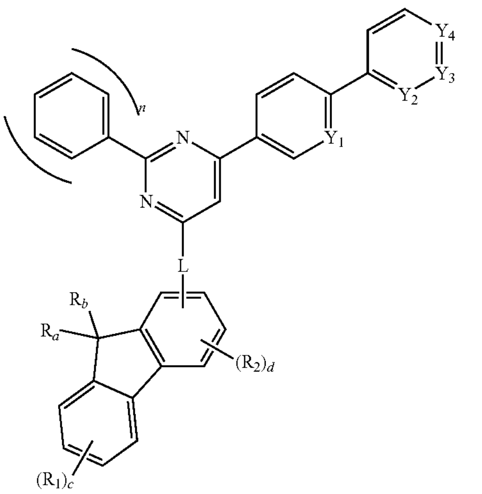

[Chemical Formula 6]

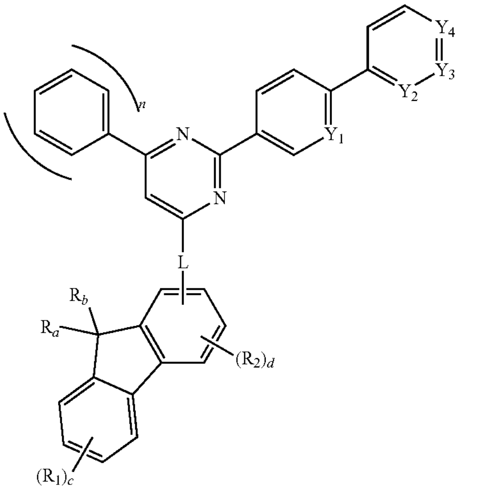

3. The compound of claim 1, wherein in Chemical Formula 1, X is selected from the group consisting of the following structures represented by X1-X4:

X-1

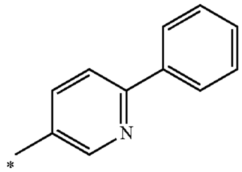

-continued

X-2

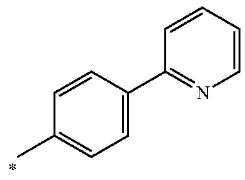

X-3

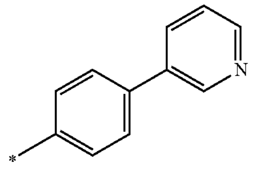

X-4

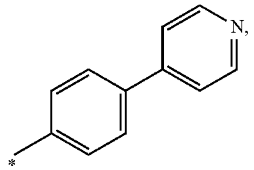

4. The compound of claim 1, wherein in Chemical Formula 1, A is selected from the group consisting of the following structures represented by A-1 and A-3 to A-6:

A-1

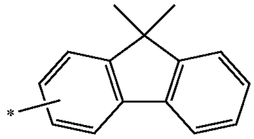

A-3

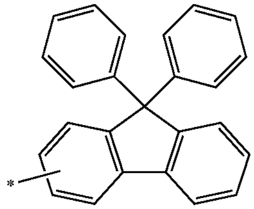

A-4

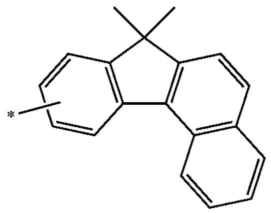

A-5

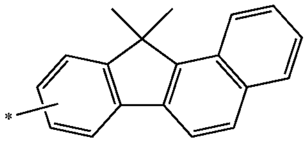

-continued
A-6
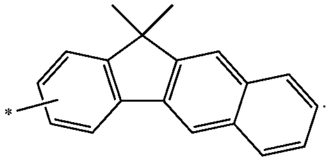
5. The compound of claim 1, wherein in Chemical Formula 1, L is a linking group selected from the following structures represented by L-1 to L-7:
L-1
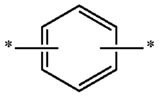
L-2
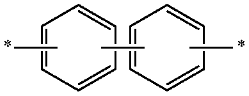
L-3
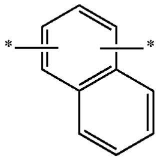
L-4
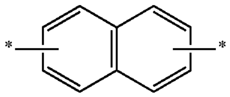
L-5
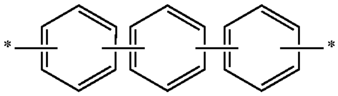
L-6
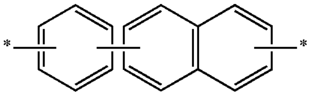
L-7
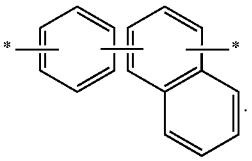
6. The compound of claim 1, wherein the compound represented by Chemical Formula 1 is selected from the group consisting of the following compounds represented by 106, 108-111, 113-116, 118-121, 123-126, 128-131, 133-135, 166, 168-171, 173-176, 178-181, 183-186, 188-191, 193-195, 316, 317-321, 323-326, 328-330, 346, 348-351, 353-356, 358-360, 376, 378-381, 383-386, 388-390, 406, 408-411, 413-416, 418-420, 541, 543-546, 548-551, 553-556, 558-561, 563-566, 568-570, 601, 603-606, 608-611, 613-616, 618-621, 623-626, 628-631, 633-636, 638-641, 643-645, 661, 663-666, 668-671, 673-675, 691, 693-696, 698-701, 703-705, 721, 723-726, 728-731, 733-735:
106
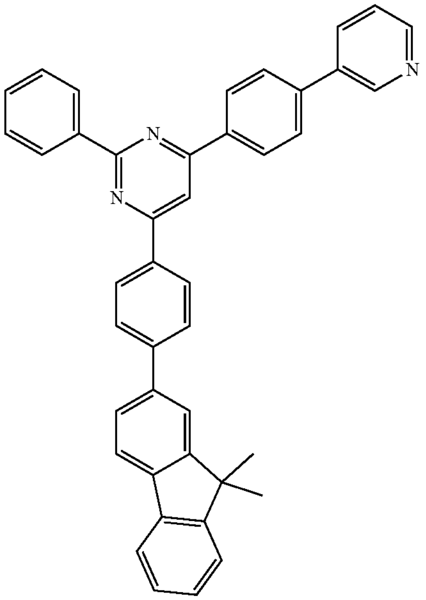
108
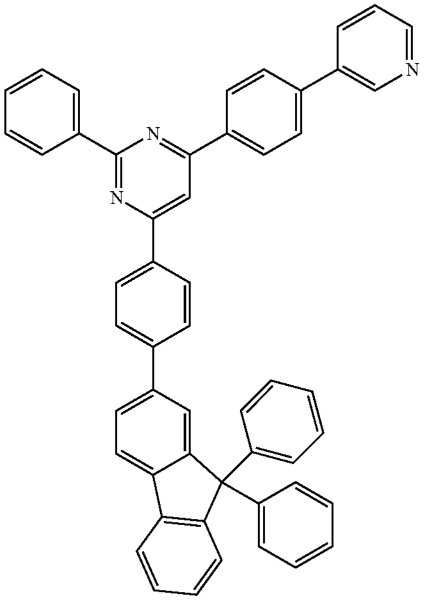

-continued
109
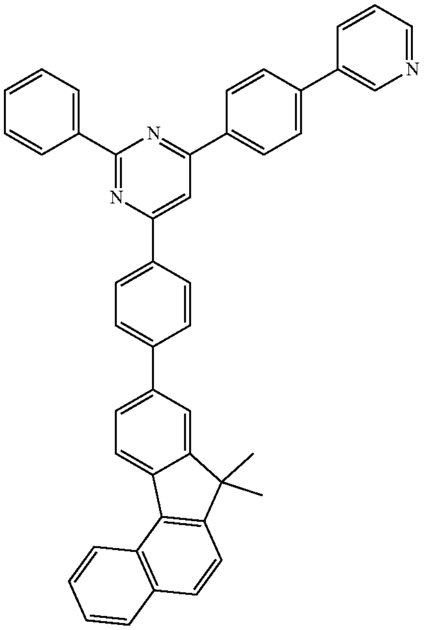
110
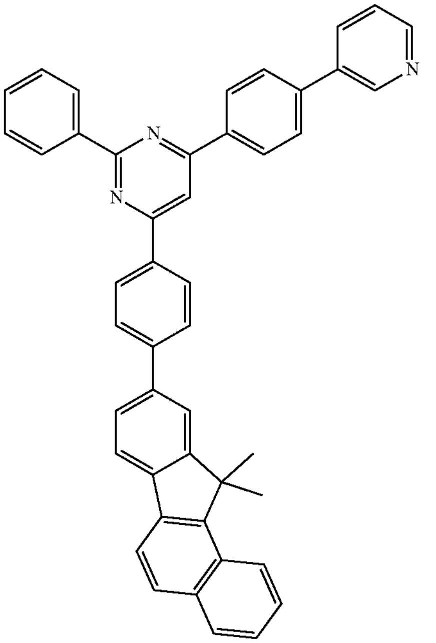
-continued
111
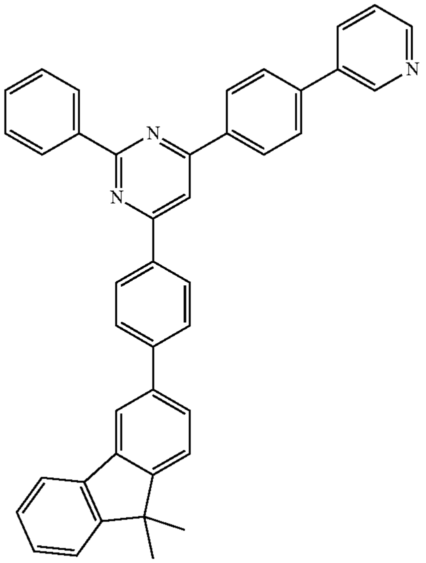
113
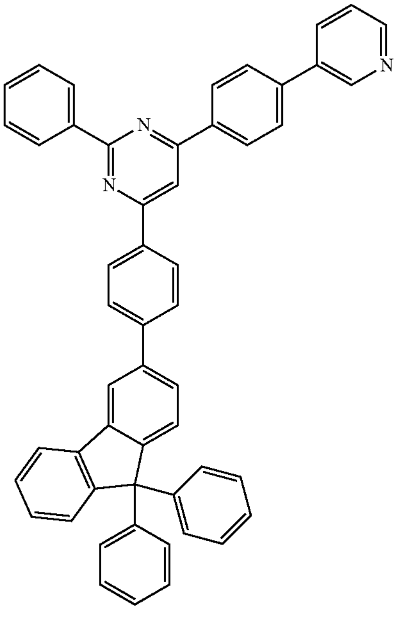

-continued
114
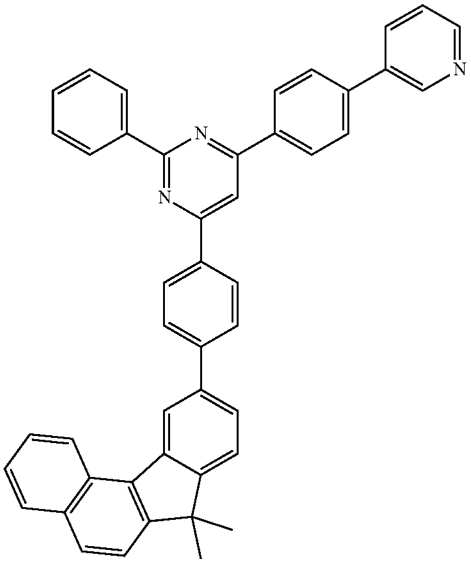
115
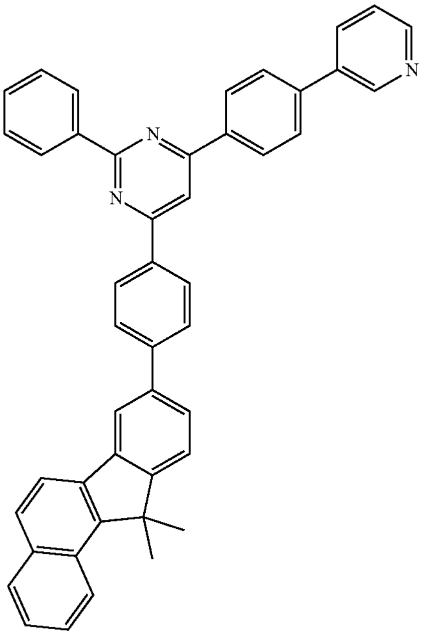
-continued
116
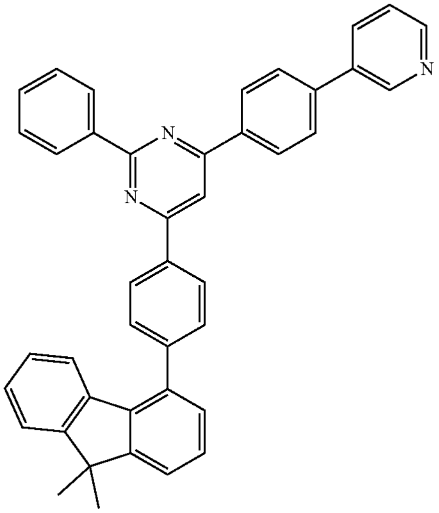
118
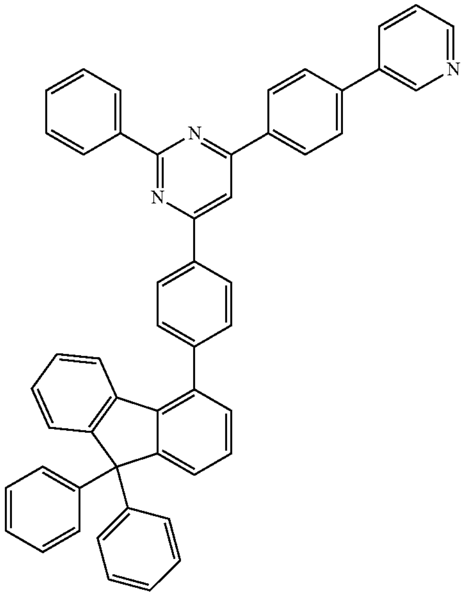
119
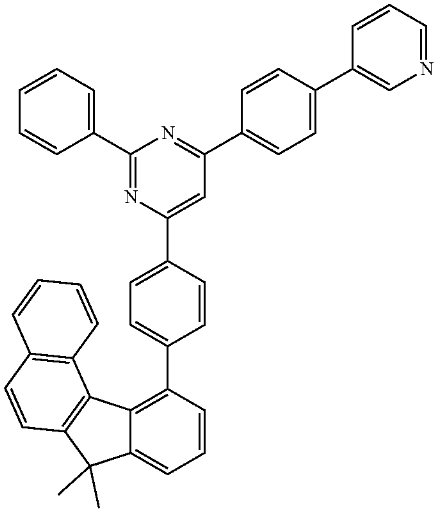

-continued
120
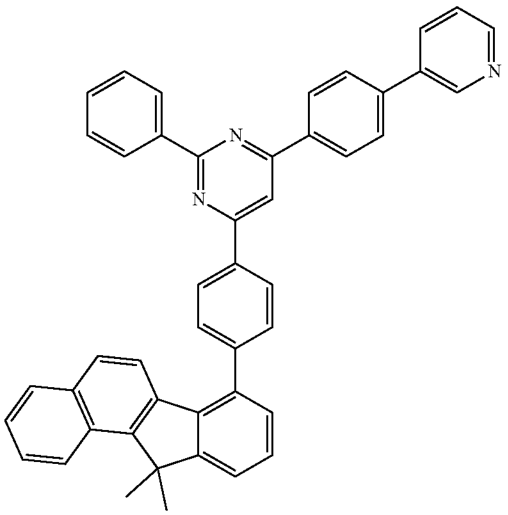
121
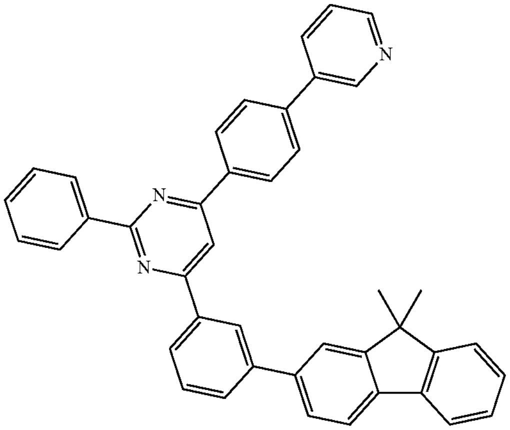
123
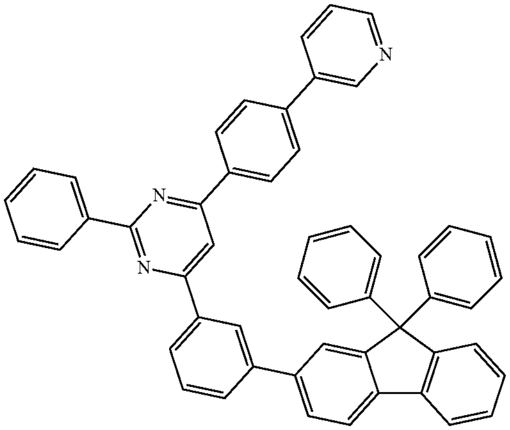
-continued
124
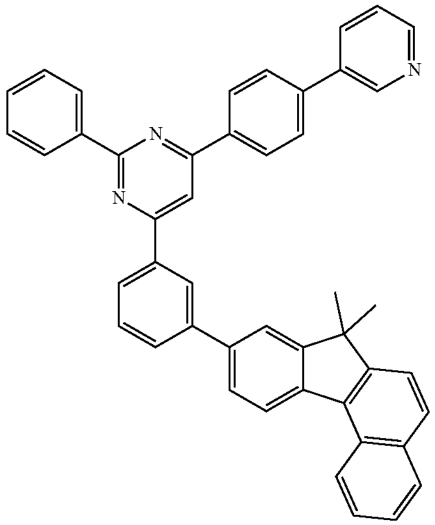
125
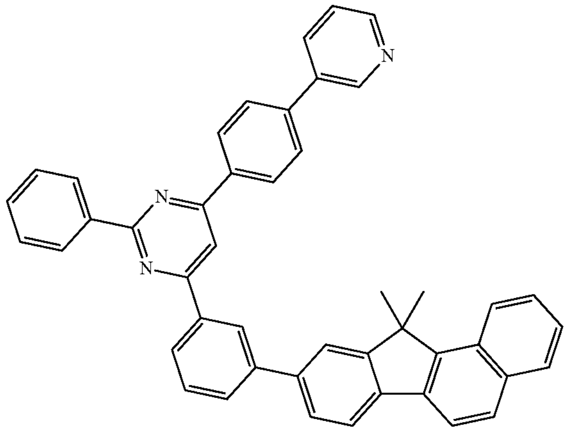
126
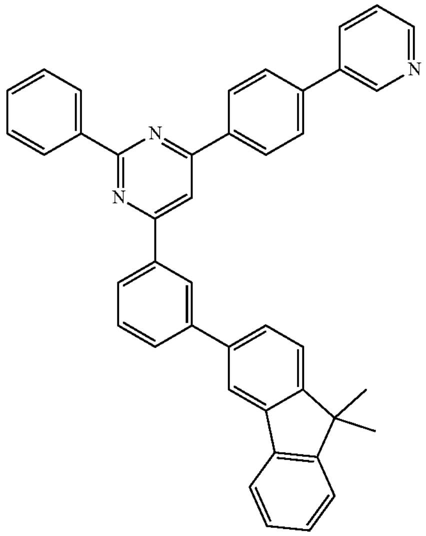

-continued
128
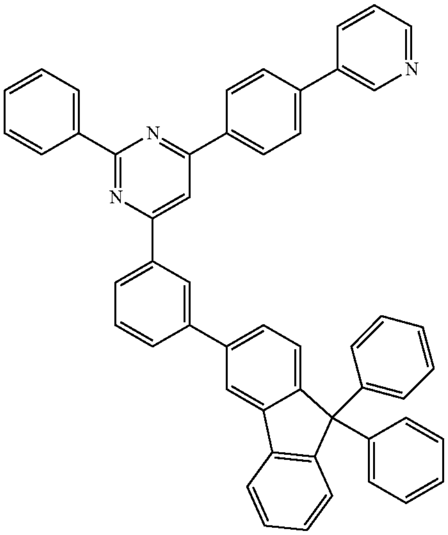
129
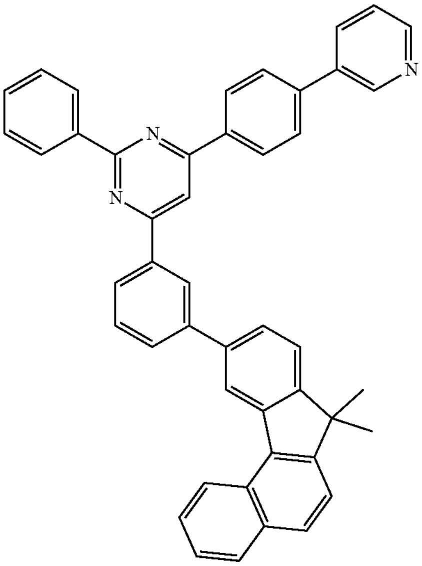
-continued
130
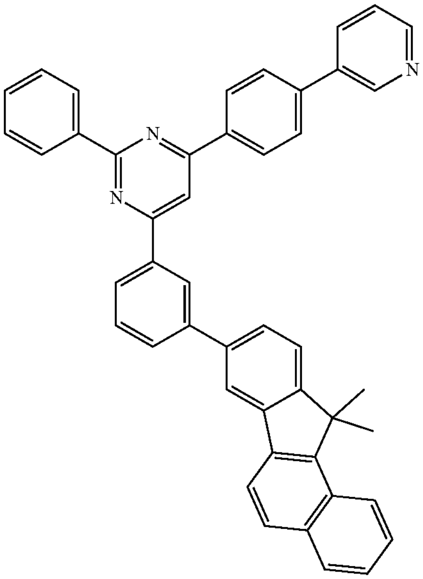
131
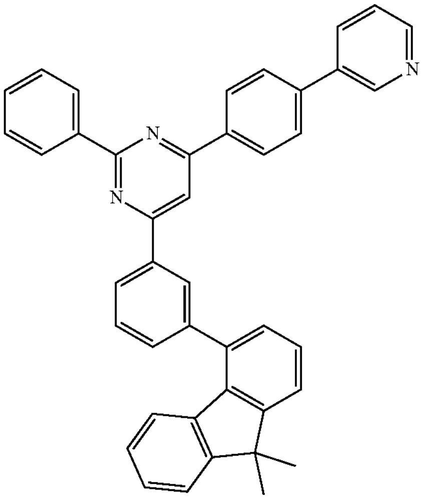
133
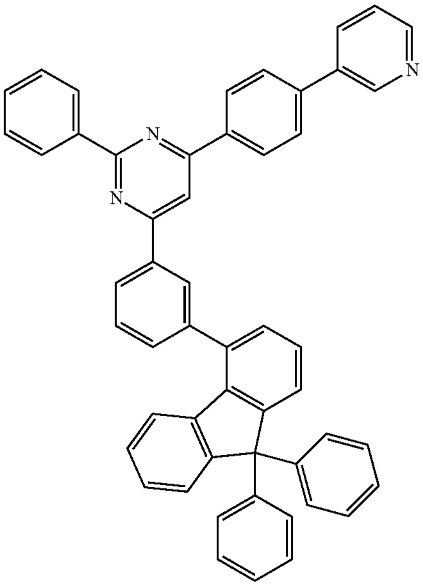

-continued
134
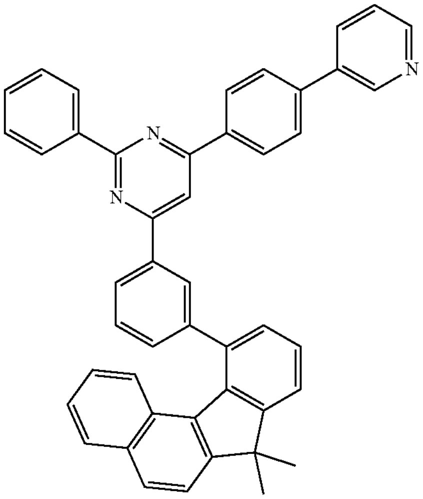
166
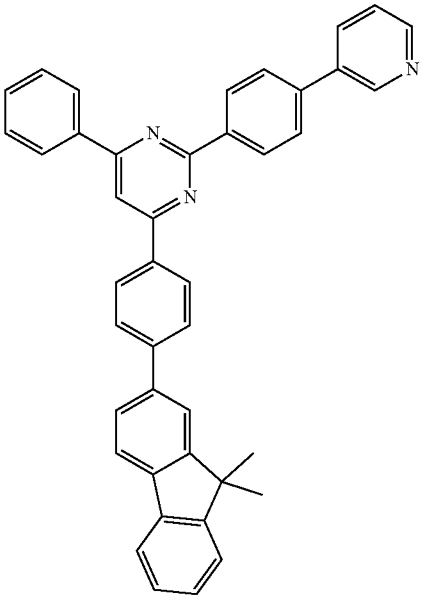
135
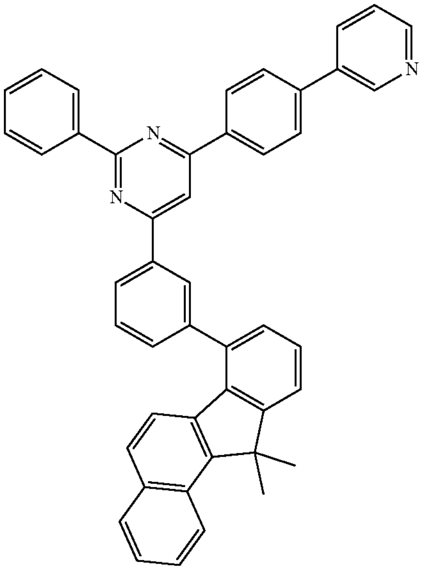
168
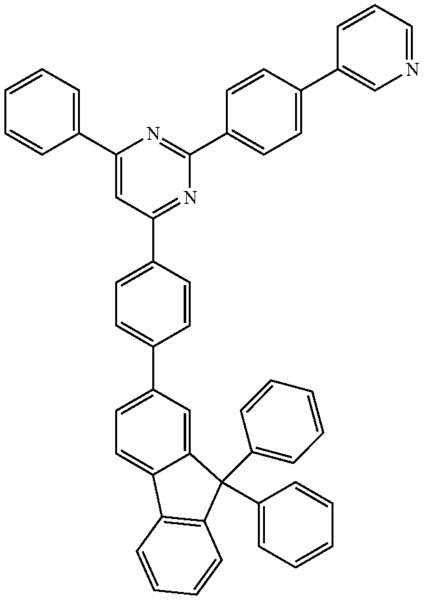

-continued
169
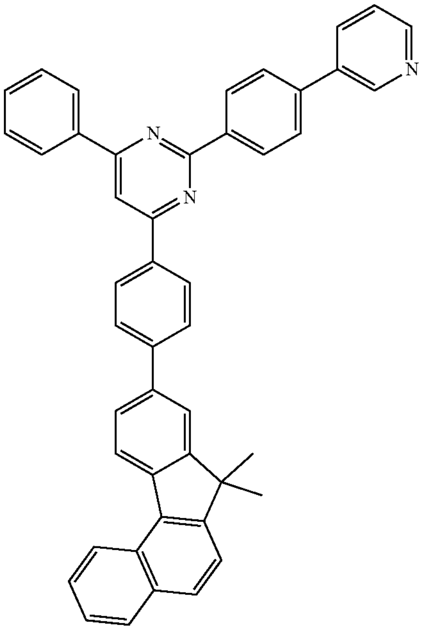
170
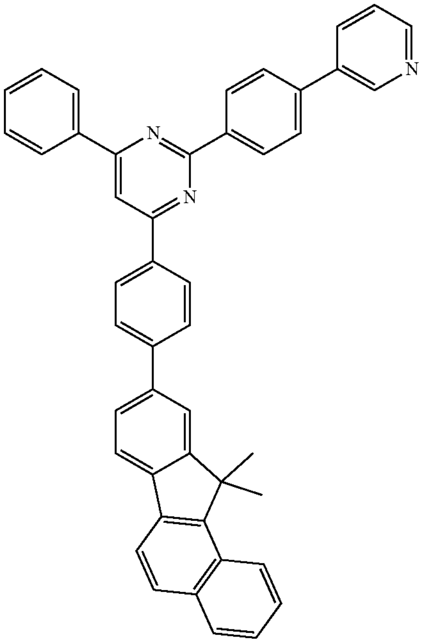
-continued
171
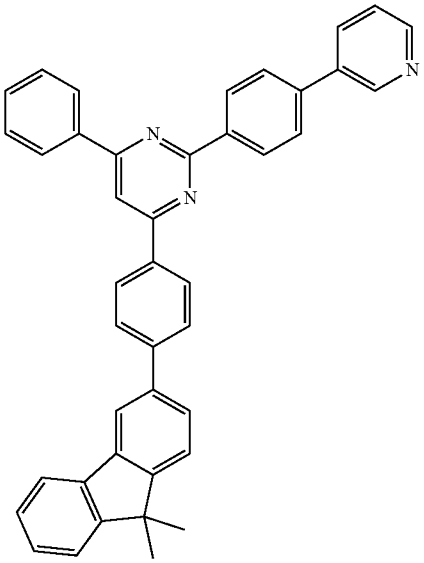
173
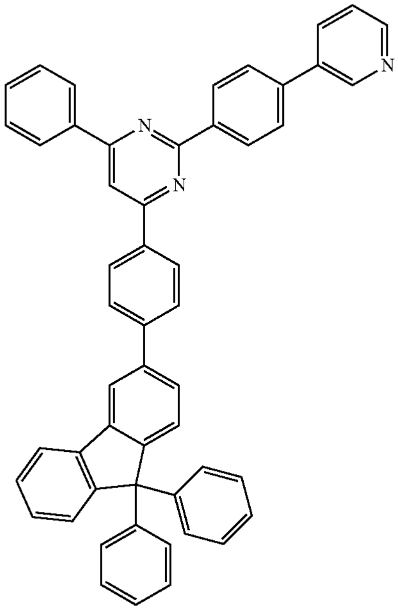

-continued
174
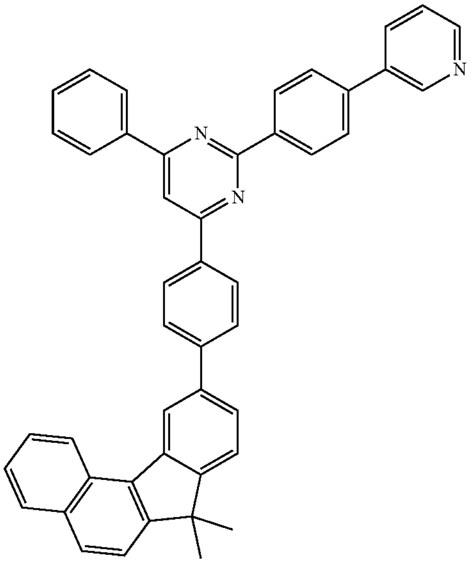
175
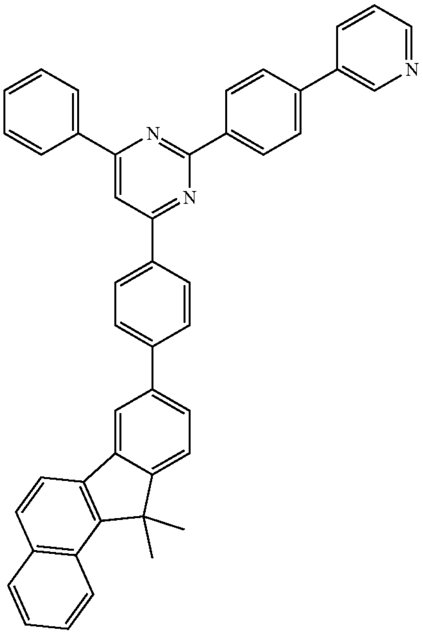
-continued
176
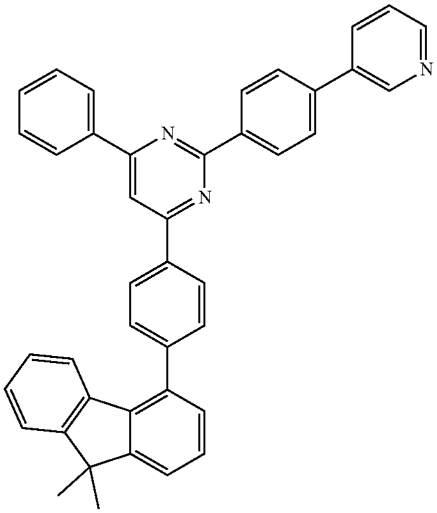
178
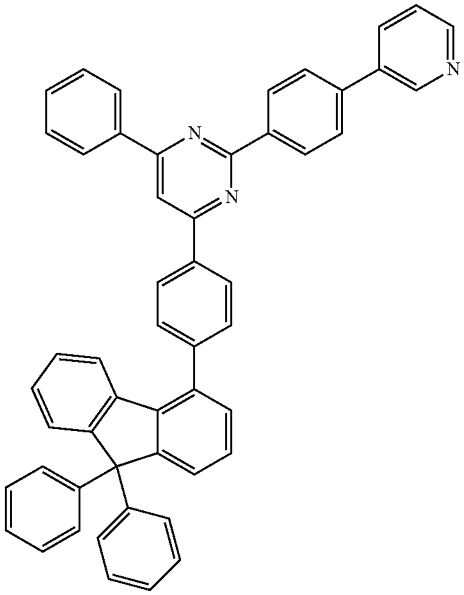
179
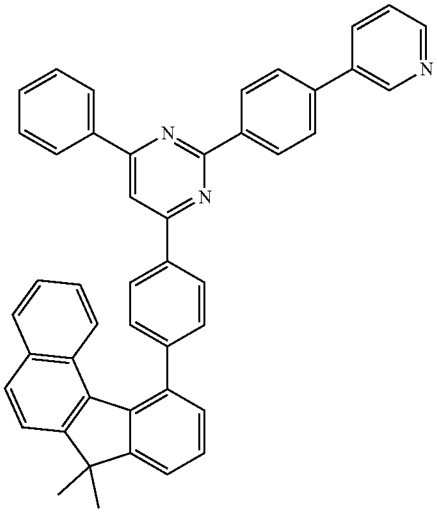

180
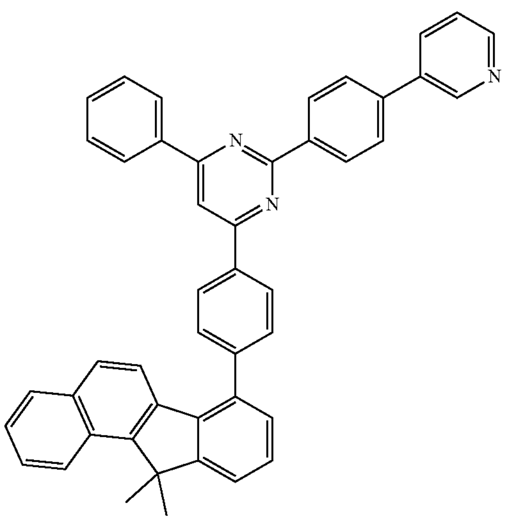
181
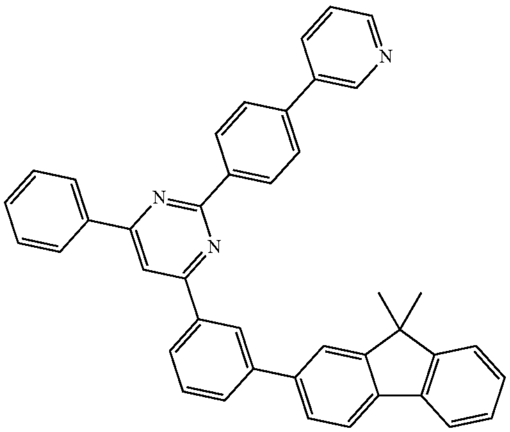
183
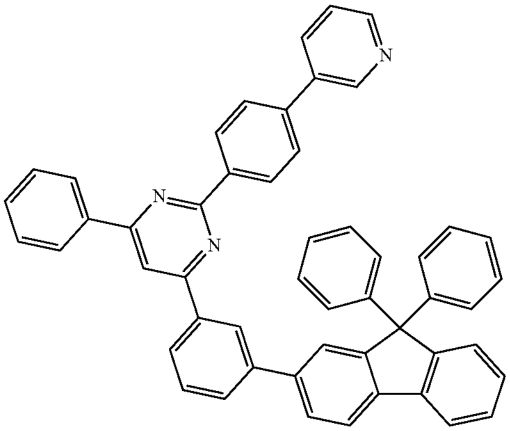
184
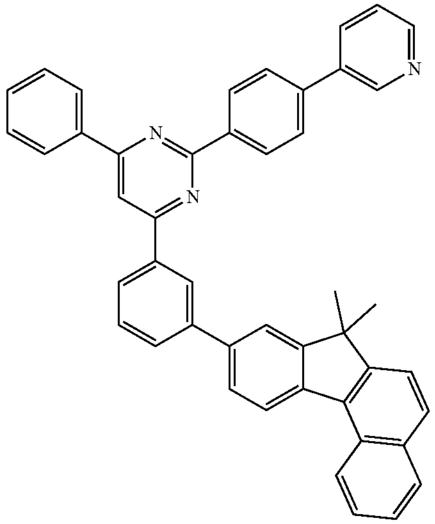
185
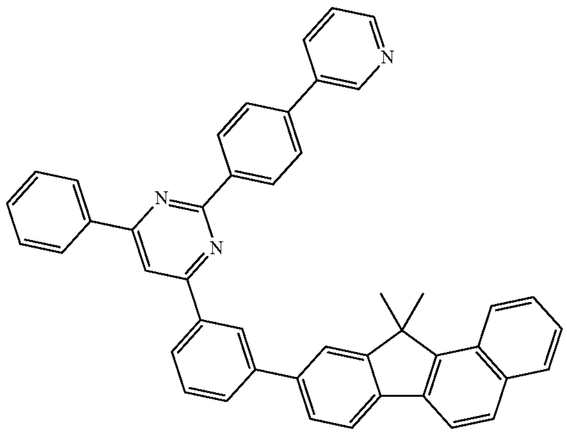
186
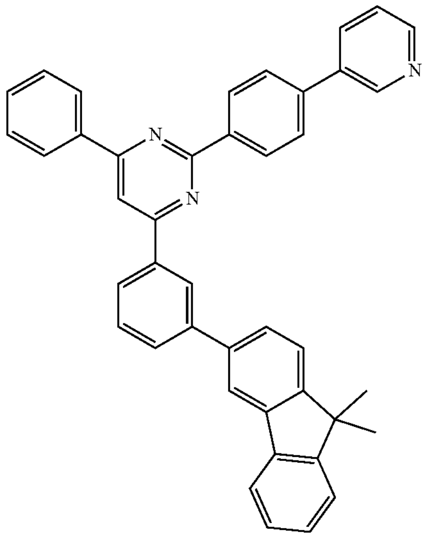

-continued
188
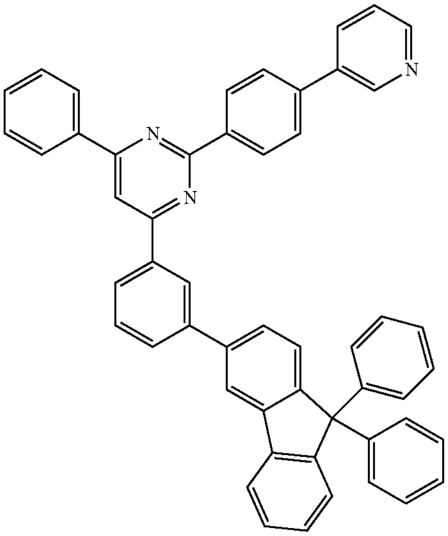
189
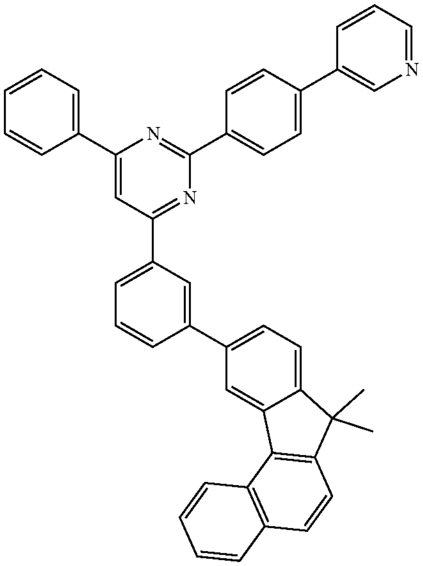
-continued
190
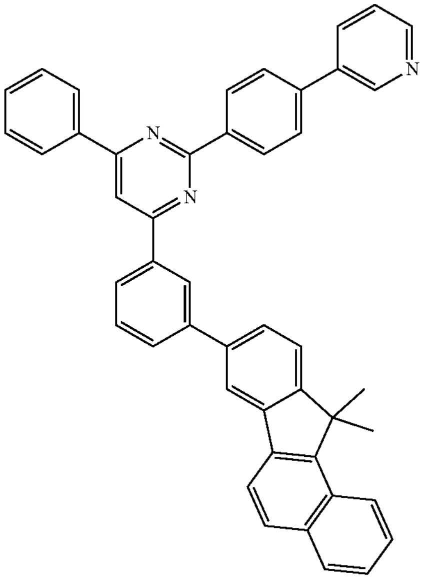
191
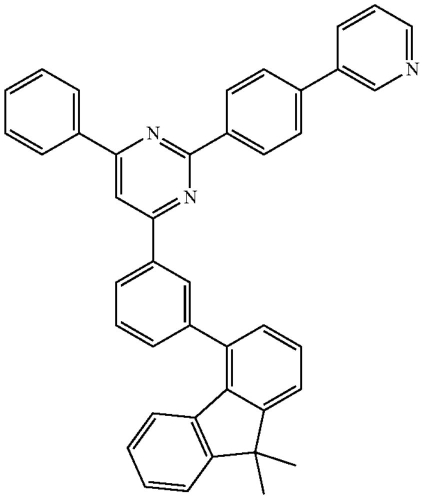
193
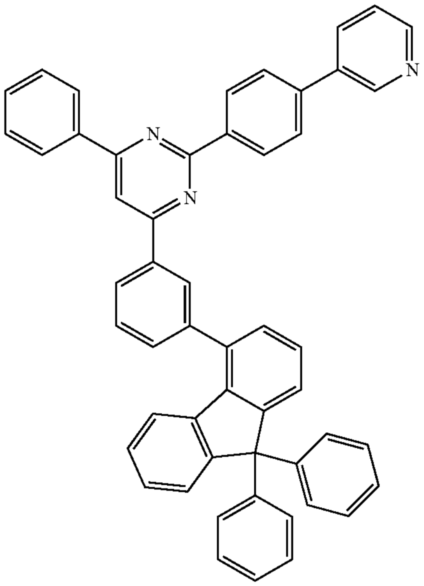

-continued
194
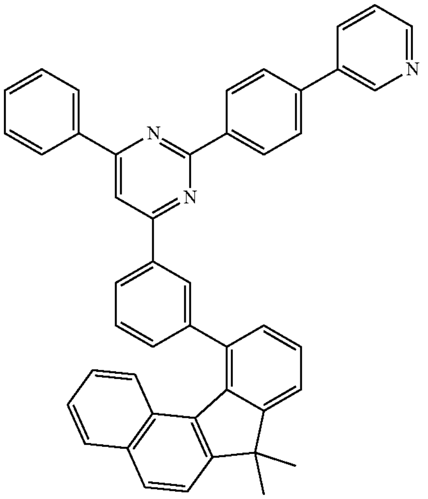
195
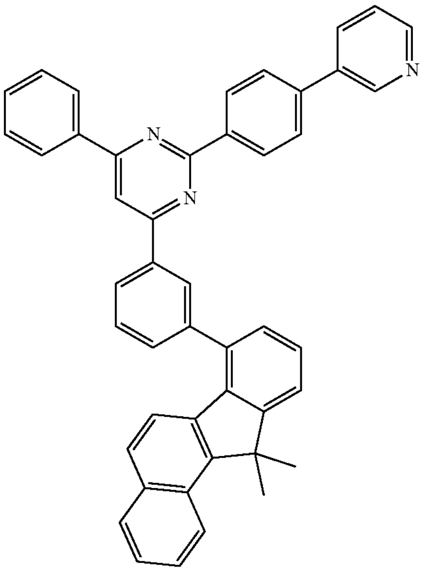
-continued
316
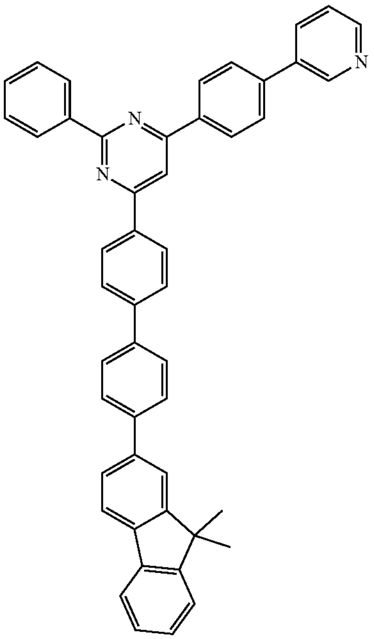
317
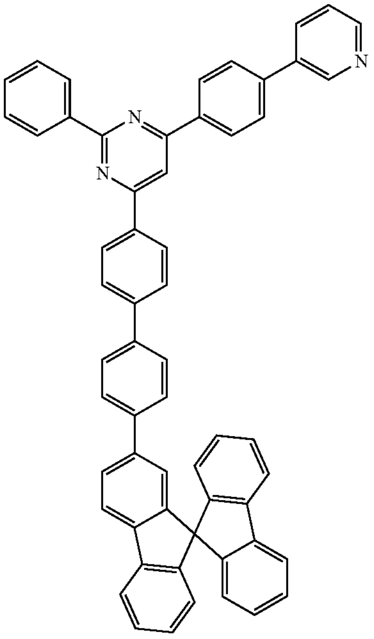

-continued
318
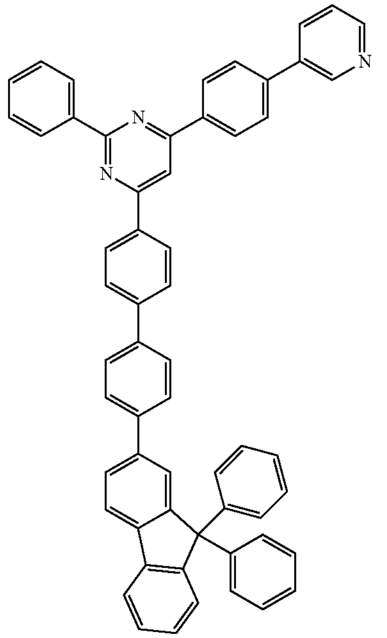
319
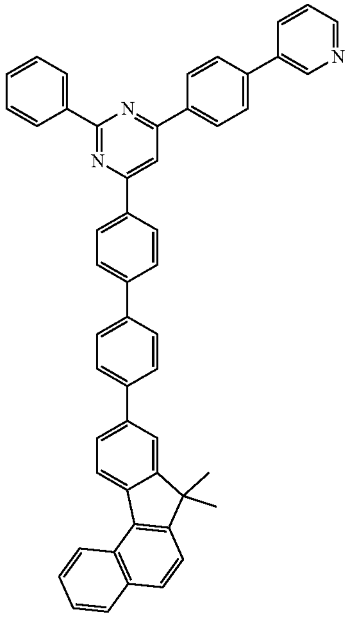
-continued
320
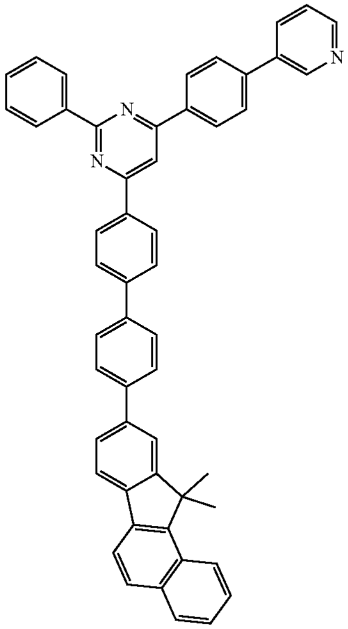
321
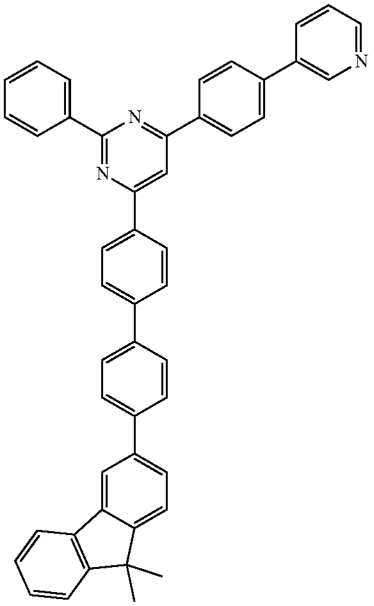

-continued
323
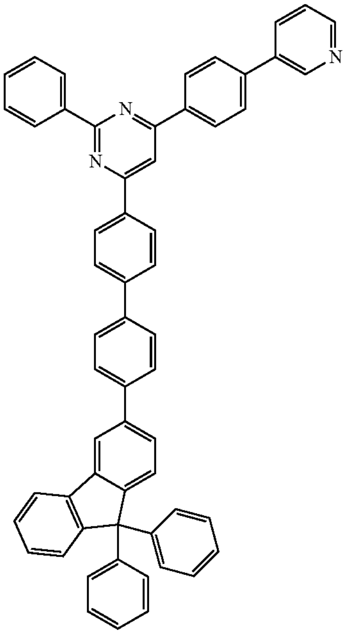
-continued
325
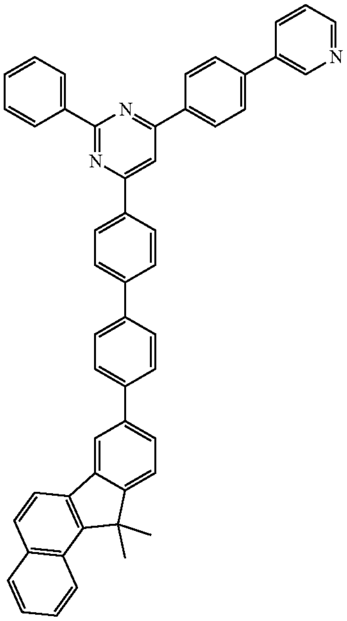
324
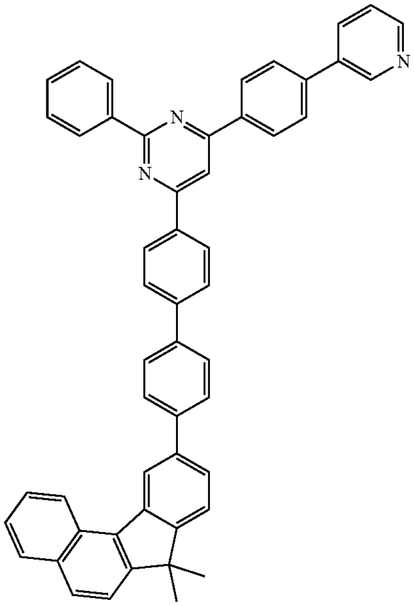
326
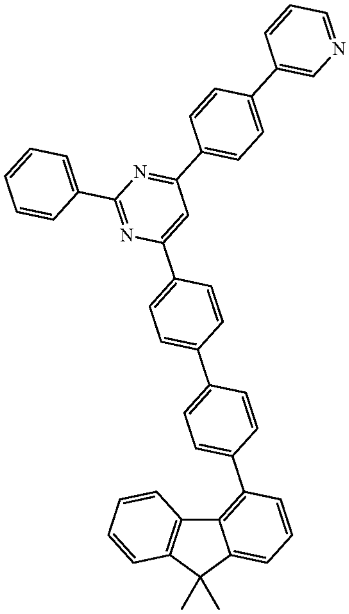

-continued
328
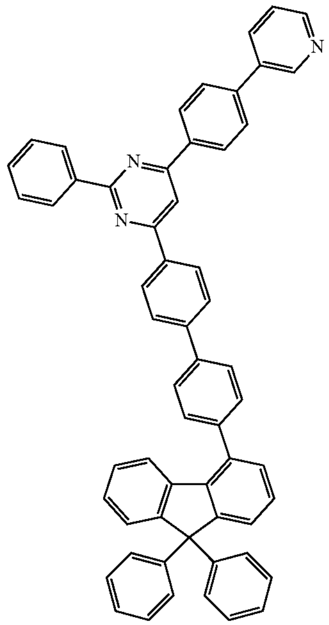
330
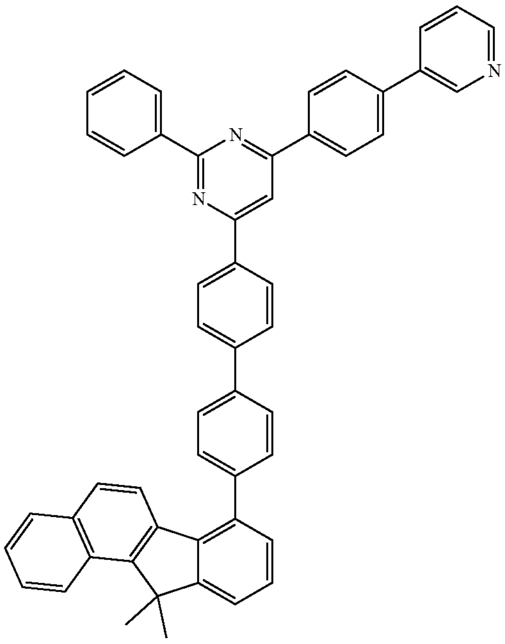
329
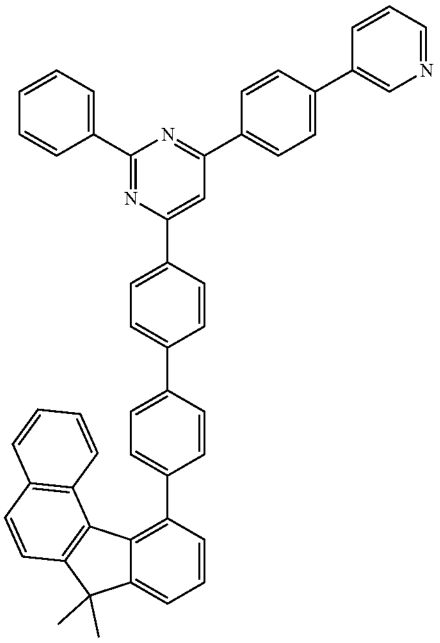
346
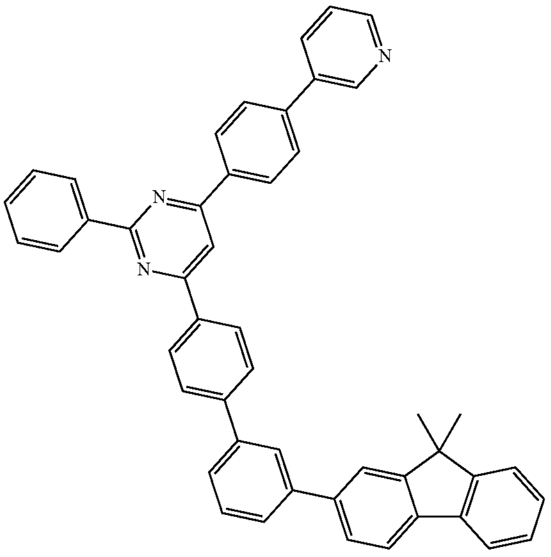

-continued
348
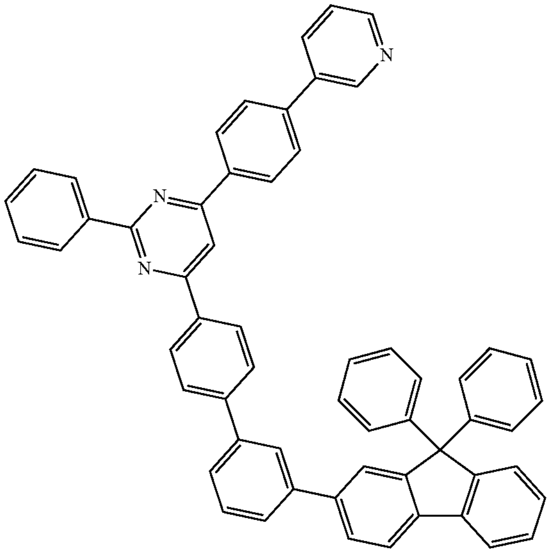
-continued
350
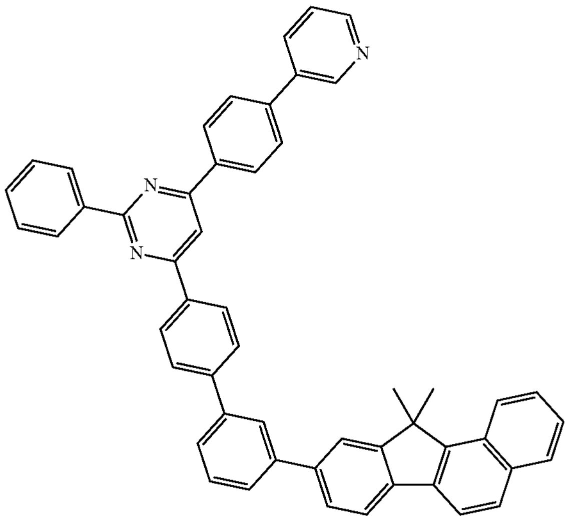
349
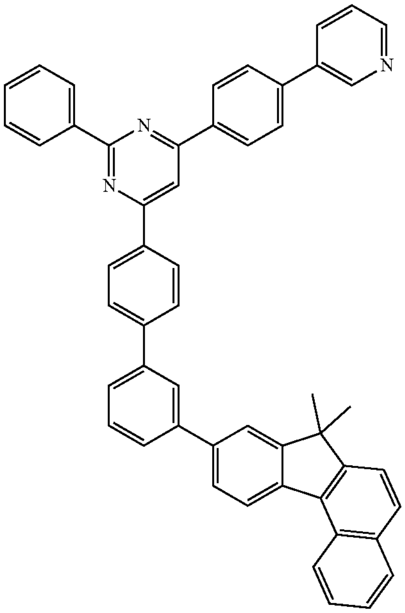
351
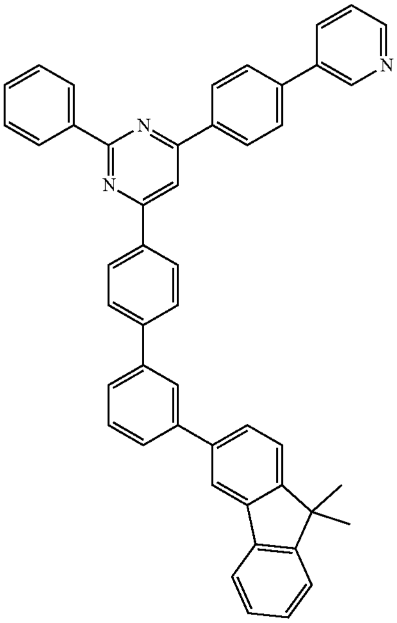

353
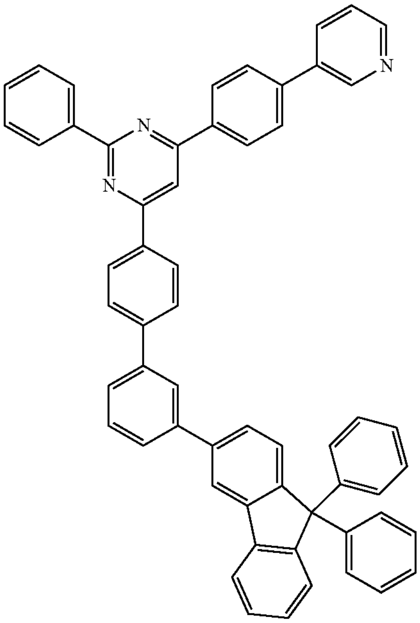
354
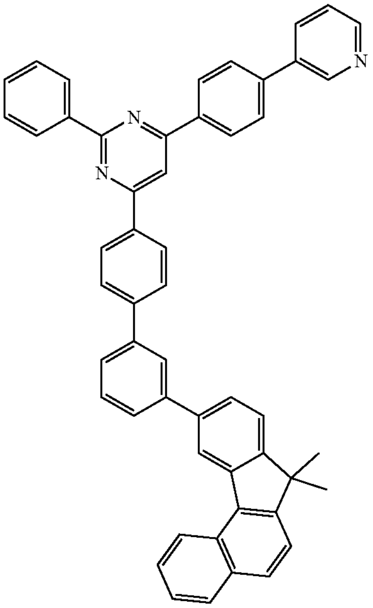
355
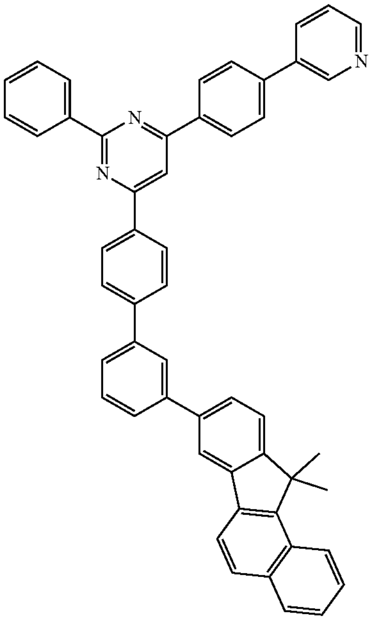
356
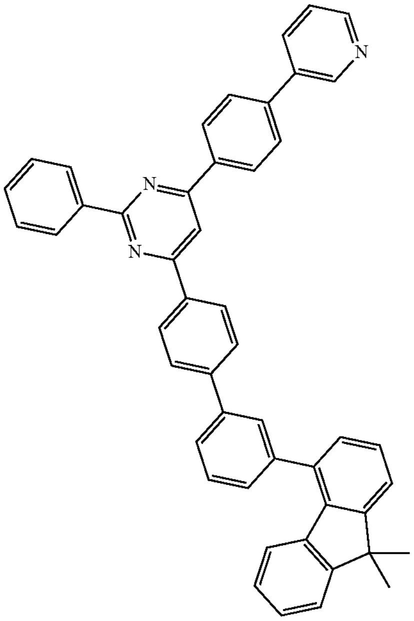

-continued
358
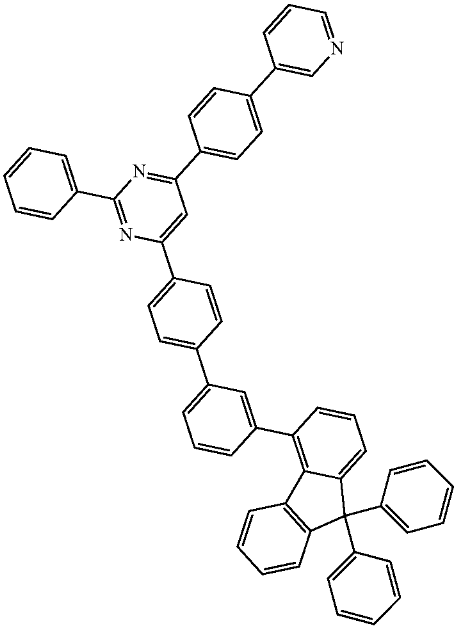
359
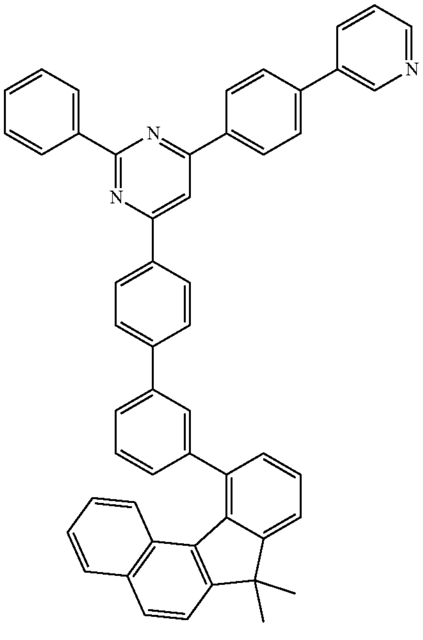
-continued
360
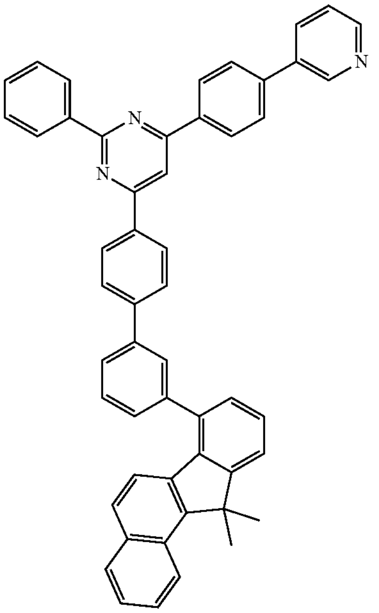
376
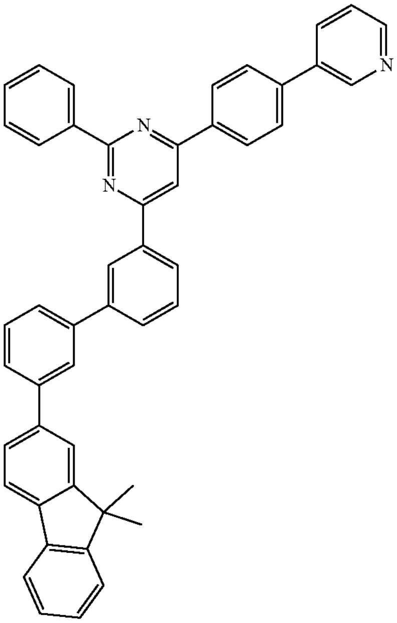

-continued
378
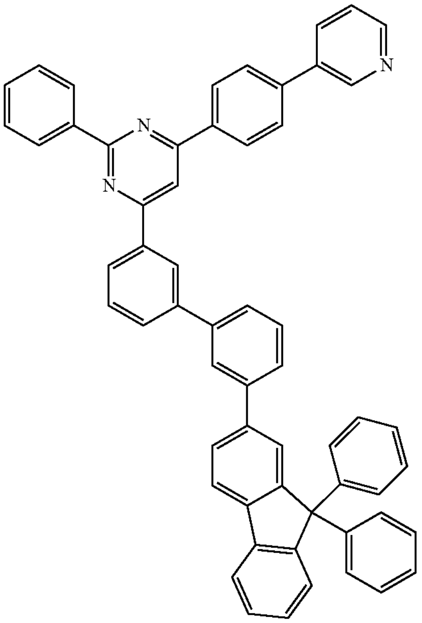
380
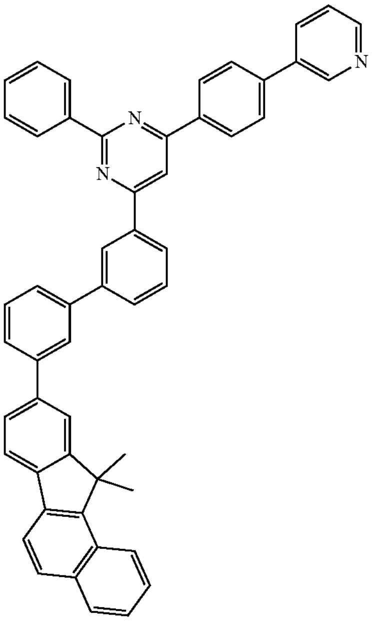
379
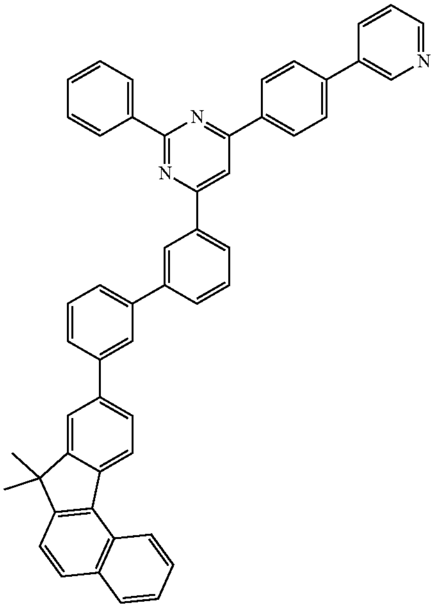
381
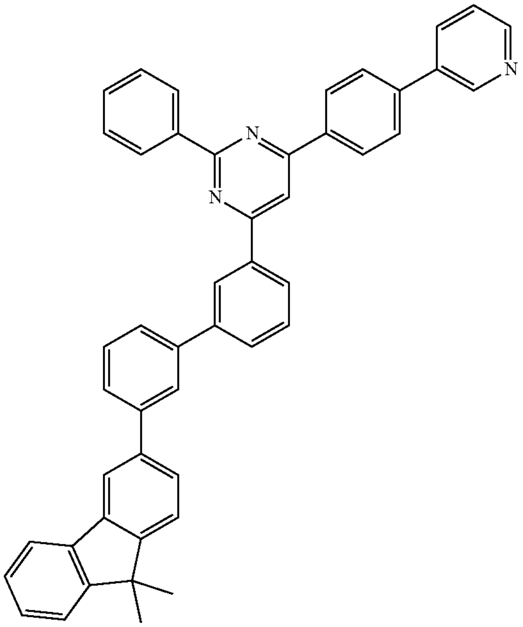

-continued
383
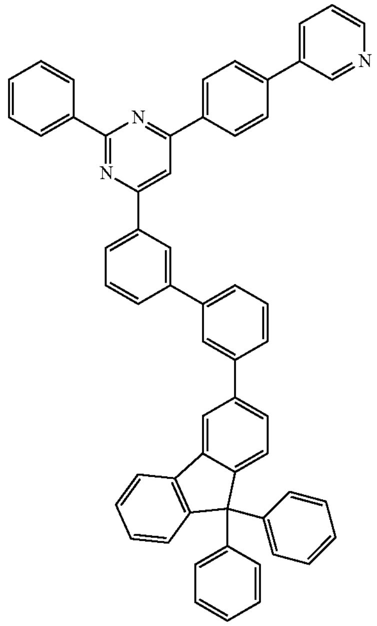
384
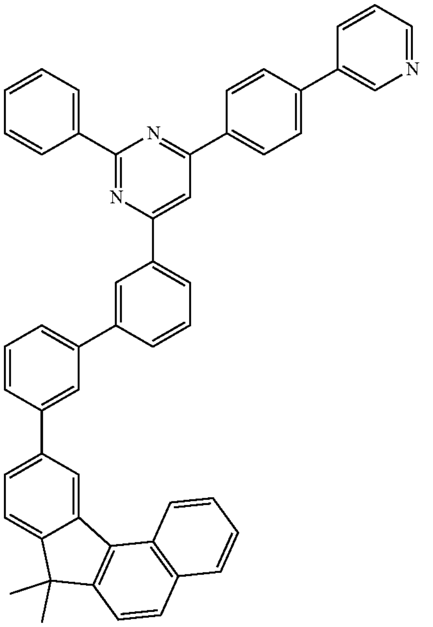
-continued
385
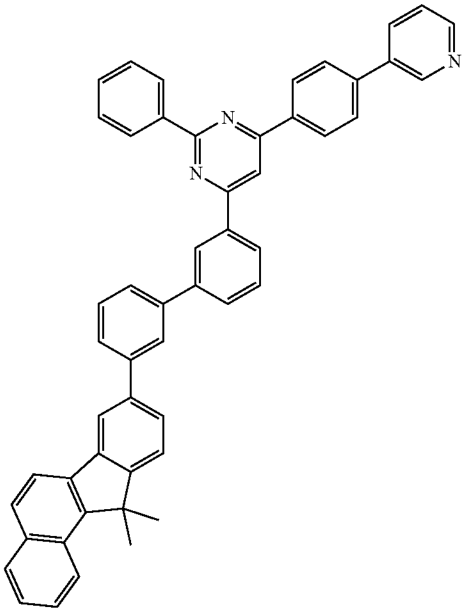
386
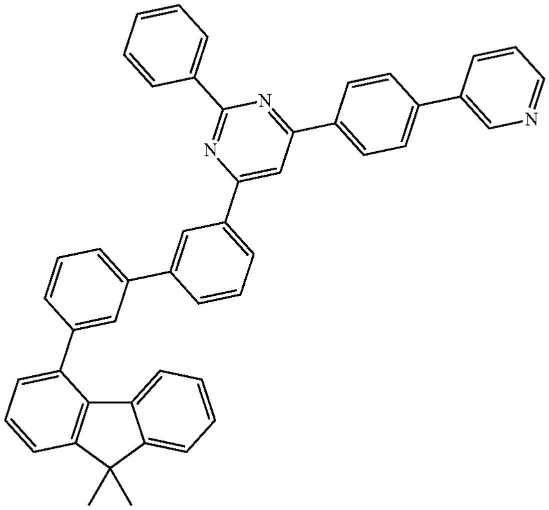

-continued
388
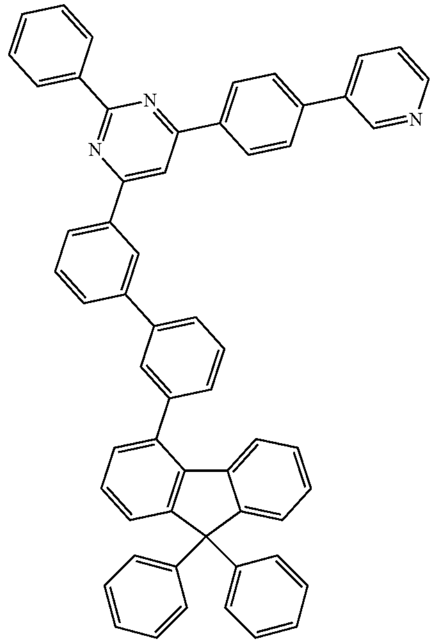
389
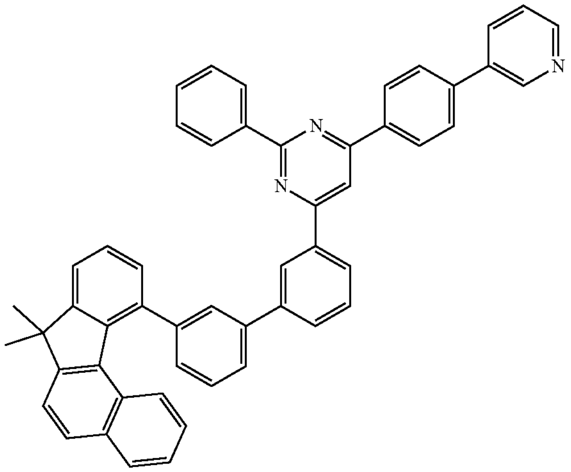
-continued
390
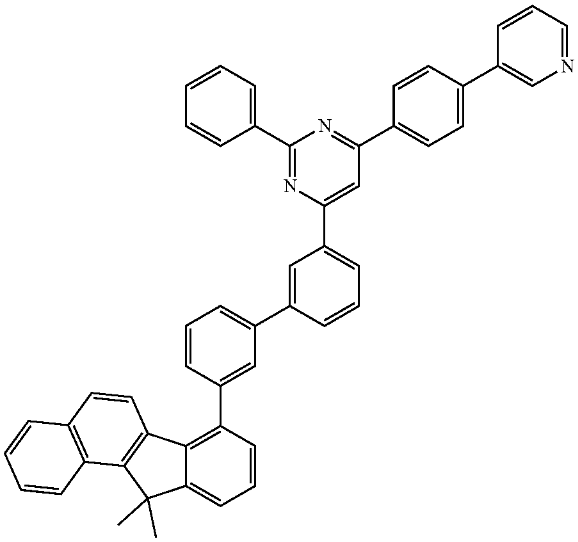
406
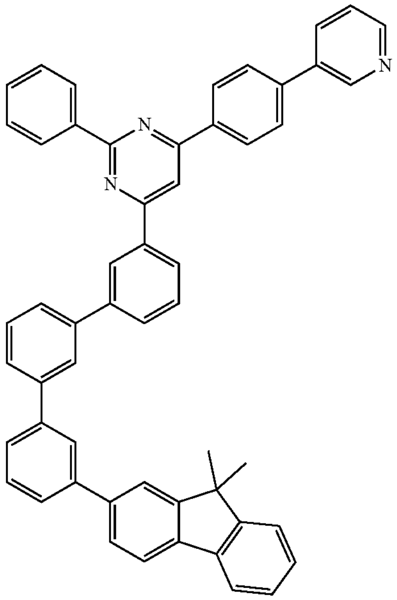

-continued
408
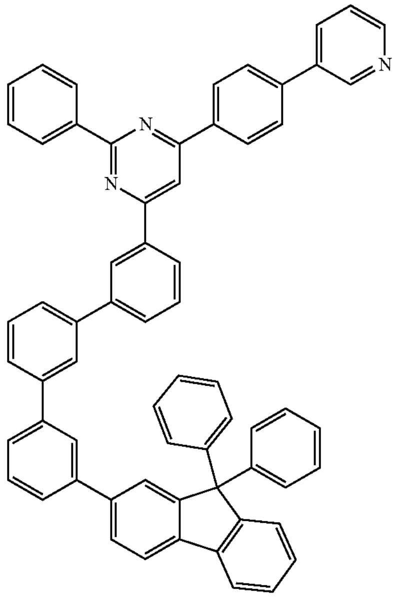
-continued
410
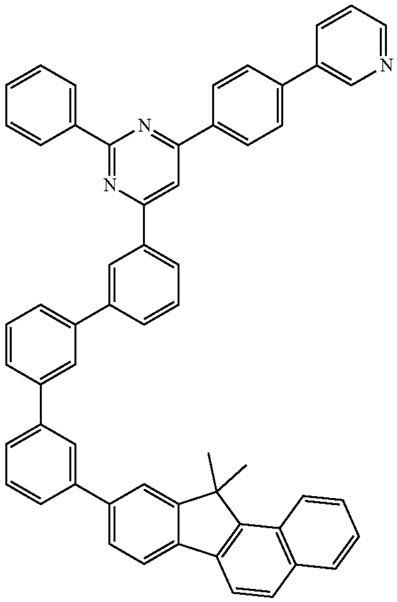
409
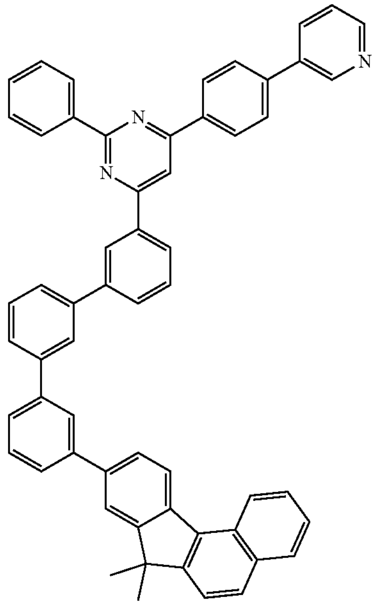
411
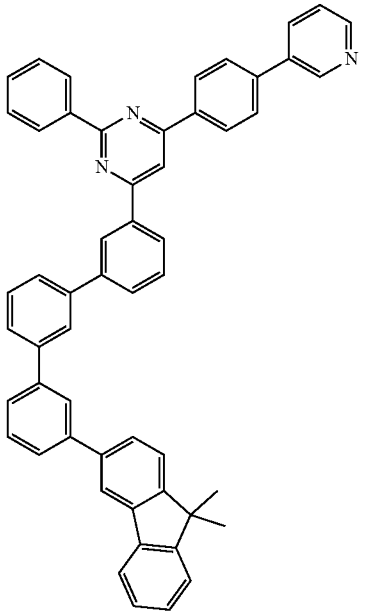

-continued
413
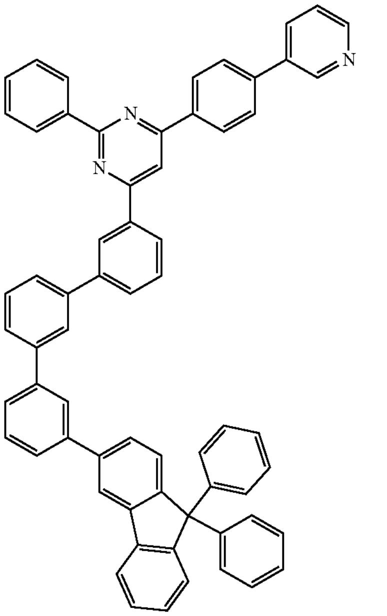
-continued
415
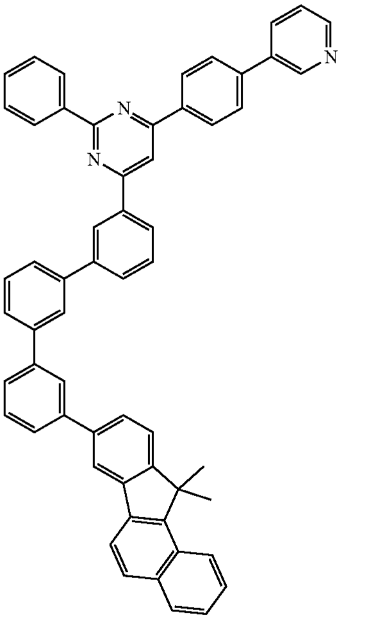
414
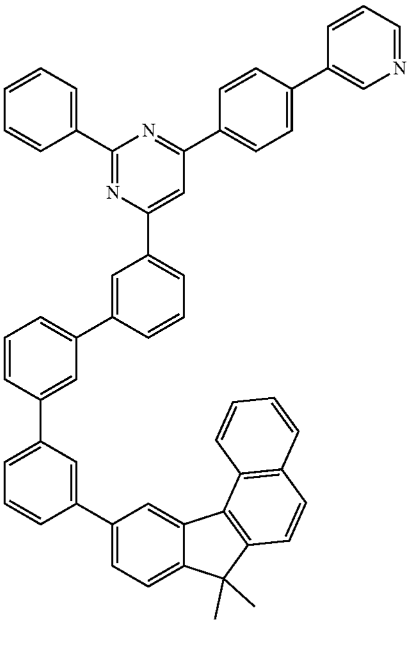
416
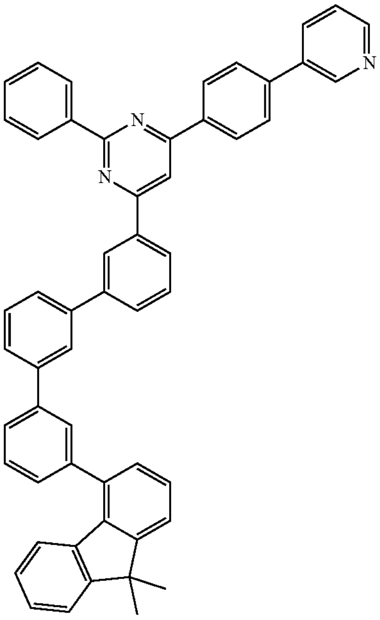

-continued
418
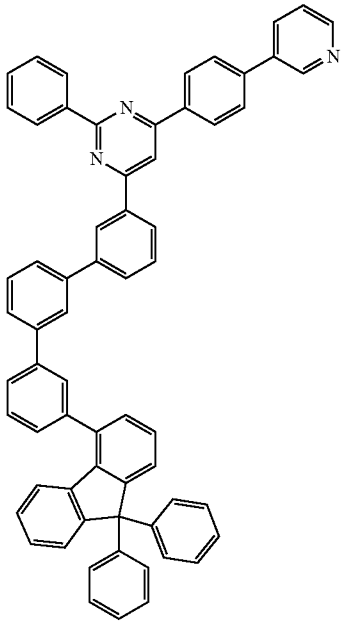
-continued
420
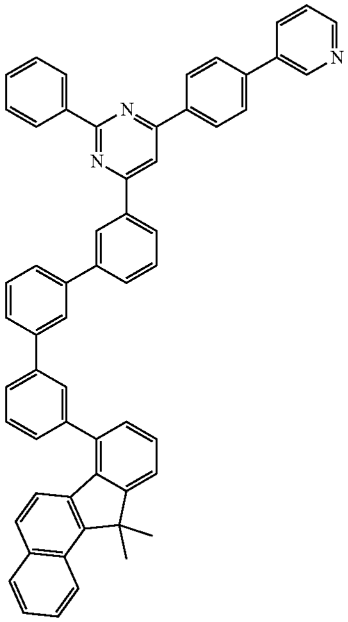
419
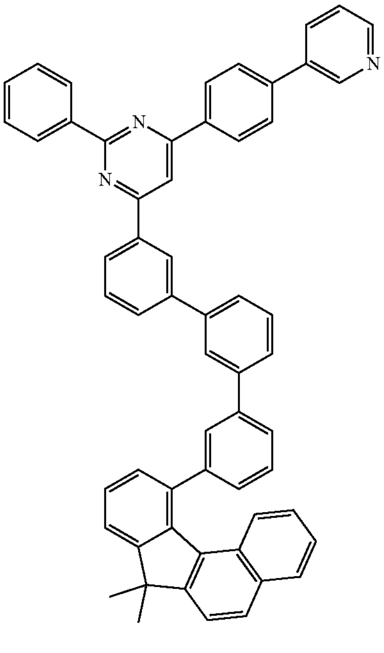
541
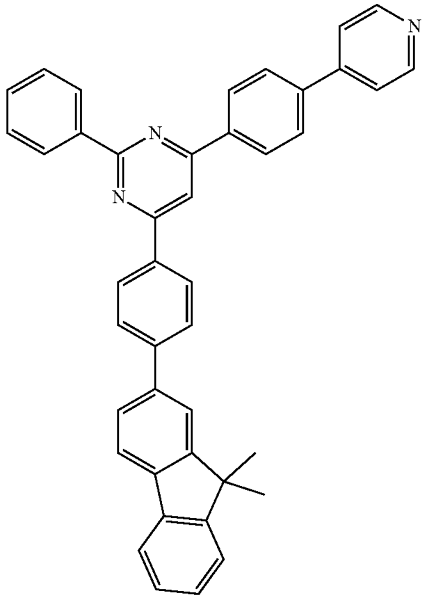

-continued
543
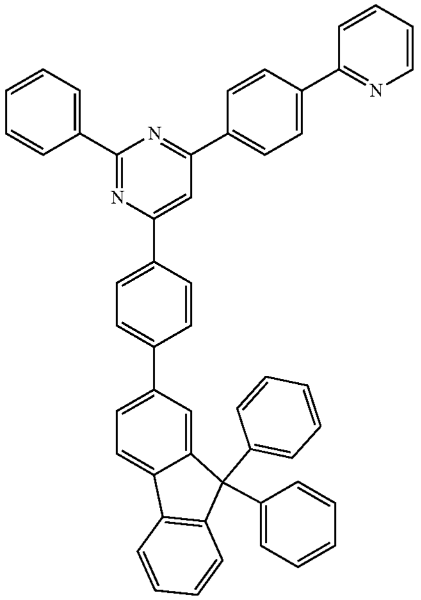
545
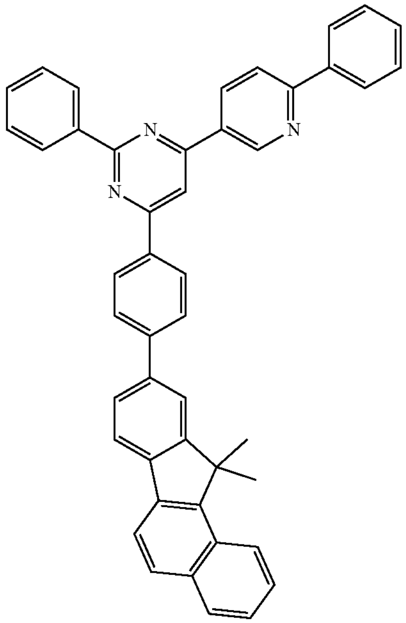
544
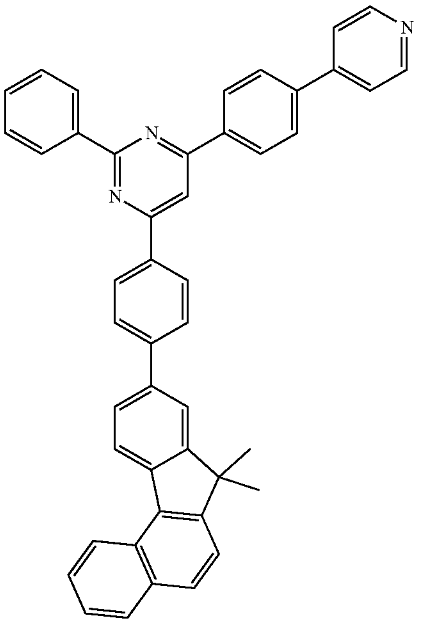
546
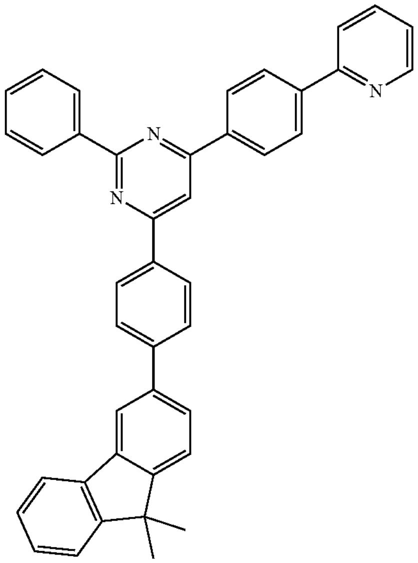

-continued
548
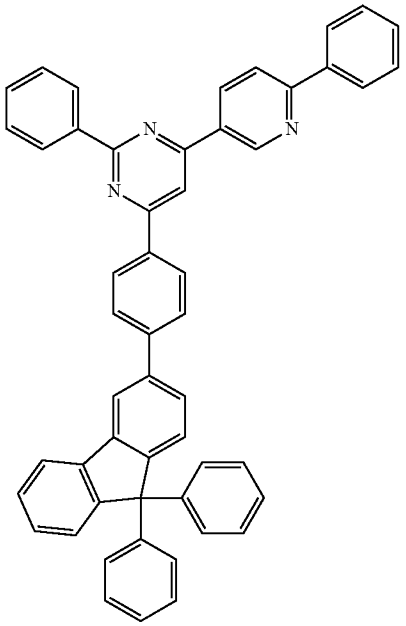
549
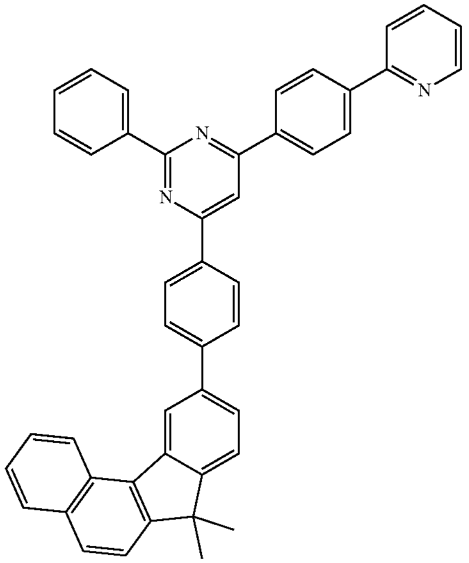
-continued
550
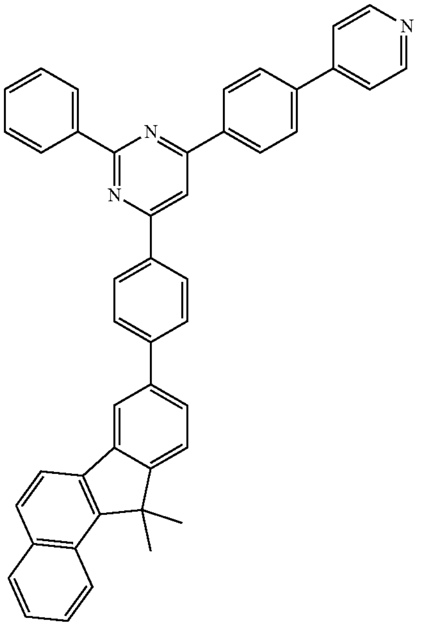
551
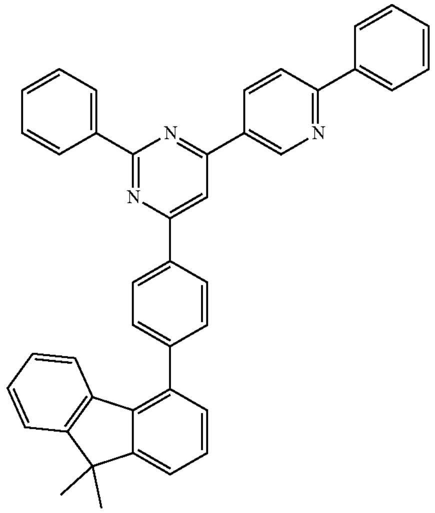

-continued
553
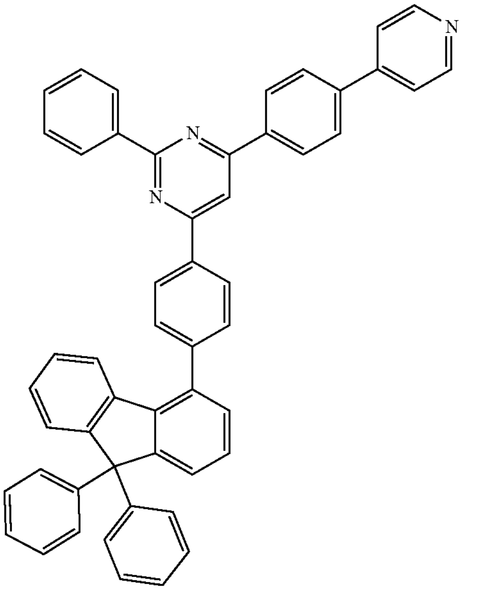
554
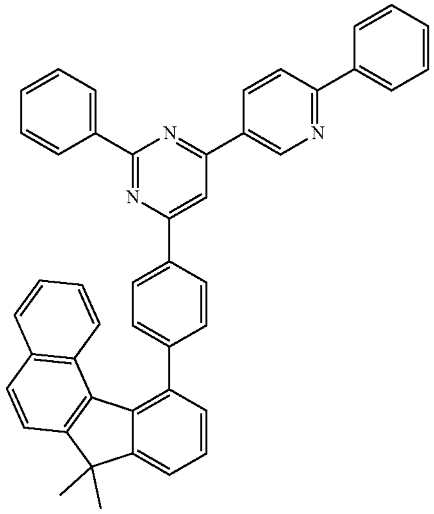
555
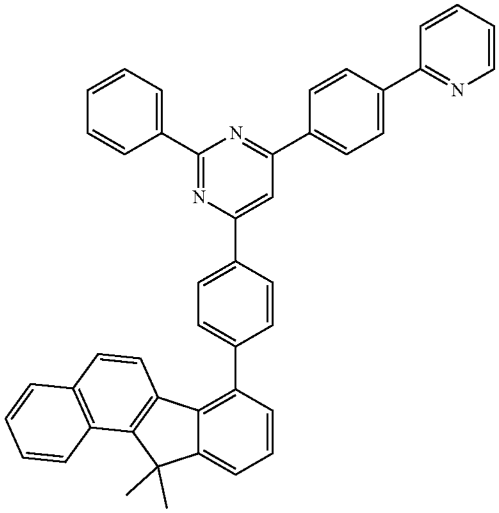
-continued
556
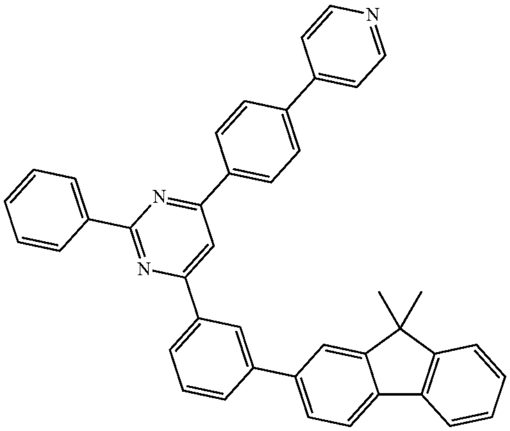
558
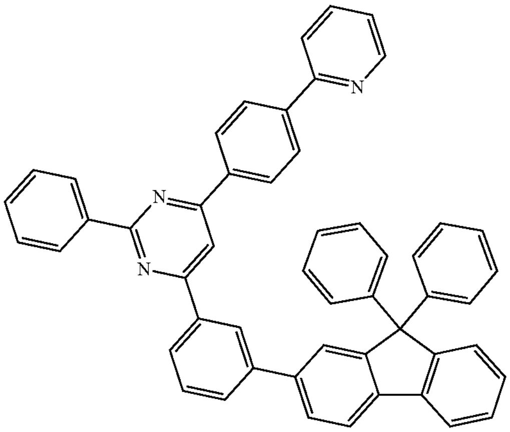
559
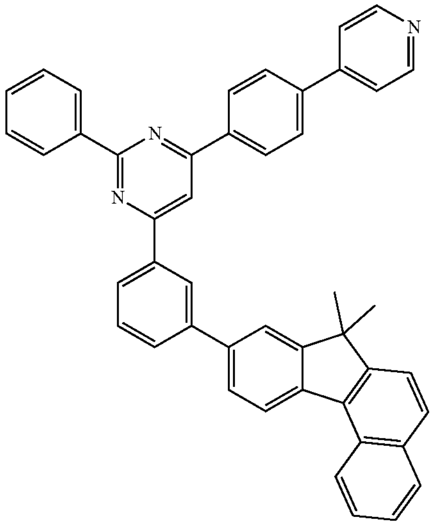

-continued
560
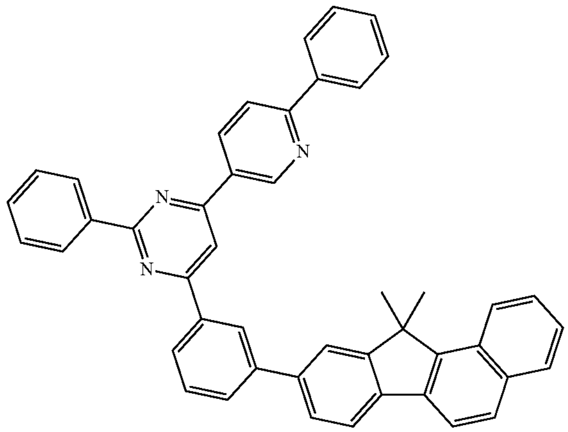
561
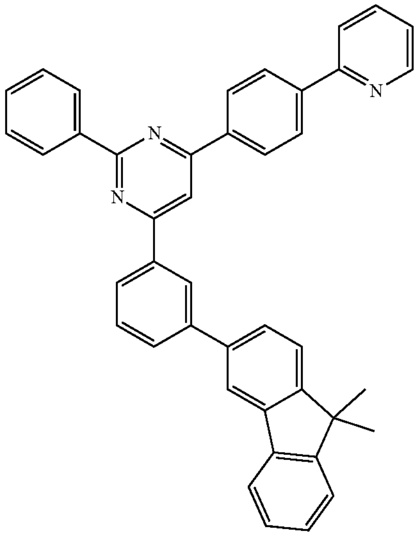
563
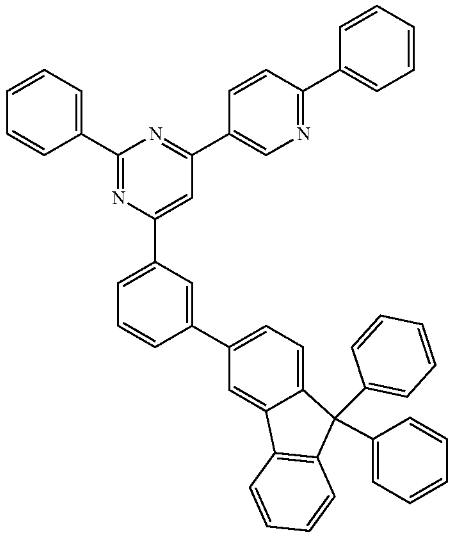
-continued
564
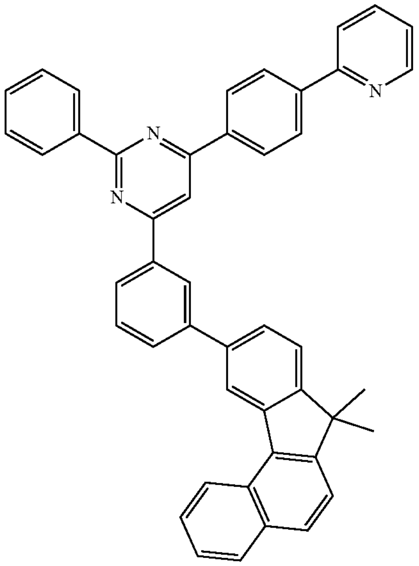
565
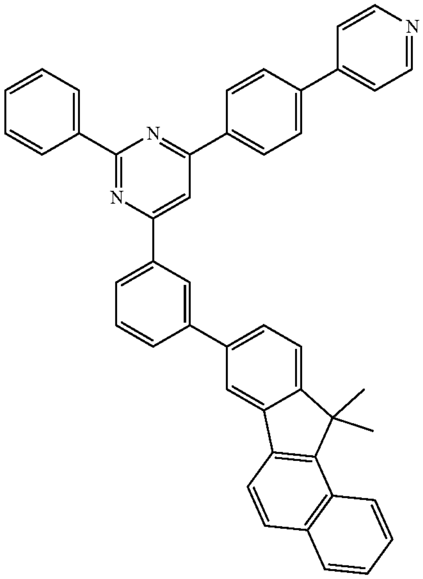
566
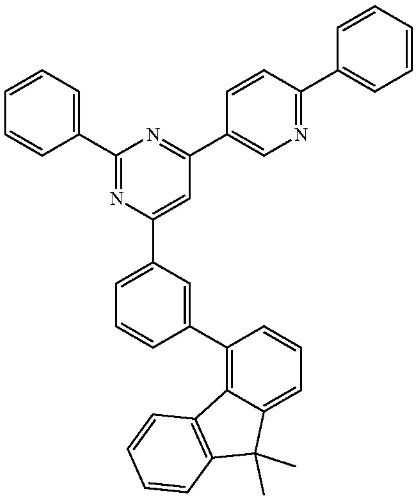

-continued
568
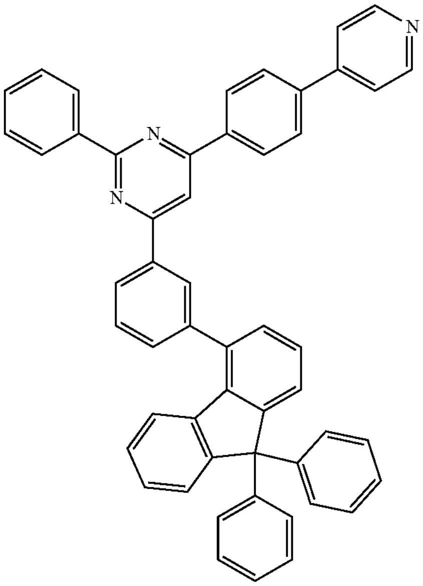
569
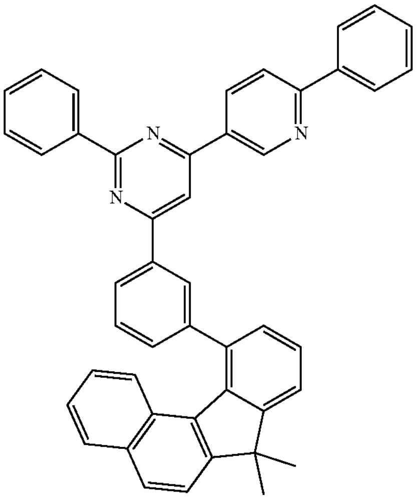
570
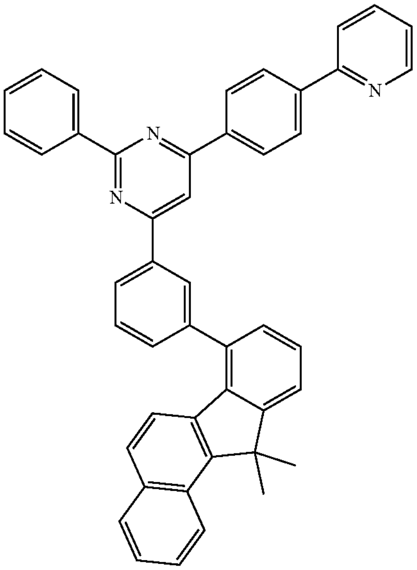
-continued
601
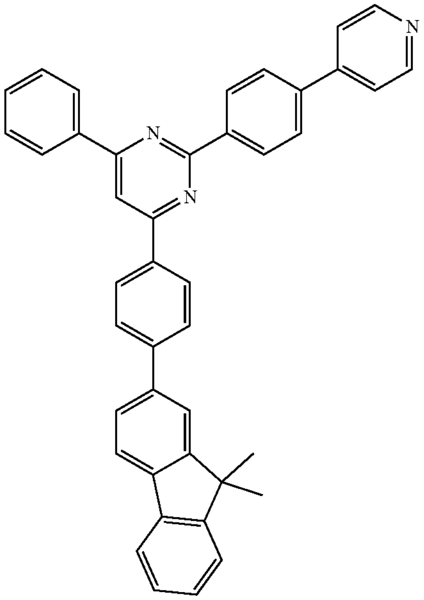
603
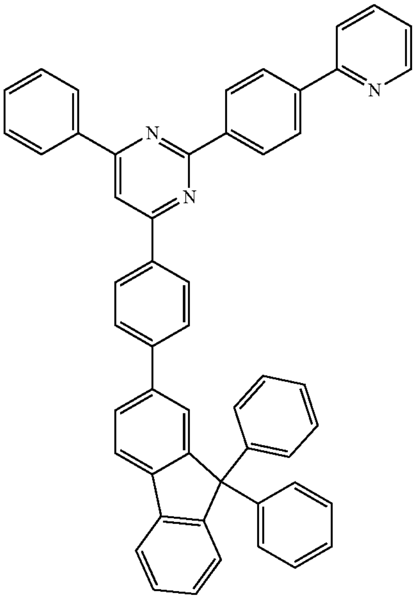

604
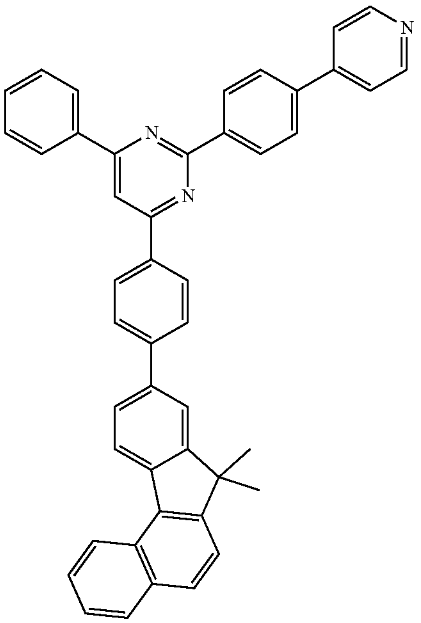
605
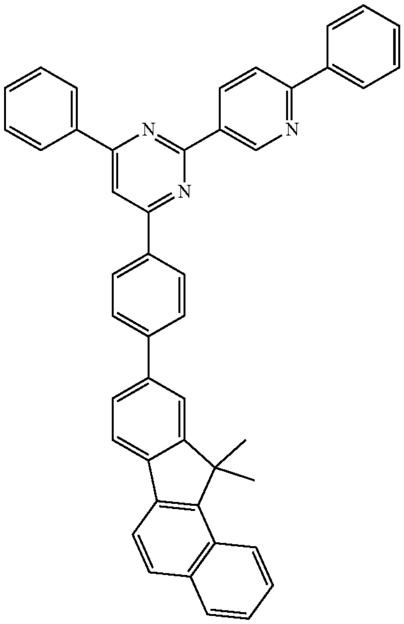
606
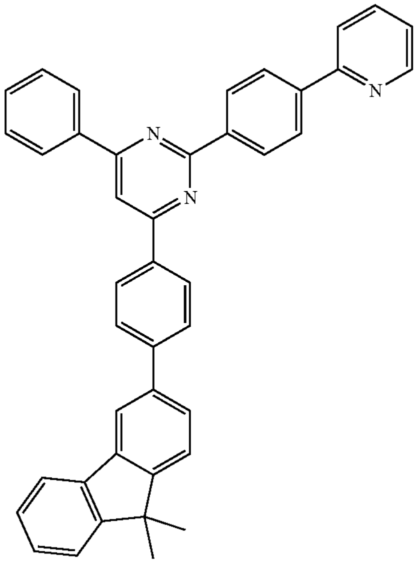
608
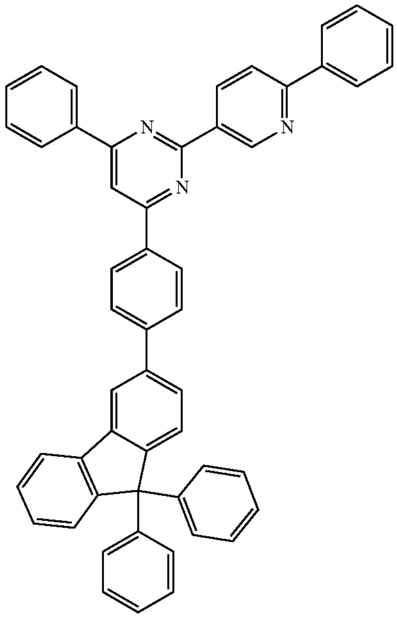

-continued
609
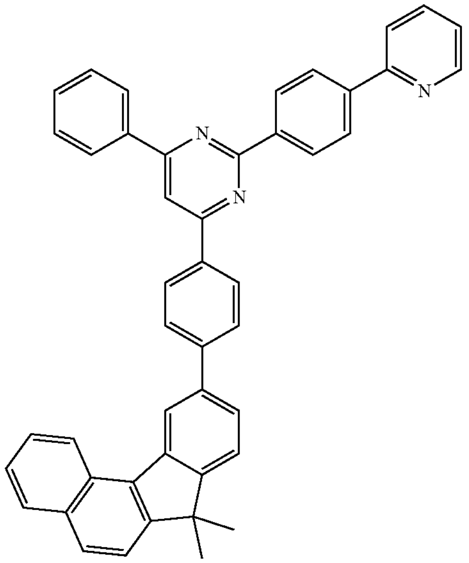
610
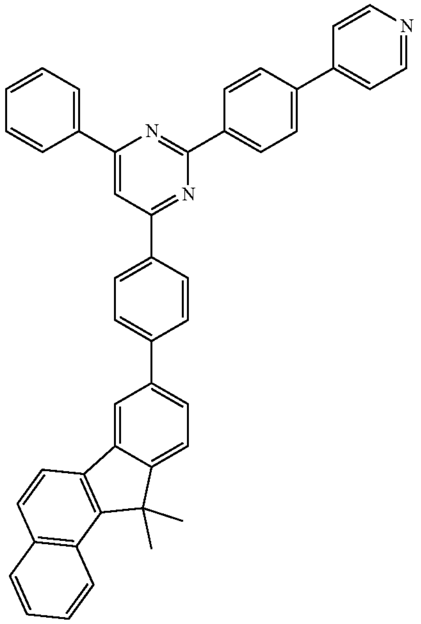
-continued
611
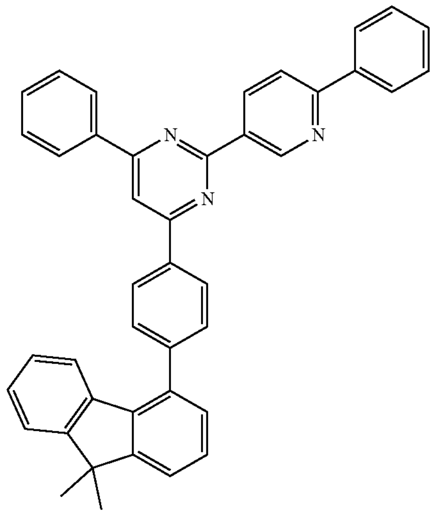
613
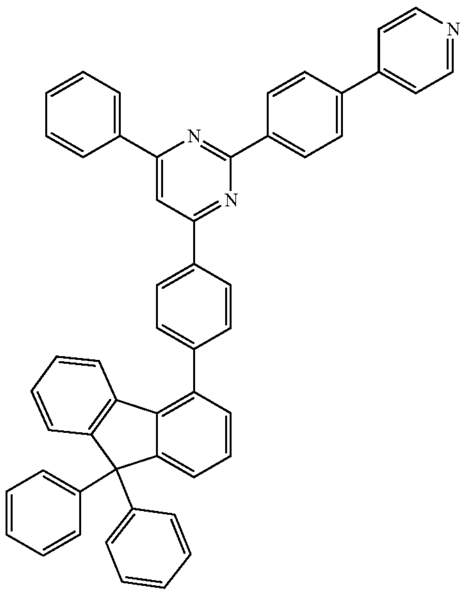
614
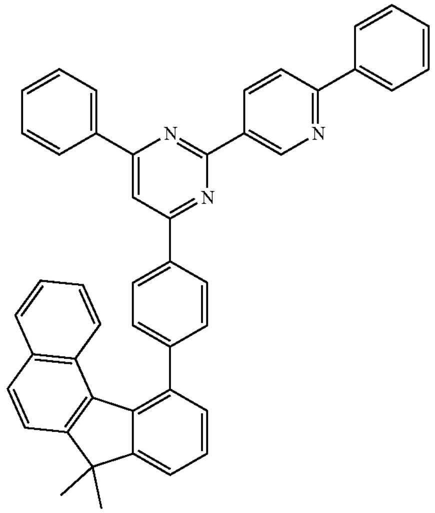

-continued
615
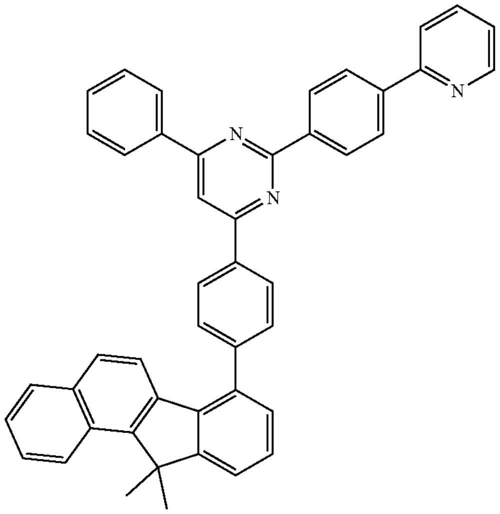
616
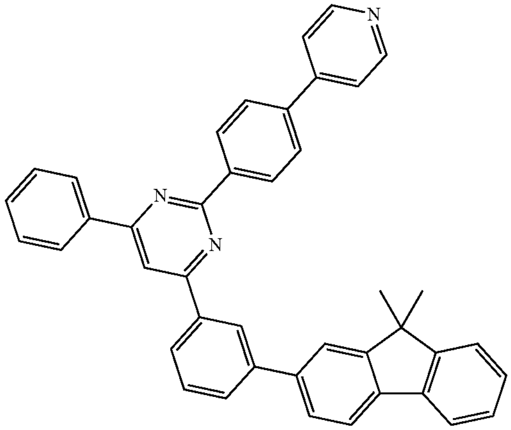
618
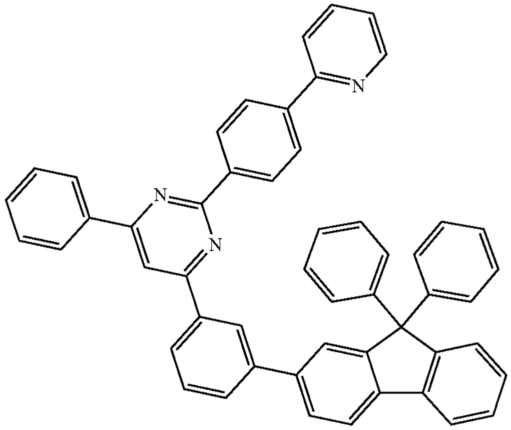
-continued
619
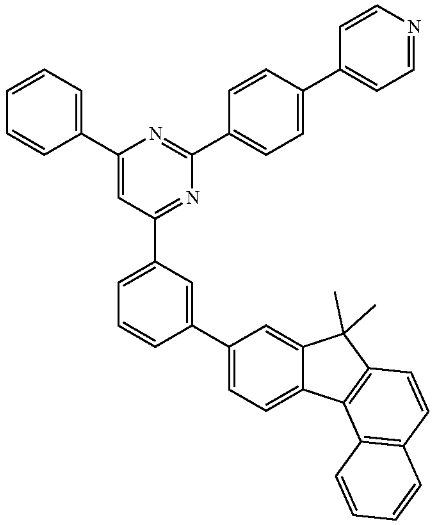
620
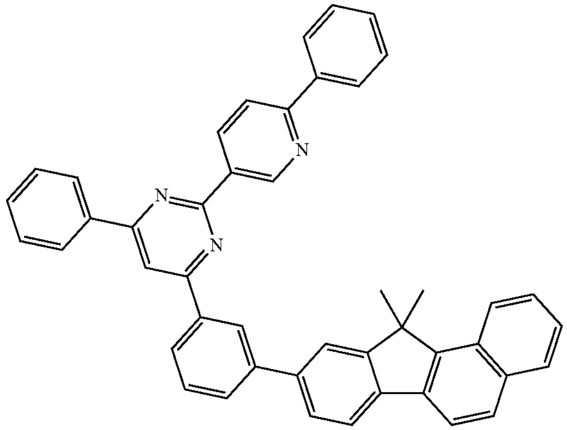
621
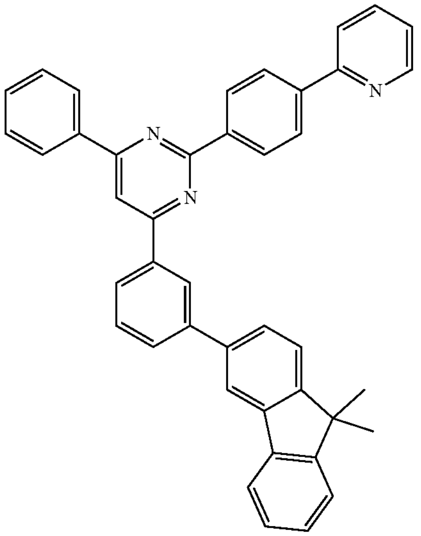

-continued
623
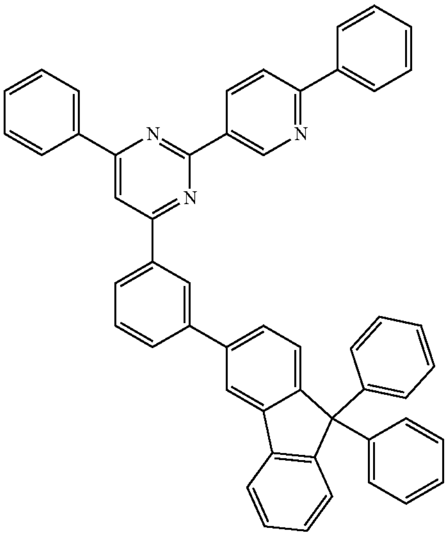
624
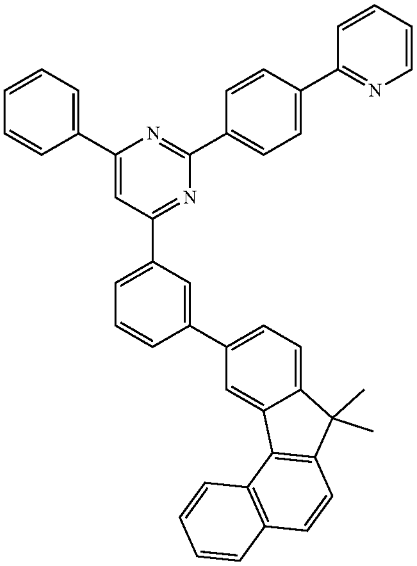
-continued
625
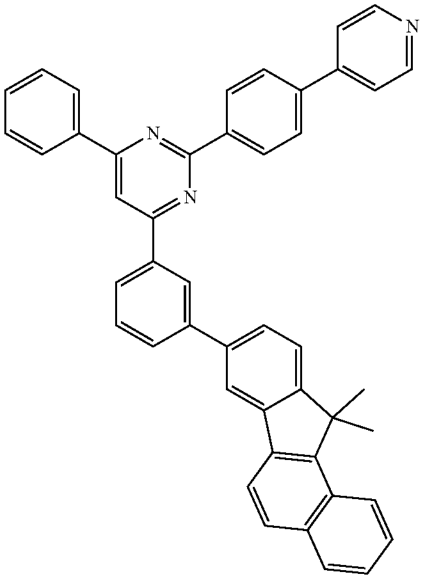
626
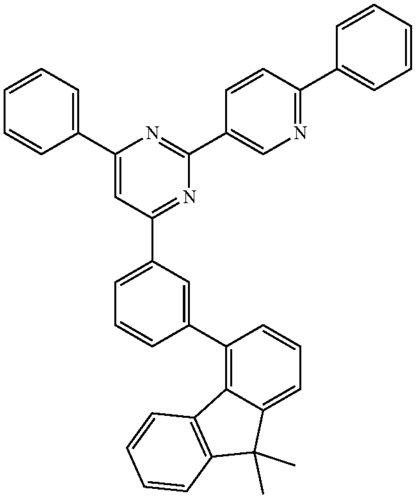
628
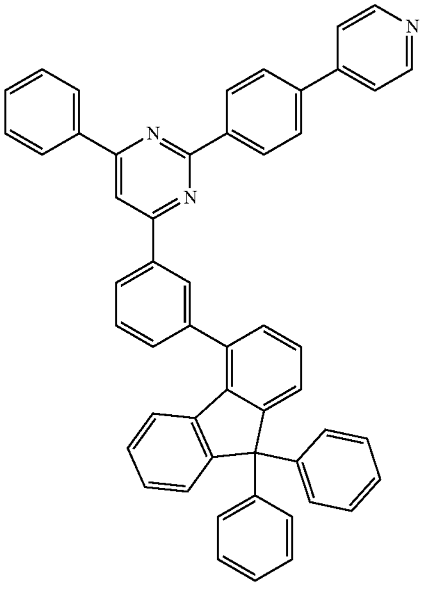

-continued
629
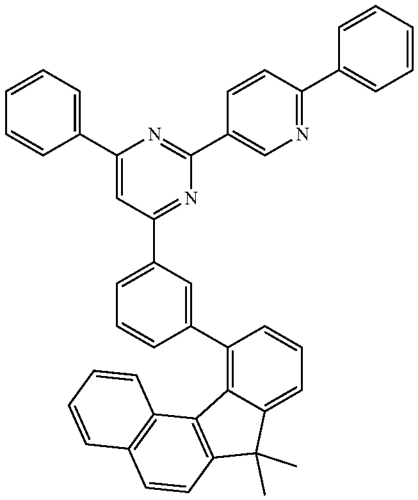
630
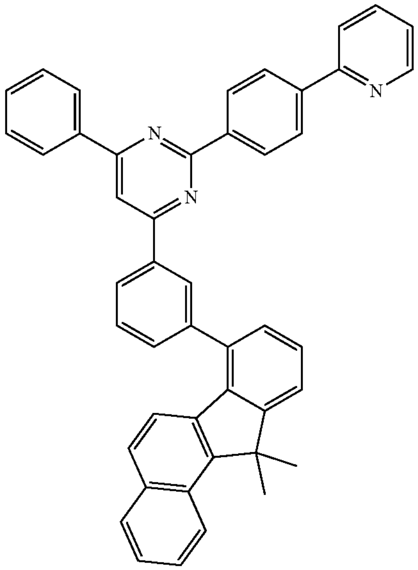
-continued
631
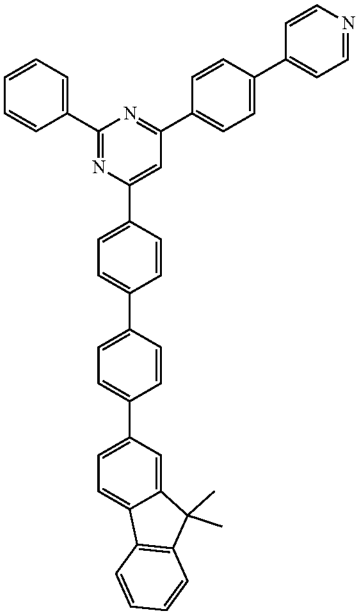
633
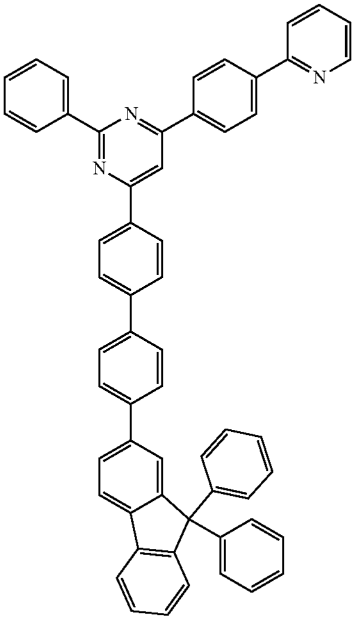

-continued
634
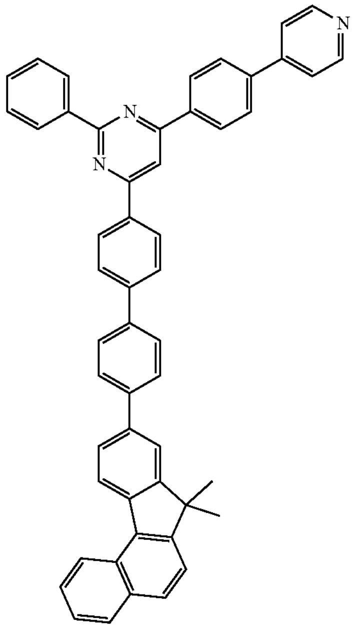
635
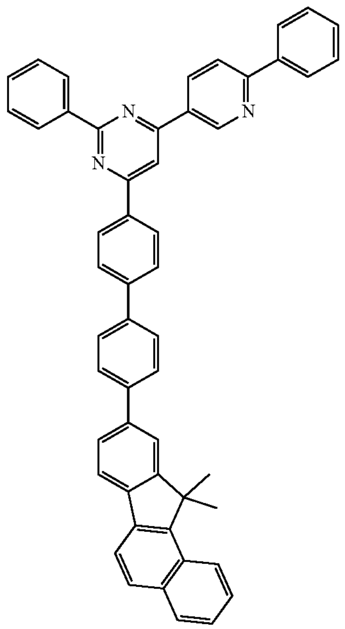
-continued
636
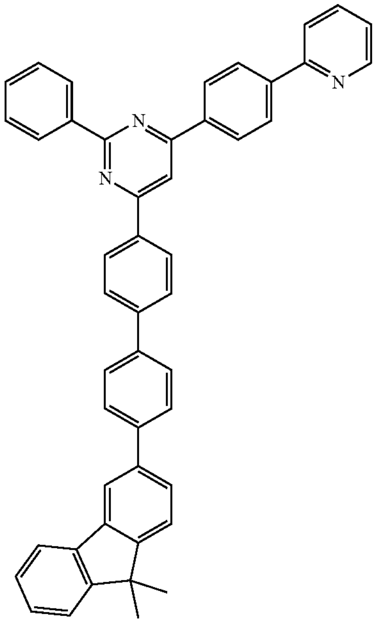
638
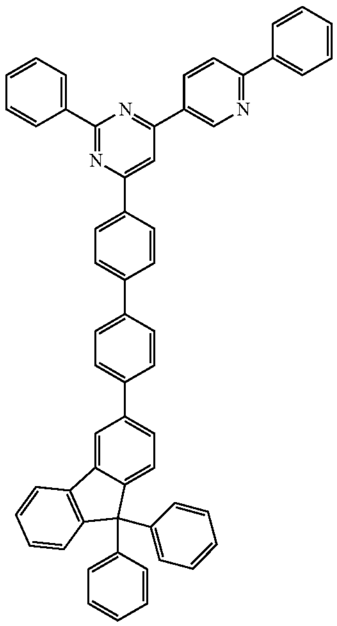

639
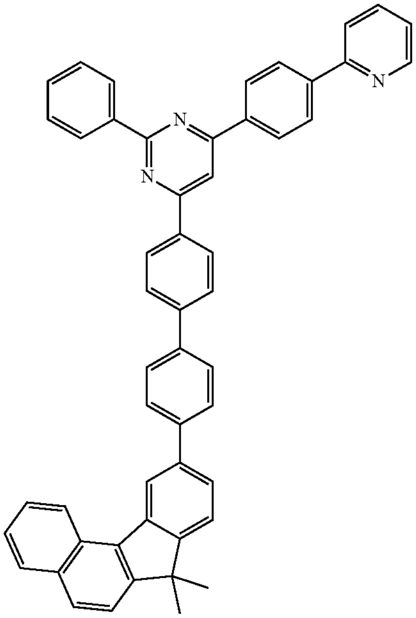
640
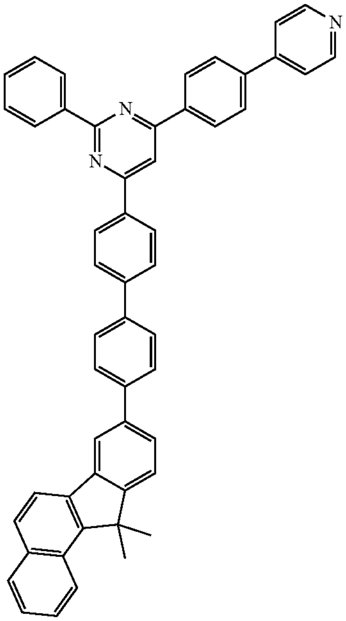
641
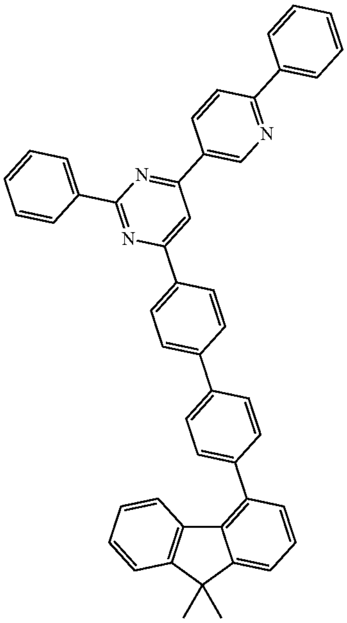
643
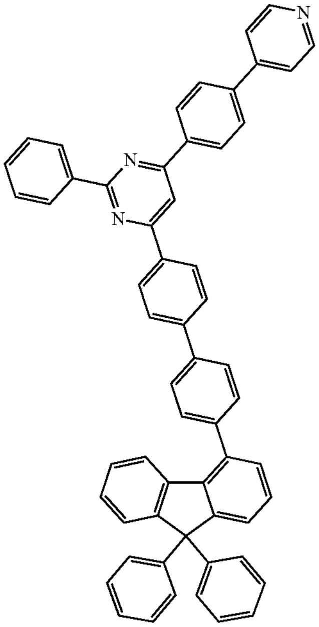

-continued
644
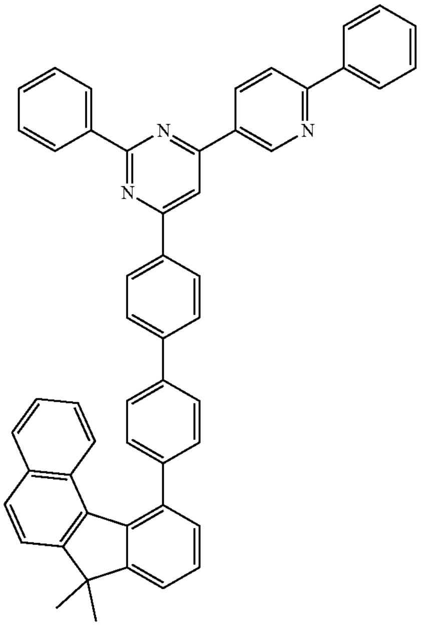
645
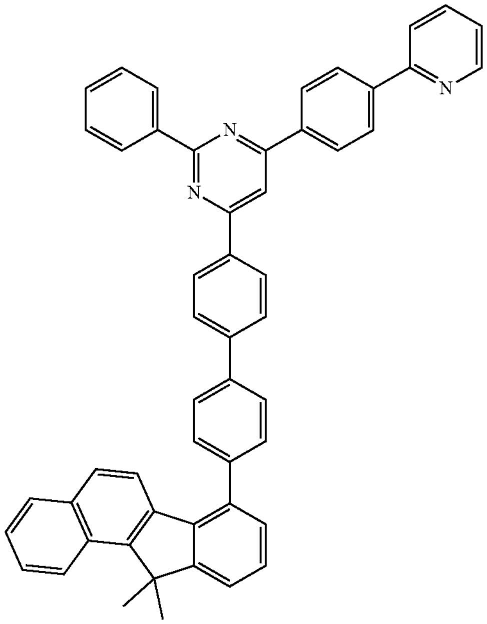
-continued
661
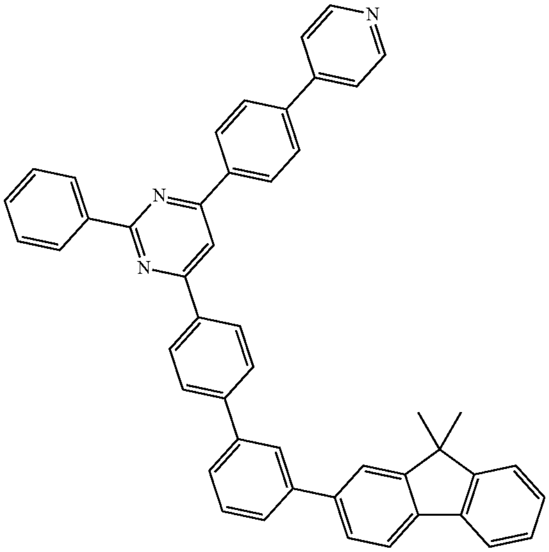
663
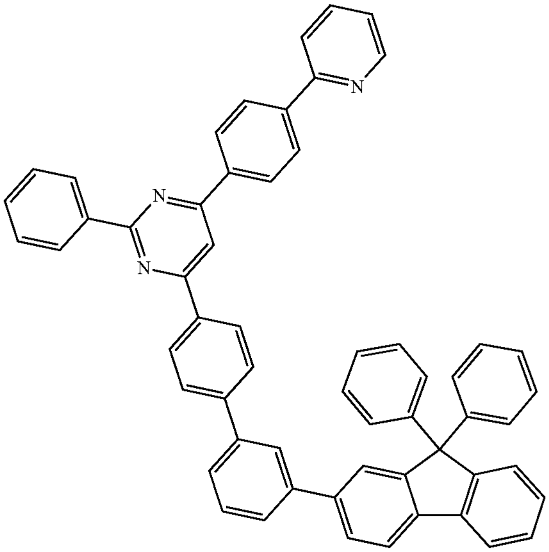

664
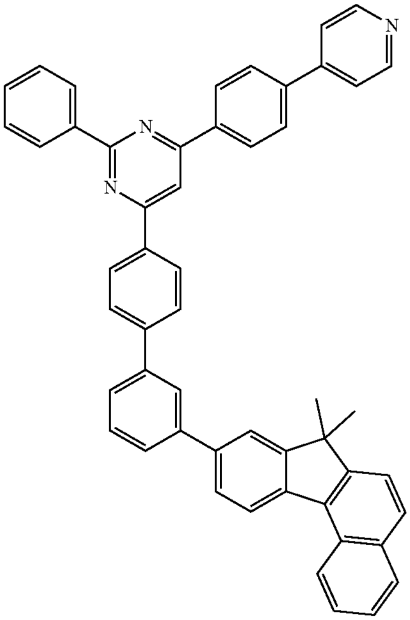
665
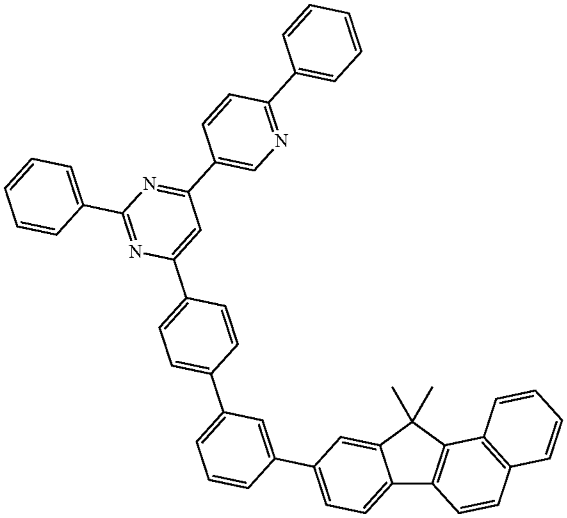
666
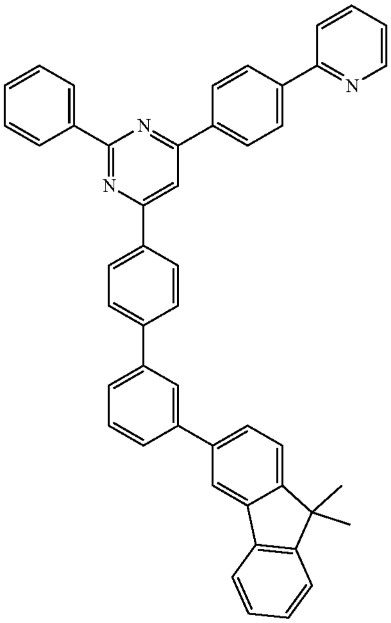
668
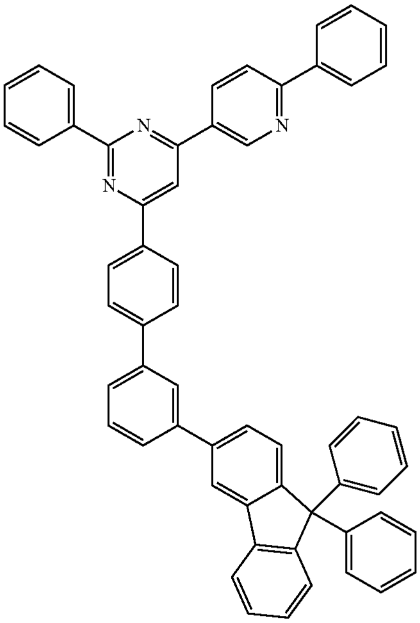

-continued
669
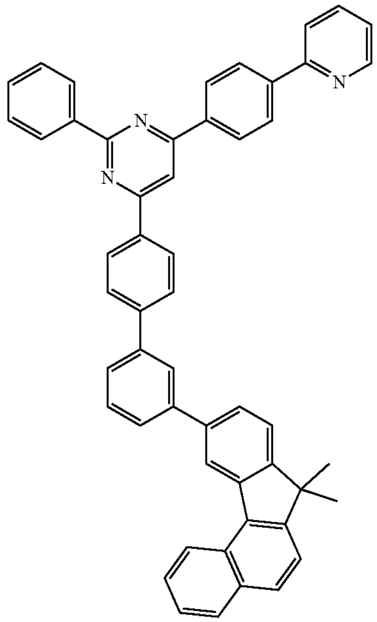
670
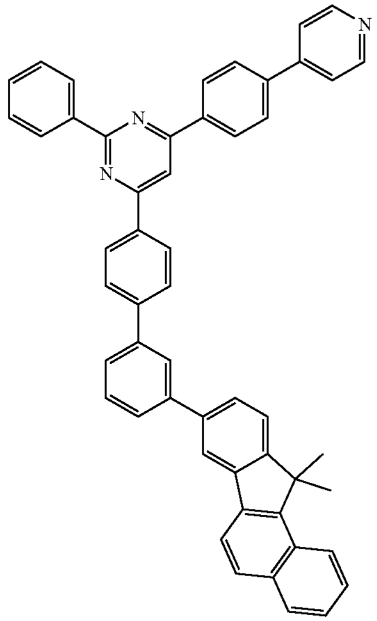
-continued
671
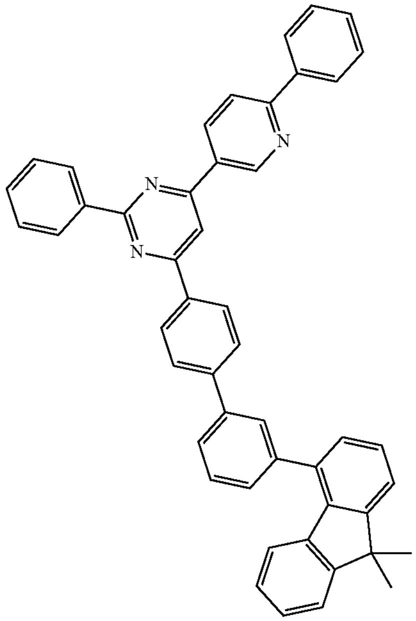
673
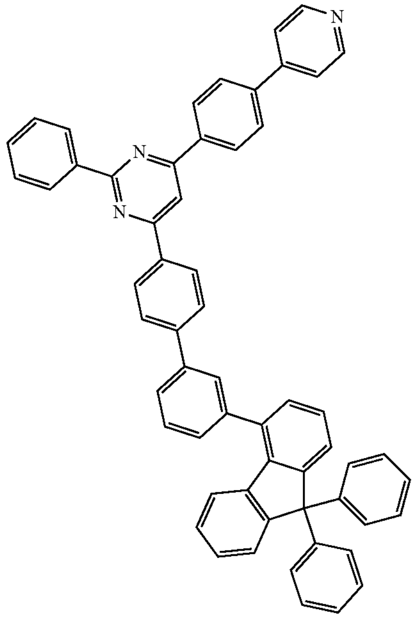

-continued
674
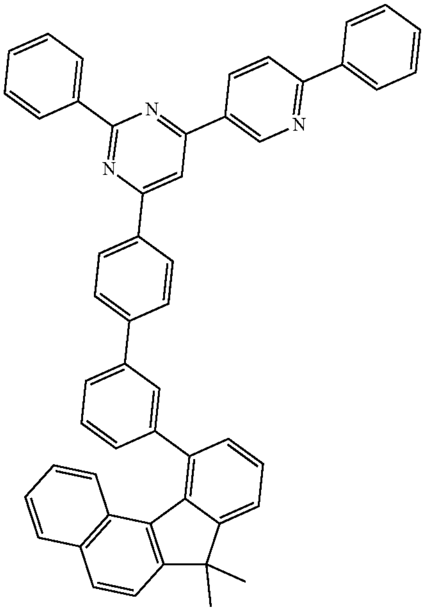
691
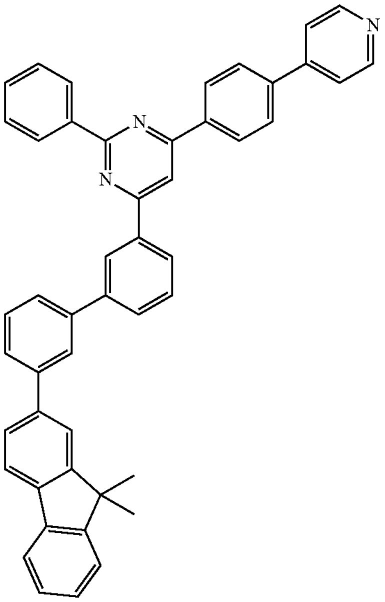
675
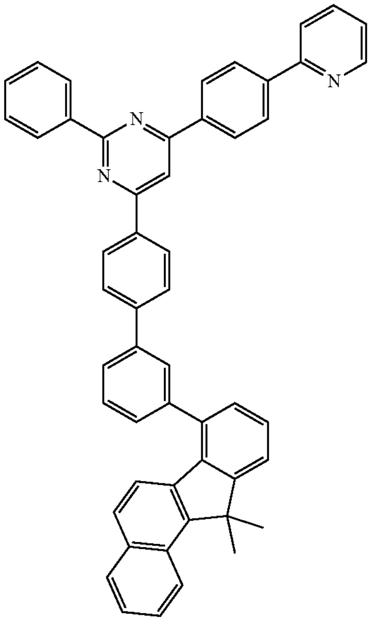
693
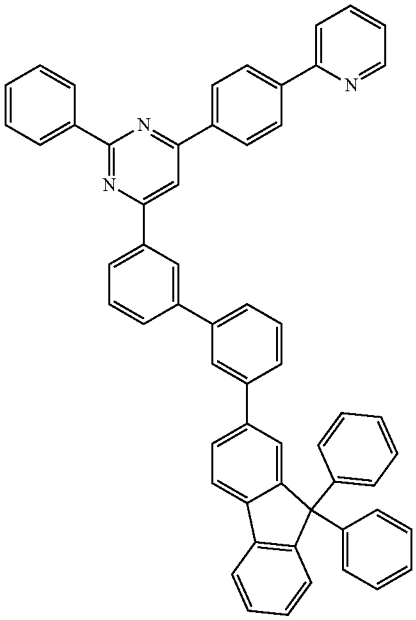

-continued
694
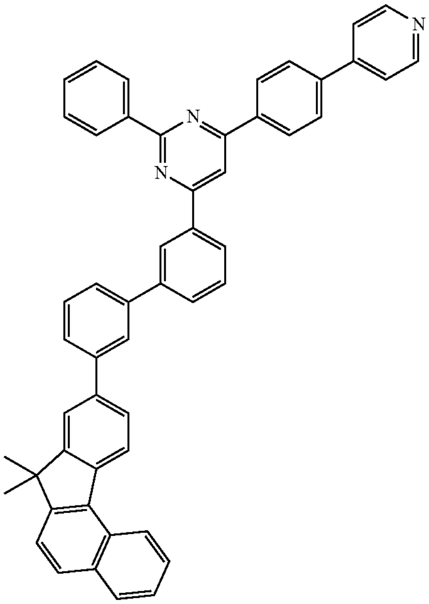
695
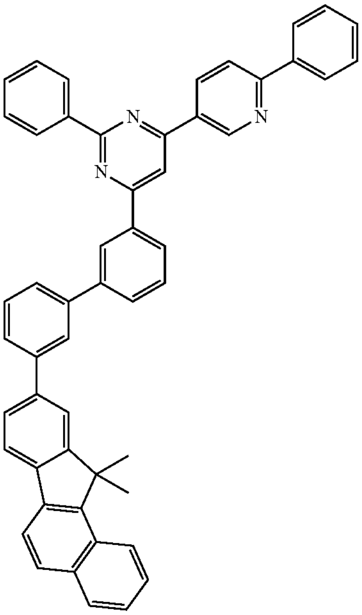
-continued
696
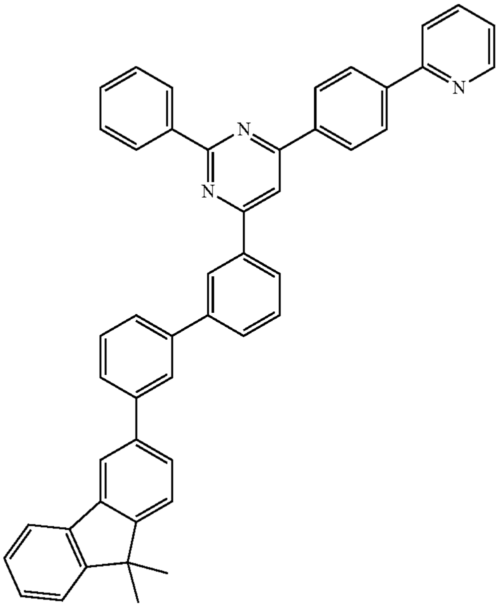
698
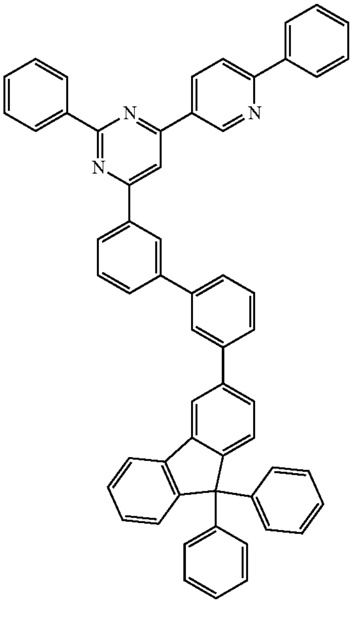

-continued
699
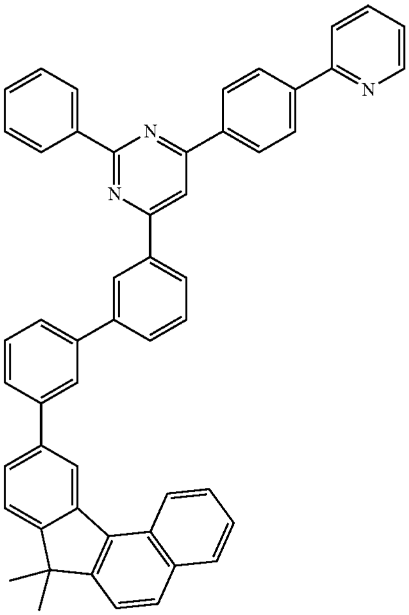
700
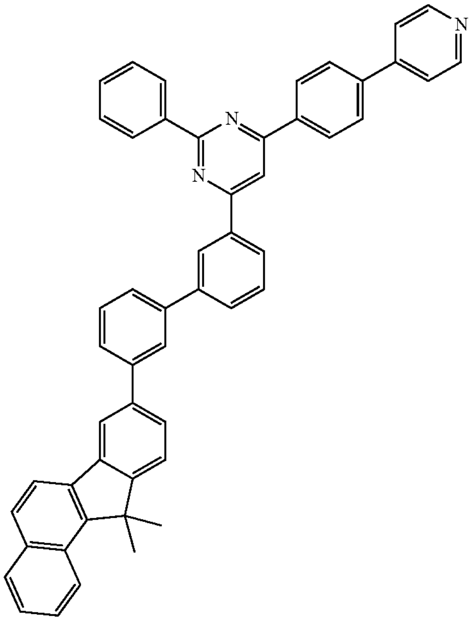
-continued
701
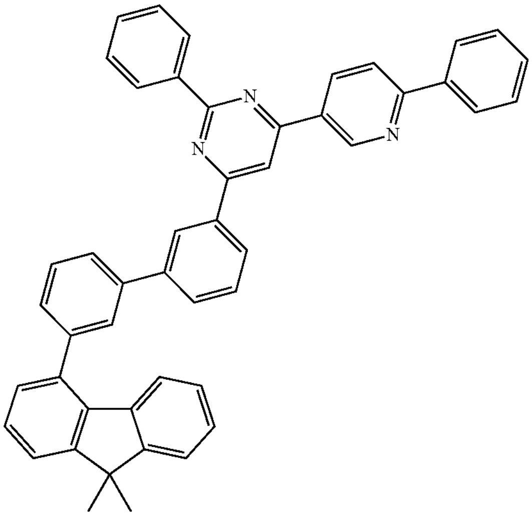
703
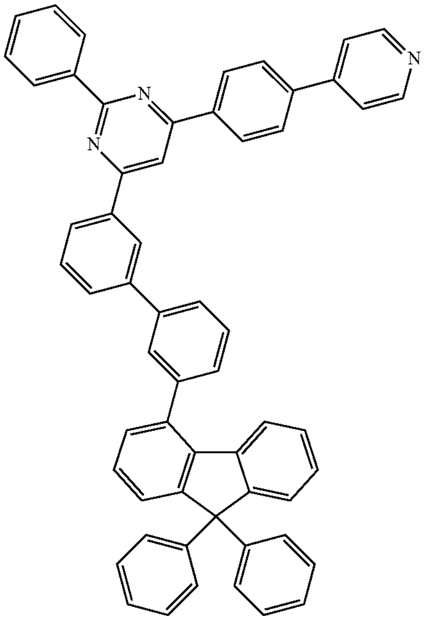
704
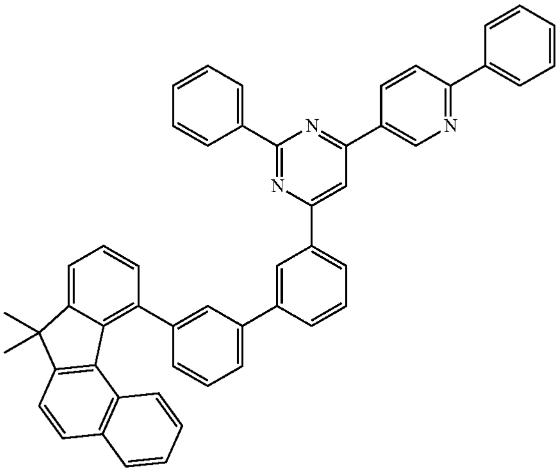

-continued
705
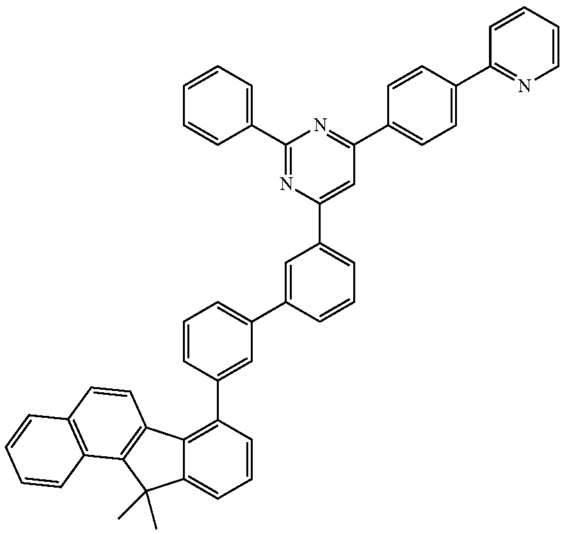
721
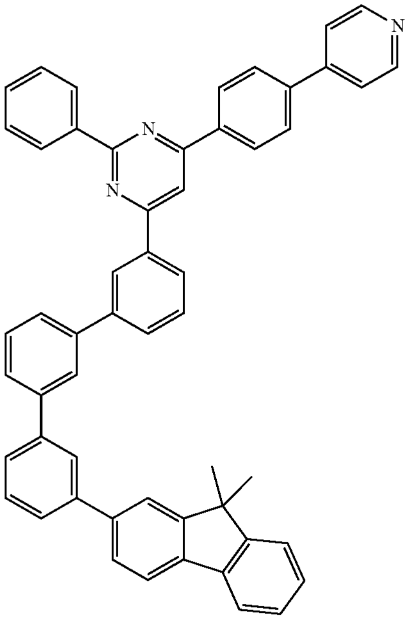
-continued
723
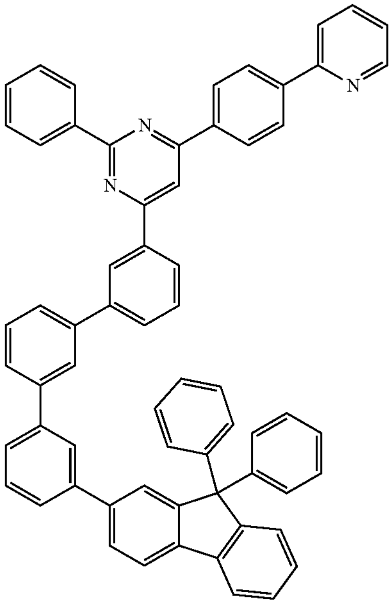
724
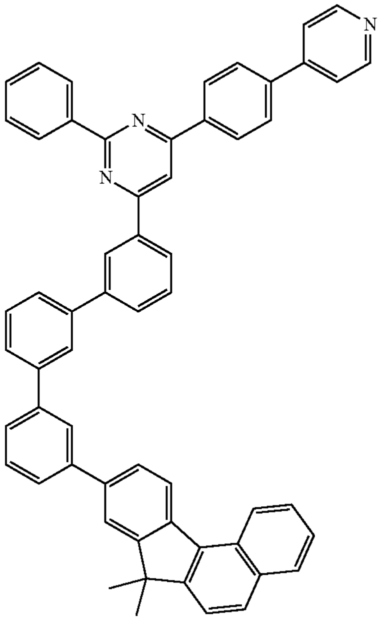

-continued
725
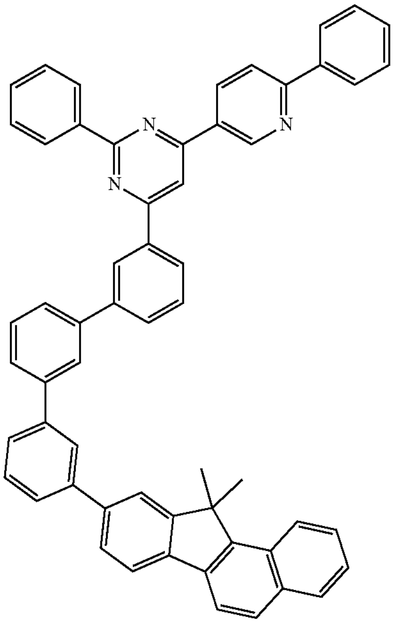
726
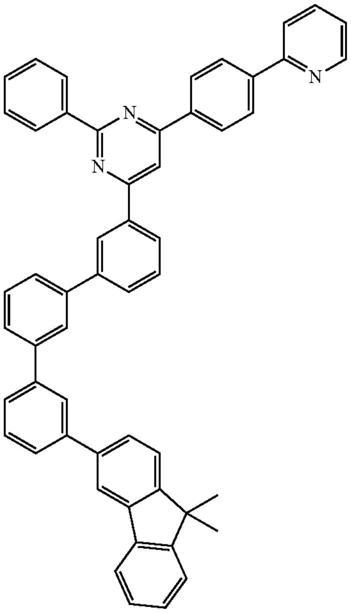
-continued
728
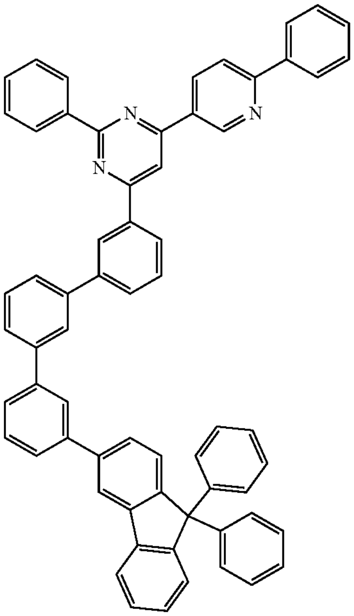
729
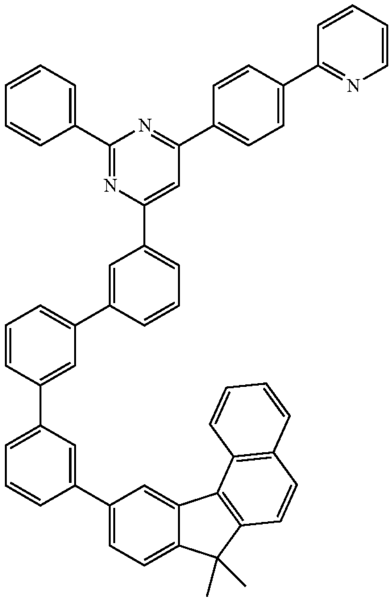

-continued
730
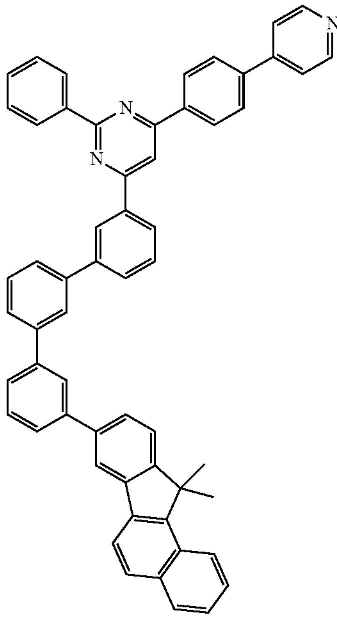
733
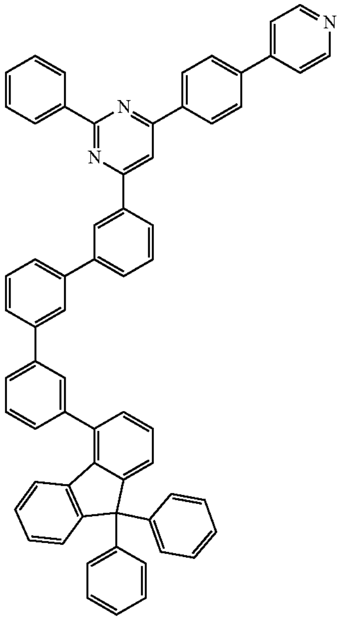
731
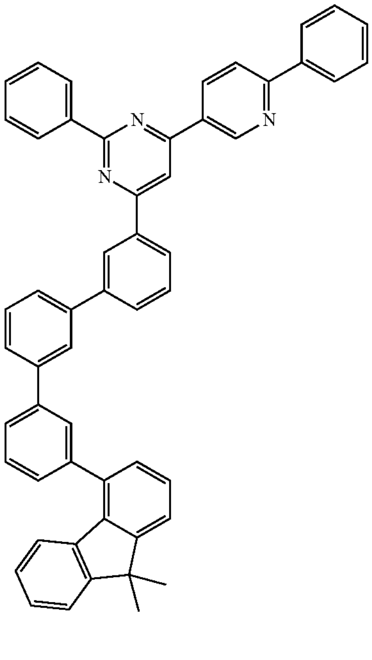
734
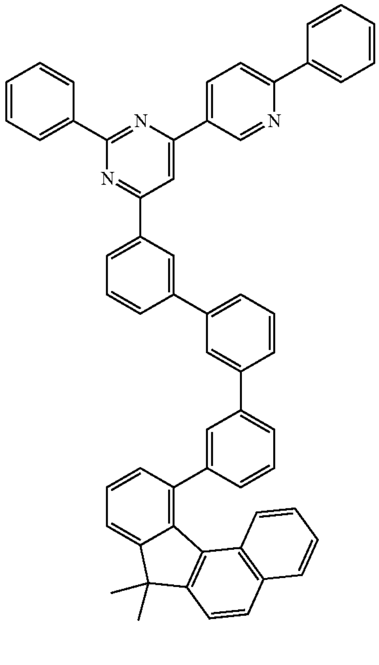

-continued

735

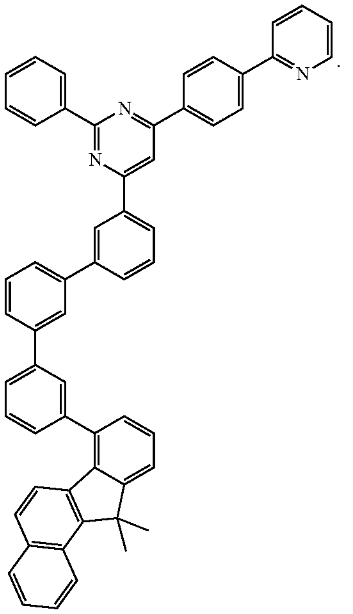

7. An organic electroluminescent device, comprising an anode, a cathode and one or more organic layers disposed between the anode and the cathode, wherein at least one of the one or more organic layers comprises the compound according to claim 1.

8. The organic electroluminescent device of claim 7, wherein the compound represented by Chemical Formula 1 is a compound represented by the following Chemical Formula 5 or Chemical Formula 6:

[Chemical Formula 5]

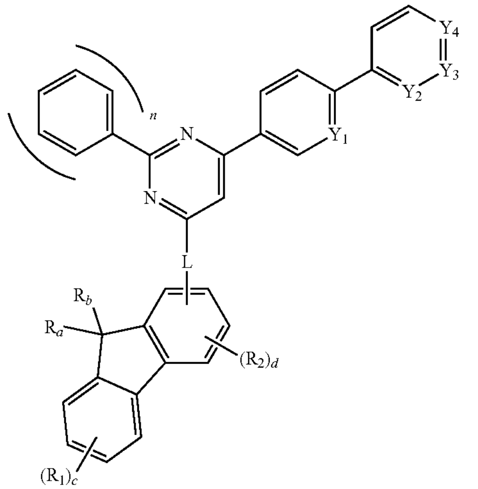

-continued

[Chemical Formula 6]

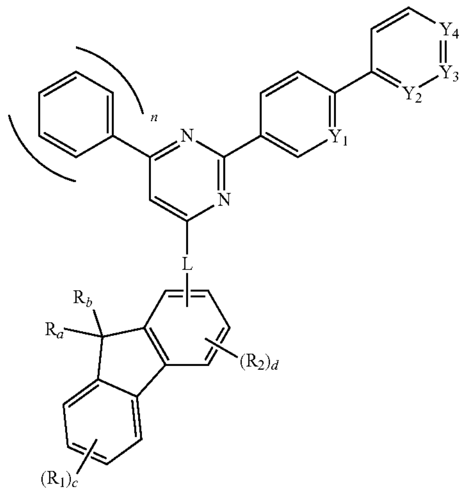

9. The organic electroluminescent device of claim 7, wherein in Chemical Formula 1, X is selected from the group consisting of the following structures represented by X-1 to X4:

X-1

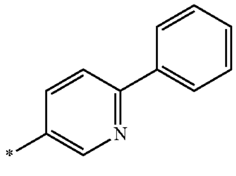

X-2

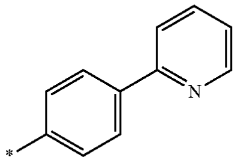

X-3

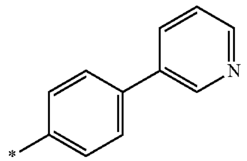

X-4

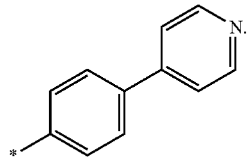

10. The organic electroluminescent device of claim 7, wherein $R_a$ and $R_b$ are each independently a methyl group or a phenyl group.

11. The organic electroluminescent device of claim 7, wherein in Chemical Formula 1, A is selected from the group of consisting of the following structures represented by A-1 and A-3 to A-6:

A-1

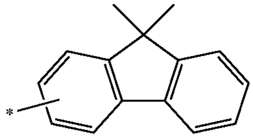

A-3

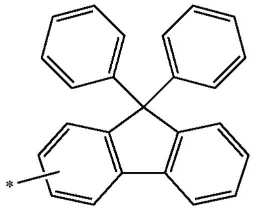

A-4

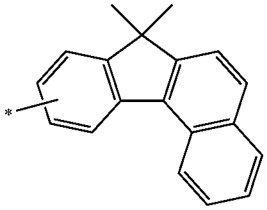

A-5

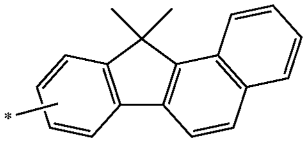

A-6

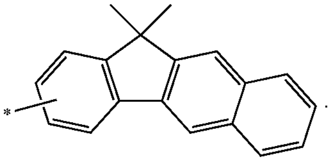

12. The organic electroluminescent device of claim 7, wherein in Chemical Formula 1, is selected from the following structures represented by L-1 to L-7:

L-1

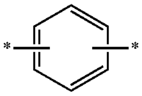

-continued

L-2

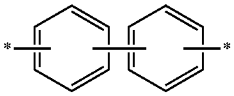

L-3

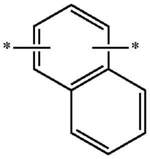

L-4

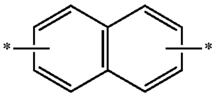

L-5

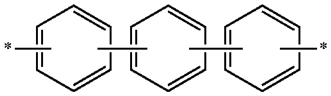

L-6

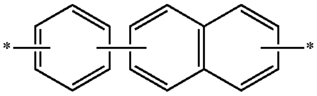

L-7

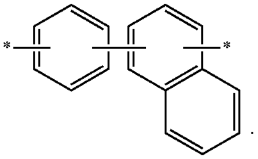

13. The organic electroluminescent device of claim 7, wherein the organic layer comprising the compound is selected from the group consisting of: a hole injection layer, a hole transporting layer, a light emitting auxiliary layer, a light emitting layer, an electron transporting layer, and an electron injection layer.

14. The organic electroluminescent device of claim 7, wherein the organic layer comprising the compound is selected from the group consisting of: an electron transporting layer and an electron transport auxiliary layer.

* * * * *